(12) United States Patent
Sakamoto

(10) Patent No.: US 11,968,891 B2
(45) Date of Patent: Apr. 23, 2024

(54) ORGANIC ELECTROLUMINESCENCE DEVICE AND HETEROCYCLIC COMPOUND FOR ORGANIC ELECTROLUMINESCENCE DEVICE

(71) Applicant: SAMSUNG DISPLAY CO., LTD., Yongin-si (KR)

(72) Inventor: Naoya Sakamoto, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 600 days.

(21) Appl. No.: 16/382,346

(22) Filed: Apr. 12, 2019

(65) Prior Publication Data

US 2019/0393422 A1    Dec. 26, 2019

(30) Foreign Application Priority Data

Jun. 26, 2018  (KR) .................. 10-2018-0073189

(51) Int. Cl.
| | |
|---|---|
| *H10K 85/60* | (2023.01) |
| *C07D 405/14* | (2006.01) |
| *C07D 409/14* | (2006.01) |
| *C09K 11/06* | (2006.01) |
| *H10K 50/11* | (2023.01) |

(Continued)

(52) U.S. Cl.
CPC ......... *H10K 85/654* (2023.02); *C07D 405/14* (2013.01); *C07D 409/14* (2013.01);
(Continued)

(58) Field of Classification Search
CPC ............. H01L 51/0067; H01L 51/0072; H01L 51/0073; H01L 51/0074; H01L 51/5012;
(Continued)

(56) References Cited

U.S. PATENT DOCUMENTS

| | | |
|---|---|---|
| 9,604,972 B2 | 3/2017 | Yoshida et al. |
| 9,670,185 B2 | 6/2017 | Xia et al. |
| (Continued) | | |

FOREIGN PATENT DOCUMENTS

| | | |
|---|---|---|
| CN | 108424411 A | 8/2018 |
| EP | 3 200 255 A2 | 8/2017 |
| (Continued) | | |

OTHER PUBLICATIONS

European Partial Search Report for patent application No. 19182182.6, dated Aug. 9, 2019, 10 pages.

(Continued)

*Primary Examiner* — Michael Y Sun
(74) *Attorney, Agent, or Firm* — Lewis Roca Rothgerber Christie LLP

(57) ABSTRACT

An organic electroluminescence device and a heterocyclic compound, the device including a first electrode; a hole transport region on the first electrode; an emission layer on the hole transport region; an electron transport region on the emission layer; and a second electrode on the electron transport region, wherein the emission layer includes a heterocyclic compound that includes a nitrogen-containing monocycle, at least one linker, and two or more carbazole moieties, the at least one linker is a substituted or unsubstituted dibenzofuran group or a substituted or unsubstituted dibenzothiophene group, and at least one of the carbazole moieties and the nitrogen-containing monocycle are bonded to the at least one linker in an ortho relationship.

23 Claims, 2 Drawing Sheets

(51) Int. Cl.
*H10K 50/15* (2023.01)
*H10K 50/16* (2023.01)
*H10K 50/17* (2023.01)
*H10K 50/18* (2023.01)

(52) U.S. Cl.
CPC .......... *C09K 11/06* (2013.01); *H10K 85/6572* (2023.02); *H10K 85/6574* (2023.02); *H10K 85/6576* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02)

(58) Field of Classification Search
CPC ............. H01L 51/5056; H01L 51/5072; H01L 51/5088; H01L 51/5092; H01L 51/5096; H01L 51/5024; H01L 51/0071; C07D 405/14; C09K 11/06; C09K 2211/1018; C09K 2211/1007; C09K 2211/1029; C09K 2211/1044; C09K 2211/1059; C09K 2211/1088; C09K 2211/1092

See application file for complete search history.

(56) References Cited

U.S. PATENT DOCUMENTS

| | | | |
|---|---|---|---|
| 9,732,069 B2 | 8/2017 | Lee et al. | |
| 11,084,806 B2 | 8/2021 | Jang et al. | |
| 2011/0240983 A1* | 10/2011 | Sekiguchi | H05B 33/14 257/40 |
| 2017/0194574 A1 | 7/2017 | Ishidai et al. | |
| 2018/0037546 A1 | 2/2018 | Sugino et al. | |
| 2018/0166634 A1* | 6/2018 | Numata | C07D 487/04 |
| 2018/0212158 A1* | 7/2018 | Aspuru-Guzik | C07D 471/04 |

FOREIGN PATENT DOCUMENTS

| | | | | |
|---|---|---|---|---|
| EP | 3 257 850 A1 | 12/2017 | | |
| KR | 10-2015-0134248 A | 12/2015 | | |
| KR | 10-2017-0082447 A | 7/2017 | | |
| KR | 20170082447 A | * 7/2017 | ......... | H01L 51/0085 |
| KR | 10-2017-0102000 A | 9/2017 | | |
| KR | 10-2018-0007243 A | 1/2018 | | |
| KR | 10-1856728 B1 | 5/2018 | | |
| KR | 10-2018-0062208 A | 6/2018 | | |
| WO | WO 2016/129672 A1 | 8/2016 | | |
| WO | 2017/011531 A2 | 1/2017 | | |
| WO | WO 2017/018795 A2 | 2/2017 | | |

OTHER PUBLICATIONS

Dias, Fernando, et al., "Photophysics of thermally activated delayed fluorescence molecules," Methods and Applications in Fluorescence, vol. 5, Mar. 2017, 26 pages.

EPO Extended Search Report dated Nov. 13, 2019, issued in European Patent Application No. 19182182.6, (11 pages).

* cited by examiner

ORGANIC ELECTROLUMINESCENCE DEVICE AND HETEROCYCLIC COMPOUND FOR ORGANIC ELECTROLUMINESCENCE DEVICE

CROSS-REFERENCE TO RELATED APPLICATION

Korean Patent Application No. 10-2018-0073189, filed on Jun. 26, 2018, in the Korean Intellectual Property Office, and entitled: "Organic Electroluminescence Device and Heterocyclic Compound for Organic Electroluminescence Device," is incorporated by reference herein in its entirety.

BACKGROUND

1. Field

Embodiments relates to an organic electroluminescence device and a heterocyclic compound used for the organic electroluminescence device.

2. Description of the Related Art

The development of an organic electroluminescence display as an image display device is being actively conducted. Different from a liquid crystal display device, the organic electroluminescence display is a self-luminescent display in which holes and electrons injected from a first electrode and a second electrode recombine in an emission layer, and a light-emitting material which is an organic compound included in the emission layer emits light to attain display.

An organic electroluminescence device may include, e.g., an organic device including a first electrode, a hole transport layer on the first electrode, an emission layer on the hole transport layer, an electron transport layer on the emission layer, and a second electrode on the electron transport layer. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and electrons injected into the emission layer recombine to produce excitons in the emission layer. The organic electroluminescence device emits light using light generated by the transition of the excitons to a ground state.

SUMMARY

The embodiments may be realized by providing an organic electroluminescence device including a first electrode; a hole transport region on the first electrode; an emission layer on the hole transport region; an electron transport region on the emission layer; and a second electrode on the electron transport region, wherein the emission layer includes a heterocyclic compound that includes a nitrogen-containing monocycle, at least one linker, and two or more carbazole moieties, the at least one linker is a substituted or unsubstituted dibenzofuran group or a substituted or unsubstituted dibenzothiophene group, and at least one of the carbazole moieties and the nitrogen-containing monocycle are bonded to the at least one linker in an ortho relationship.

The embodiments may be realized by providing an organic electroluminescence device including a first electrode; a hole transport region on the first electrode; an emission layer on the hole transport region; an electron transport region on the emission layer; and a second electrode on the electron transport region, wherein the emission layer includes a heterocyclic compound represented by the following Formula 1:

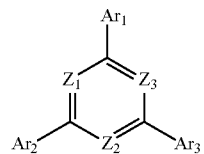

[Formula 1]

in Formula 1, $Z_1$ to $Z_3$ are each independently $CR_1$ or N, at least one of $Z_1$ to $Z_3$ is N, $R_1$ is a hydrogen atom, a deuterium atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $Ar_1$ to $Ar_3$ are each independently a group represented by the following Formula 2, a substituted or unsubstituted aryl group having 6 to 30 ring carbon atoms, or a substituted or unsubstituted heteroaryl group having 2 to 30 carbon atoms for forming a ring, and at least one of $Ar_1$ to $Ar_3$ is a group represented by Formula 2:

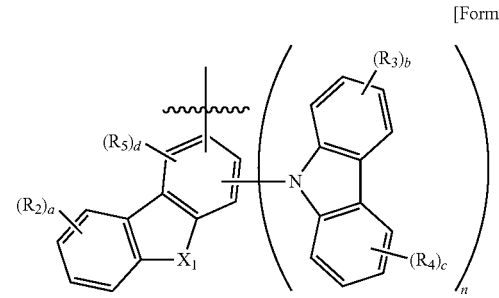

[Formula 2]

in Formula 2, $X_1$ is O or S, "n" is an integer of 1 to 3, "a" to "c" are each independently an integer of 0 to 4, "d" is an integer of 0 to 2, and $R_2$ to $R_5$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, when only one of $Ar_1$ to $Ar_3$ is a group represented by Formula 2 above, "n" is 2 or 3, and at least one of the carbazole moieties in Formula 2 is bonded in an ortho relationship with respect to the nitrogen-containing monocycle of Formula 1.

The embodiments may be realized by providing a heterocyclic compound represented by the following Formula 1:

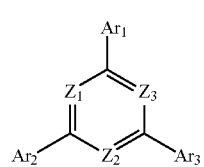

[Formula 1]

wherein, in Formula 1, $Z_1$ to $Z_3$ are each independently $CR_1$ or N, at least one of $Z_1$ to $Z_3$ is N, $R_1$ is a hydrogen atom, a deuterium atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $Ar_1$ to $Ar_3$ are each independently a group represented by the following Formula 2, a substituted or unsubstituted aryl group having 6 to 30 ring carbon atoms, or a substituted or unsubstituted heteroaryl group having 2 to 30 ring carbon atoms, and at least one of $Ar_1$ to $Ar_3$ is a group represented by Formula 2:

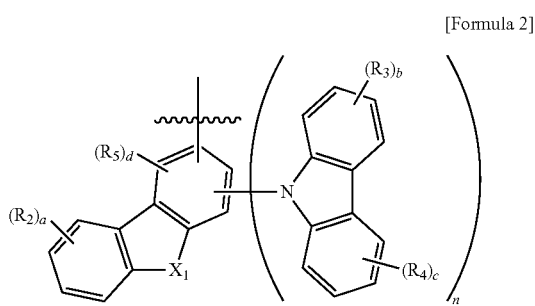

[Formula 2]

in Formula 2, $X_1$ is O or S, "n" is an integer of 1 to 3, "a" to "c" are each independently an integer of 0 to 4, "d" is an integer of 0 to 2, and $R_2$ to $R_5$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, when only one of $Ar_1$ to $Ar_3$ is a group represented by Formula 2 above, "n" is 2 or 3, and at least one of the carbazole moieties in Formula 2 is bonded in an ortho relationship with respect to the nitrogen-containing monocycle of Formula 1.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
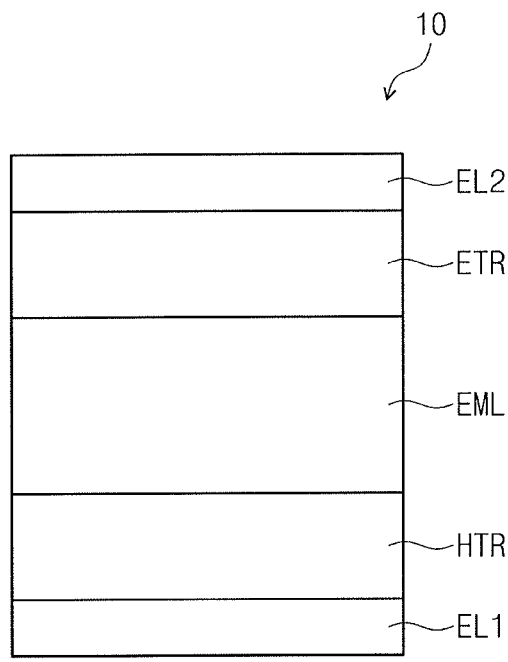
FIG. 1 illustrates a cross-sectional view of an organic electroluminescence device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "includes," "including," "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be "directly on" the other part, or intervening layers may also be present.

First, organic electroluminescence devices according to exemplary embodiments will be explained referring to FIG. 1 to FIG. 3.

FIG. 1 illustrates a cross-sectional view of an organic electroluminescence device according to an embodiment.

Figure 2:
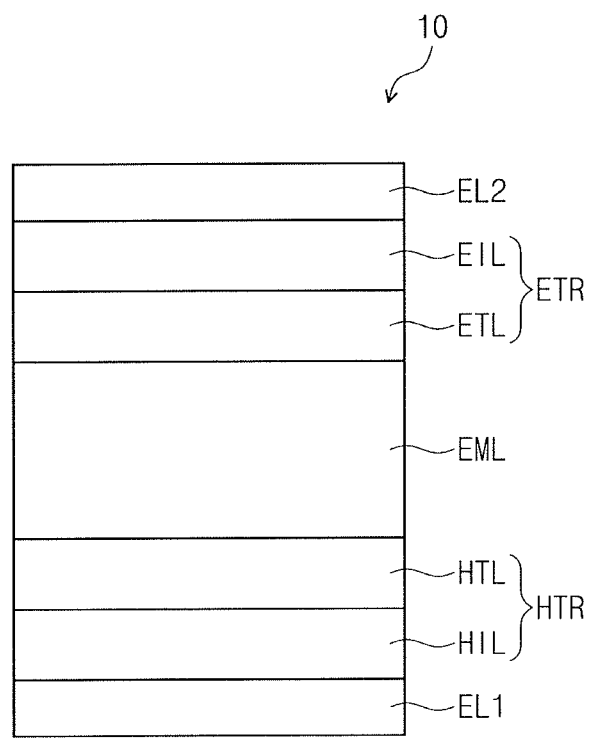
FIG. 2 illustrates a cross-sectional view of an organic electroluminescence device according to an embodiment.

FIG. 2 illustrates a cross-sectional view of an organic electroluminescence device according to an embodiment.

Figure 3:
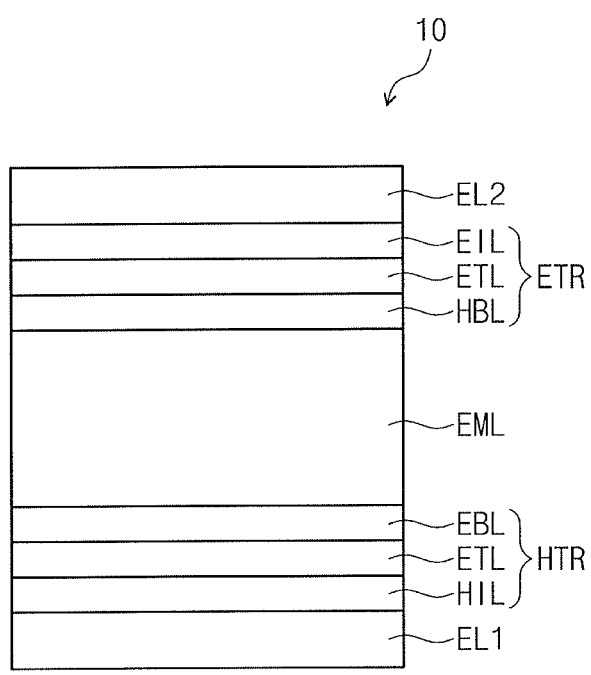
FIG. 3 illustrates a cross-sectional view of an organic electroluminescence device according to an embodiment.

FIG. 3 illustrates a cross-sectional view of an organic electroluminescence device according to an embodiment.

Referring to FIG. 1 to FIG. 3, an organic electroluminescence device 10 according to an embodiment may include a first electrode EL1, a hole transport region HTR, an emission layer EML, an electron transport region ETR, and a second electrode EL2.

The first electrode EL1 has conductivity. The first electrode EL1 may be a pixel electrode or an anode. The first electrode EL1 may be a transmissive electrode, a transflective electrode, or a reflective electrode. If the first electrode EL1 is the transmissive electrode, the first electrode EL1 may include a transparent metal oxide such as indium tin oxide (ITO), indium zinc oxide (IZO), zinc oxide (ZnO), or indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer or transflective layer formed using the above materials, or a transparent layer formed using ITO, IZO, ZnO, or ITZO. For example, the first electrode EL1 may have a three-layer structure of ITO/Ag/ITO.

The thickness of the first electrode EL1 may be from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer EBL. The thickness of the hole transport region HTR may be, for example, from about 1,000 Å to about 1,500 Å

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL and a hole transport layer HTL, and may have a structure of a single layer formed using a hole injection material and a hole transport material. In an implementation, the hole transport region HTR may have a structure of a single layer formed using a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/ electron blocking layer EBL.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4', 4"-tris(N,N-diphenylamino)triphenylamine (TDATA), 4,4', 4"-tris {N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-dinaphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL may include, for example, carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris (N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 100 Å to about 10,000 Å, for example, from about 100 Å to about 1,000 Å. If the hole transport region HTR includes both the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. If the thicknesses of the hole transport region HTR, the hole injection layer HIL, and the hole transport layer HTL satisfy the above-described ranges, satisfactory hole transport properties may be obtained without substantial increase of a driving voltage.

The hole transport region HTR may further include a charge generating material in addition to the above-described materials to increase conductivity. The charge generating material may be dispersed uniformly or non-uniformly in the hole transport region HTR. The charge generating material may be, for example, a p-dopant. In an implementation, the p-dopant may be one of quinone derivatives, metal oxides, or cyano group-containing compounds. Examples of the p-dopant may include quinone derivatives such as tetracyanoquinodimethane (TCNQ) and 2,3,5,6-tetrafluoro-tetracyanoquinodimethane (F4-TCNQ), metal oxides such as tungsten oxide, and molybdenum oxide.

As described above, the hole transport region HTR may further include at least one of a hole buffer layer or an electron blocking layer in addition to the hole injection layer HIL and the hole transport layer HTL. The hole buffer layer may compensate a resonance distance according to the wavelength of light emitted from the emission layer EML and increase light emission efficiency. Materials included in the hole transport region HTR may be used as materials included in the hole buffer layer. The electron blocking layer is a layer preventing electron injection from the electron transport region ETR to the hole transport region HTR.

The emission layer EML may be provided on the hole transport region HTR. In an implementation, the emission layer EML may have a thickness of about 100 Å to about 1,000 Å, e.g., about 100 Å to about 300 Å. In an implementation, the emission layer EML may have a single layer formed using a single material, a single layer formed using a plurality of different materials, or a multilayer structure having a plurality of layers formed using a plurality of different materials.

The emission layer EML may include, e.g., a heterocyclic compound including a nitrogen-containing monocycle, a (e.g., at least one) linker, and two or more carbazole moieties. In an implementation, the linker may be, e.g., a substituted or unsubstituted dibenzofuran group or a substituted or unsubstituted dibenzothiophene.

At least one of the carbazole moieties and the nitrogen-containing monocycle may be bonded the linker in an ortho relationship. For example, the nitrogen-containing monocycle and the carbazole moieties may be connected via the linker, and at least one of the carbazole moieties and the nitrogen-containing monocycle are bonded to the linker in ortho relationship. For example, the nitrogen-containing monocycle may be bound to one ring atom of the linker, and one of the carbazole moieties may be bound to another ring atom of the linker, which other ring atom of the linker is directly adjacent to the one ring atom of the linker on the ring (e.g., the one ring atom of the linker may be at a 3-position of the linker and the other ring atom of the linker may be at a 4-position of the linker).

In an implementation, if two carbazole moieties are included, only one of the two may be bonded in the ortho relationship with respect to the nitrogen-containing monocycle, and the other carbazole moiety may be bonded in meta or para relationship with respect to the nitrogen-containing monocycle. In an implementation, each (e.g., both) of the two carbazole moieties may be bonded to the linker in the ortho relationship with respect to the nitrogen-containing monocycle. In an implementation, the heterocyclic compound may include two linkers.

In an implementation, the heterocyclic compound may include one or two linkers. If the heterocyclic compound includes one linker, each of two or more carbazole moieties may be bonded to the linker. If the heterocyclic compound includes two linkers, at least one carbazole moiety may be bonded each of the linkers.

In an implementation, the nitrogen-containing monocycle may be, e.g., a substituted or unsubstituted pyridine group, a substituted or unsubstituted pyrimidine group, or a substituted or unsubstituted triazine group. In an implementation, the nitrogen-containing monocycle may be, e.g., a substituted or unsubstituted triazine group.

In an implementation, the nitrogen-containing monocycle may be substituted with at least one substituted or unsubstituted phenyl group. In an implementation, if the heterocyclic compound includes one linker, the nitrogen-containing monocycle may be unsubstituted or may be di-substituted with two substituted or unsubstituted phenyl groups. In an implementation, if the heterocyclic compound includes two linkers, the nitrogen-containing monocycle may be substituted with one substituted or unsubstituted phenyl group. In an implementation, the nitrogen-containing monocycle may be, e.g., substituted with one or two unsubstituted phenyl groups.

In an implementation, the heterocyclic compound may be, e.g., represented by the following Formula 1.

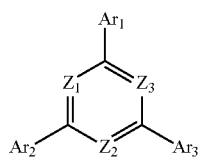

[Formula 1]

In Formula 1, $Z_1$ to $Z_3$ may each independently be, e.g., $CR_1$ or N, at least one of $Z_1$ to $Z_3$ is N. $R_1$ may be, e.g., a hydrogen atom, a deuterium atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. $Ar_1$ to $Ar_3$ may each independently be, e.g., a group represented by Formula 2, below, a substituted or unsubstituted aryl group having 6 to 30 ring carbon atoms, or a substituted or unsubstituted heteroaryl group having 2 to 30 ring carbon atoms. In an implementation, at least one of $Ar_1$ to $Ar_3$ may be a group represented by Formula 2. It may be understood that the substituted or unsubstituted aryl group having 6 to 30 ring carbon atoms and the substituted or unsubstituted heteroaryl group having 2 to 30 ring carbon atoms are different from the group represented by Formula 2.

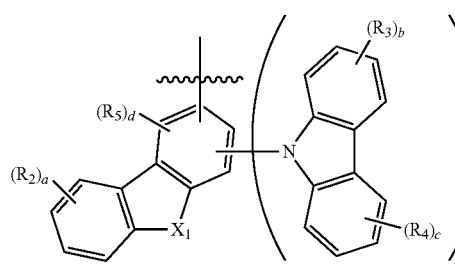

[Formula 2]

In Formula 2, $X_1$ may be, e.g., O or S. "n" may be, e.g., an integer of 1 to 3, "a" to "c" may each independently be, e.g., an integer of 0 to 4, and "d" may be, e.g., an integer of 0 to 2. $R_2$ to $R_5$ may each independently be, e.g., a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $R_2$ to $R_5$ may each independently be, e.g., a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, when n of Formula 2 is 1, the compound represented by Formula 1 may include another carbazole moiety thereon.

In the description, ⌇ means a part to be connected or a bonding location (e.g., at a location of $Ar_1$ to $Ar_3$ of Formula 1).

In the description, "substituted or unsubstituted" may mean substituted with at least one substituent selected from a deuterium atom, a halogen atom, a cyano group, a nitro group, an amino group, a silyl group, a boron group, a phosphine group, an alkyl group, an alkenyl group, an aryl group, and a heterocycle, or unsubstituted. In addition, each of the substituent illustrated above may be substituted or unsubstituted. For example, a biphenyl group may be interpreted as an aryl group, or a phenyl group substituted with a phenyl group.

In the description, the halogen atom may include a fluorine atom, a chlorine atom, a bromine atom and an iodine atom.

In the description, the alkyl may be a linear, branched or cyclic type. The carbon number of the alkyl may be from 1 to 30, from 1 to 20, 1 to 10, or from 1 to 4. The alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the description, the aryl group means an optional functional group or substituent derived from an aromatic hydrocarbon ring. The aryl group may be a monocyclic aryl group or a heterocyclic aryl group. The carbon number for forming a ring in the aryl group may be, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc.

In the description, the fluorenyl group may be substituted, and two substituents may be combined with each other to form a spiro structure. If the fluorenyl group is substituted, examples are shown below.

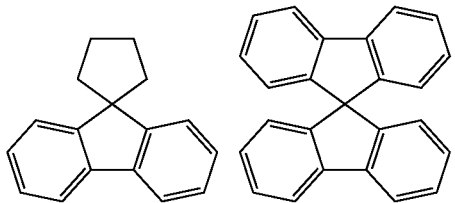

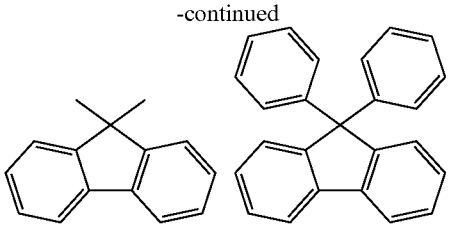

In the description, the heteroaryl group may be a heteroaryl group including at least one of O, N, P, Si or S as a heteroatom. If the heteroaryl group includes two heteroatoms, two heteroatoms may be the same or different. The carbon number for forming a ring of the heteroaryl group may be 2 to 30 or 2 to 20. The heteroaryl group may be a monocyclic heteroaryl group or a polycyclic heteroaryl group. The polycyclic heteroaryl group may have, for example, a two-ring or a three-ring structure. Examples of the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc.

In the description, the silyl group includes an alkyl silyl group and an aryl silyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc.

In the description, the boron group includes an alkyl boron group and an aryl boron group. Examples of the boron group may include trimethylboron, triethylboron, t-butyldimethylboron, triphenylboron, diphenylboron, phenylboron, etc.

In the description, the alkenyl group may be a linear chain or a branched chain. The carbon number is not specifically limited, but may be from 2 to 30, 2 to 20, or 2 to 10. Examples of the alkenyl group may include vinyl, I-butenyl, 1-pentenyl, 1,3-butadienyl aryl, styrenyl, styrylvinyl, etc.

In the description, the carbon number of the amino group is not specifically limited, but may be 1 to 30. The amino group may include an alkyl amino group and an aryl amino group. Examples of the amino group include a methylamino group, a dimethylamino group, a phenylamino group, a diphenylamino group, a naphthylamino group, a 9-methylanthracenylamino group, a triphenylamino group, etc.

In an implementation, $R_1$ may be, e.g., a hydrogen atom. For example, $Z_1$ to $Z_3$ may be each independently CH or N.

In an implementation, each (e.g., all) of $Z_1$ to $Z_3$ may be N.

In an implementation, at least one among $Ar_1$ to $Ar_3$ that is not represented by Formula 2 may be, e.g., a substituted or unsubstituted aryl group having 6 to 30 ring carbon atoms. In an implementation, at least one among $Ar_1$ to $Ar_3$ that is not represented by Formula 2 may be, e.g., substituted or unsubstituted phenyl group, a substituted or unsubstituted biphenyl group, a substituted or unsubstituted terphenyl group, a substituted or unsubstituted naphthyl group, a substituted or unsubstituted anthracene group, or a substituted or unsubstituted phenanthrene group.

In an implementation, if only one of $Ar_1$ to $Ar_3$ is represented by Formula 2, "n" of Formula 2 is 2 or 3.

In an implementation, at least one of the carbazole moieties in Formula 2 may be bonded in the ortho relationship with respect to the nitrogen-containing monocycle of Formula 1.

In an implementation, $X_1$ may be O. In an implementation, $X_1$ may be S.

If "a" is 2, 3, or 4, the 2, 3, or 4 $R_2$ groups may be the same or different, if "b" is 2, 3, or 4, the 2, 3, or 4 $R_3$ groups may be the same or different, if "c" is 2, 3, or 4, the 2, 3, or 4 $R_4$ groups may be the same or different, and if "d" is 2, the 2 $R_5$ groups may be the same or different.

In an implementation, if "a" is 1, $R_2$ may not be a hydrogen atom, if "b" is 1, $R_3$ may not be a hydrogen atom, if "c" is 1, $R_4$ may not be a hydrogen atom, and/or if "d" is 1, $R_5$ may not be a hydrogen atom.

In an implementation, if "a" is 1, 2, 3, or 4, $R_2$ may be, e.g., a deuterium atom, a halogen atom, a substituted or unsubstituted alkyl group having 1 to 5 carbon atoms, a substituted or unsubstituted phenyl group, a substituted or unsubstituted biphenyl group, a substituted or unsubstituted naphthyl group, or a substituted or unsubstituted heteroaryl group having 2 to 15 ring carbon atoms.

In an implementation, if "b" is 1, 2, 3, or 4, $R_3$ may be a deuterium atom, a halogen atom, a substituted or unsubstituted alkyl group having 1 to 5 carbon atoms, a substituted or unsubstituted phenyl group, a substituted or unsubstituted biphenyl group, a substituted or unsubstituted naphthyl group, or a substituted or unsubstituted heteroaryl group having 2 to 15 ring carbon atoms.

In an implementation, if "c" is 1, 2, 3, or 4, $R_4$ may be a deuterium atom, a halogen atom, a substituted or unsubstituted alkyl group having 1 to 5 carbon atoms, a substituted or unsubstituted phenyl group, a substituted or unsubstituted biphenyl group, a substituted or unsubstituted naphthyl group, or a substituted or unsubstituted heteroaryl group having 2 to 15 ring carbon atoms.

In an implementation, if "d" is 1 or 2, $R_5$ may be a deuterium atom, a halogen atom, a substituted or unsubstituted alkyl group having 1 to 5 carbon atoms, a substituted or unsubstituted phenyl group, a substituted or unsubstituted biphenyl group, a substituted or unsubstituted naphthyl group, or a substituted or unsubstituted heteroaryl group having 2 to 15 ring carbon atoms.

In an implementation, each (e.g., all) of "a" to "d" may be 0.

In an implementation, the compound represented by Formula 1 may be represented by the following Formula 1-1.

[Formula 1-1]

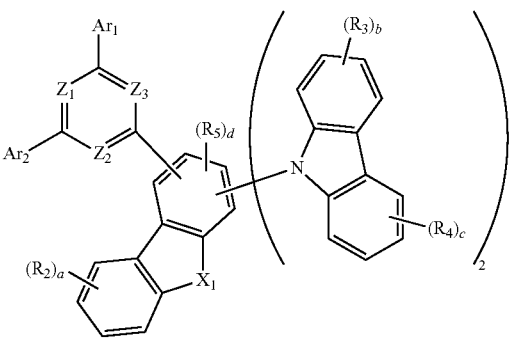

In Formula 1-1, $Z_1$ to $Z_3$, $Ar_1$, $Ar_2$, $R_2$ to $R_5$, "a" to "d" and $X_1$ may be defined the same as those of Formulae 1 and 2. In an implementation, "d" may be 0 or 1.

In an implementation, in Formula 1-1, $Ar_1$ and $Ar_2$ may each independently be, e.g., a substituted or unsubstituted aryl group having 6 to 18 ring carbon atoms or a substituted or unsubstituted heteroaryl group having 2 to 15 ring carbon atoms. For example, $Ar_1$ and $Ar_2$ may be each independently a substituted or unsubstituted phenyl group, a substituted or unsubstituted biphenyl group, a substituted or unsubstituted terphenyl group, a substituted or unsubstituted naphthyl group, a substituted or unsubstituted anthracene group, a substituted or unsubstituted phenanthrene group, a substituted or unsubstituted dibenzofuran group, or a substituted or unsubstituted dibenzothiophene group.

At least one of the two carbazole moieties of Formula 1-1 may be bonded in an ortho relationship with respect to the nitrogen-containing monocycle (e.g., including $Z_1$ to $Z_3$).

In an implementation, the compound represented by Formula 1 may be represented by the following Formula 1-2.

[Formula 1-2]

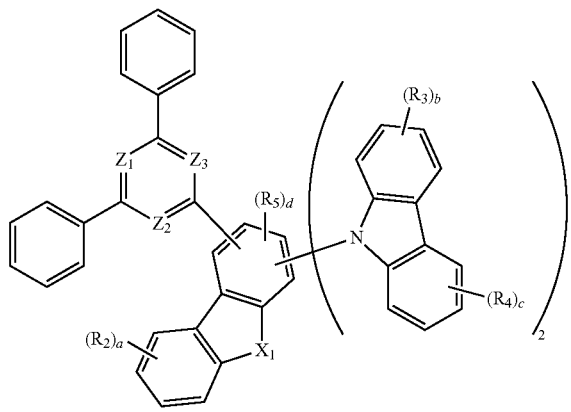

In Formula 1-2, $Z_1$ to $Z_3$, $R_2$ to $R_5$, "a" to "d" and $X_1$ may be defined the same as those of Formulae 1 and 2. In an implementation, "d" may be 0 or 1.

In an implementation, in Formula 1-2, each of "a" to "d" may be 0.

At least one of two carbazole moieties in Formula 1-2 may be bonded in an ortho relationship with respect to the nitrogen-containing monocycle (e.g., including $Z_1$ to $Z_3$).

In an implementation, the compound represented by Formula 1 may be represented by the following Formula 1-3.

[Formula 1-3]

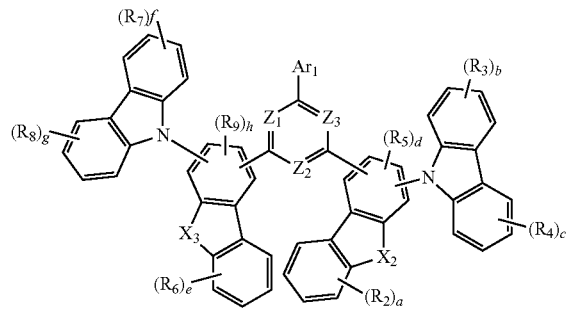

In Formula 1-3, $X_2$ and $X_3$ may each independently be, e.g., O or S. $R_2$ to $R_9$ may each independently be, a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. "a" to "c" and "e" to "g" may each independently be, e.g., an integer of 0 to 4, "d" and "h" may each independently be, e.g., an integer of 0 to 2. $Z_1$ to $Z_3$, and $Ar_1$ may be defined the same as those of Formula 1.

In an implementation, in Formula 1-3, $X_2$ and $X_3$ may be the same.

In an implementation, in Formula 1-3, $Ar_1$ may be, e.g., a substituted or unsubstituted aryl group having 6 to 18 ring carbon atoms. In an implementation, $Ar_1$ may be, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracene group, or a substituted or unsubstituted phenanthrene group.

At least one of two carbazole moieties in Formula 1-3 may be bonded in an ortho relationship with respect to the nitrogen-containing monocycle (e.g., including $Z_1$ to $Z_3$).

In an implementation, the compound represented by Formula 1-3 may be represented by the following Formula 1-4.

[Formula 1-4]

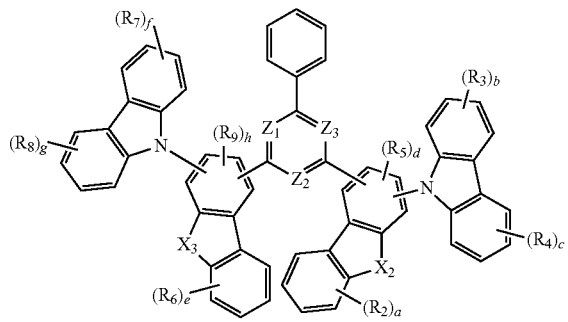

In Formula 1-4, $X_2$ and $X_3$ may each independently be, e.g., O or S. $R_2$ to $R_9$ may each independently be, e.g., a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, "a" to "c" and "e" to "g" may each independently be, e.g., an integer of 0 to 4, "d" and "h" may each independently be, e.g., an integer of 0 to 2. $Z_1$ to $Z_3$ may be defined the same as those Formula 1.

In an implementation, in Formula 1-4, $X_2$ and $X_3$ may be the same.

At least one of two carbazole moieties in Formula 1-4 is substituted in ortho relationship with respect to a ring including $Z_1$ to $Z_3$.

In an implementation, the compound represented by Formula 1 may be represented by the following Formula 1-5 or Formula 1-6.

[Formula 1-5]

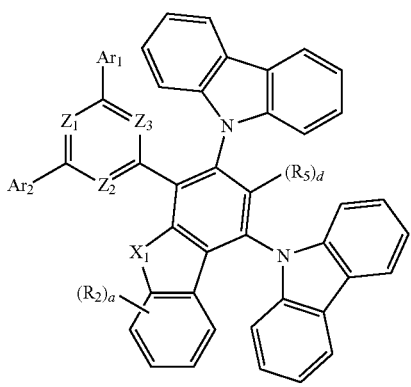

[Formula 1-6]

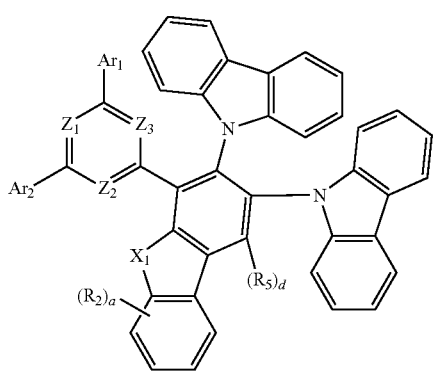

In Formulae 1-5 and 1-6, $Z_1$ to $Z_3$, $Ar_1$, $Ar_2$, $R_2$, $R_5$, "a", "d" and $X_1$ may be defined the same as those of Formulae 1 and 2. In an implementation, "d" may be 0 or 1.

In an implementation, the compound represented by Formula 1 may be represented by one of the following Formulae 1-7 to 1-9.

[Formula 1-7]

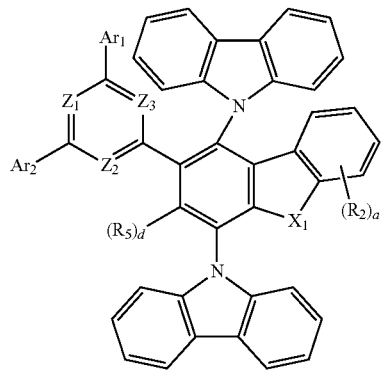

[Formula 1-8]

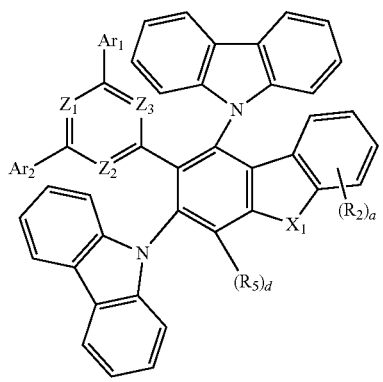

[Formula 1-9]

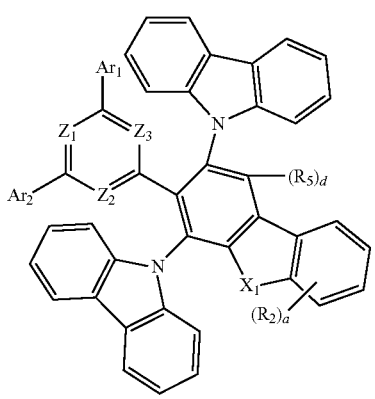

In Formulae 1-7 to 1-9, $Z_1$ to $Z_3$, $Ar_1$, $Ar_2$, $R_2$, $R_5$, "a", "d" and $X_1$ may be defined the same as those of Formulae 1 and 2.

In an implementation, the compound represented by Formula 1 may be represented by one of the following Formulae 1-10 to 1-12.

[Formula 1-10]

[Formula 1-11]

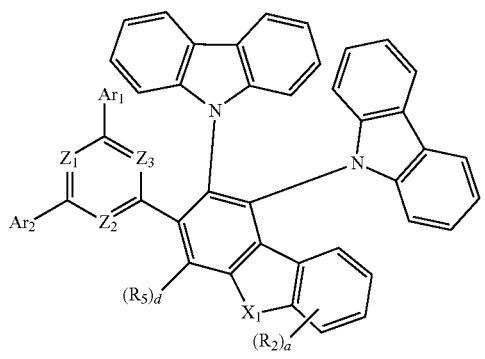

[Formula 1-14]

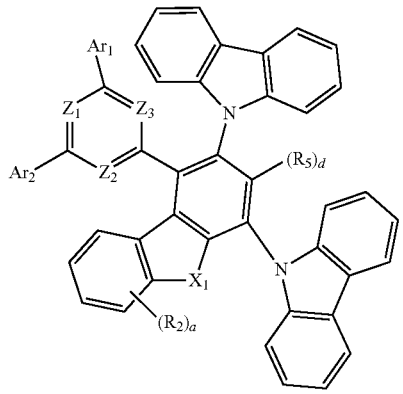

In Formulae 1-13 and 1-14, $Z_1$ to $Z_3$, $Ar_1$, $Ar_2$, $R_2$, $R_5$, "a", "d" and $X_1$ may be defined the same as those of Formulae 1 and 2.

In an implementation, the compound represented by Formula 1 may be represented by one of the following Formulae 1-15 to 1-17.

[Formula 1-12]

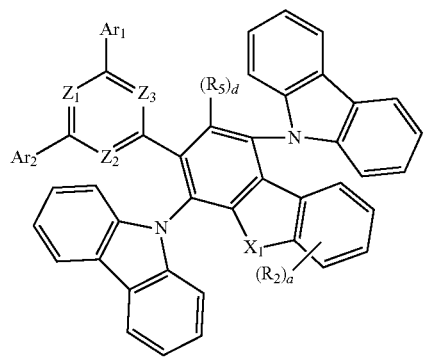

[Formula 1-15]

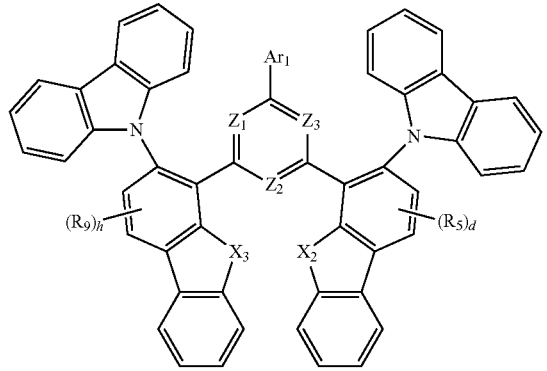

In Formulae 1-10 to 1-12, $Z_1$ to $Z_3$, $Ar_1$, $Ar_2$, $R_2$, $R_5$, "a", "d" and $X_1$ may be defined the same as those of Formulae 1 and 2.

In an implementation, the compound represented by Formula 1 may be represented by the following Formula 1-13 or Formula 1-14.

[Formula 1-13]

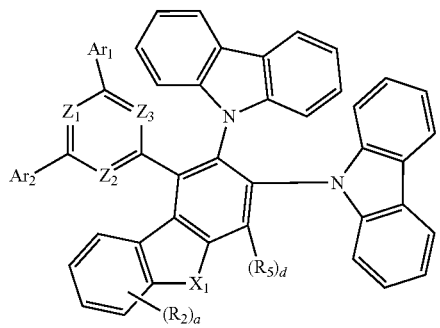

[Formula 1-16]

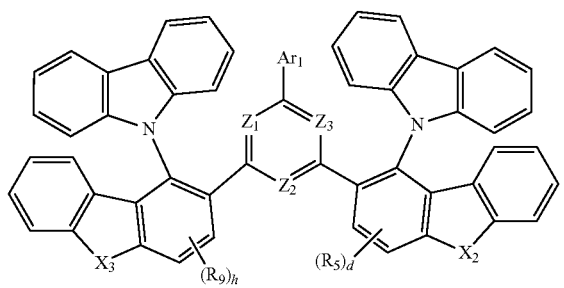

[Formula 1-17]
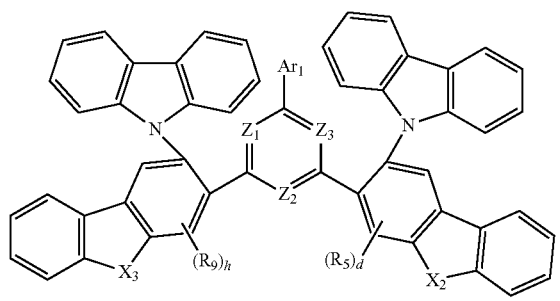
In Formulae 1-15 to 1-17, $Z_1$ to $Z_3$, An, $Ar_2$, $R_2$, $R_5$, "a", and "d" may be defined the same as those of Formula 1, and $X_2$ and $X_3$ may be O or S.
In an implementation, the heterocyclic compound may be, e.g., a compound of the following Compound Group 1.
[Compound Group 1]
1
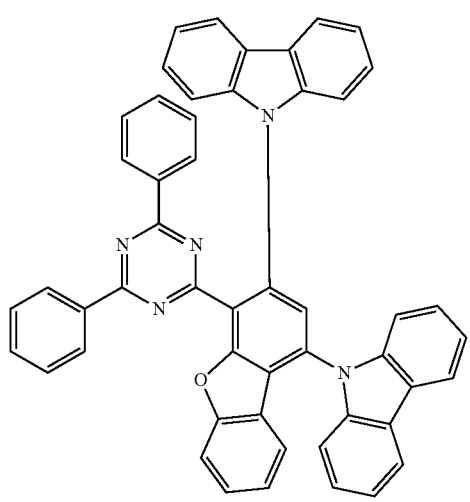
2
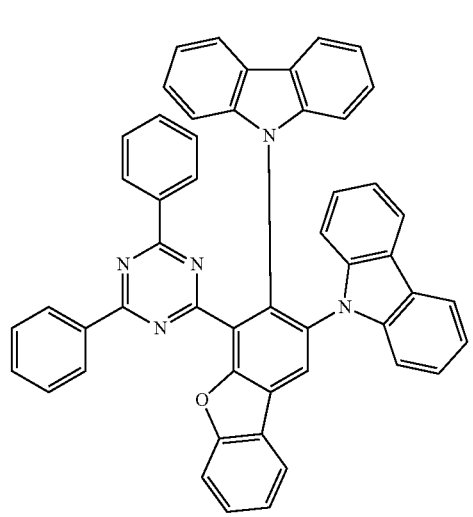
3
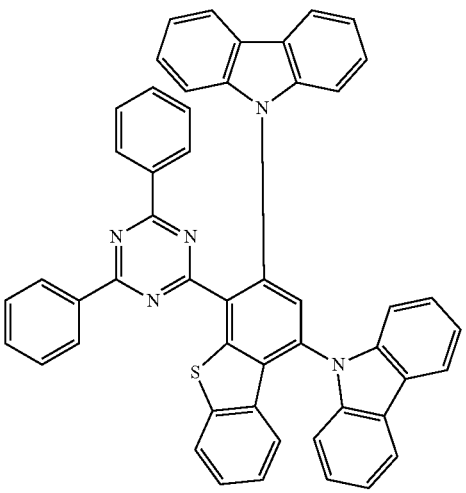
4
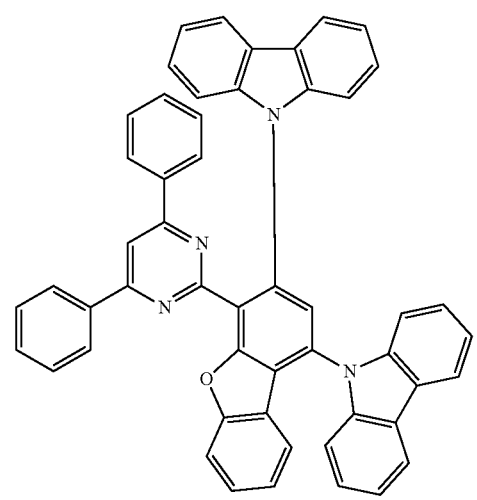

19
-continued
6
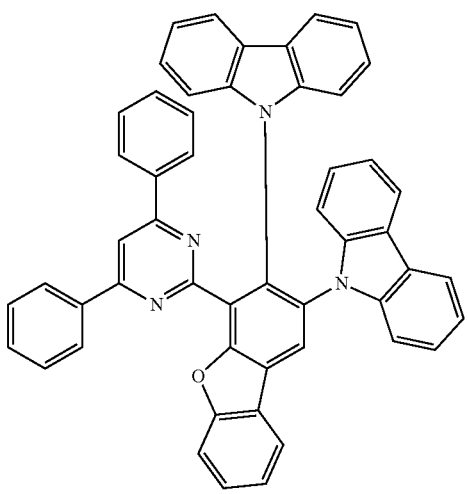
7
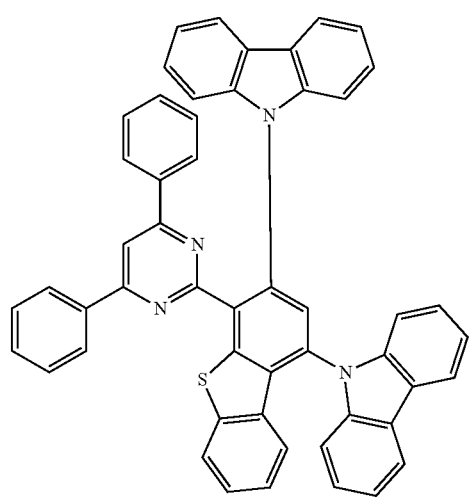
8
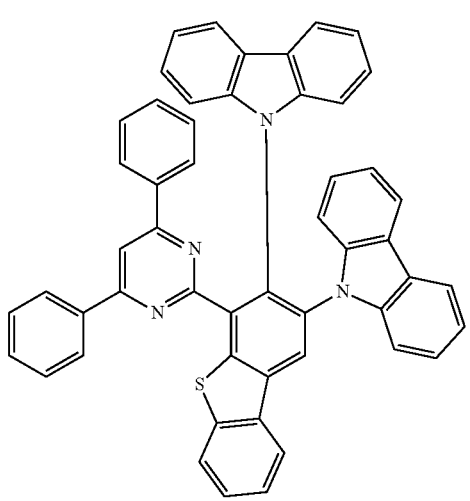
20
-continued
9
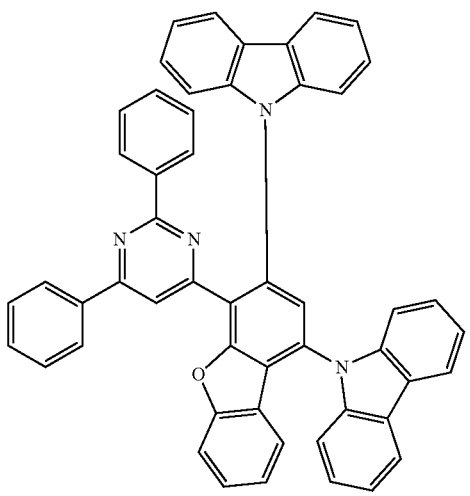
10
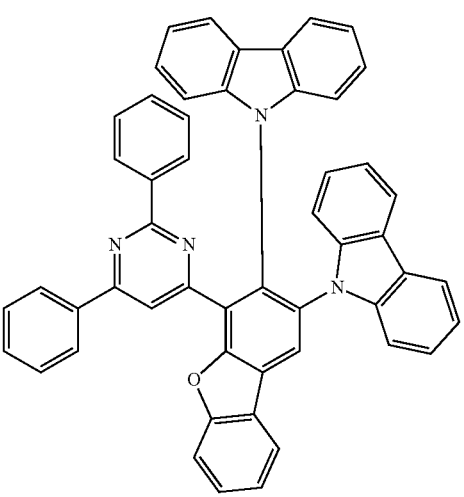
11
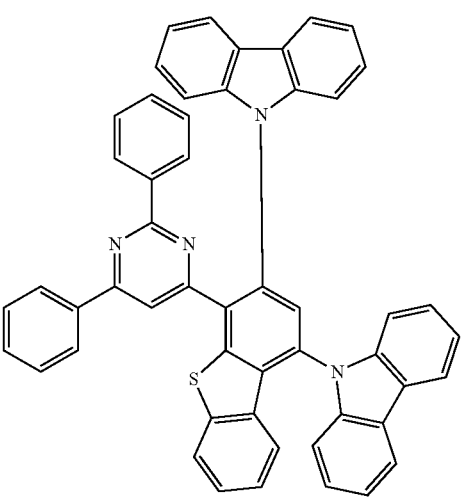

12
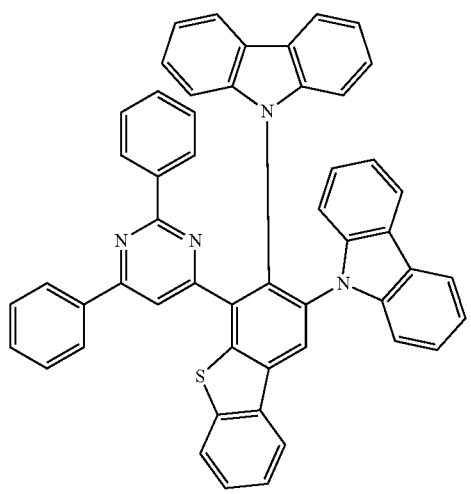
13
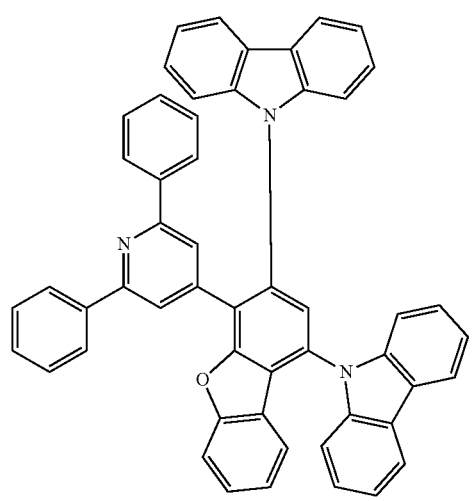
14
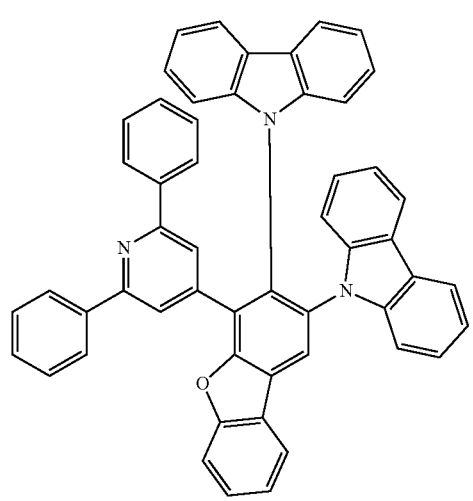
15
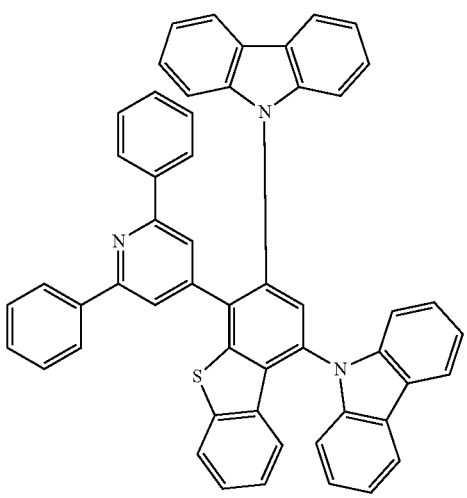
16
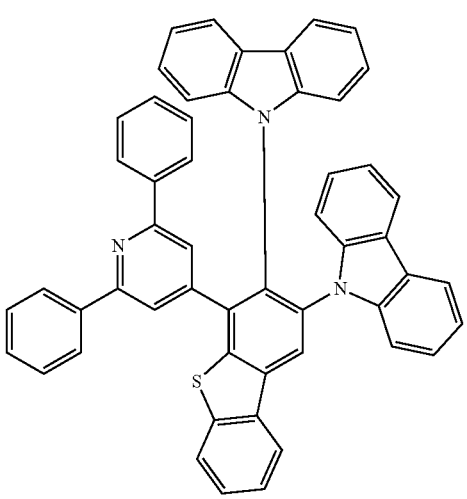
17
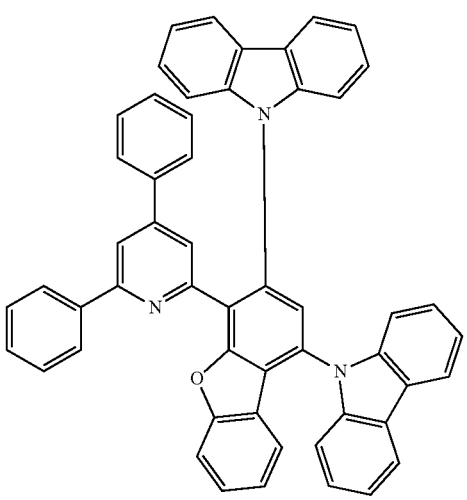

18
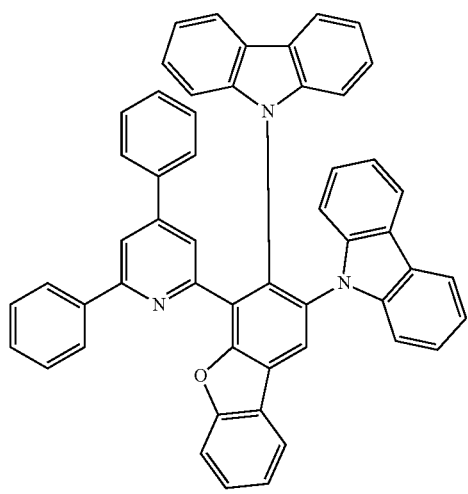
19
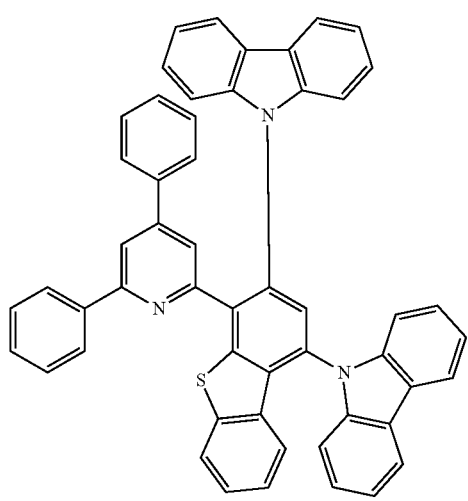
20
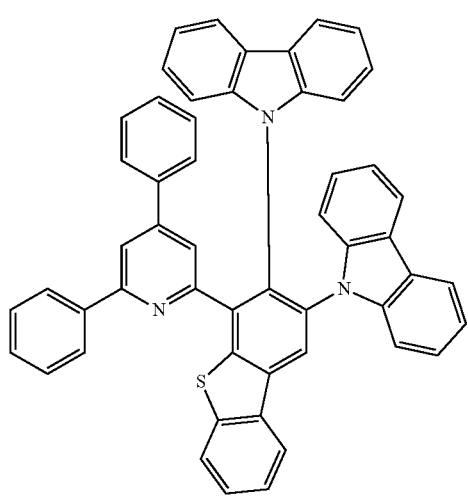
21
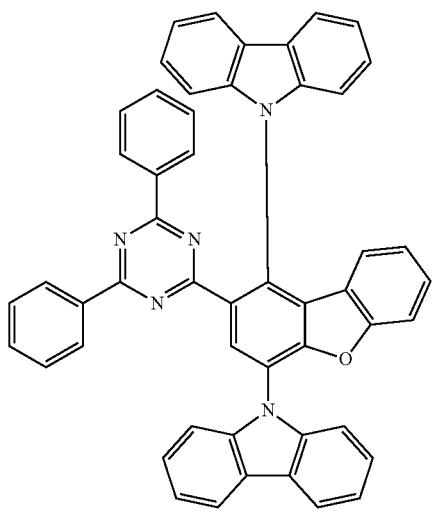
22
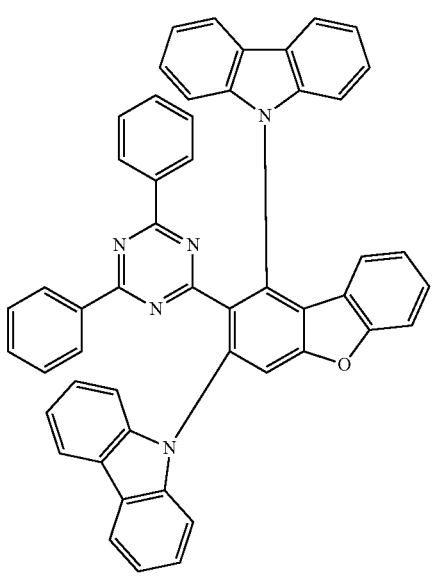
23
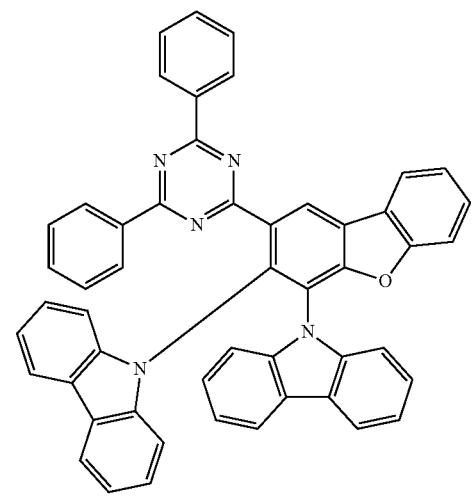

24
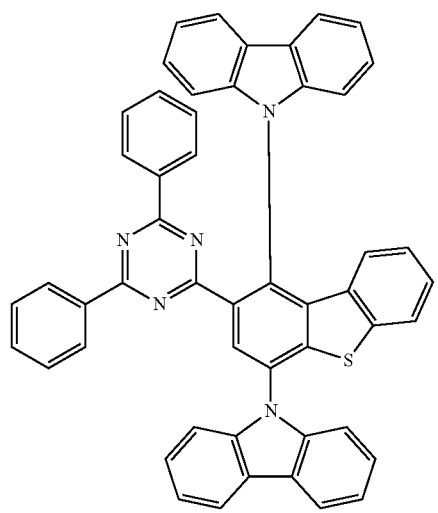
25
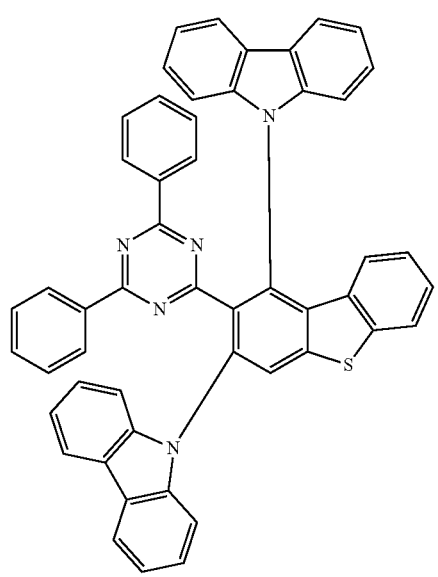
26
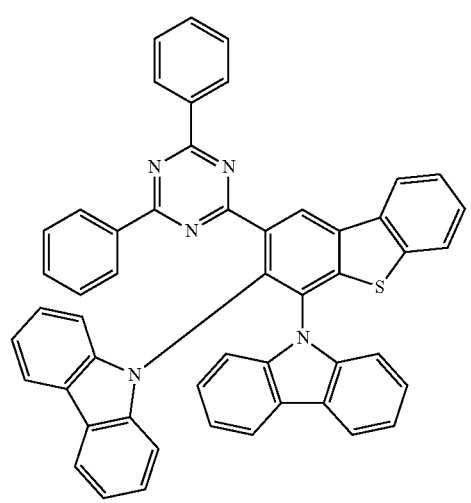
27
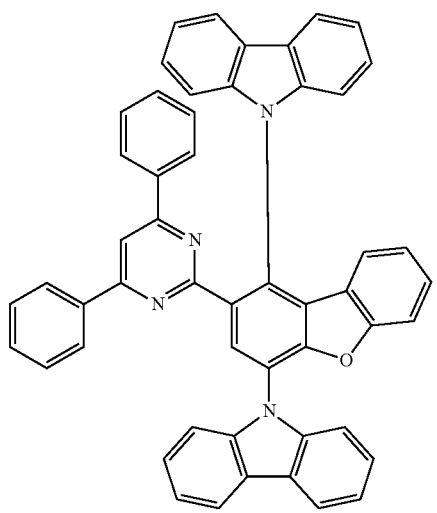
28
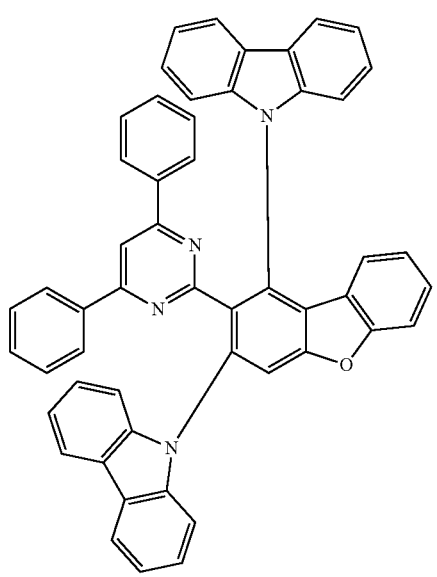
29
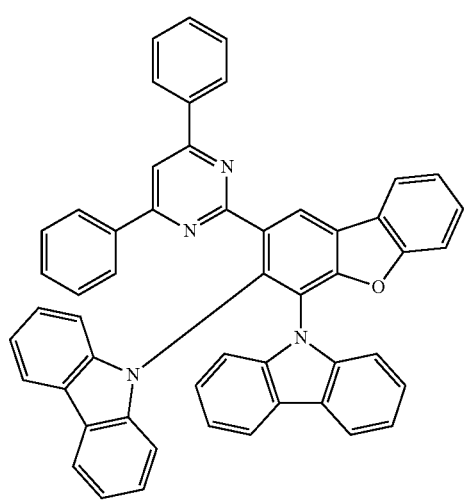

27
-continued
30
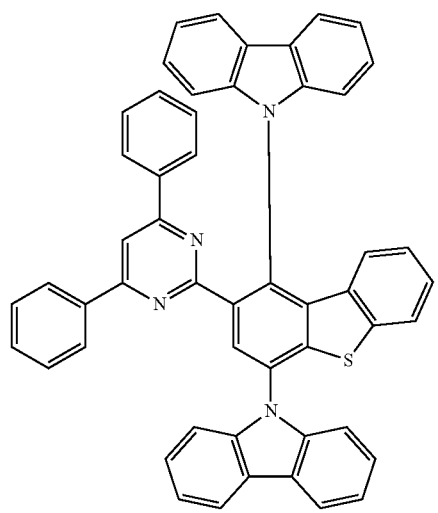
31
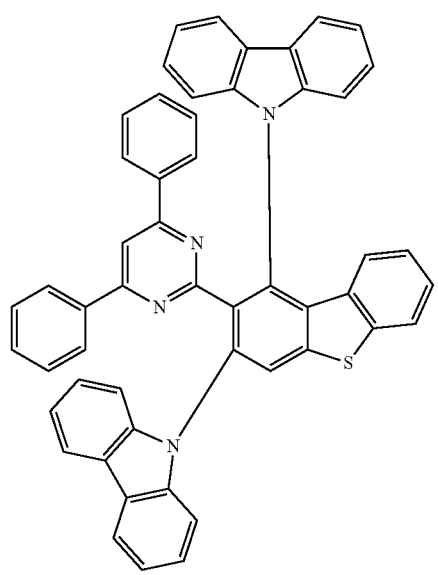
32
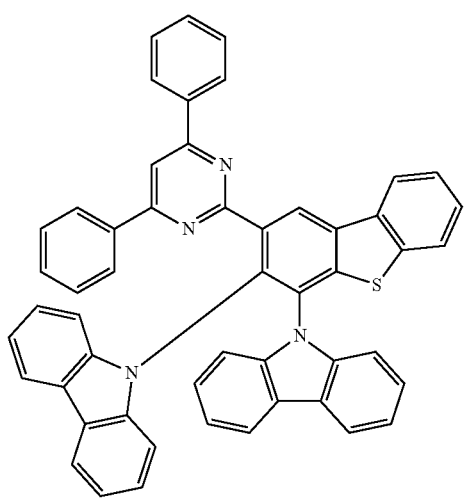
28
-continued
33
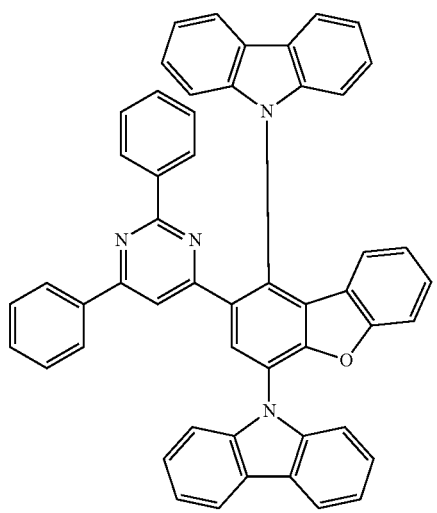
34
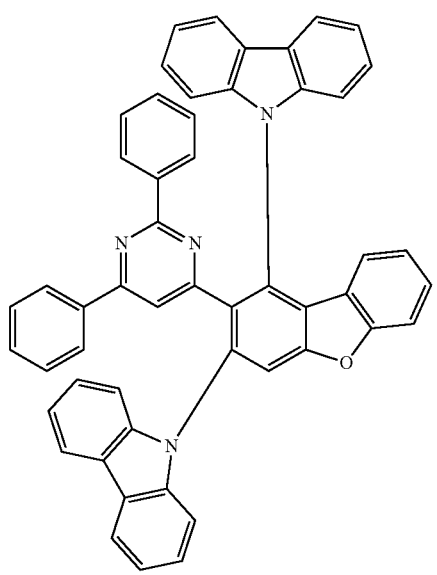
35
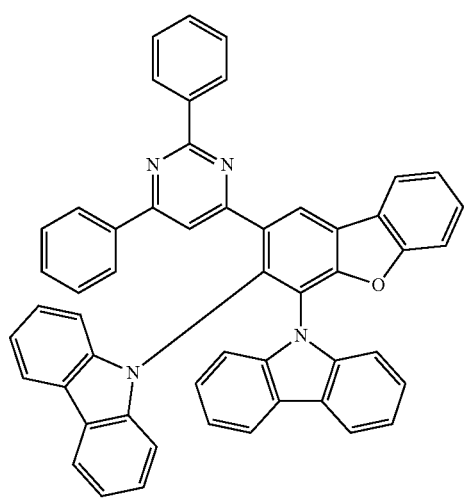

-continued
36
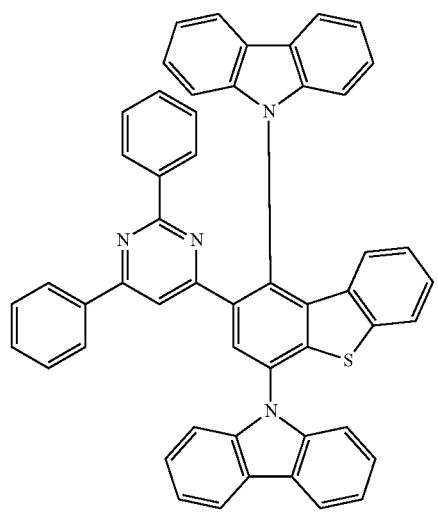
37
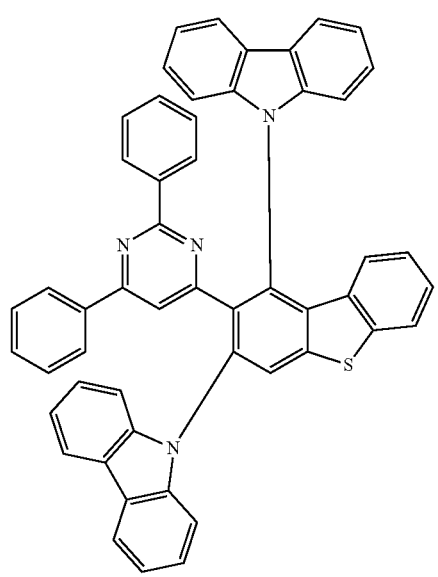
38
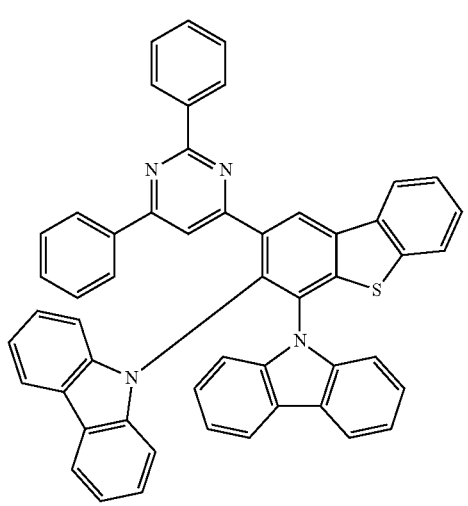
-continued
39
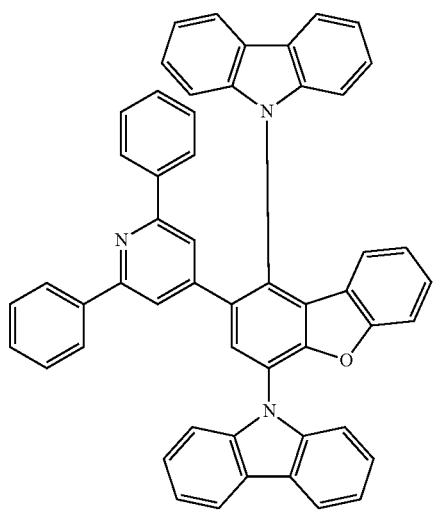
40
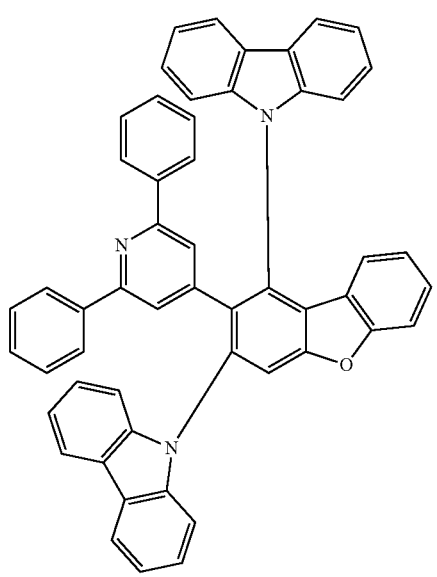
41
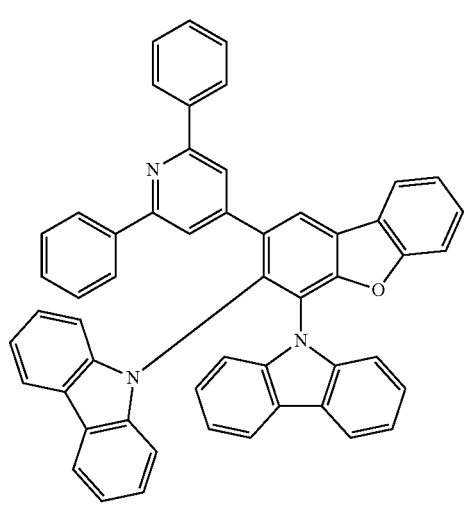

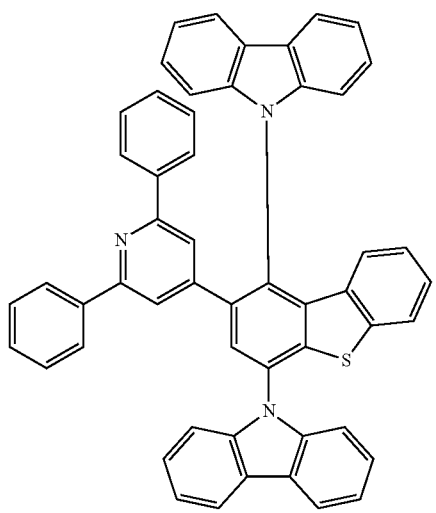
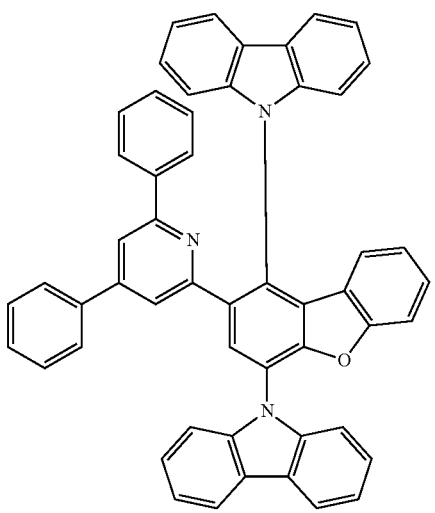

-continued
48
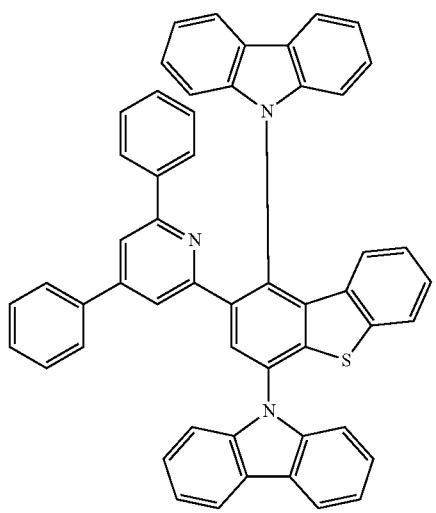
49
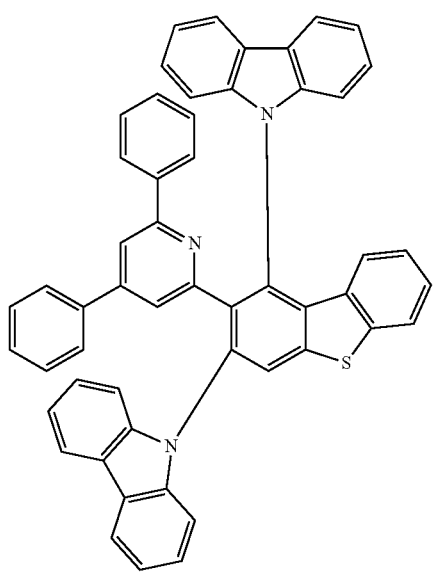
50
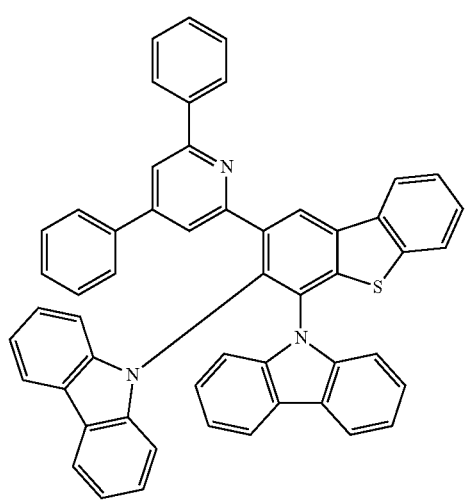
-continued
51
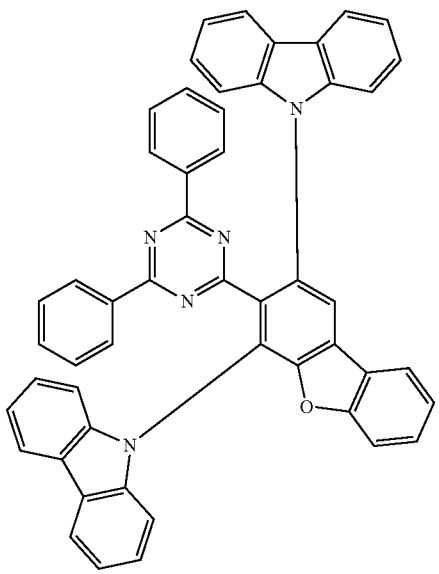
52
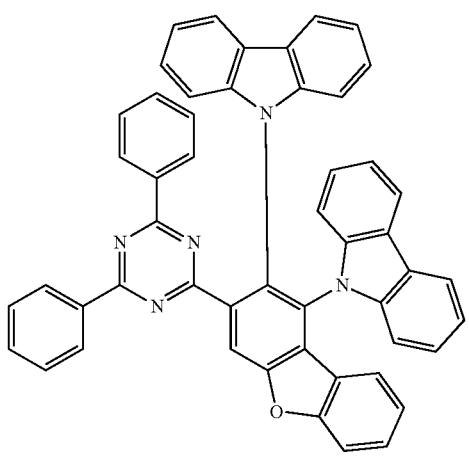
53
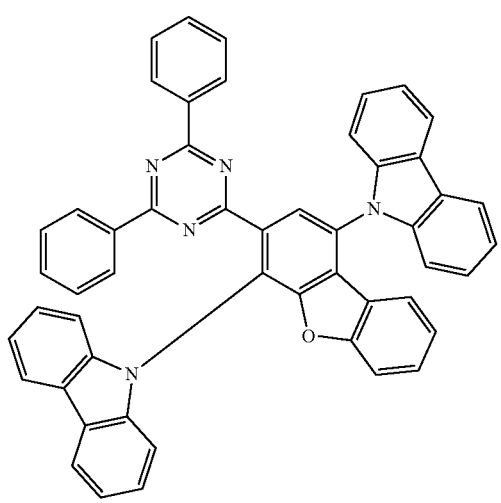

54
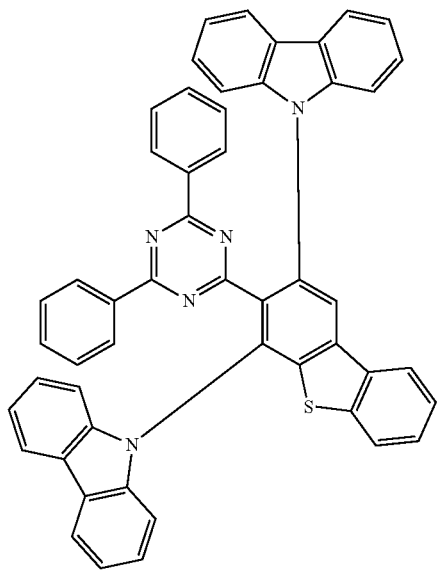
55
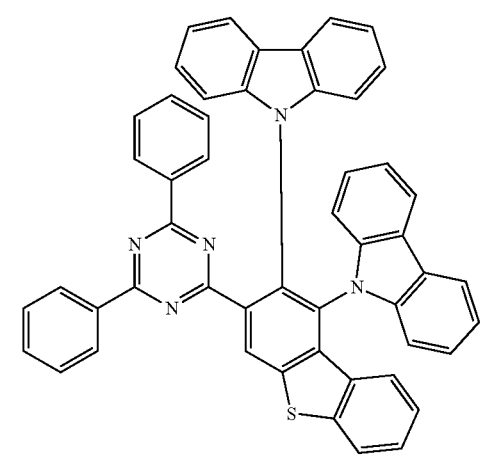
56
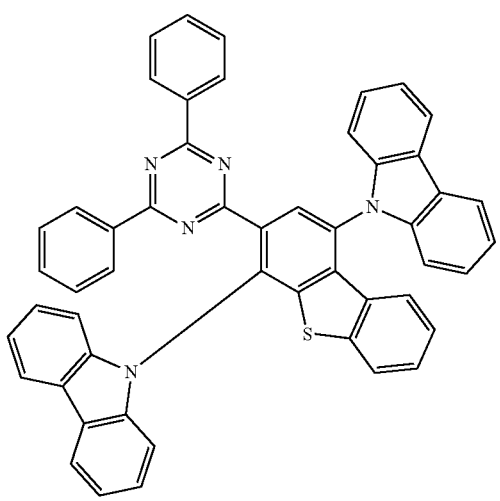
57
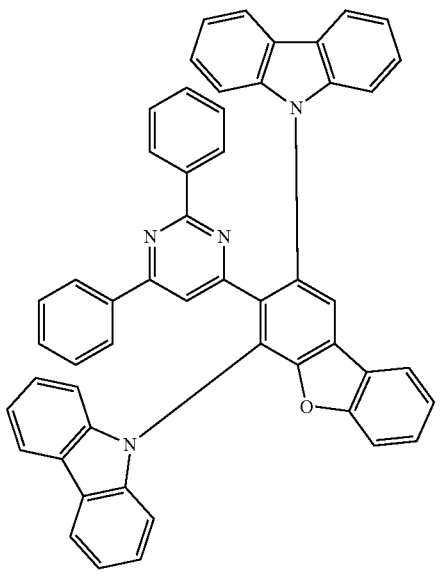
58
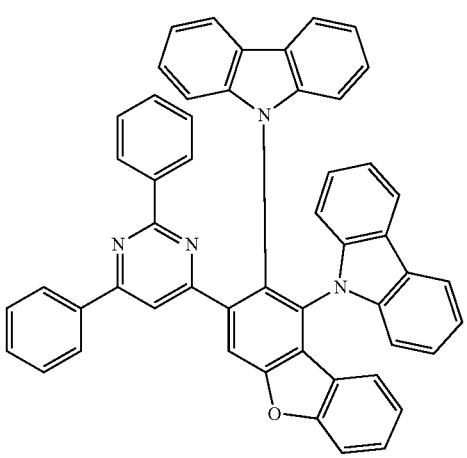
59
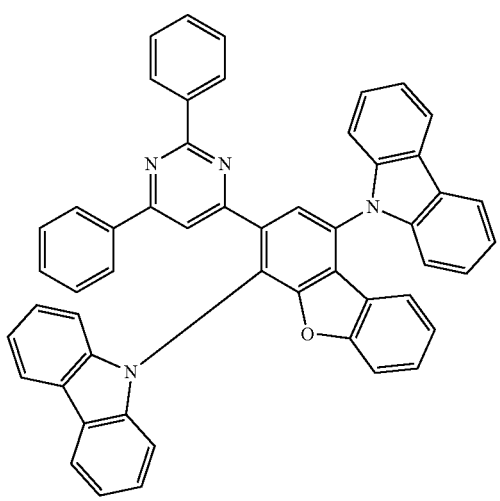

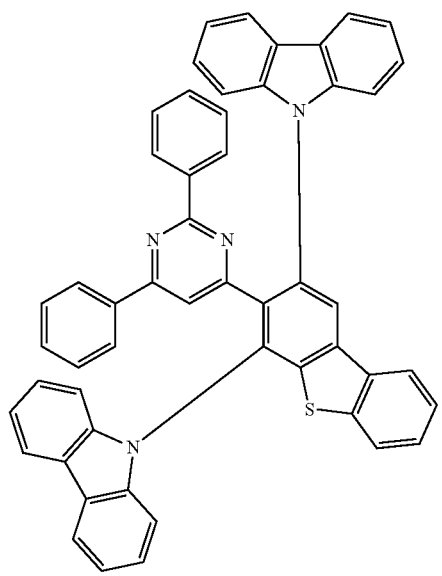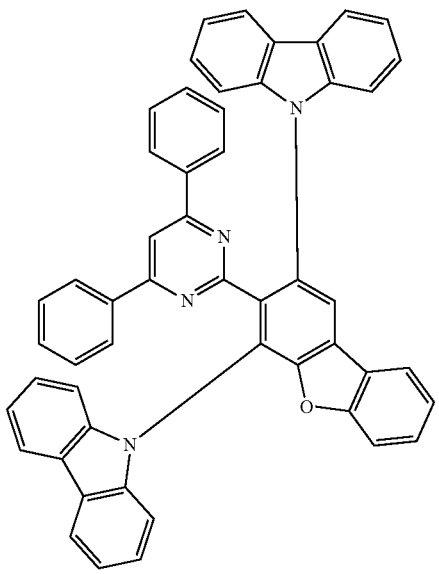

66
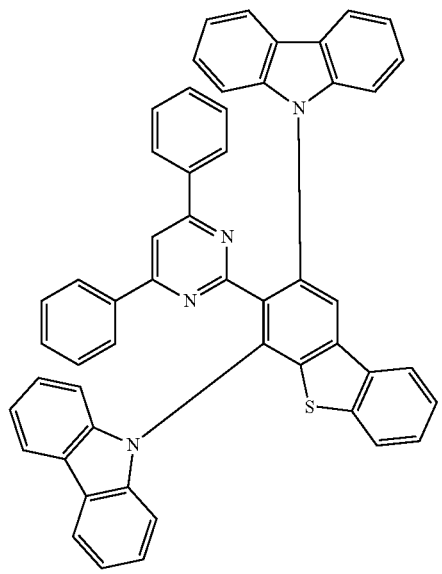
67
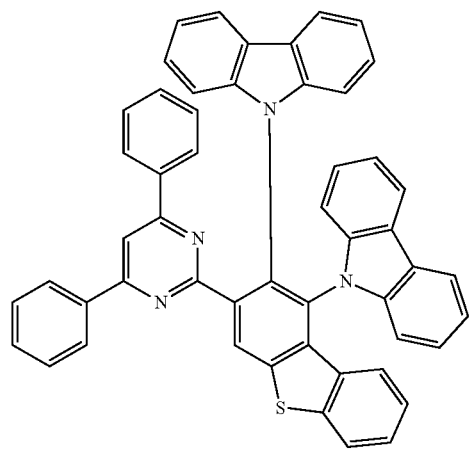
68
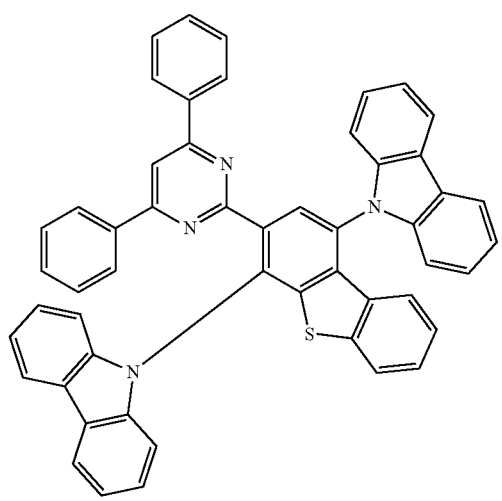
69
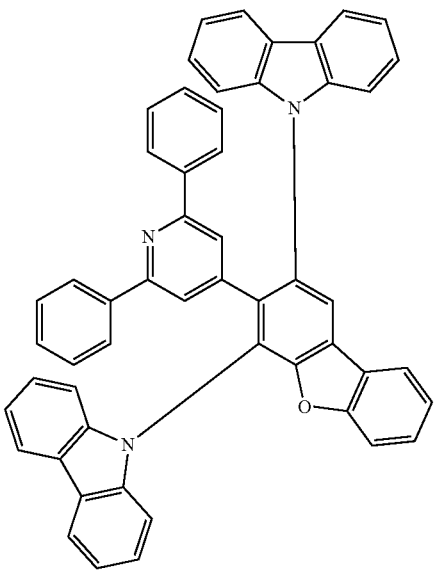
70
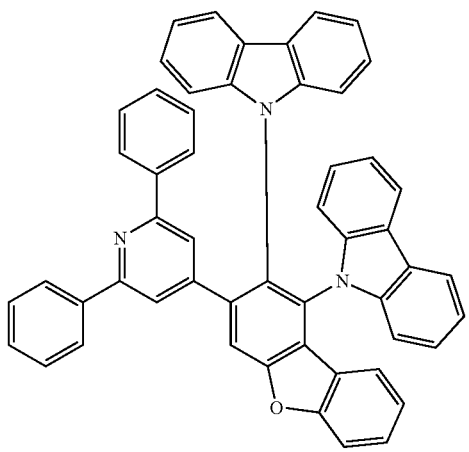
71
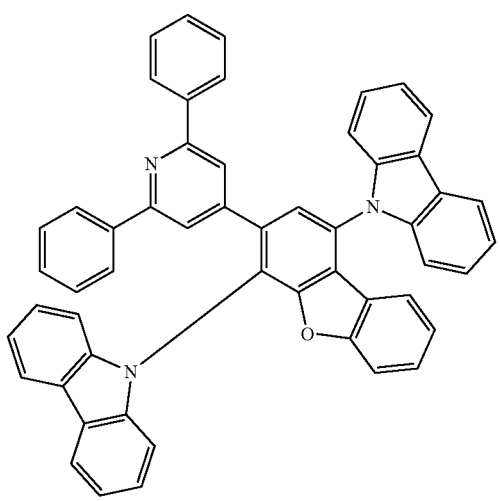

-continued
| 72 | 75 |
|---|---|
| 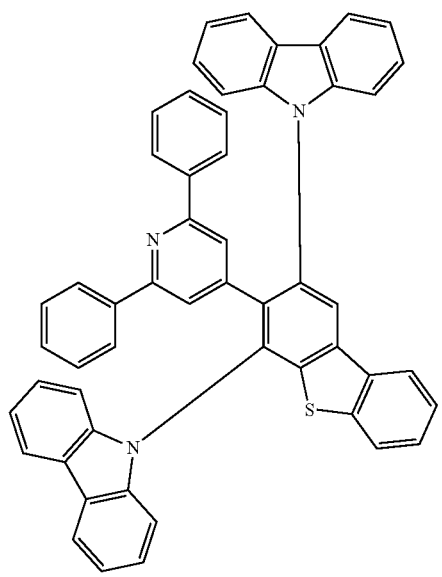 | 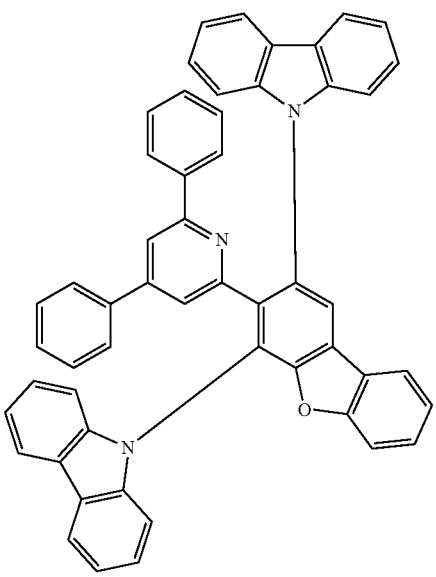 |
| 73 | 76 |
| 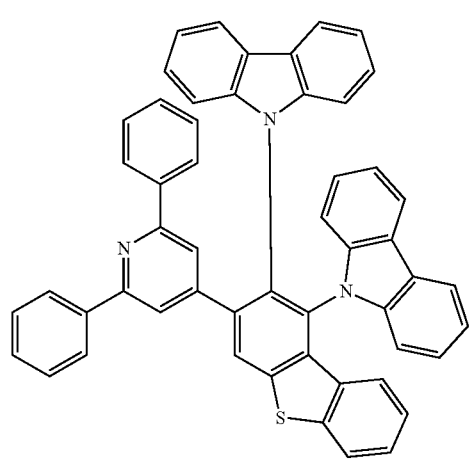 | 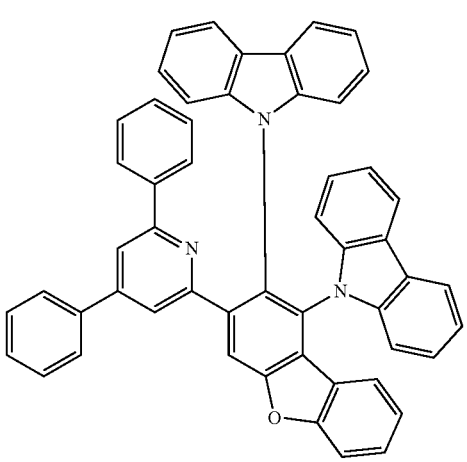 |
| 74 | 77 |
| 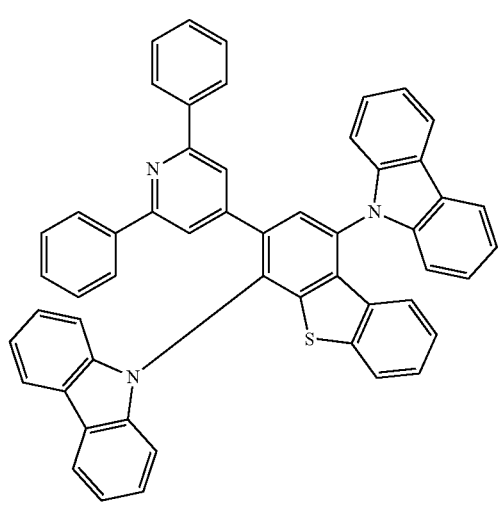 | 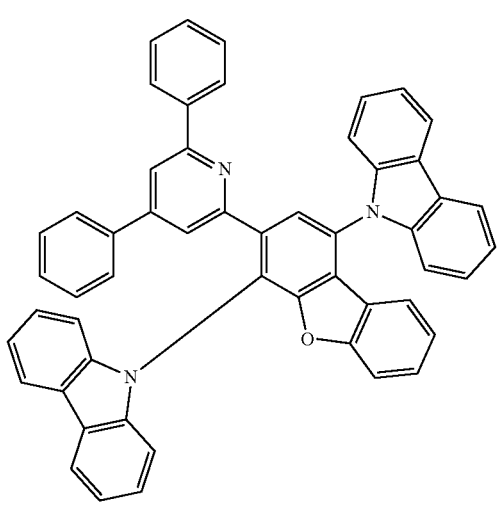 |

78
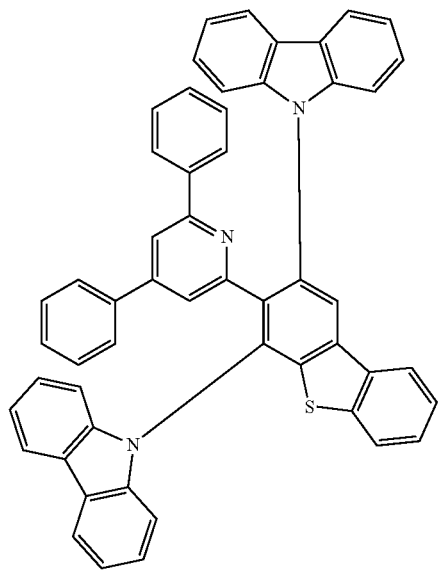
79
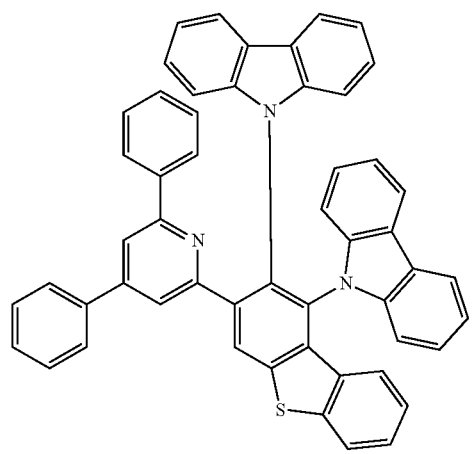
80
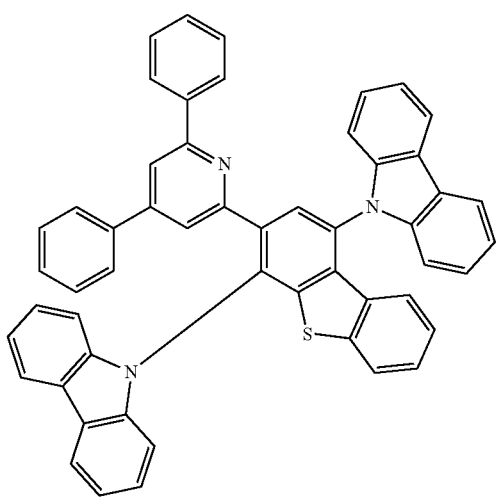
81
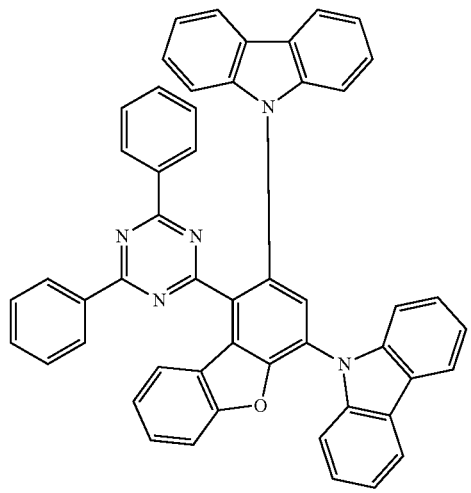
82
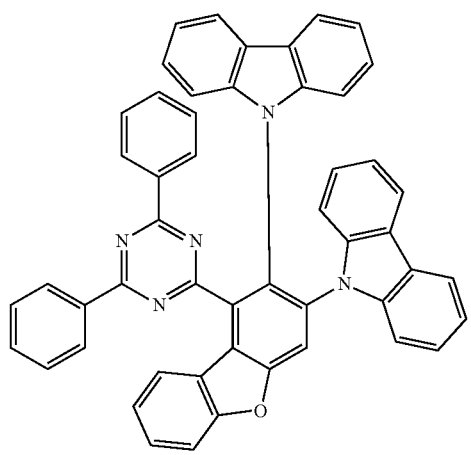
83
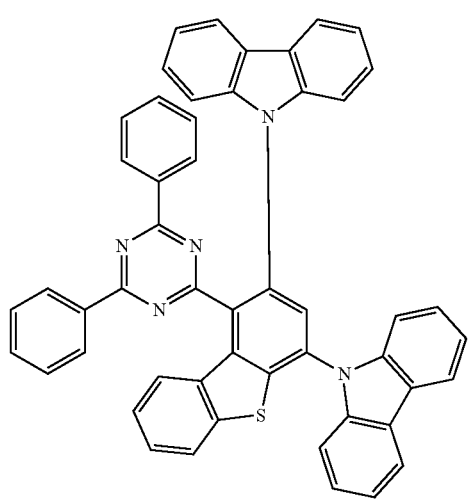

84
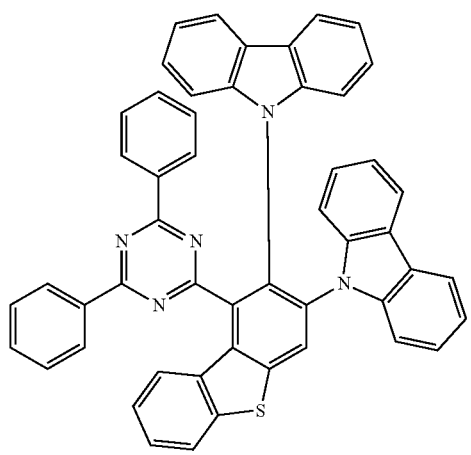
85
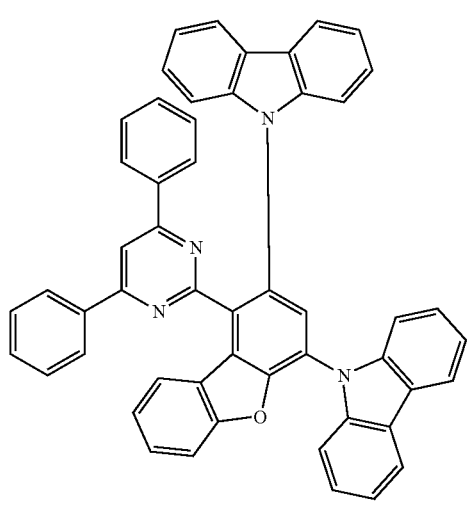
86
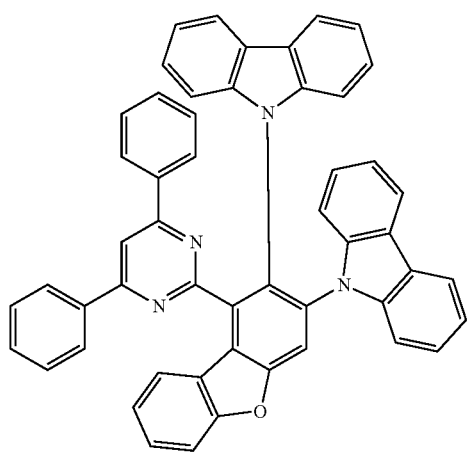
87
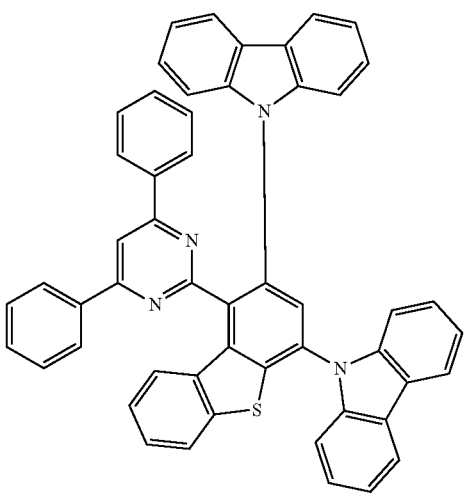
88
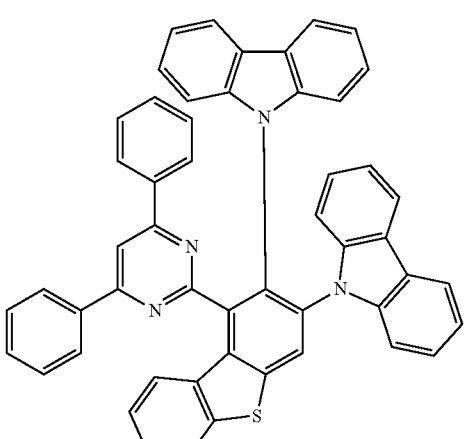
89
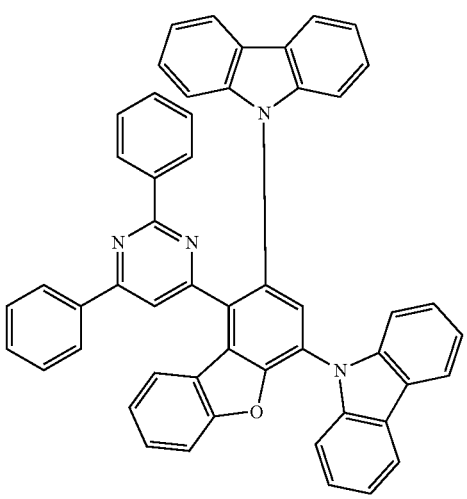

90
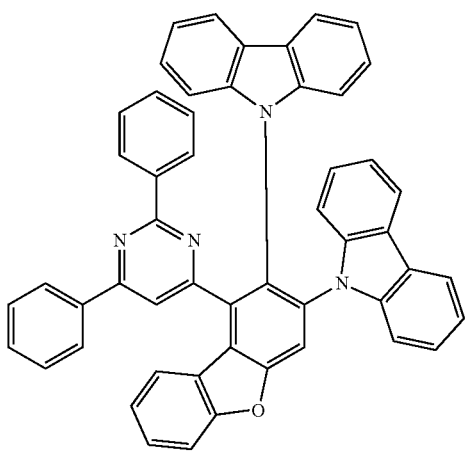
91
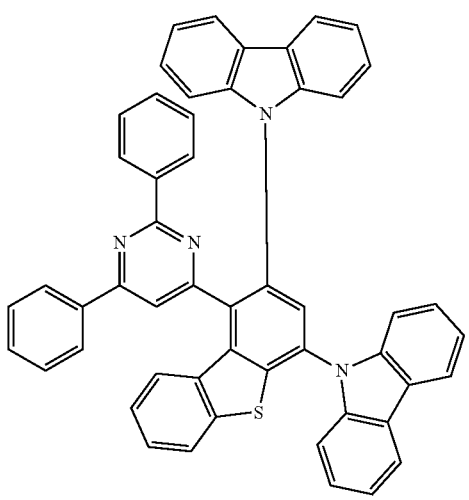
92
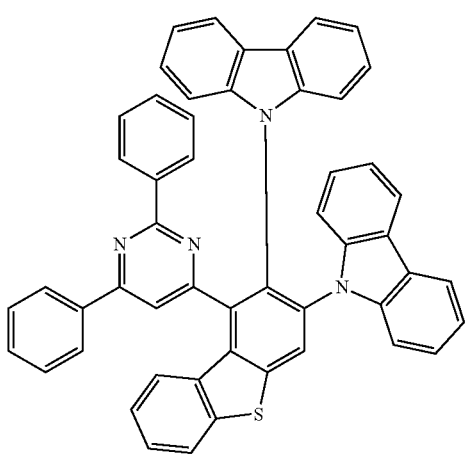
93
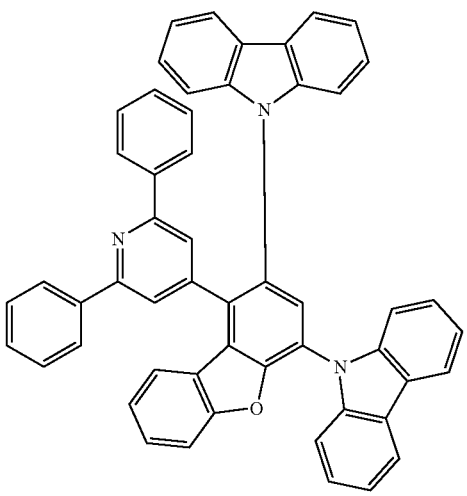
94
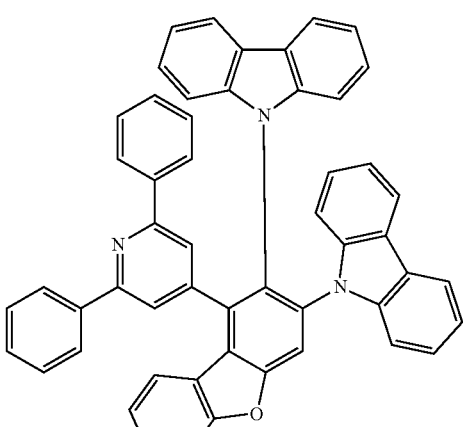
95
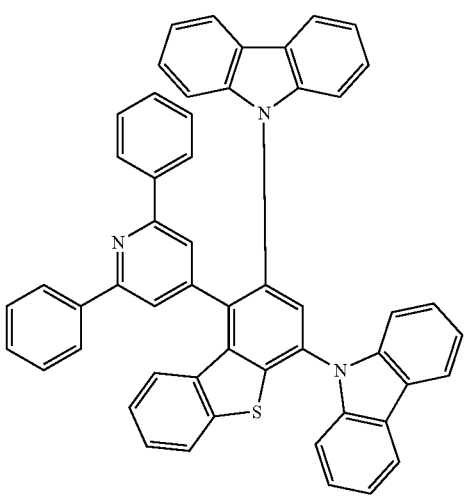

96
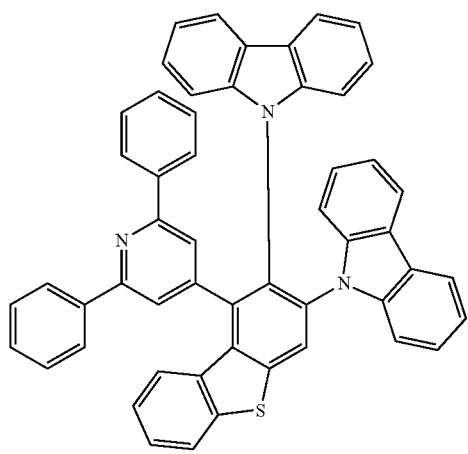
97
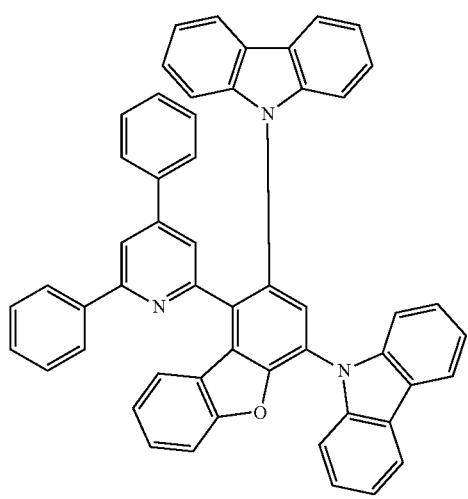
98
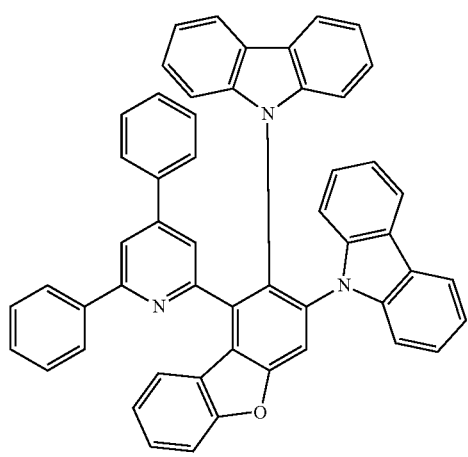
99
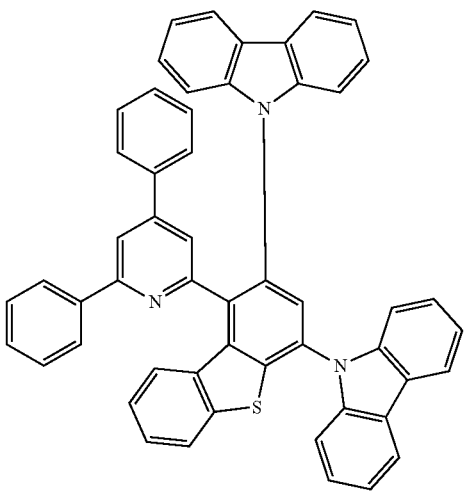
100
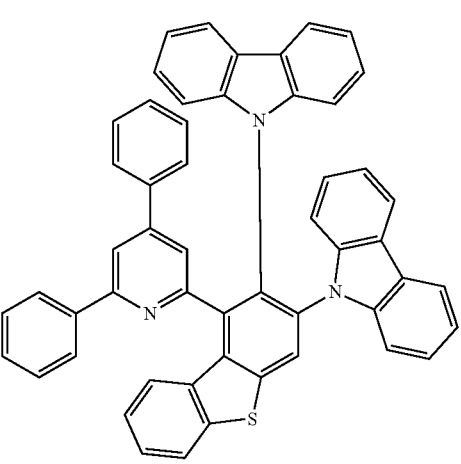
101
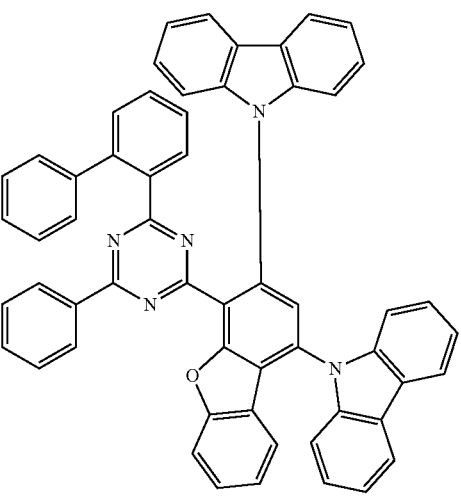

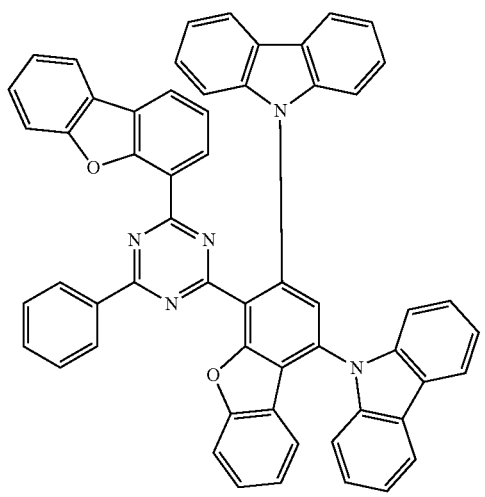
102
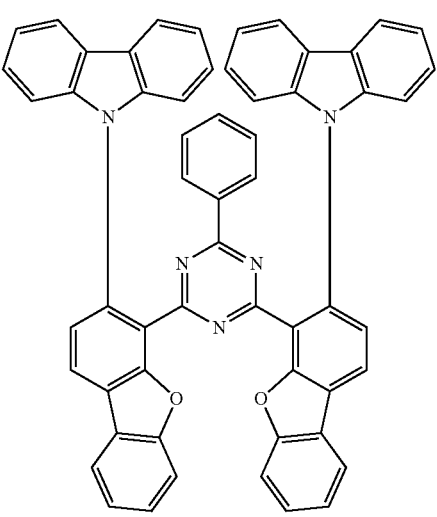
105
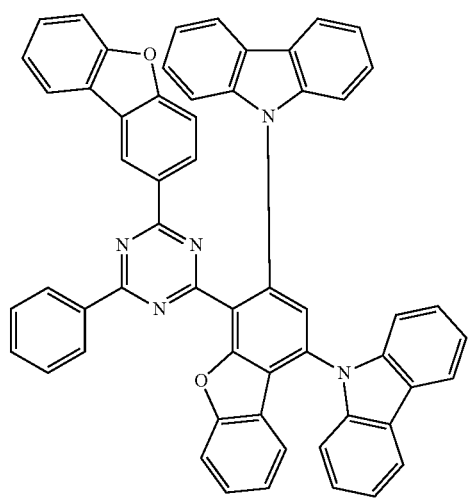
103
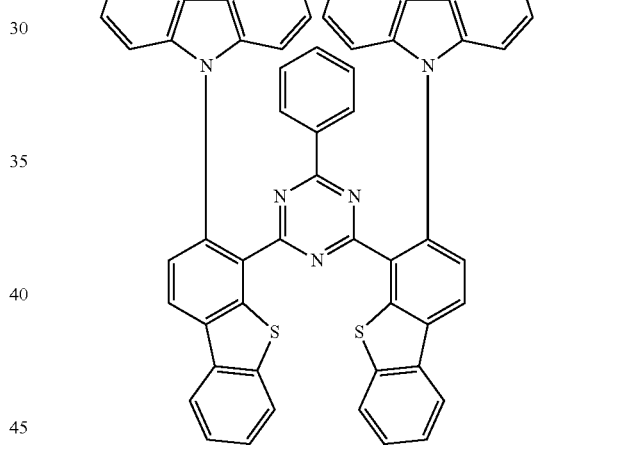
106
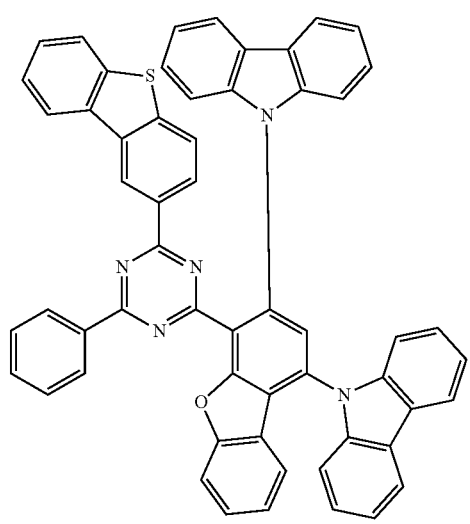
104
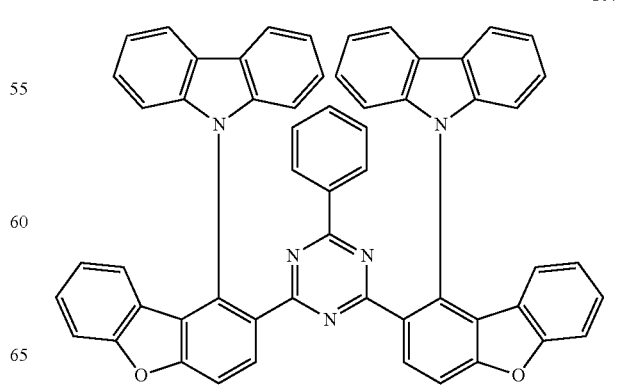
107

53
-continued
108
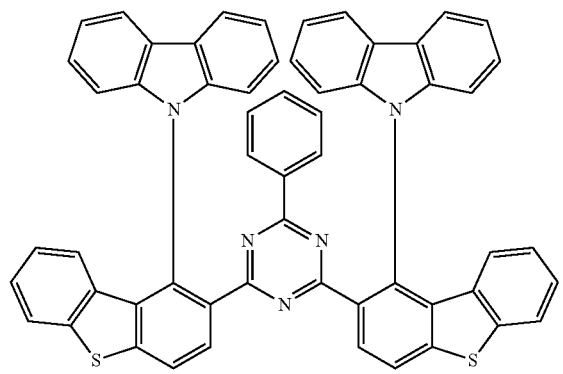
109
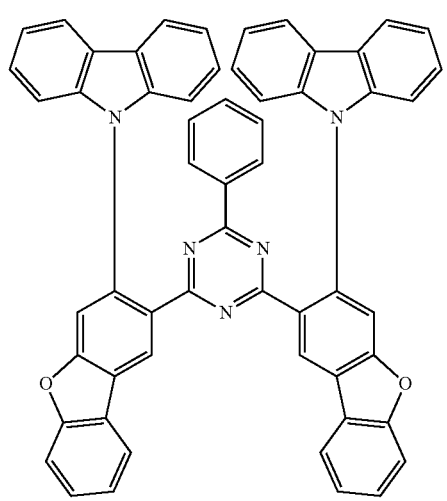
110
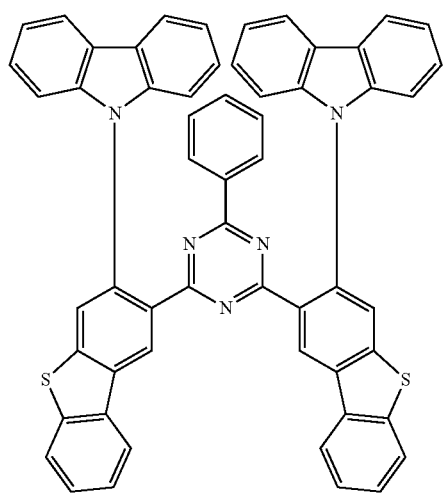
54
-continued
111
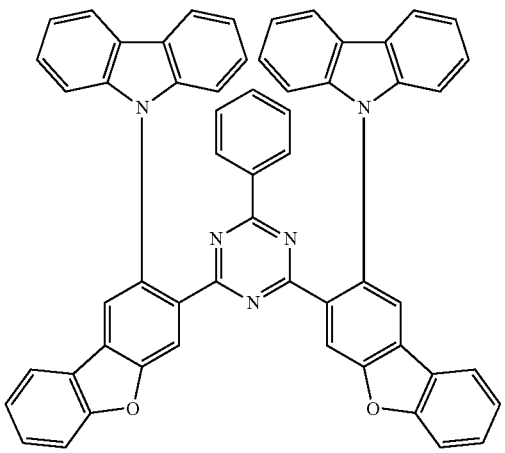
112
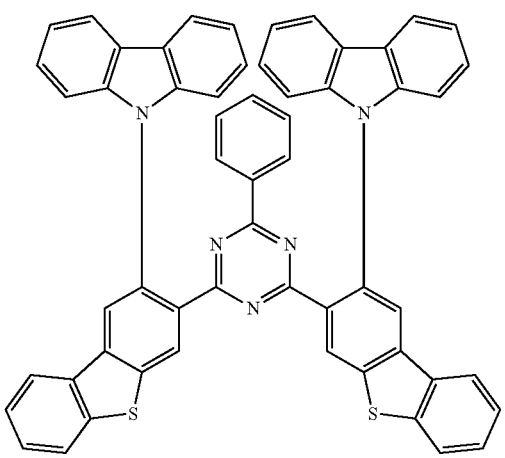
113
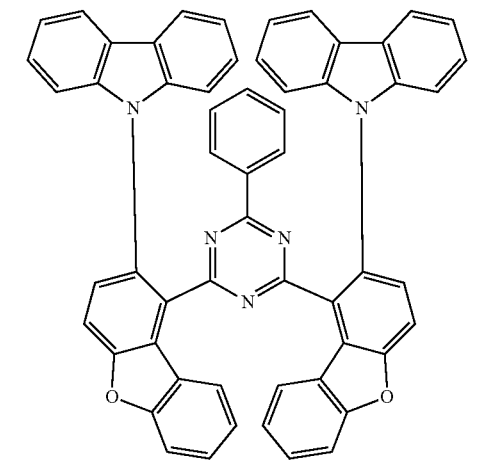

-continued
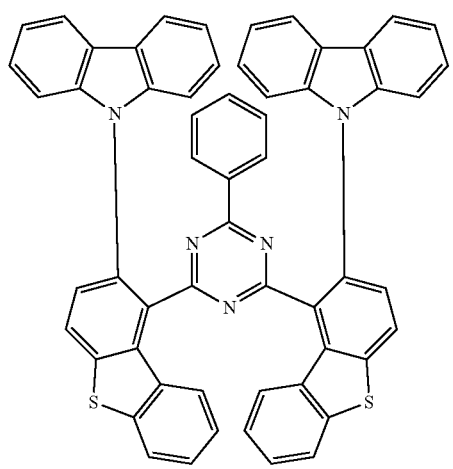
114
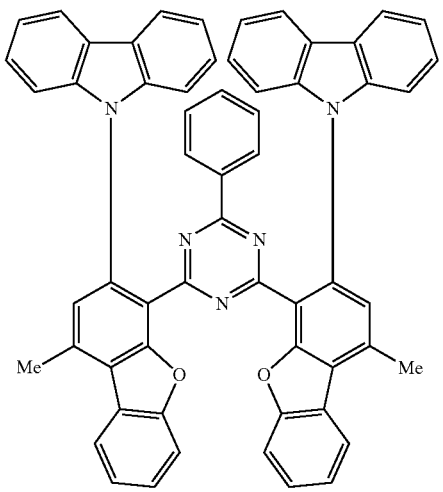
117
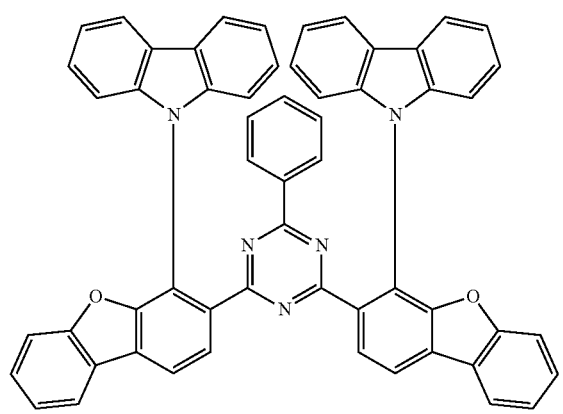
115
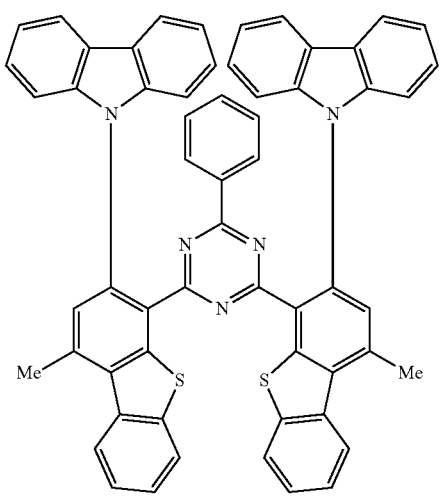
118
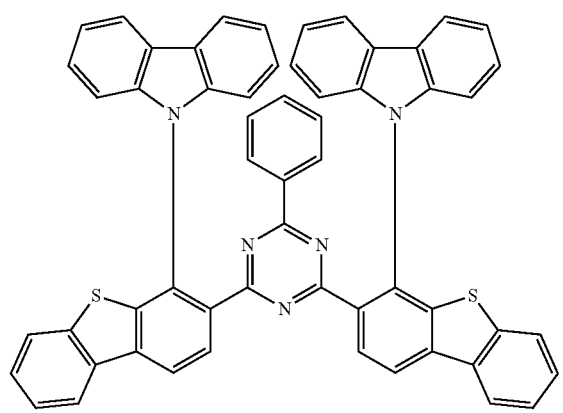
116
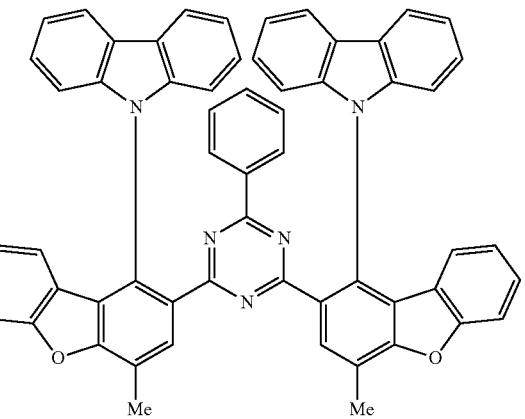
119

120
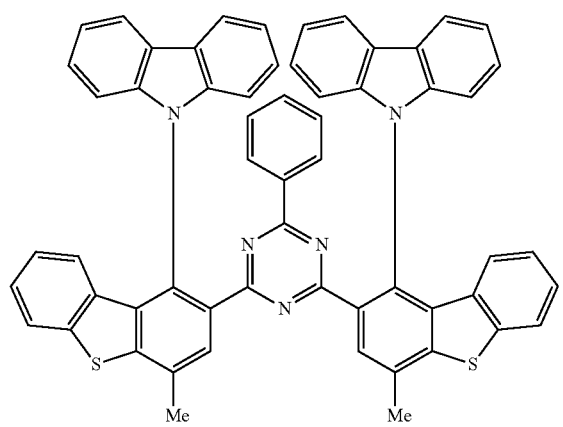
121
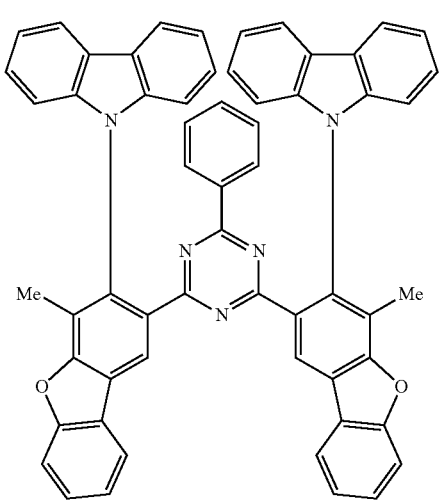
122
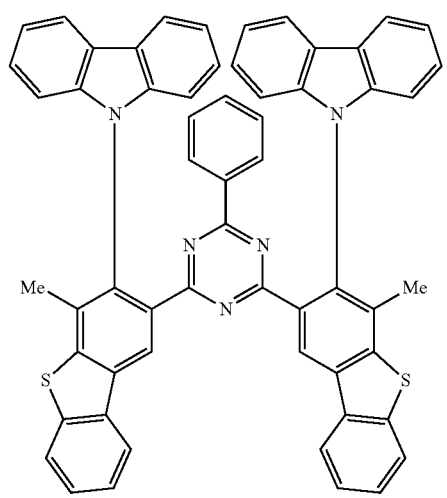
123
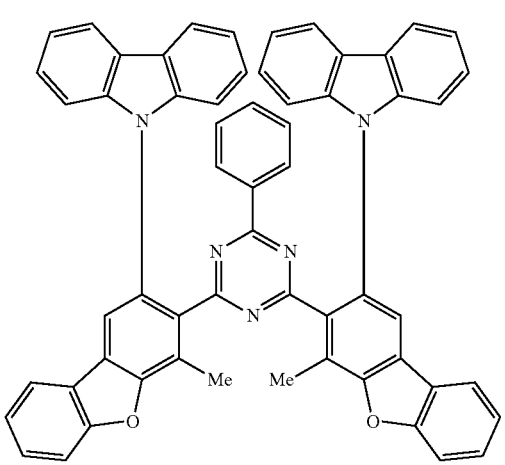
124
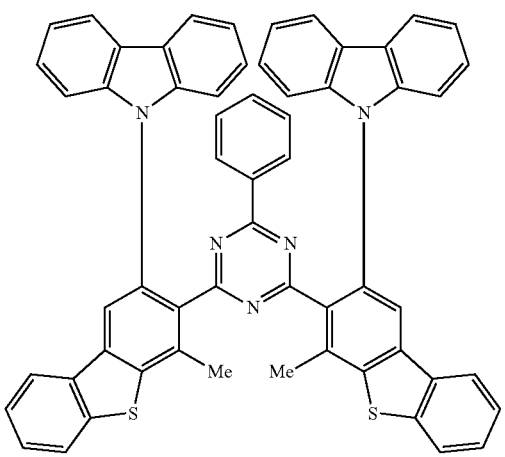
125
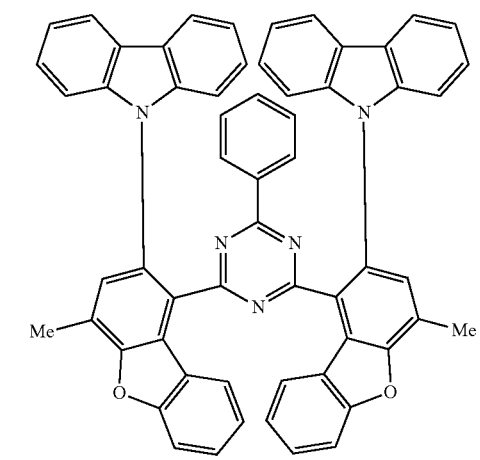

-continued
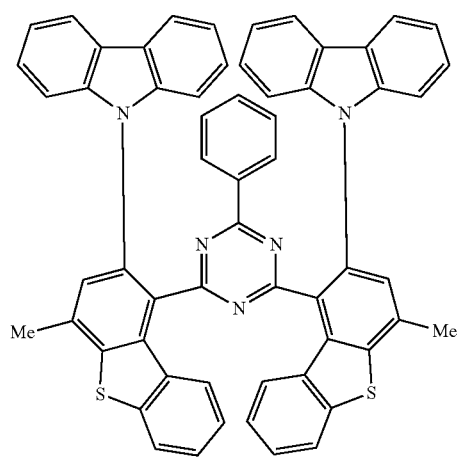
126
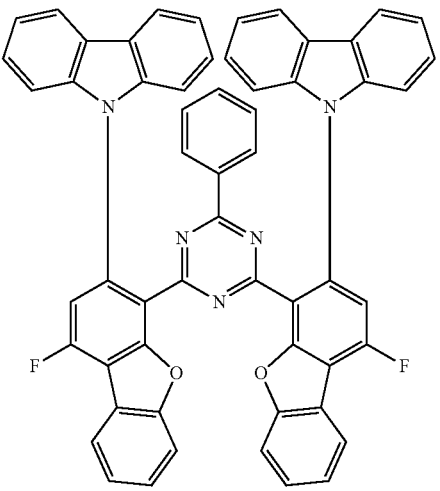
129
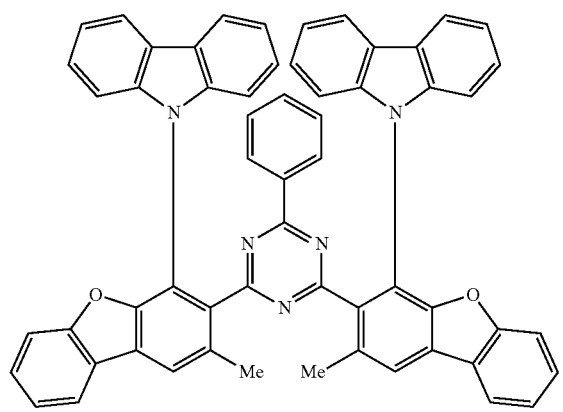
127
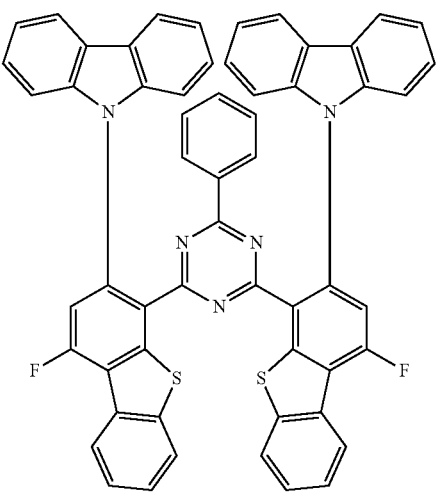
130
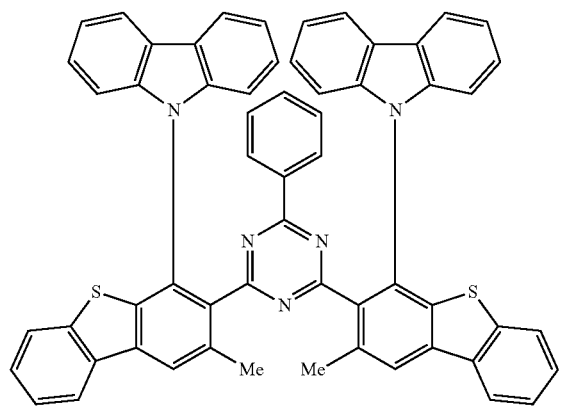
128
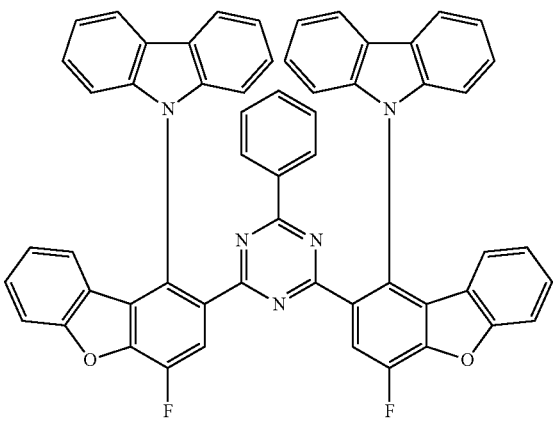
131

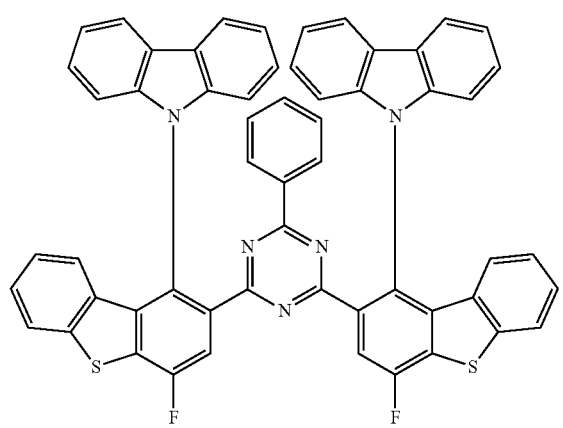
132
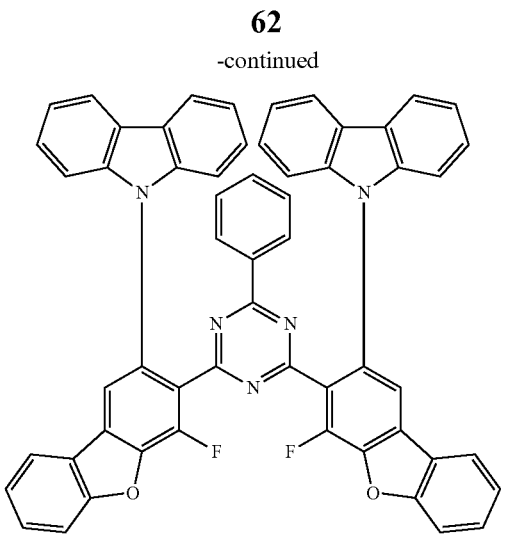
135
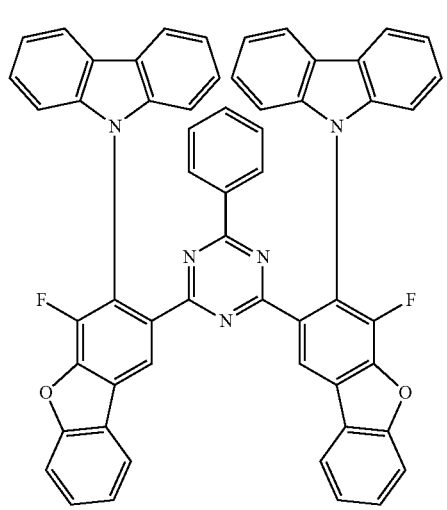
133
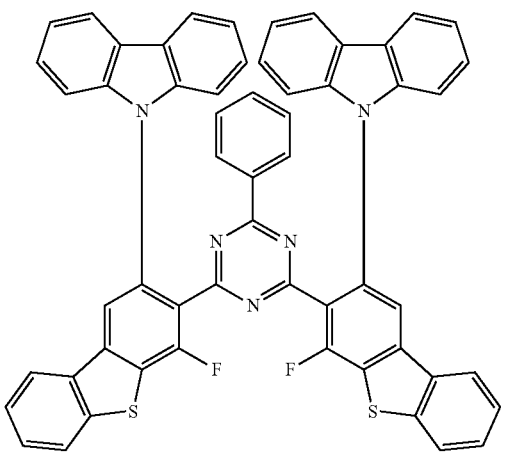
136
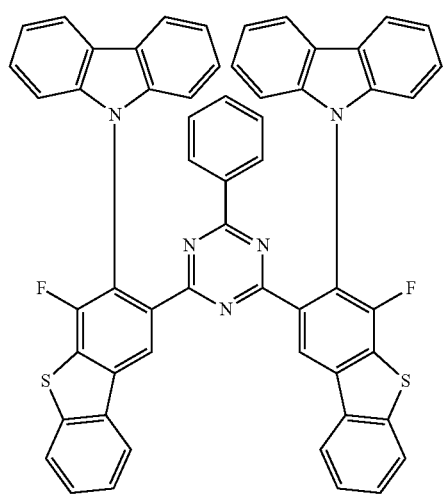
134
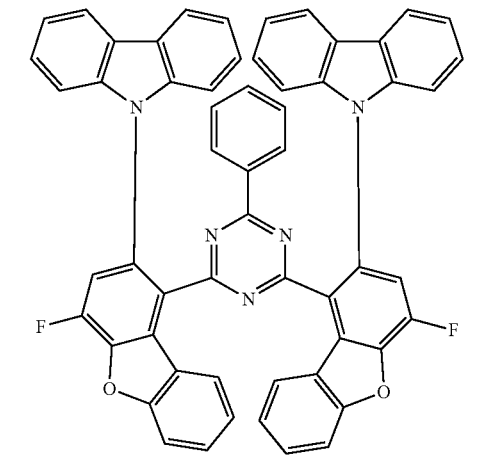
137

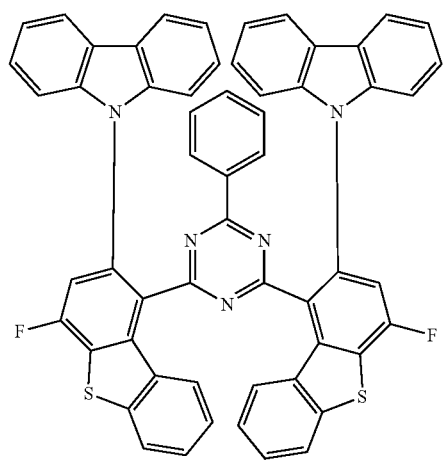
138
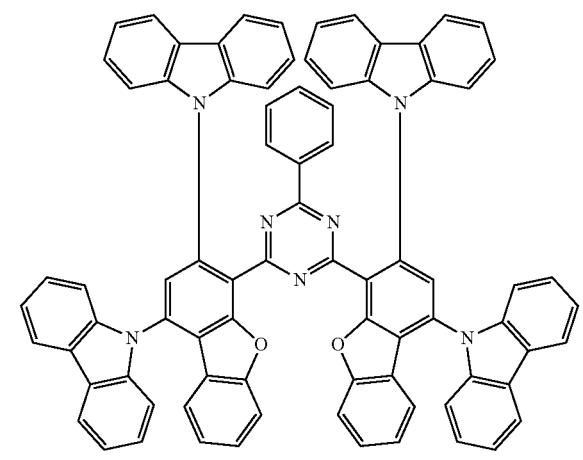
141
139
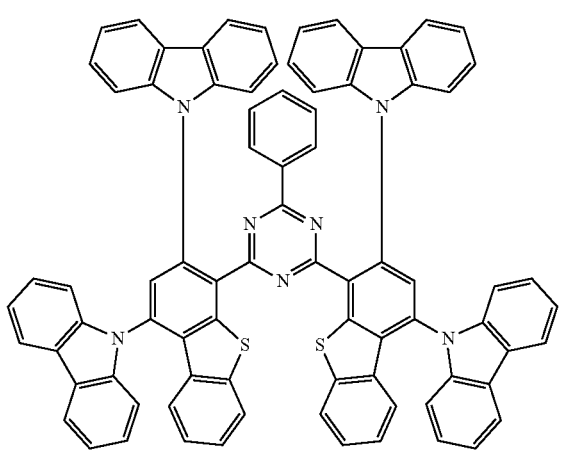
142
140
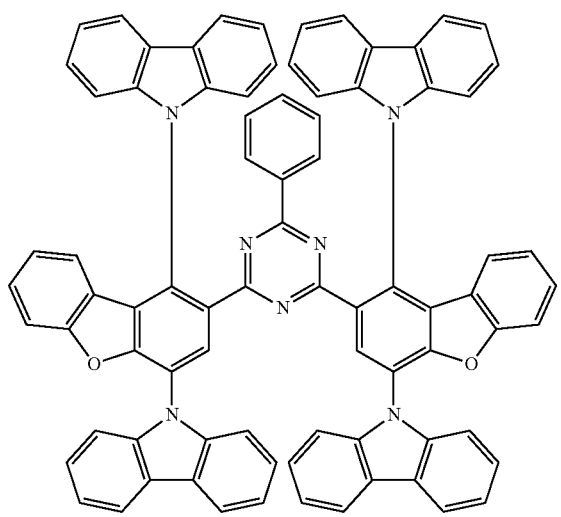
143

144
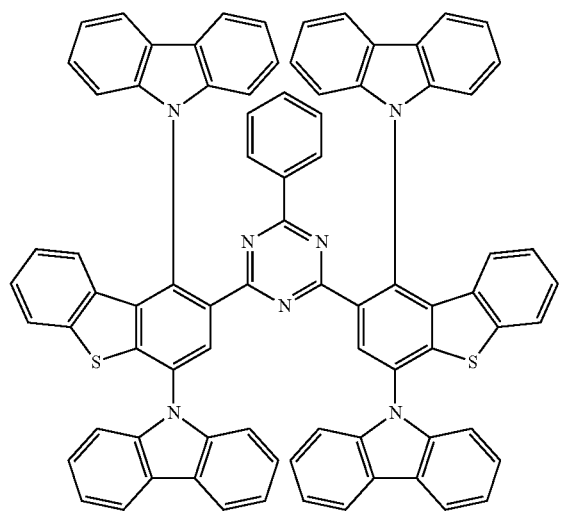
145
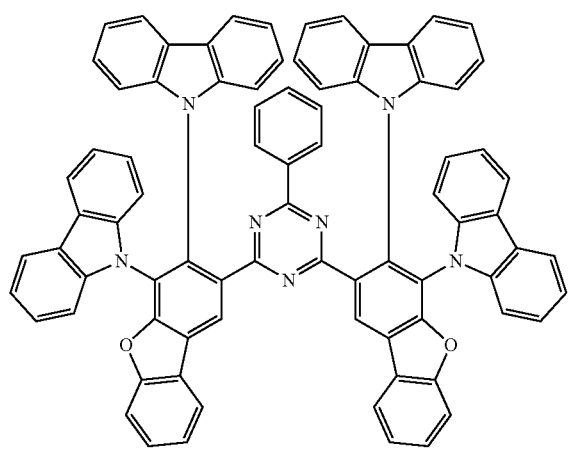
146
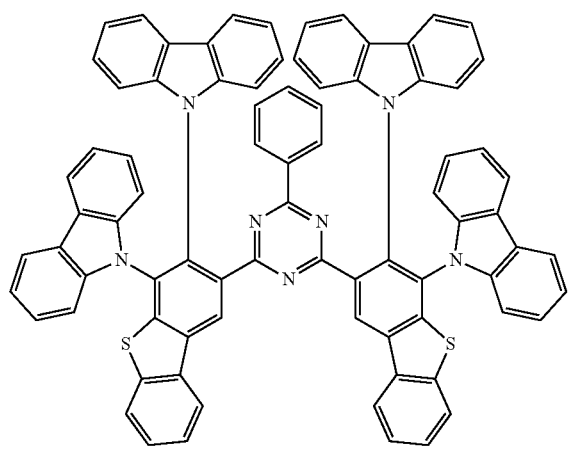
147
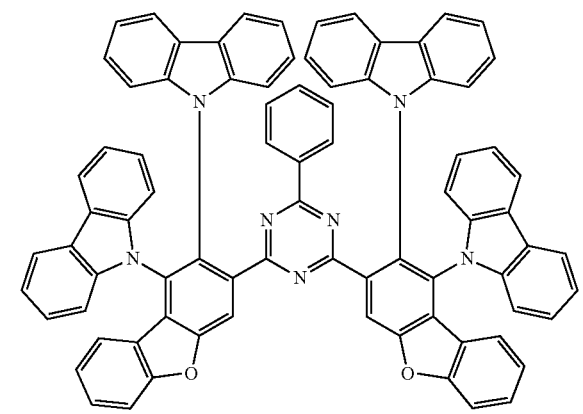
148
149
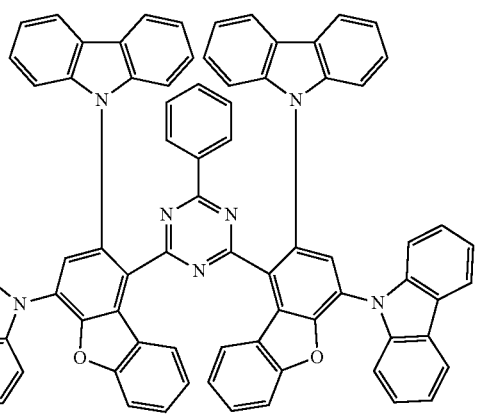

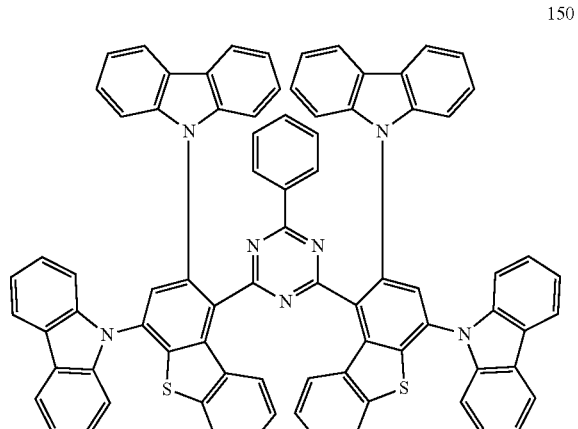
150
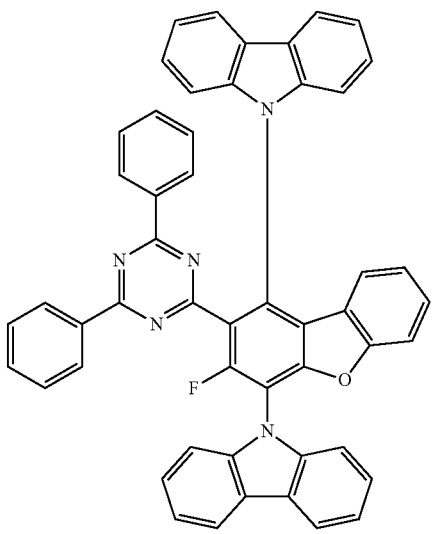
153
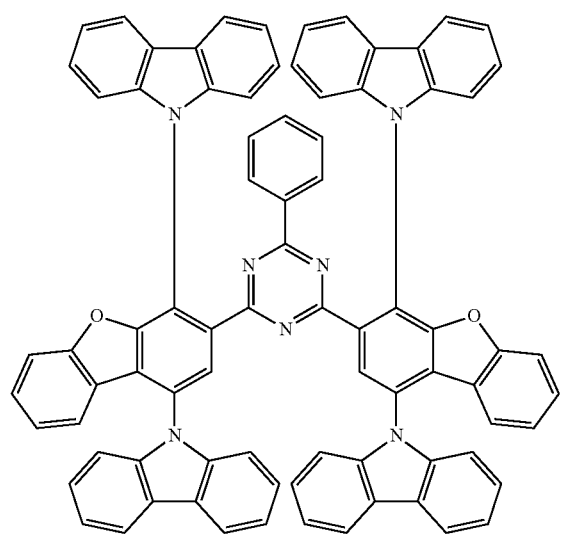
151
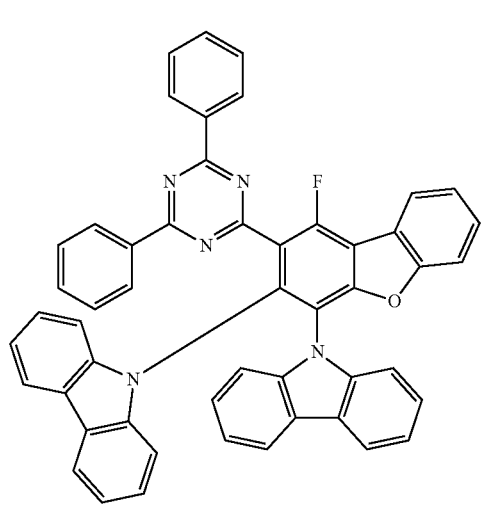
154
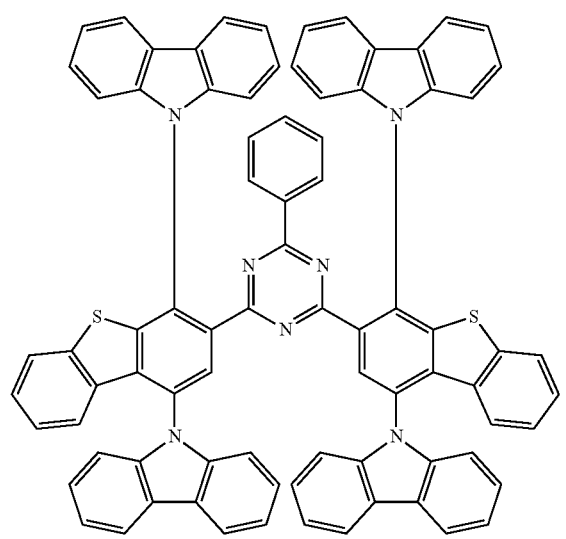
152
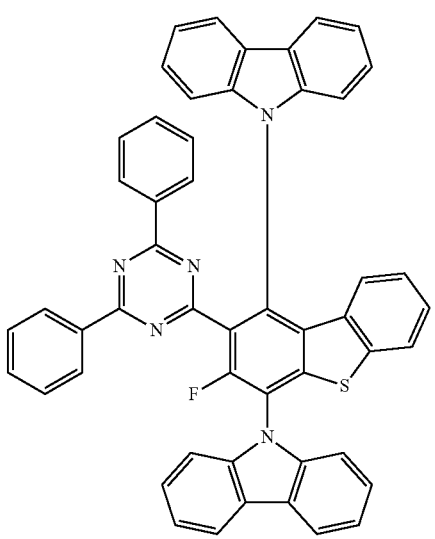
155

156
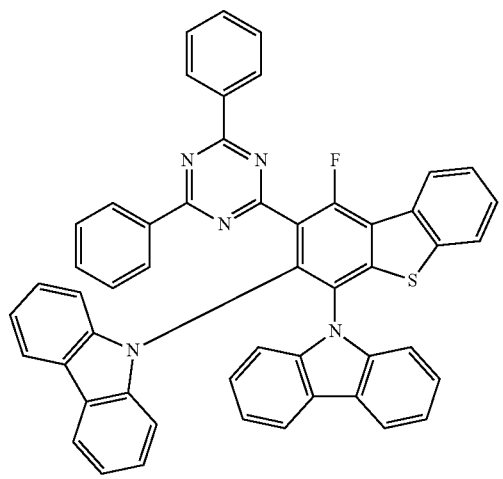
157
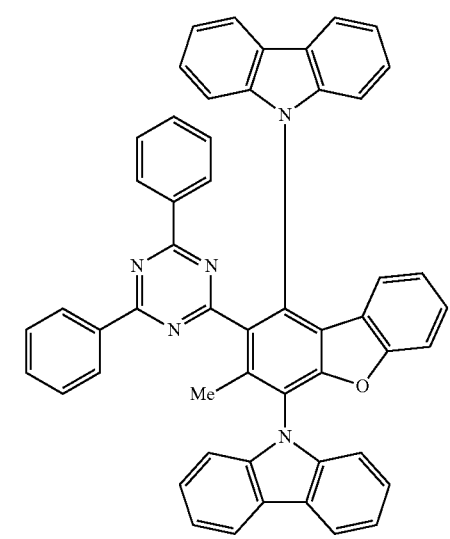
158
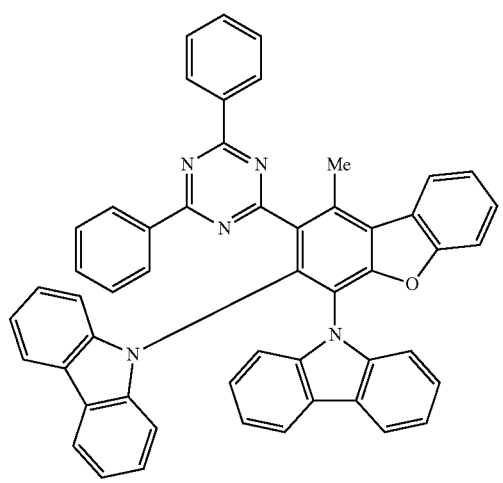
159
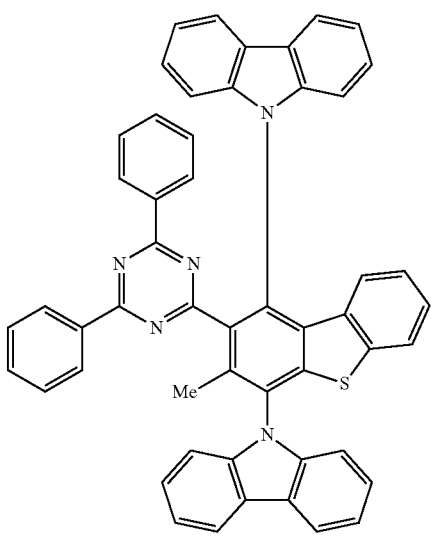
160
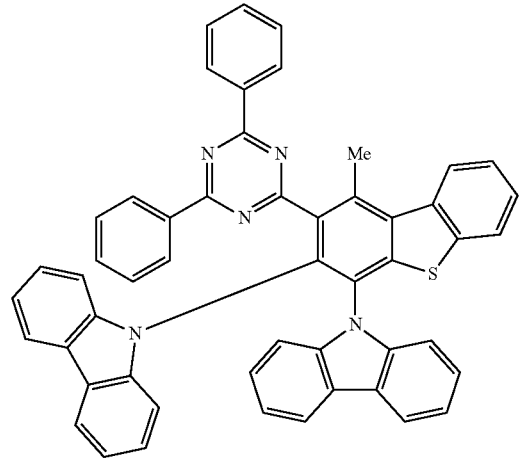
161
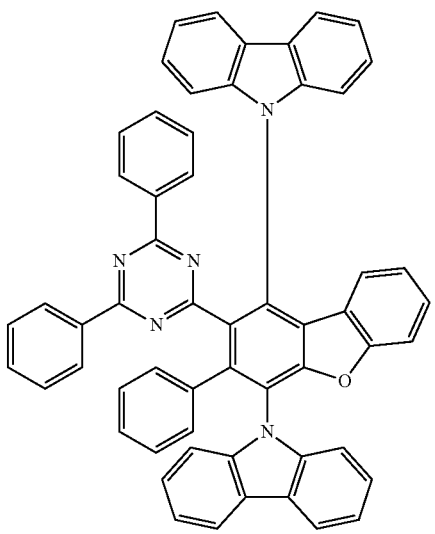

162
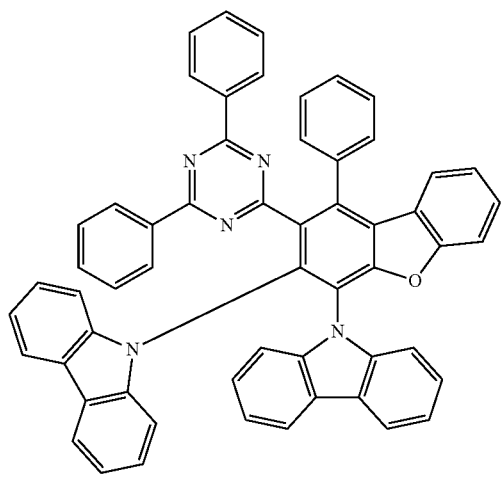
163
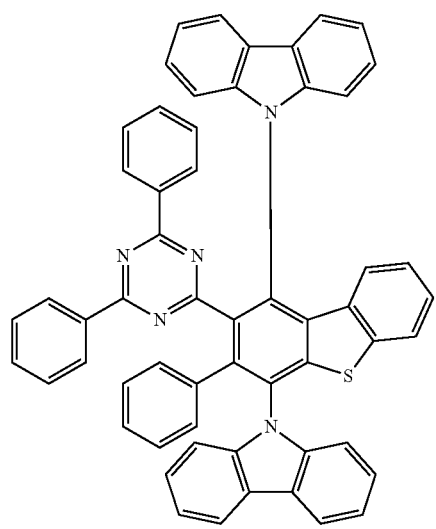
164
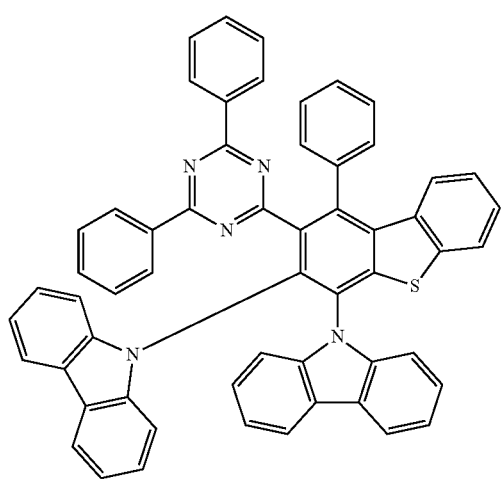
165
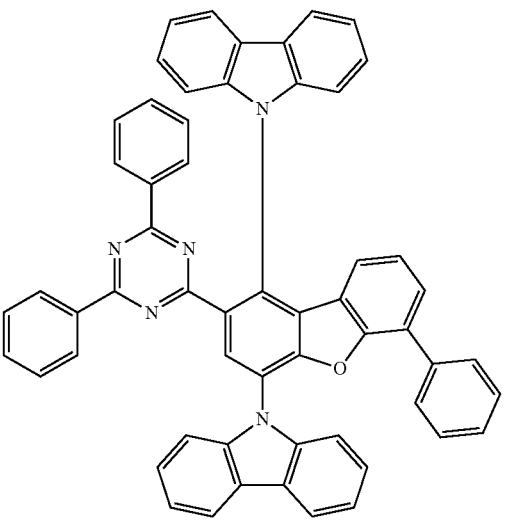
166
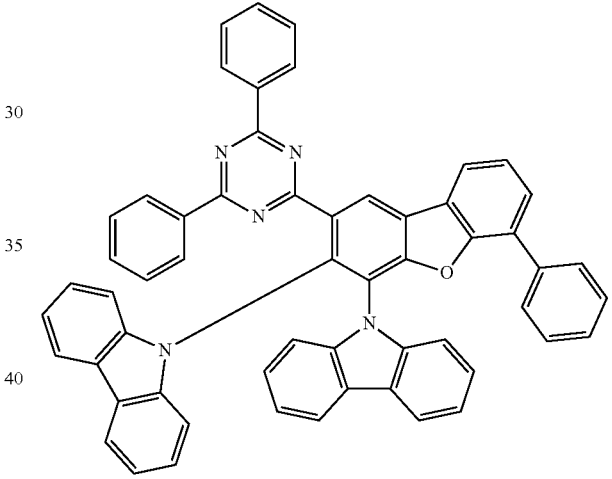
167
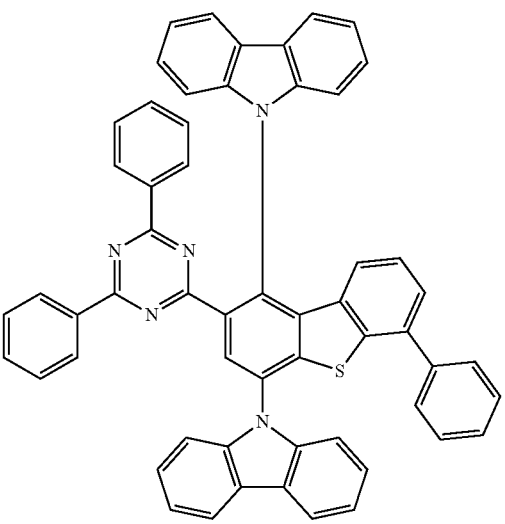

73
-continued
168
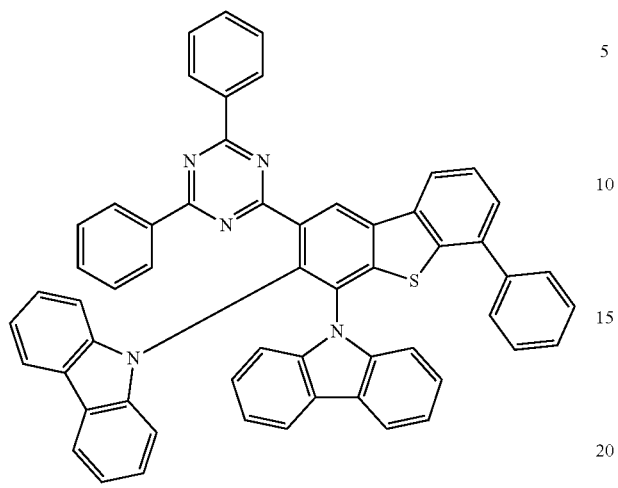
169
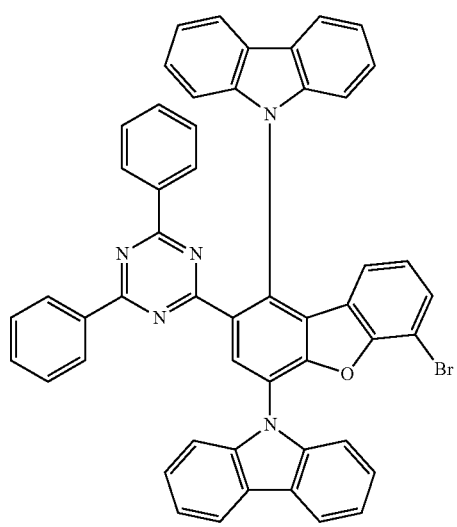
170
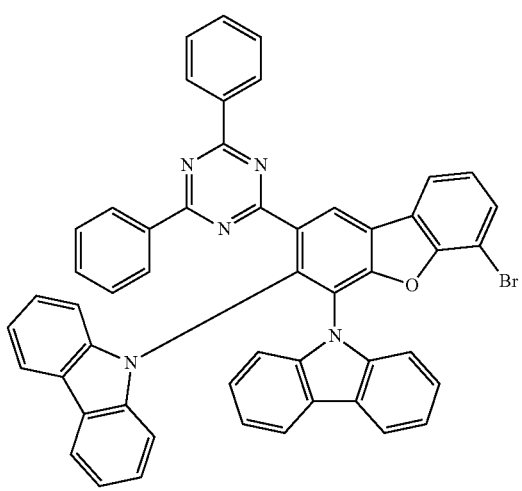
74
-continued
171
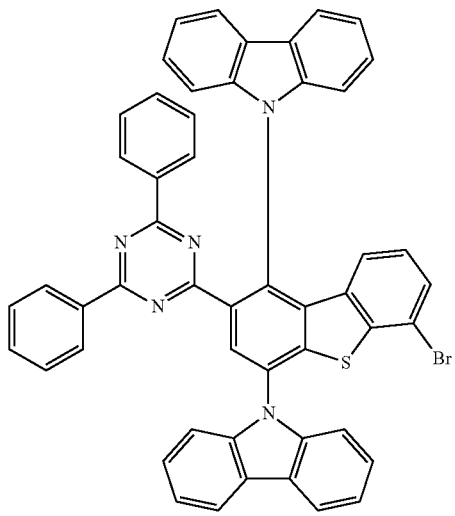
172
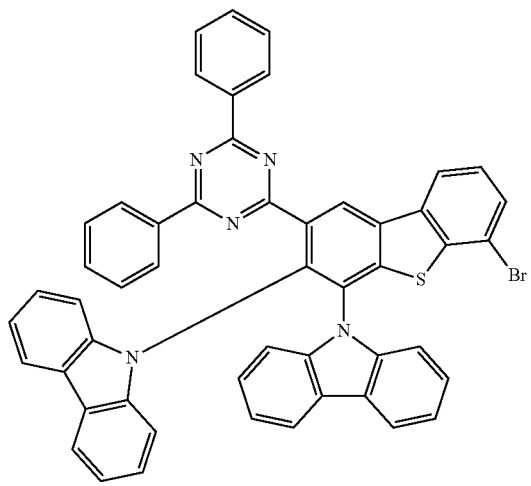
173
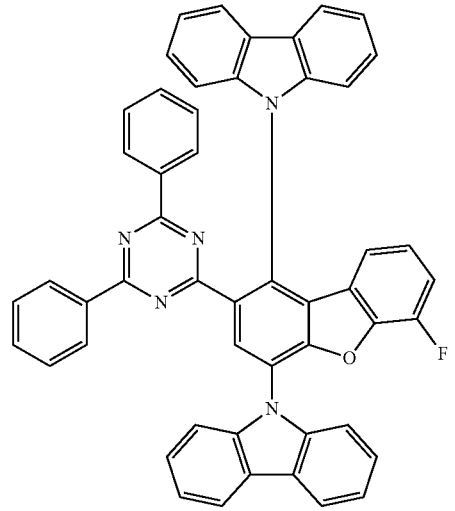

174
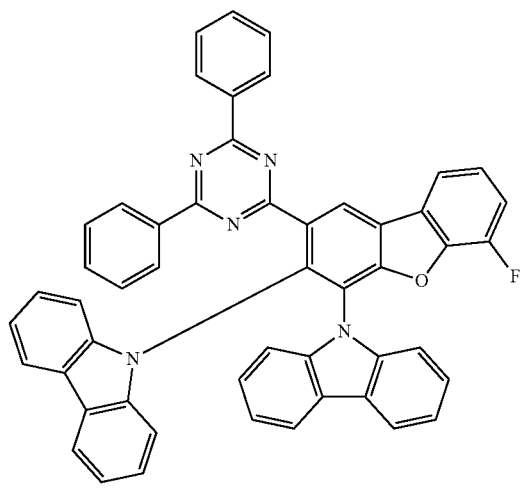
175
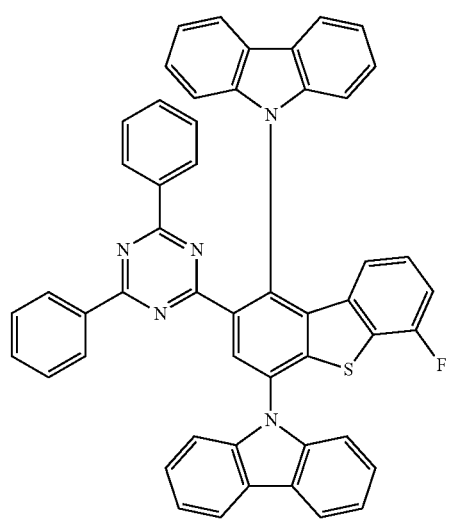
176
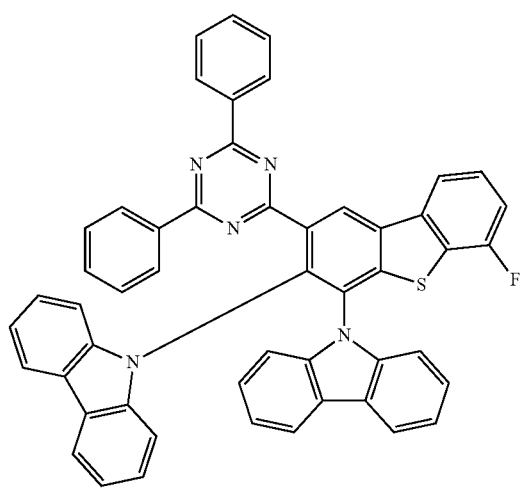
177
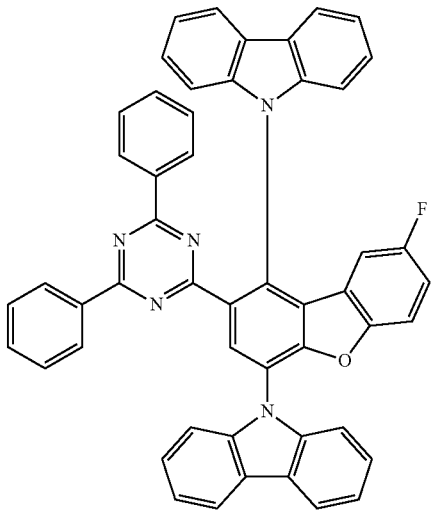
178
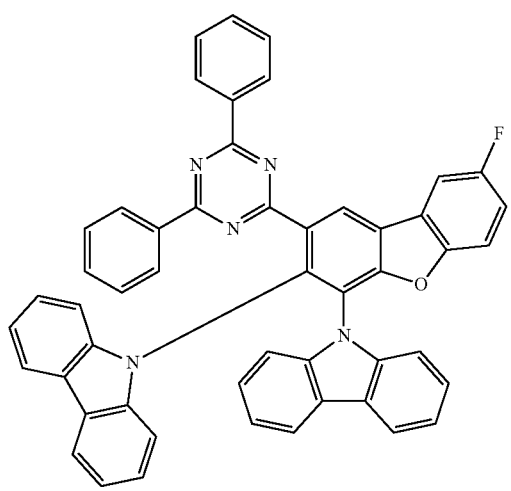
179
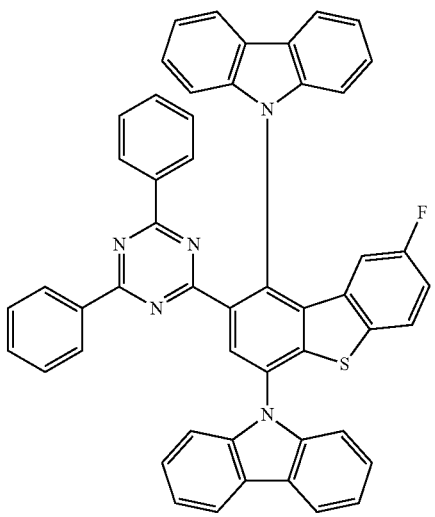

77
-continued
180
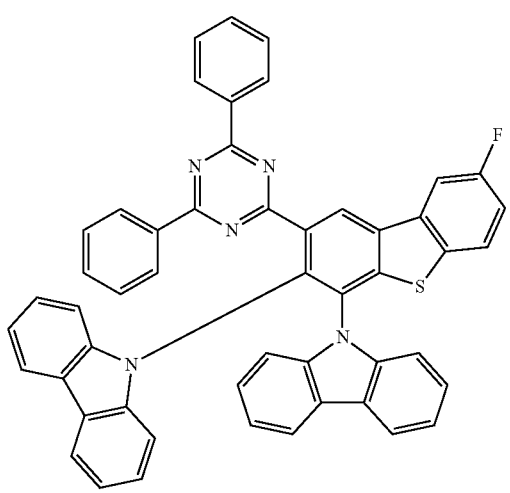
181
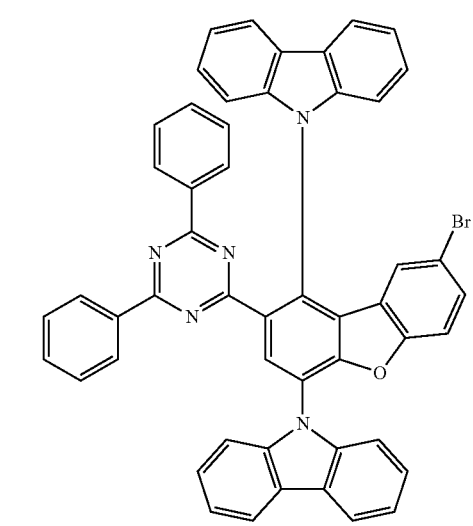
182
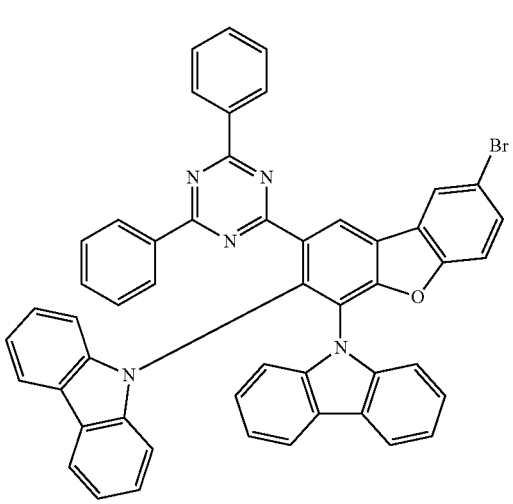
78
-continued
183
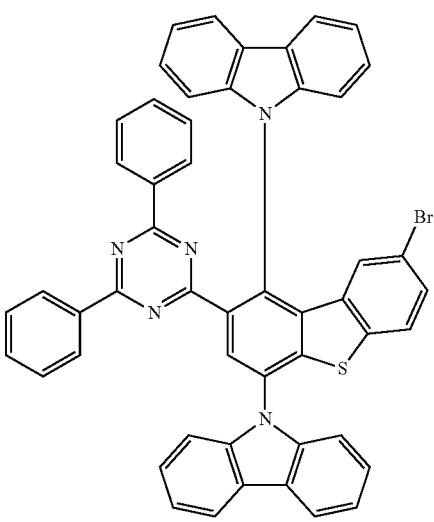
184
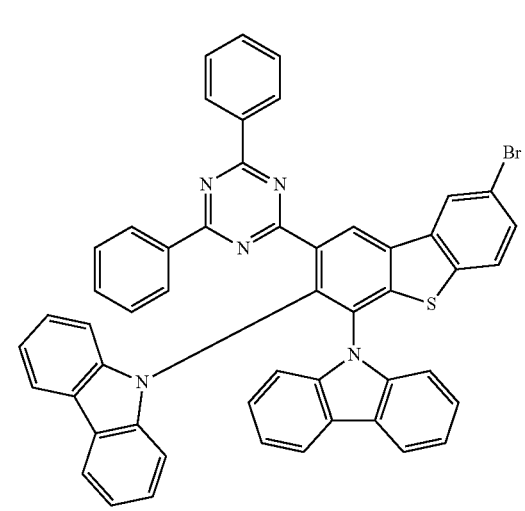
185
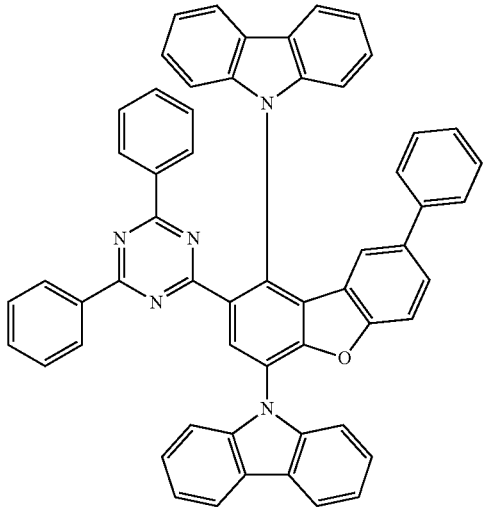

-continued

186

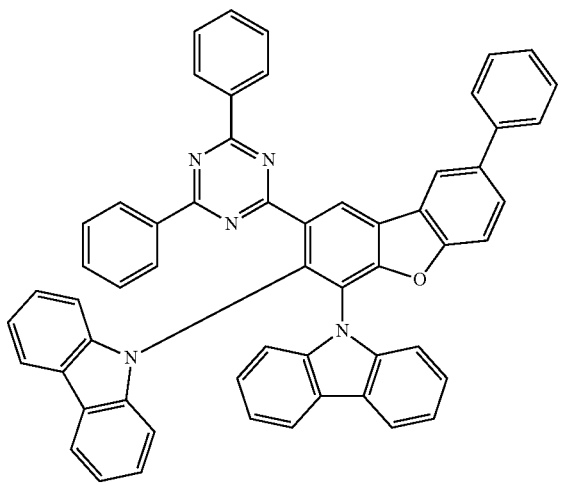

187

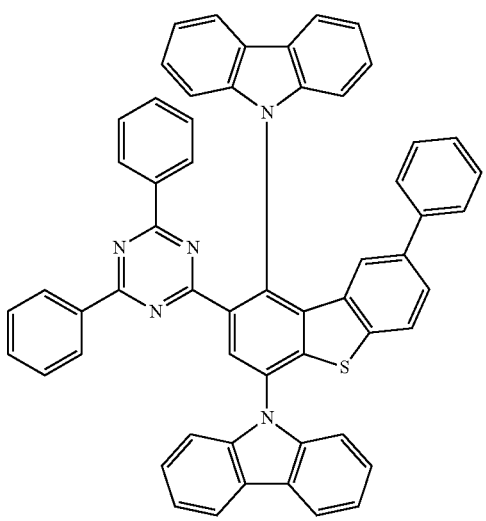

188

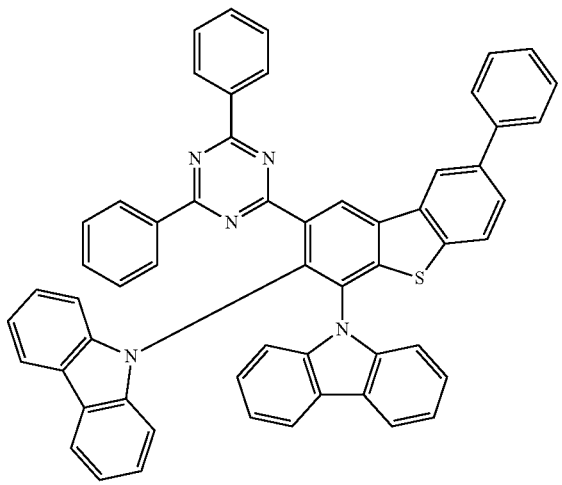

In an implementation, the emission layer EML may include one kind or two or more kinds of the heterocyclic compound. In an implementation, the emission layer EML may further include other suitable materials in addition to the heterocyclic compound.

In an implementation, the emission layer EML may include a host and a dopant, and the dopant may include the heterocyclic compound. In an implementation, the heterocyclic compound represented by Formula 1 may be included in the emission layer EML as a dopant. In an implementation, the heterocyclic compound represented by Formula 1 may be included in the emission layer EML as a dopant for thermally activated delayed fluorescence. The emission layer EML includes the heterocyclic compound and may be a blue emission layer emitting blue light having a wavelength region of less than about 470 nm. For example, the heterocyclic compound may be included in the emission layer EML as a dopant emitting deep blue light having a wavelength region of about 440 nm to about 470 nm, or about 450 nm to about 470 nm.

In an implementation, the host material may include suitable materials. For example, at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4''-tris(carbazol-9-yl)-triphenylamine (TcTa) or 1,3,5-tris(N-phenylbenzimidazole-2-yl)benzene (TPBi) may be included. For example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), etc., may be used as the host material.

In an implementation, in addition to the heterocyclic compound, the emission layer EML may further include as a dopant, at least one of N,N,N',N'-tetraphenyl-pyrene-1,6-diamine (TPD), 4,4'-bis(2-(9-ethyl-9H-carbazol-3-yl)vinyl)-1,1'-biphenyl (BCzVBi); 4,4'-bis(9-ethyl-3-carbazovinylene)-1,1'-biphenyl, 10-phenyl-10H,10'H-spiro[acridine-9,9'-anthracene]-10'-one (ACRSA), 3,4,5,6-tetra-9H-carbazol-9-yl-1,2-benzenedicarbonitrile (4CzPN), 2,4,5,6-tetra-9H-carbazol-9-yl-isophthalonitrile (4CzIPN), bis[4-9,9-dimethyl-9,10-dihydroacridine]phenyl]sulfone (DMAC-DPS), and 2-phenoxazine-4,6-diphenyl-1,3,5-triazine (PSZ-TRZ). In addition, the emission layer EML may further include, as known dopant materials, styryl derivatives (for example, 1,4-bis[2-(3-N-ethylcarbazoryl)vinyl]benzene (BCzVB), 4-(di-p-tolylamino)-4'-[(di-p-tolylamino)styryl] stilbene (DPAVB), and N-(4-((E)-2-(6-((E)-4-(diphenylamino)styryl)naphthalen-2-yl)vinyl)phenyl)-N-phenyl-benzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

The emission layer EML may be a blue emission layer that emits blue light. The emission layer EML may be a fluorescence emission layer radiating fluorescence. The emission layer EML may be a delayed fluorescence emission layer radiating delayed fluorescence.

The electron transport region ETR is provided on the emission layer EML. The electron transport region ETR may include at least one of a hole blocking layer HBL, an electron transport layer ETL, or an electron injection layer EIL.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure having a plurality of different materials, or a structure laminated from the emission layer EML of electron transport layer ETL/electron injection layer EIL, or hole blocking layer HBL/electron transport layer ETL/electron injection layer EIL. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes an electron transport layer ETL, the electron transport region ETR may include tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate ($Bebq_2$), 9,10-di(naphthalene-2-yl)anthracene (ADN), and a mixture thereof. The thickness of the electron transport layers ETL may be from about 100 Å to about 1,000 Å, for example, from about 150 Å to about 500 Å. If the thickness of the electron transport layers ETL satisfies the above-described range, satisfactory electron transport properties may be obtained without substantial increase of a driving voltage.

If the electron transport region ETR includes an electron injection layer EIL, the electron transport layer ETL may use LiF, lithium quinolate (LiQ), $Li_2O$, BaO, NaCl, CsF, a metal in lanthanides such as Yb, or a metal halide such as RbCl, and RbI. The electron injection layer EIL may also be formed using a mixture material of an electron transport material and an insulating organo metal salt. The organo metal salt may be a material having an energy band gap of about 4 eV or more. Particularly, the organo metal salt may include, for example, metal acetates, metal benzoates, metal acetoacetates, metal acetylacetonates, or metal stearates. The thickness of the electron injection layer EIL may be from about 1 Å to about 100 Å, from about 3 Å to about 90 Å. If the thickness of the electron injection layer EIL satisfies the above-described range, satisfactory electron injection properties may be obtained without substantial increase of a driving voltage.

The electron transport region ETR may include a hole blocking layer as described above. The hole blocking layer may include, for example, 2,9-dimethyl-4,7-diphenyl-1,10-phenanthroline (BCP), 4,7-diphenyl-1,10-phenanthroline (Bphen), or bis[2-(diphenylphosphino)phenyl]ether oxide (DPEPO).

The second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

In an implementation, the second electrode EL2 may be connected with an auxiliary electrode. If the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via transition from an excited state to a ground state.

If the organic electroluminescence device 10 is a top emission type, the first electrode EL1 may be a reflective electrode and the second electrode EL2 may be a transmissive electrode or a transflective electrode. If the organic electroluminescence device 10 is a bottom emission type, the first electrode EL1 may be a transmissive electrode or a transflective electrode and the second electrode EL2 may be a reflective electrode.

The organic electroluminescence device 10 according to an embodiment may include the heterocyclic compound represented by Formula 1, and thus, high efficiency and blue emission (e.g., deep blue emission) may be achieved at the same time.

An embodiment provides a heterocyclic compound represented by Formula 1. The above-described explanation on Formula 1 will be applied unless otherwise explained. For example, the heterocyclic compound according to an embodiment may be represented by the following Formula 1.

[Formula 1]

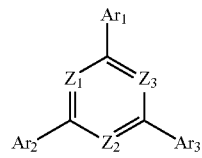

In Formula 1, $Z_1$ to $Z_3$ may each independently be, e.g., $CR_1$ or N. In an implementation, at least one of $Z_1$ to $Z_3$ may be N. In an implementation, $R_1$ may be, e.g., a hydrogen atom, a deuterium atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, $Ar_1$ to $Ar_3$ may each independently be, e.g., a group represented by Formula 2, a substituted or unsubstituted aryl group having 6 to 30 ring carbon atoms, or a substituted or unsubstituted heteroaryl group having 2 to 30 ring carbon atoms. In an implementation, at least one of $Ar_1$ to $Ar_3$ may be a group represented by Formula 2.

[Formula 2]

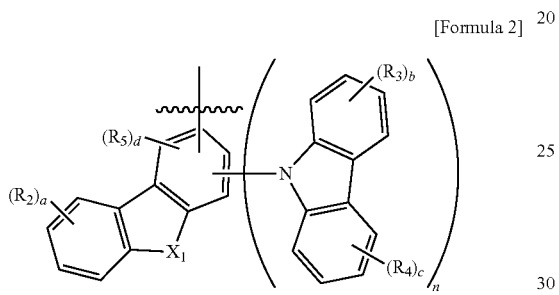

In Formula 2, $X_1$ may be, e.g., O or S "n" may be, e.g., an integer of 1 to 3, "a" to "c" may each independently be, e.g., an integer of 0 to 4, and "d" may be, e.g., an integer of 0 to 2. $R_2$ to $R_5$ may each independently be, e.g., a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms. In an implementation, if only one of $Ar_1$ to $Ar_3$ is a group represented by Formula 2, "n" may be 2 or 3. In an implementation, at least one of the carbazole moieties in Formula 2 may be bonded in ortho relationship with respect to the nitrogen-containing monocycle of Formula 1.

In an implementation, the heterocyclic compound according to an embodiment may be a compound of Compound Group 1, above.

The heterocyclic compound according to an embodiment may have a difference between a singlet energy level and a triplet energy level of about 0.2 eV or less, and as a result, may be used as a material for thermally activated delayed fluorescence. The heterocyclic compound according to an embodiment may be applied as a material for an organic electroluminescence device and may contribute to the increase of efficiency.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthetic Examples

Heterocyclic compounds according to embodiments may be synthesized, e.g., as follows.

1. Synthesis of Compound 1

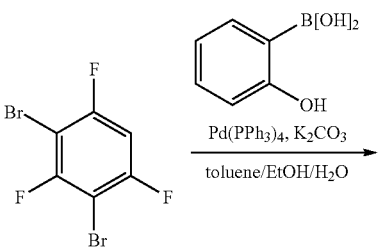

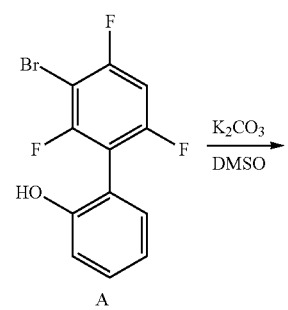

A

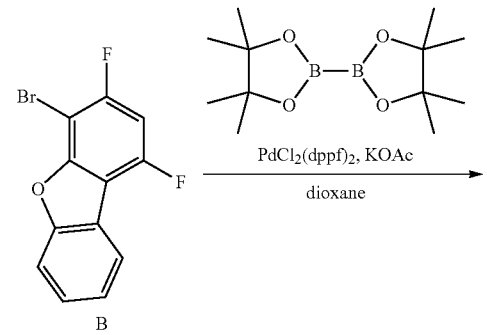

B

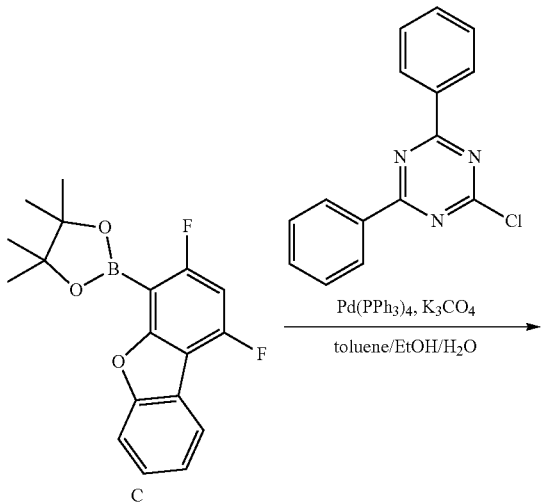

C

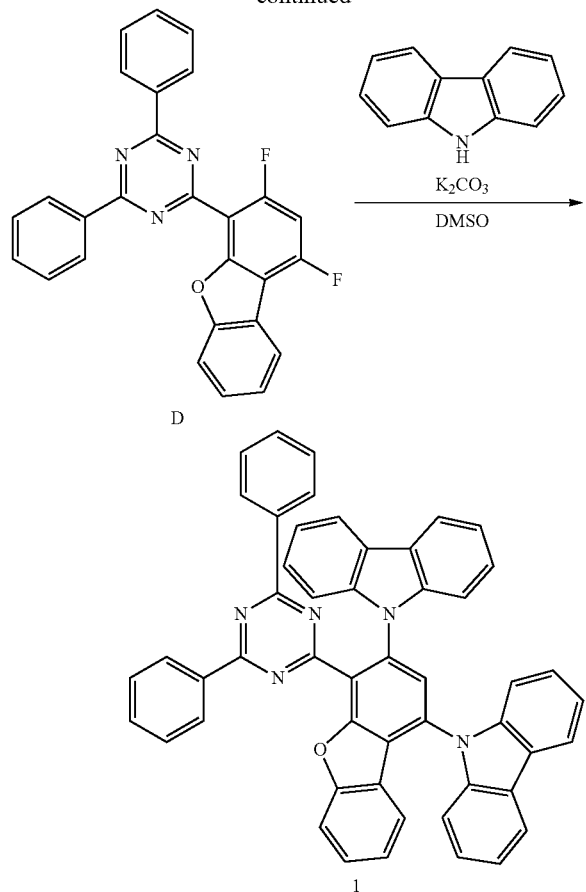

(Synthesis of Intermediate A)

Under an argon (Ar) atmosphere, in a 500 ml, three-neck flask, 2,4-dibromo-1,3,5-trifluorobenzene (10.00 g), (2-hydroxyphenyl)boronic acid (4.76 g), tetrakis(triphenylphosphine)palladium(0) (Pd(PPh$_3$)$_4$, 1.99 g), and potassium carbonate (K$_2$CO$_3$, 9.54 g) were dissolved in a mixed solvent of degassed toluene/ethanol/water (10:1:2, 180 ml), followed by stirring at about 80° C. for about 10 hours. After finishing the reaction, water was added, and organic layers extracted with CH$_2$Cl$_2$ were collected and dried with MgSO$_4$. Solvents were distilled off under a reduced pressure. The crude product thus obtained was separated by silica gel column chromatography to obtain 8.57 g (yield 82%) of Intermediate A. The molecular weight of Intermediate A measured by FAB-MS was 303.

(Synthesis of Intermediate B)

Under an argon (Ar) atmosphere, in a 300 ml, three-neck flask, Intermediate A (8.50 g) and K$_2$CO$_3$ (7.75 g) were dissolved in dehydrated DMSO (100 ml), followed by stirring at about 110° C. for about 6 hours. After decreasing the temperature to ambient temperature, the reaction solution was poured into 1,000 ml of water and stirred. The precipitate thus produced was recovered by suction filtration, dissolved in CH$_2$Cl$_2$ (300 ml) and dried with MgSO$_4$, and solvents were removed by distillation under a reduced pressure. The crude product thus obtained was separated by silica gel column chromatography and recrystallization to obtain 3.57 g (yield 45%) of Intermediate B. The molecular weight of Intermediate B measured by FAB-MS was 283.

(Synthesis of Intermediate C)

Under an argon (Ar) atmosphere, in a 200 ml, three neck flask, Intermediate B (3.50 g), bis(pinacolato)diboron (3.14 g), [1,1'-bis(diphenylphosphino)ferrocene]dichloropalladium(II) dichloromethane adduct (PdCl$_2$(dppf), 1.01 g), and potassium acetate (KOAc, 2.43 g) were dissolved in dehydrated 1,4-dioxane (70 ml), followed by stirring at about 90° C. for about 8 hours. After cooling in air, water was added, and organic layers extracted with CH$_2$Cl$_2$ were collected and dried with MgSO$_4$. Solvents were removed by distillation under a reduced pressure. The crude product thus obtained was separated by silica gel column chromatography to obtain 3.18 g (yield 78%) of Intermediate C. The molecular weight of Intermediate C measured by FAB-MS was 330.

(Synthesis of Intermediate D)

Under an argon (Ar) atmosphere, in a 200 ml, three-neck flask, Intermediate C (3.00 g), 2-chloro-4,6-diphenyl-1,3,5-triazine (2.43 g), Pd(PPh$_3$)$_4$ (0.53 g), and tripotassium phosphate (K$_3$PO$_4$, 3.86 g) were dissolved in a mixed solvent of degassed toluene/ethanol/water (10:1:2, 60 ml), followed by stirring at about 80° C. for about 10 hours. After finishing the reaction, water was added, and organic layers extracted with CH$_2$Cl$_2$ were collected and dried with MgSO$_4$. Solvents were distilled off under a reduced pressure. The crude product thus obtained was separated by silica gel column chromatography to obtain 2.85 g (yield 72%) of Intermediate D. The molecular weight of Intermediate D measured by FAB-MS was 435.

(Synthesis of Compound 1)

Under an argon (Ar) atmosphere, in a 200 ml, three-neck flask, Intermediate D (2.80 g), carbazole (2.15 g), and K$_2$CO$_3$ (4.45 g) were dissolved in dehydrated DMSO (30 ml), followed by stirring at about 150° C. for about 6 hours. After decreasing the temperature to ambient temperature, the reaction solution was poured into 300 ml of water and stirred. The precipitate thus produced was recovered by suction filtration, dissolved in CH$_2$Cl$_2$ (150 ml), and dried with MgSO$_4$, and solvents were removed by distillation under a reduced pressure. The crude product thus obtained was separated by recrystallization to obtain 3.75 g (yield 80%) of Compound 1. The molecular weight of Compound 1 measured by FAB-MS was 729.

2. Synthesis of Compound 24

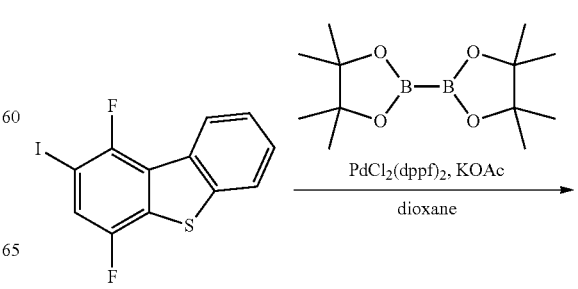

-continued

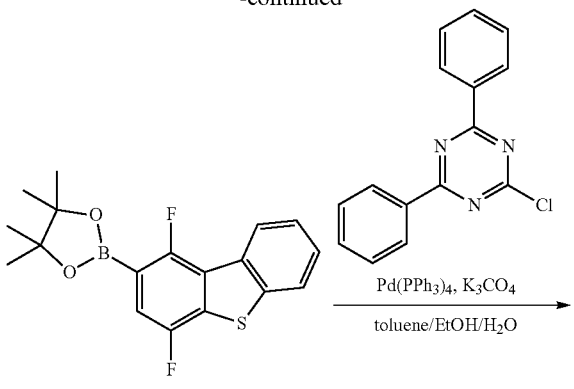

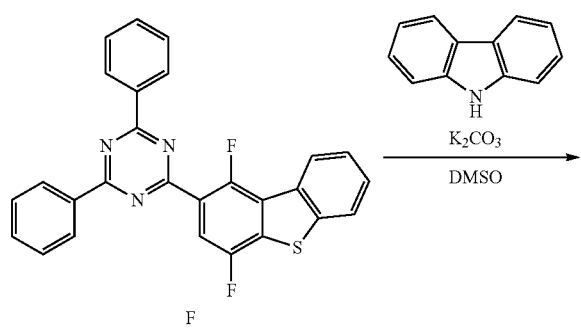

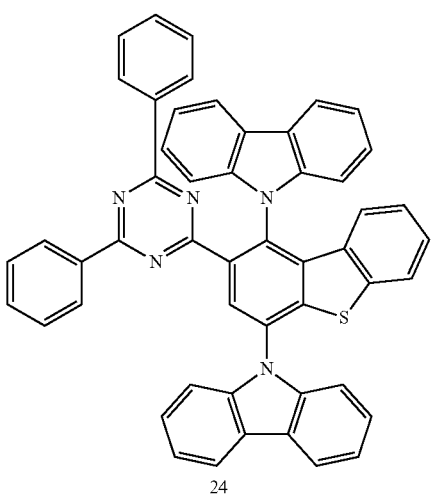

(Synthesis of Intermediate E)

Under an argon (Ar) atmosphere, in a 200 ml, three-neck flask, 1,4-difluoro-2-iododibenzo[b,d]thiophene (5.00 g), bis(pinacolato)diboron (3.66 g), PdCl$_2$(dppf) (1.18 g), and KOAc (2.84 g) were dissolved in dehydrated 1,4-dioxane (80 ml), followed by stirring at about 90° C. for about 8 hours. After cooling in the air, water was added, and organic layers extracted with CH$_2$Cl$_2$ were collected and dried with MgSO$_4$. Then, solvents were removed by distillation under a reduced pressure. The crude product thus obtained was separated by silica gel column chromatography to obtain 3.10 g (yield 62%) of Intermediate E. The molecular weight of Intermediate E measured by FAB-MS was 346.

(Synthesis of Intermediate F)

Under an argon (Ar) atmosphere, in a 200 ml, three-neck flask, Intermediate E (3.00 g), 2-chloro-4,6-diphenyl-1,3,5-triazine (2.32 g), Pd(PPh$_3$)$_4$ (0.50 g), and K$_3$PO$_4$ (3.68 g) were dissolved in a mixed solvent of degassed toluene/ethanol/water (10:1:2, 50 ml), followed by stirring at about 80° C. for about 10 hours. After finishing the reaction, water was added, and organic layers extracted with CH$_2$Cl$_2$ were collected and dried with MgSO$_4$. Solvents were distilled off under a reduced pressure. The crude product thus obtained was separated by silica gel column chromatography to obtain 2.74 g (yield 70%) of Intermediate F. The molecular weight of Intermediate F measured by FAB-MS was 451.

(Synthesis of Compound 24)

Under an argon (Ar) atmosphere, in a 200 ml, three-neck flask, Intermediate F (2.70 g), carbazole (2.61 g), and K$_2$CO$_3$ (5.39 g) were dissolved in dehydrated DMSO (30 ml), followed by stirring at about 150° C. for about 6 hours. After decreasing the temperature to ambient temperature, the reaction solution was poured into 300 ml of water and stirred. The precipitate thus produced was recovered by suction filtration, dissolved in CH$_2$Cl$_2$ (150 ml) and dried with MgSO$_4$, and solvents were removed by distillation under a reduced pressure. The crude product thus obtained was separated by recrystallization to obtain 4.94 g (yield 85%) of Compound 24. The molecular weight of Compound 24 measured by FAB-MS was 745.

3. Synthesis of Compound 107

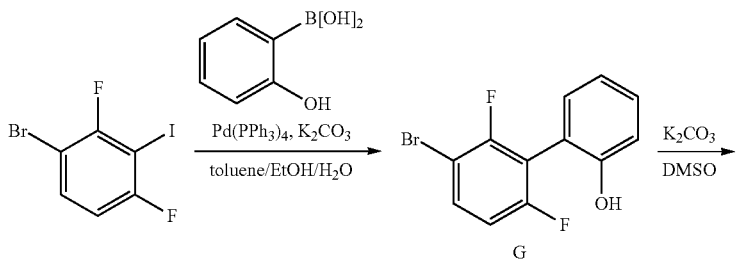

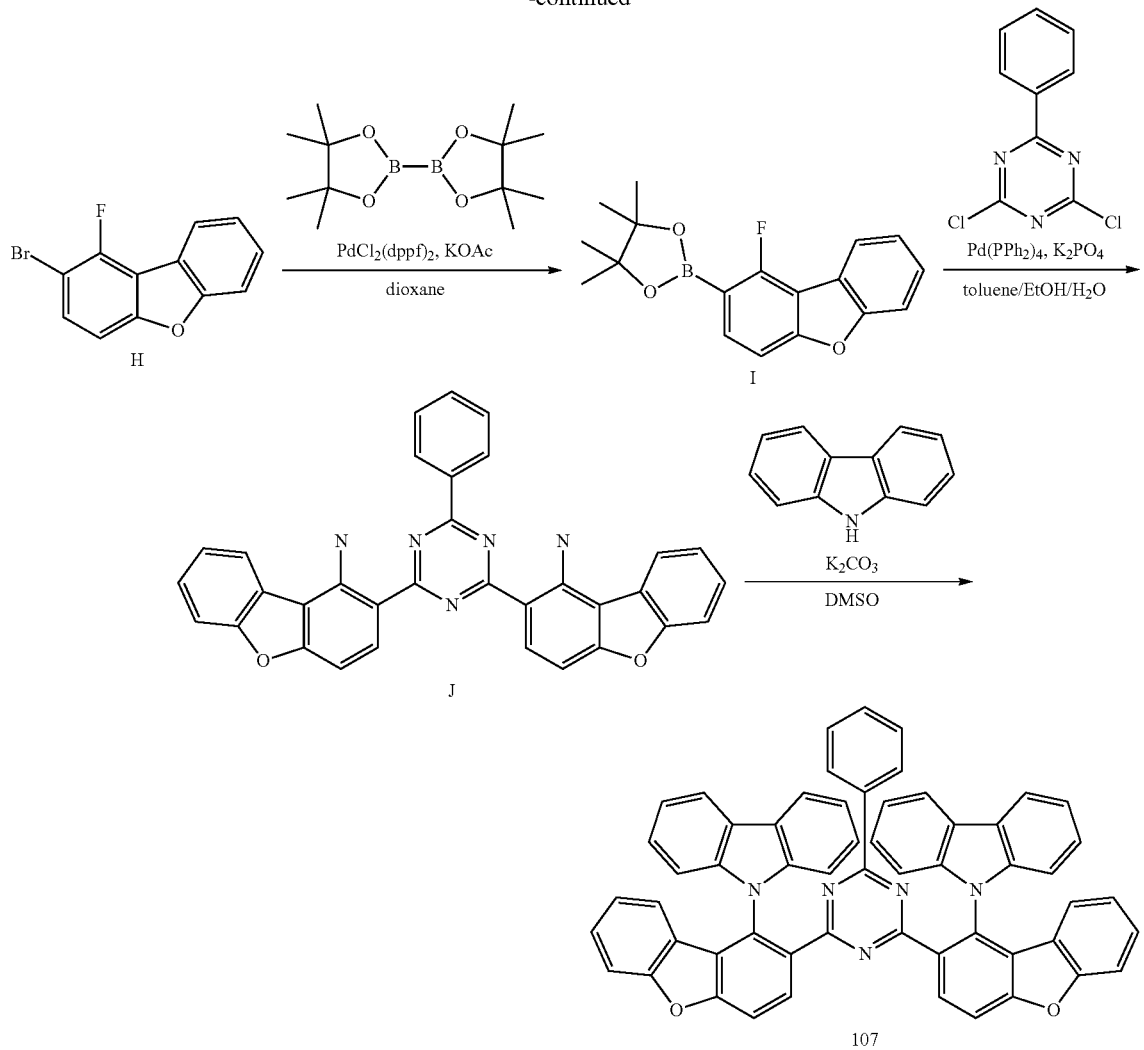

(Synthesis of Intermediate G)

Under an argon (Ar) atmosphere, in a 500 ml, three-neck flask, 1-bromo-2,4-difluoro-3-iodobenzene (10.00 g), (2-hydroxyphenyl)boronic acid (4.33 g), Pd(PPh$_3$)$_4$ (1.81 g), and K$_2$CO$_3$ (8.69 g) were dissolved in a mixed solvent of degassed toluene/ethanol/water (10:1:2, 160 ml), followed by stirring at about 80° C. for about 10 hours. After finishing the reaction, water was added, and organic layers extracted with CH$_2$Cl$_2$ were collected and dried with MgSO$_4$. Solvents were distilled off under a reduced pressure. The crude product thus obtained was separated by silica gel column chromatography to obtain 7.69 g (yield 86%) of Intermediate G. The molecular weight of Intermediate G measured by FAB-MS was 285.

(Synthesis of Intermediate H)

Under an argon (Ar) atmosphere, in a 300 ml, three-neck flask, Intermediate G (7.60 g) and K$_2$CO$_3$ (7.37 g) were dissolved in dehydrated DMSO (100 ml), followed by stirring at about 110° C. for about 6 hours. After decreasing the temperature to ambient temperature, the reaction solution was poured into 1,000 ml of water and stirred. The precipitate thus produced was recovered by suction filtration, dissolved in CH$_2$Cl$_2$ (300 ml) and dried with MgSO$_4$, and solvents were removed by distillation under a reduced pressure. The crude product thus obtained was separated by silica gel column chromatography and recrystallization to obtain 2.69 g (yield 38%) of Intermediate H. The molecular weight of Intermediate H measured by FAB-MS was 265.

(Synthesis of Intermediate I)

Under an argon (Ar) atmosphere, in a 200 ml, three neck flask, Intermediate H (2.60 g), bis(pinacolato)diboron (2.49 g), PdCl$_2$(dppf) (0.80 g), and KOAc (1.93 g) were dissolved in dehydrated 1,4-dioxane (50 ml), followed by stirring at about 90° C. for about 8 hours. After cooling in air, water was added, and organic layers extracted with CH$_2$Cl$_2$ were collected and dried with MgSO$_4$. Solvents were removed by distillation under a reduced pressure. The crude product thus obtained was separated by silica gel column chromatography to obtain 1.84 g (yield 60%) of Intermediate I. The molecular weight of Intermediate I measured by FAB-MS was 312.

(Synthesis of Intermediate J)

Under an argon (Ar) atmosphere, in a 200 ml, three-neck flask, Intermediate I (3.00 g), 2,4-dichloro-6-phenyl-1,3,5-triazine (0.65 g), Pd(PPh$_3$)$_4$ (0.33 g), and K$_3$PO$_4$ (2.45 g) were dissolved in a mixed solvent of degassed toluene/ethanol/water (10:1:2, 50 ml), followed by stirring at about 80° C. for about 10 hours. After finishing the reaction, water was added, and organic layers extracted with CH$_2$Cl$_2$ were collected and dried with MgSO$_4$. Solvents were distilled off under a reduced pressure. The crude product thus obtained was separated by silica gel column chromatography to obtain 2.27 g (yield 75%) of Intermediate J. The molecular weight of Intermediate J measured by FAB-MS was 525.

(Synthesis of Compound 107)

Under an argon (Ar) atmosphere, in a 200 ml, three-neck flask, Intermediate J (2.20 g), carbazole (1.40 g), and K$_2$CO$_3$ (2.89 g) were dissolved in dehydrated DMSO (30 ml), followed by stirring at about 150° C. for about 6 hours. After decreasing the temperature to ambient temperature, the reaction solution was poured into 300 ml of water and stirred. The precipitate thus produced was recovered by suction filtration, dissolved in CH$_2$Cl$_2$ (150 ml) and dried with MgSO$_4$, and solvents were removed by distillation under a reduced pressure. The crude product thus obtained was separated by recrystallization to obtain 2.75 g (yield 80%) of Compound 107. The molecular weight of Compound 107 measured by FAB-MS was 819.

4. Synthesis of Compound 109

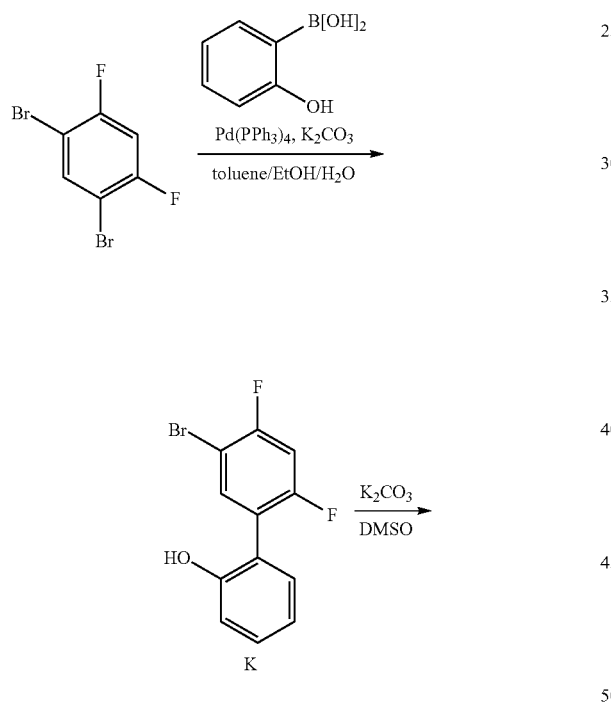

K

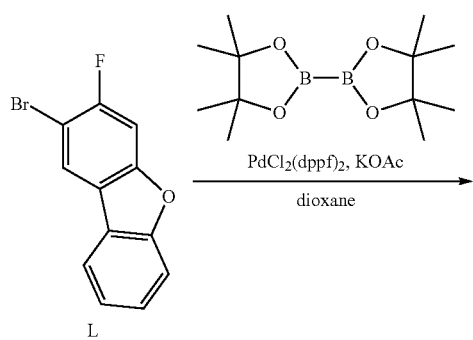

L

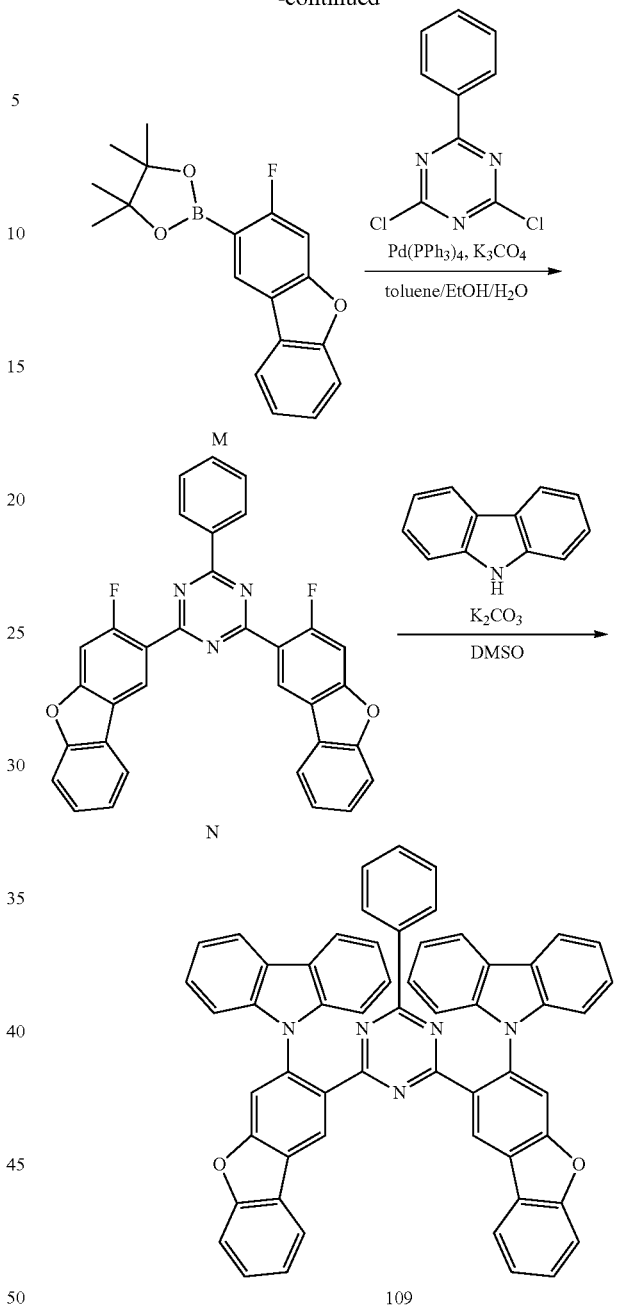

M

N

109

(Synthesis of Intermediate K)

Under an argon (Ar) atmosphere, in a 500 ml, three-neck flask, 1,5-dibromo-2,4-difluorobenzene (10.00 g), (2-hydroxyphenyl)boronic acid (5.07 g), Pd(PPh$_3$)$_4$ (2.13 g), and K$_2$CO$_3$ (10.17 g) were dissolved in a mixed solvent of degassed toluene/ethanol/water (10:1:2, 180 ml), followed by stirring at about 80° C. for about 10 hours. After finishing the reaction, water was added, and organic layers extracted with CH$_2$Cl$_2$ were collected and dried with MgSO$_4$. Solvents were distilled off under a reduced pressure. The crude product thus obtained was separated by silica gel column chromatography to obtain 8.91 g (yield 85%) of Intermediate K. The molecular weight of Intermediate K measured by FAB-MS was 285.

(Synthesis of Intermediate L)

Under an argon (Ar) atmosphere, in a 300 ml, three-neck flask, Intermediate K (8.90 g) and $K_2CO_3$ (8.63 g) were dissolved in dehydrated DMSO (100 ml), followed by stirring at about 110° C. for about 6 hours. After decreasing the temperature to ambient temperature, the reaction solution was poured into 1,000 ml of water and stirred. The precipitate thus produced was recovered by suction filtration, dissolved in $CH_2Cl_2$ (300 ml) and dried with $MgSO_4$, and solvents were removed by distillation under a reduced pressure. The crude product thus obtained was separated by silica gel column chromatography and recrystallization to obtain 7.20 g (yield 87%) of Intermediate L. The molecular weight of Intermediate L measured by FAB-MS was 265.

(Synthesis of Intermediate M)

Under an argon (Ar) atmosphere, in a 500 ml, three neck flask, Intermediate L (7.20 g), bis(pinacolato)diboron (6.89 g), $PdCl_2(dppf)$ (2.22 g), and KOAc (5.33 g) were dissolved in dehydrated 1,4-dioxane (140 ml), followed by stirring at about 90° C. for about 8 hours. After cooling in air, water was added, and organic layers extracted with $CH_2Cl_2$ were collected and dried with $MgSO_4$. Solvents were removed by distillation under a reduced pressure. The crude product thus obtained was separated by silica gel column chromatography to obtain 4.41 g (yield 52%) of Intermediate M. The molecular weight of Intermediate M measured by FAB-MS was 312.

(Synthesis of Intermediate N)

Under an argon (Ar) atmosphere, in a 300 ml, three-neck flask, Intermediate M (4.40 g), 2,4-dichloro-6-phenyl-1,3,5-triazine (1.59 g), $Pd(PPh_3)_4$, (0.81 g), and $K_3PO_4$ (5.98 g) were dissolved in a mixed solvent of degassed toluene/ethanol/water (10:1:2, 70 ml), followed by stirring at about 80° C. for about 10 hours. After finishing the reaction, water was added, and organic layers extracted with $CH_2Cl_2$ were collected and dried with $MgSO_4$. Solvents were distilled off under a reduced pressure. The crude product thus obtained was separated by silica gel column chromatography to obtain 5.04 g (yield 68%) of Intermediate N. The molecular weight of Intermediate N measured by FAB-MS was 525.

(Synthesis of Compound 109)

Under an argon (Ar) atmosphere, in a 200 ml, three-neck flask, Intermediate N (2.50 g), carbazole (1.59 g), and $K_2CO_3$ (3.28 g) were dissolved in dehydrated DMSO (30 ml), followed by stirring at about 150° C. for about 6 hours. After decreasing the temperature to ambient temperature, the reaction solution was poured into 300 ml of water and stirred. The precipitate thus produced was recovered by suction filtration, dissolved in $CH_2Cl_2$ (150 ml) and dried with $MgSO_4$, and solvents were removed by distillation under a reduced pressure. The crude product thus obtained was separated by recrystallization to obtain 3.08 g (yield 79%) of Compound 109. The molecular weight of Compound 109 measured by FAB-MS was 819.

5. Synthesis of Compound 133

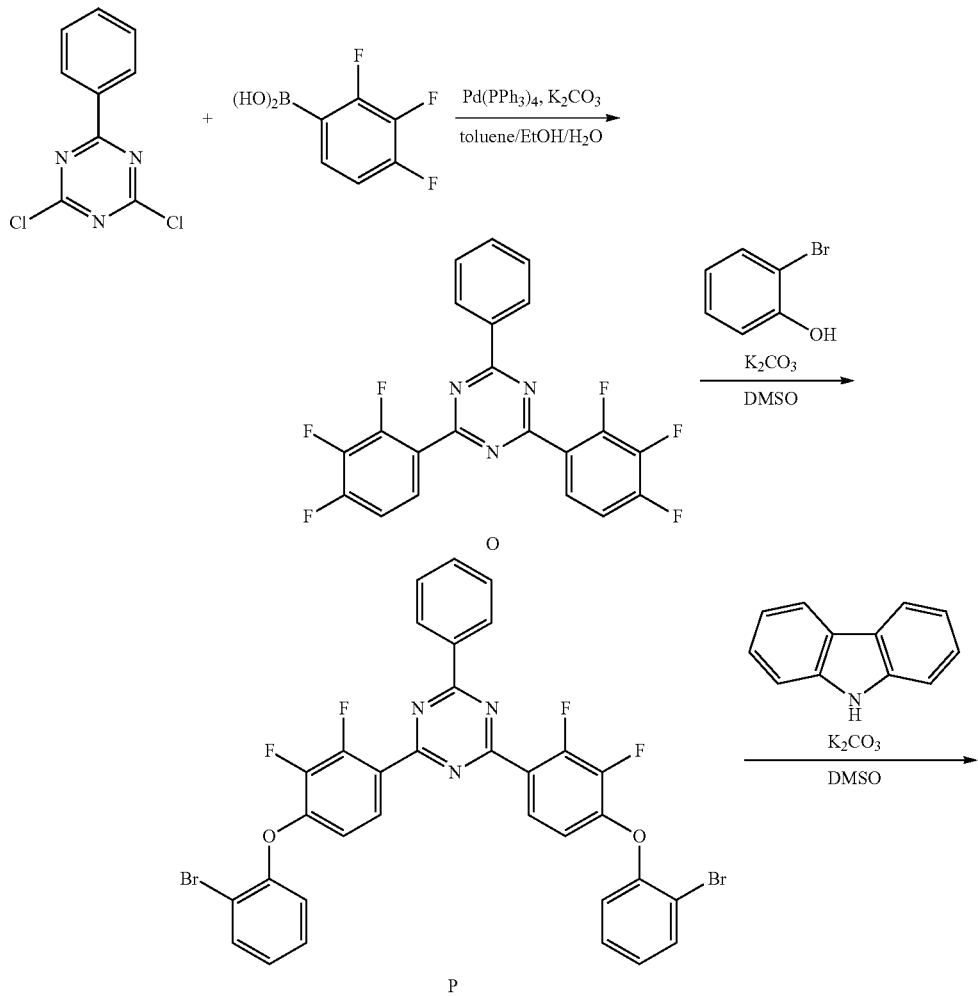

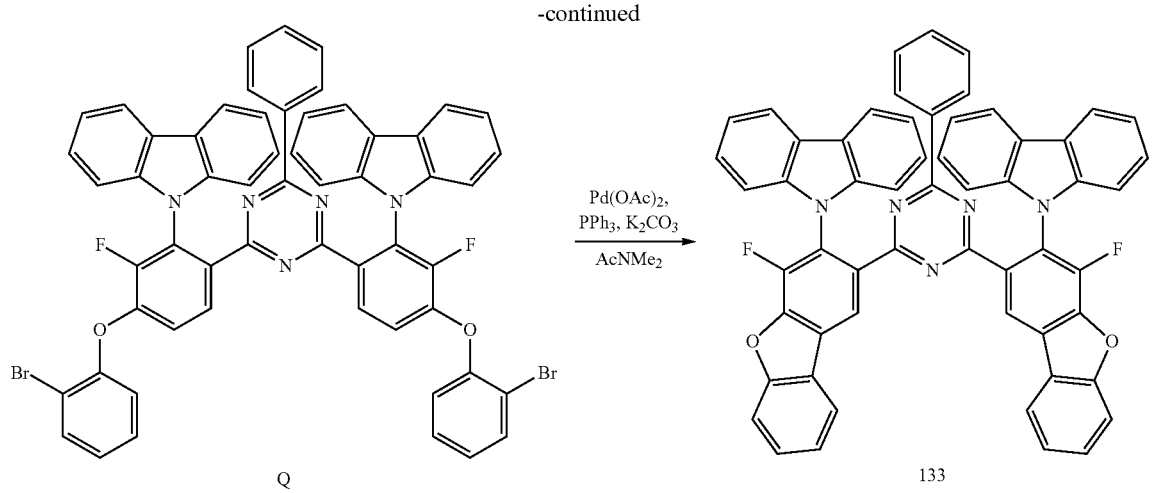

(Synthesis of Intermediate O)

Under an argon (Ar) atmosphere, in a 500 ml, three-neck flask, 2,4-dichloro-6-phenyl-1,3,5-triazine (5.00 g), 2,3,4-trifluorophenylboronic acid (7.78 g), Pd(PPh$_3$)$_4$ (2.55 g), and K$_2$CO$_3$ (12.2 g) were dissolved in a mixed solvent of degassed toluene/ethanol/water (10:1:2, 200 ml), followed by stirring at about 80° C. for about 8 hours. After finishing the reaction, water was added, and organic layers extracted with CH$_2$Cl$_2$ were collected and dried with MgSO$_4$. Solvents were distilled off under a reduced pressure. The crude product thus obtained was separated by recrystallization to obtain 4.24 g (yield 46%) of Intermediate 0. The molecular weight of Intermediate O measured by FAB-MS was 417.

(Synthesis of Intermediate P)

Under an argon (Ar) atmosphere, in a 500 ml, three-neck flask, Intermediate O (4.00 g), 2-bromophenol (3.32 g), and K$_2$CO$_3$ (5.30 g) were dissolved in dehydrated DMSO (150 ml), followed by stirring at about 60° C. for about 3 hours. After decreasing the temperature to ambient temperature, the reaction solution was poured into 1,000 ml of water and stirred. The precipitate thus produced was recovered by suction filtration, dissolved in CH$_2$Cl$_2$ (300 ml) and dried with MgSO$_4$, and solvents were removed by distillation under a reduced pressure. The crude product thus obtained was separated by recrystallization to obtain 4.15 g (yield 60%) of Intermediate P. The molecular weight of Intermediate P measured by FAB-MS was 723.

(Synthesis of Intermediate Q)

Under an Ar atmosphere, in a 300 ml, three-neck flask, Intermediate P (4.00 g), carbazole (1.85 g), and K$_2$CO$_3$ (3.06 g) were dissolved in dehydrated DMSO (50 ml), followed by stirring at about 100° C. for about 3 hours. After decreasing the temperature to ambient temperature, the reaction solution was poured into 300 ml of water and stirred. The precipitate thus produced was recovered by suction filtration, dissolved in CH$_2$Cl$_2$ (200 ml) and dried with MgSO$_4$, and solvents were removed by distillation under a reduced pressure. The crude product thus obtained was separated by recrystallization to obtain 5.34 g (yield 95%) of Intermediate Q. The molecular weight of Intermediate Q measured by FAB-MS was 1,017.

(Synthesis of Compound 133)

Under an Ar atmosphere, in a 500 ml, three-neck flask, Intermediate Q (5.00 g), Pd(OAc)$_2$ (0.11 g), K$_2$CO$_3$ (2.04 g), and PPh$_3$ (0.26 g) were dissolved in dehydrated dimethylacetamide (50 ml), followed by stirring at about 140° C. for about 1 hour. After decreasing the temperature to ambient temperature, the reaction solution was poured into 300 ml of water and stirred. The precipitate thus produced was recovered by suction filtration, dissolved in CH$_2$Cl$_2$ (200 ml) and dried with MgSO$_4$, and solvents were removed by distillation under a reduced pressure. The crude product thus obtained was separated by recrystallization to obtain 3.36 g (yield 80%) of Compound 133. The molecular weight of Compound 133 measured by FAB-MS was 855.

6. Synthesis of Compound 131

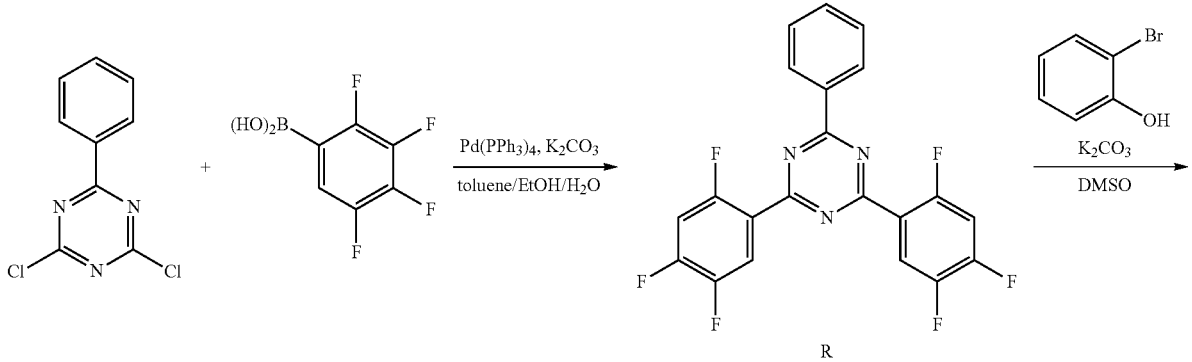

-continued

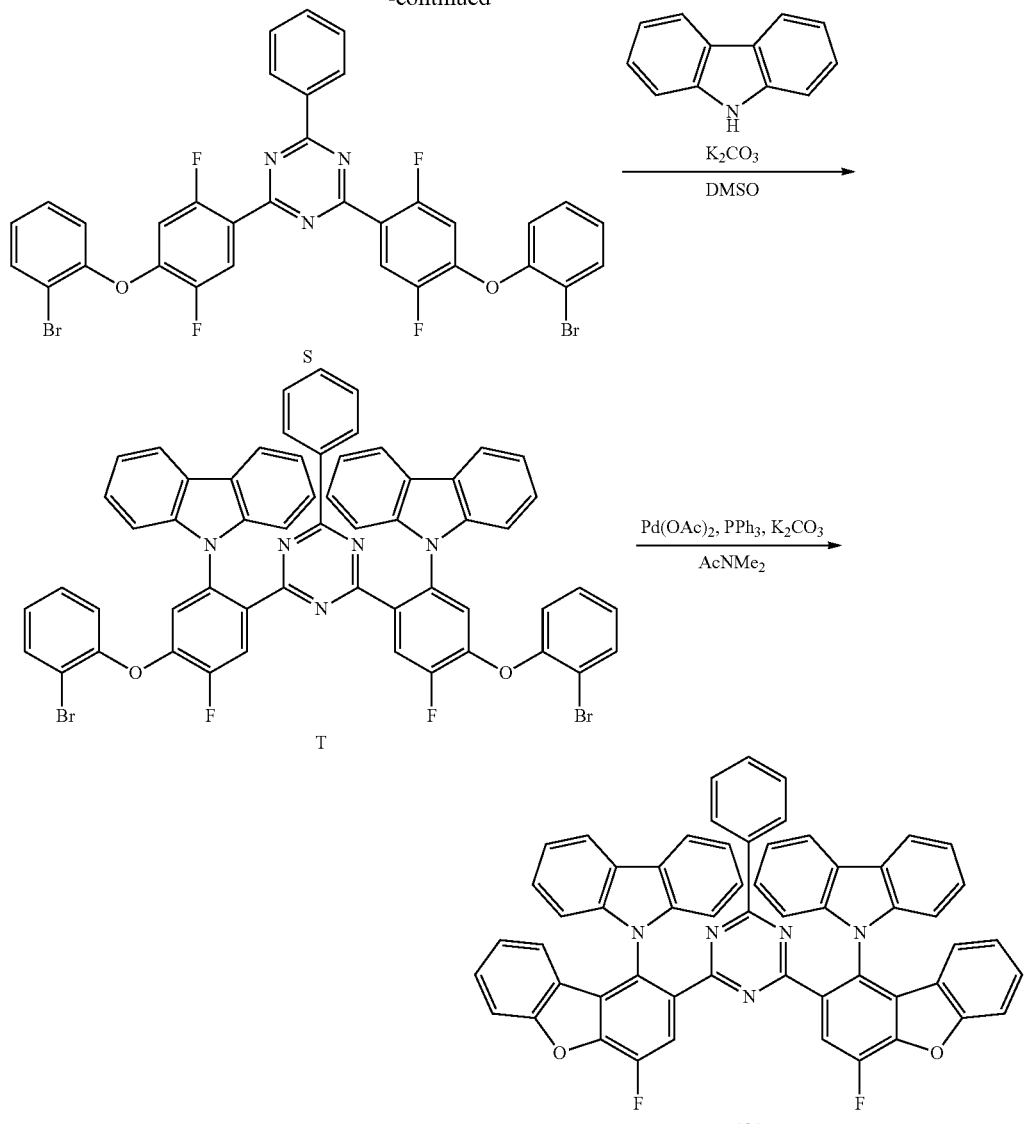

(Synthesis of Intermediate R)

Under an Ar atmosphere, in a 500 ml, three-neck flask, 2,4-dichloro-6-phenyl-1,3,5-triazine (5.00 g), 2,4,5-trifluorophenylboronic acid (7.78 g), Pd(PPh$_3$)$_4$ (2.55 g), and K$_2$CO$_3$ (12.2 g) were dissolved in a mixed solvent of degassed toluene/ethanol/water (10:1:2, 200 ml), followed by stirring at about 80° C. for about 8 hours. After finishing the reaction, water was added, and organic layers extracted with CH$_2$Cl$_2$ were collected and dried with MgSO$_4$. Solvents were distilled off under a reduced pressure. The crude product thus obtained was separated by recrystallization to obtain 4.80 g (yield 52%) of Intermediate R. The molecular weight of Intermediate R measured by FAB-MS was 417.

(Synthesis of Intermediate S)

Under an Ar atmosphere, in a 500 ml, three-neck flask, Intermediate R (4.00 g), 2-bromophenol (3.32 g), and K$_2$CO$_3$ (5.30 g) were dissolved in dehydrated DMSO (150 ml), followed by stirring at about 60° C. for about 3 hours. After decreasing the temperature to ambient temperature, the reaction solution was poured into 1,000 ml of water and stirred. The precipitate thus produced was recovered by suction filtration, dissolved in CH$_2$Cl$_2$ (300 ml) and dried with MgSO$_4$, and solvents were removed by distillation under a reduced pressure. The crude product thus obtained was separated by recrystallization to obtain 4.51 g (yield 65%) of Intermediate S. The molecular weight of Intermediate S measured by FAB-MS was 723.

(Synthesis of Intermediate T)

Under an Ar atmosphere, in a 300 ml, three-neck flask, Intermediate S (4.00 g), carbazole (1.85 g), and K$_2$CO$_3$ (3.06 g) were dissolved in dehydrated DMSO (50 ml), followed by stirring at about 100° C. for about 3 hours. After decreasing the temperature to ambient temperature, the reaction solution was poured into 300 ml of water and stirred. The precipitate thus produced was recovered by suction filtration, dissolved in CH$_2$Cl$_2$ (200 ml) and dried with MgSO$_4$, and solvents were removed by distillation under a reduced pressure. The crude product thus obtained was separated by recrystallization to obtain 5.06 g (yield 90%) of Intermediate T. The molecular weight of Intermediate T measured by FAB-MS was 1,017.

(Synthesis of Compound 131)

Under an Ar atmosphere, in a 500 ml, three-neck flask, Intermediate T (5.00 g), Pd(OAc)$_2$ (0.11 g), K$_2$CO$_3$ (2.04 g), and PPh$_3$ (0.26 g) were dissolved in dehydrated dimethylacetamide (50 ml), followed by stirring at about 140° C. for about 1 hour. After decreasing the temperature to ambient temperature, the reaction solution was poured into 300 ml of water and stirred. The precipitate thus produced was isolated by suction filtration, dissolved in CH$_2$Cl$_2$ (200 ml) and dried with MgSO$_4$, and solvents were removed by distillation under a reduced pressure. The crude product thus obtained was separated by recrystallization to obtain 3.45 g (yield 82%) of Compound 131. The molecular weight of Compound 131 measured by FAB-MS was 855.

7. Synthesis of Compound 23

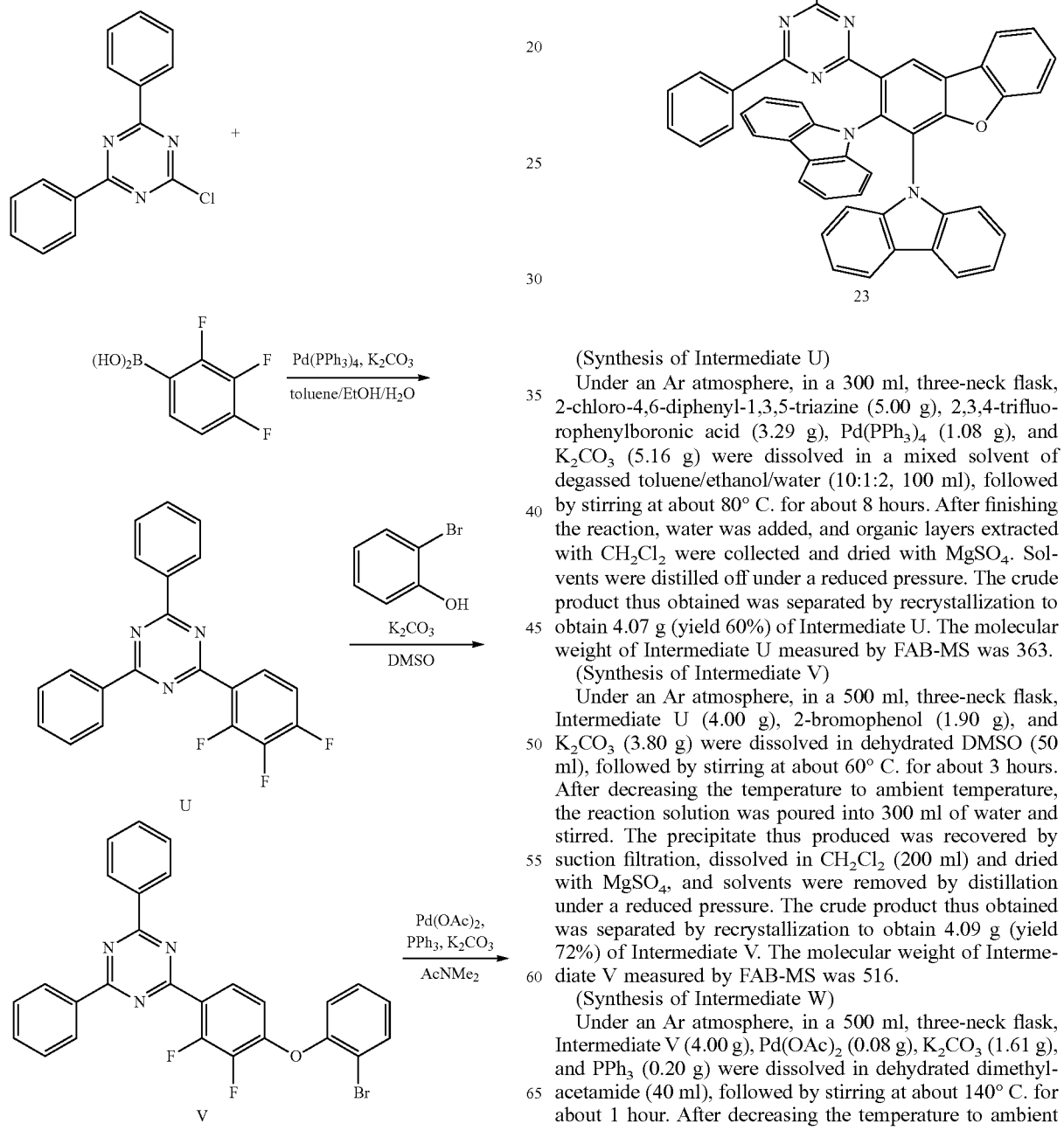

(Synthesis of Intermediate U)

Under an Ar atmosphere, in a 300 ml, three-neck flask, 2-chloro-4,6-diphenyl-1,3,5-triazine (5.00 g), 2,3,4-trifluorophenylboronic acid (3.29 g), Pd(PPh$_3$)$_4$ (1.08 g), and K$_2$CO$_3$ (5.16 g) were dissolved in a mixed solvent of degassed toluene/ethanol/water (10:1:2, 100 ml), followed by stirring at about 80° C. for about 8 hours. After finishing the reaction, water was added, and organic layers extracted with CH$_2$Cl$_2$ were collected and dried with MgSO$_4$. Solvents were distilled off under a reduced pressure. The crude product thus obtained was separated by recrystallization to obtain 4.07 g (yield 60%) of Intermediate U. The molecular weight of Intermediate U measured by FAB-MS was 363.

(Synthesis of Intermediate V)

Under an Ar atmosphere, in a 500 ml, three-neck flask, Intermediate U (4.00 g), 2-bromophenol (1.90 g), and K$_2$CO$_3$ (3.80 g) were dissolved in dehydrated DMSO (50 ml), followed by stirring at about 60° C. for about 3 hours. After decreasing the temperature to ambient temperature, the reaction solution was poured into 300 ml of water and stirred. The precipitate thus produced was recovered by suction filtration, dissolved in CH$_2$Cl$_2$ (200 ml) and dried with MgSO$_4$, and solvents were removed by distillation under a reduced pressure. The crude product thus obtained was separated by recrystallization to obtain 4.09 g (yield 72%) of Intermediate V. The molecular weight of Intermediate V measured by FAB-MS was 516.

(Synthesis of Intermediate W)

Under an Ar atmosphere, in a 500 ml, three-neck flask, Intermediate V (4.00 g), Pd(OAc)$_2$ (0.08 g), K$_2$CO$_3$ (1.61 g), and PPh$_3$ (0.20 g) were dissolved in dehydrated dimethylacetamide (40 ml), followed by stirring at about 140° C. for about 1 hour. After decreasing the temperature to ambient temperature, the reaction solution was poured into 300 ml of water and stirred. The precipitate thus produced was recovered by suction filtration, dissolved in $CH_2Cl_2$ (200 ml) and dried with $MgSO_4$, and solvents were removed by distillation under a reduced pressure. The crude product thus obtained was separated by recrystallization to obtain 2.36 g (yield 70%) of Intermediate W. The molecular weight of Intermediate W measured by FAB-MS was 435.

(Synthesis of Compound 23)

Under an Ar atmosphere, in a 300 ml, three-neck flask, Intermediate W (2.00 g), carbazole (1.54 g), and $K_2CO_3$ (3.17 g) were dissolved in dehydrated DMSO (30 ml), followed by stirring at about 180° C. for about 8 hours. After decreasing the temperature to ambient temperature, the reaction solution was poured into 300 ml of water and stirred. The precipitate thus produced was recovered by suction filtration, dissolved in $CH_2Cl_2$ (200 ml) and dried with $MgSO_4$, and solvents were removed by distillation under a reduced pressure. The crude product thus obtained was separated by recrystallization to obtain 1.94 g (yield 58%) of Compound 23. The molecular weight of Compound 23 measured by FAB-MS was 729.

8. Synthesis of Compound 29

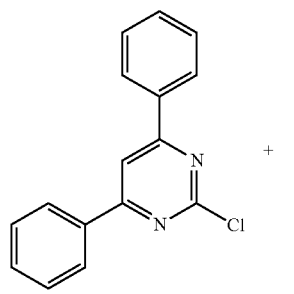

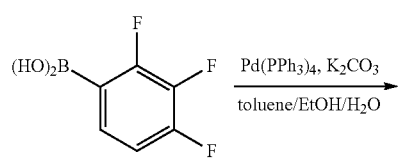

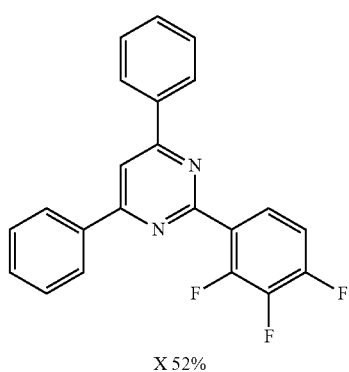

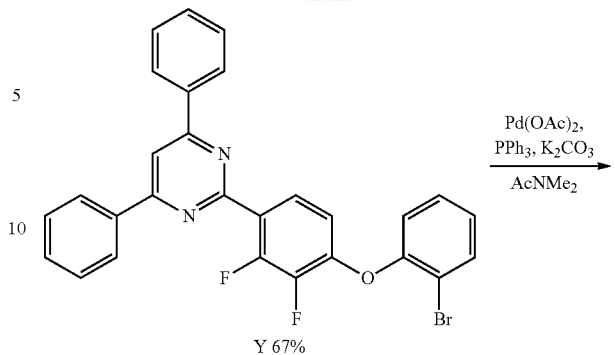

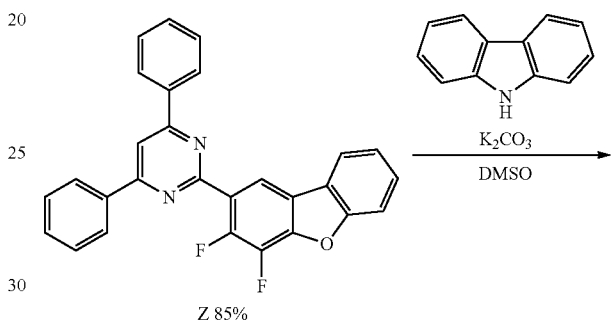

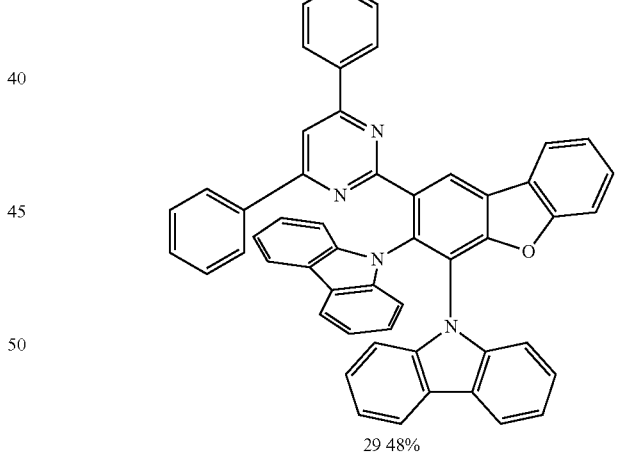

Compound 29 was synthesized by conducting the same procedure for synthesizing Compound 23 except for using 2-chloro-4,6-diphenylpyrimidine instead of 2-chloro-4,6-diphenyl-1,3,5-triazine.

Device Manufacturing Examples

Organic electroluminescence devices of Examples 1 to 4 were manufactured using Compounds 1, 24, 107 and 109 as dopant materials for an emission layer.

Example Compounds
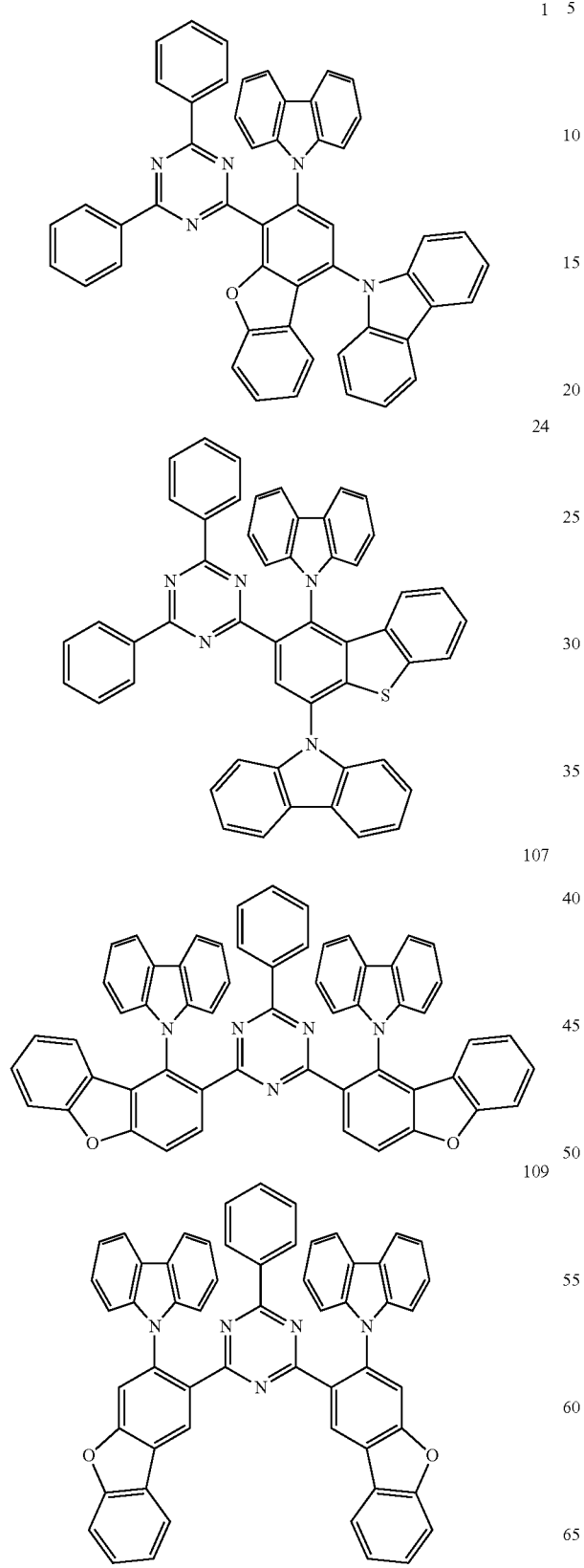
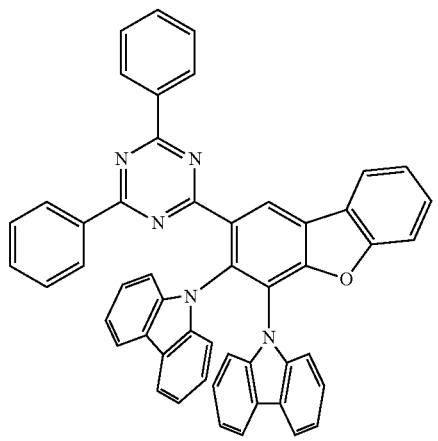
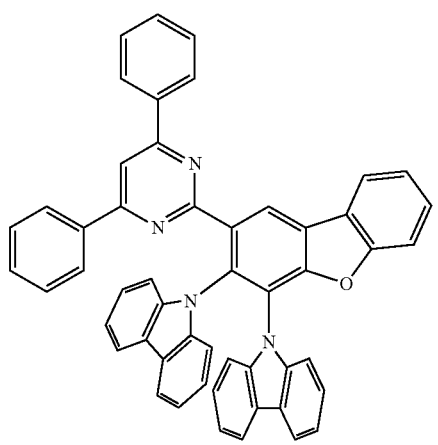
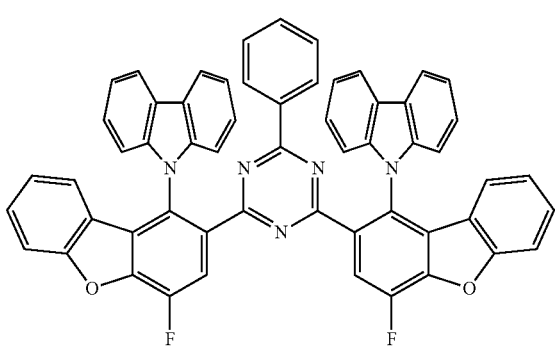

133

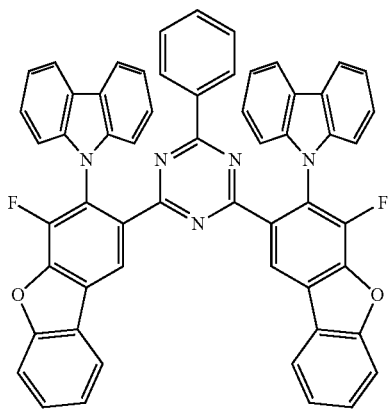

X-3

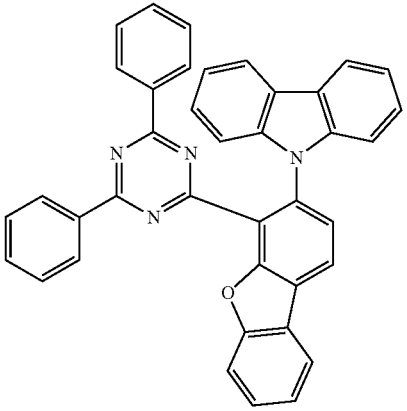

Using Compounds X-1 to X-3 below as dopant materials for an emission layer, organic electroluminescence devices of Comparative Examples 1 to 3 were manufactured.

[Comparative Compounds]

X-1

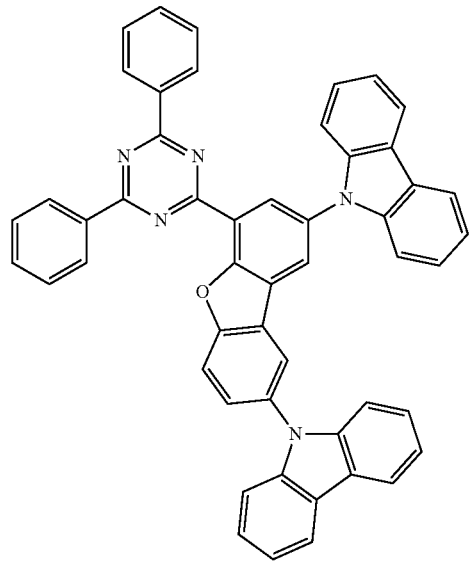

X-2

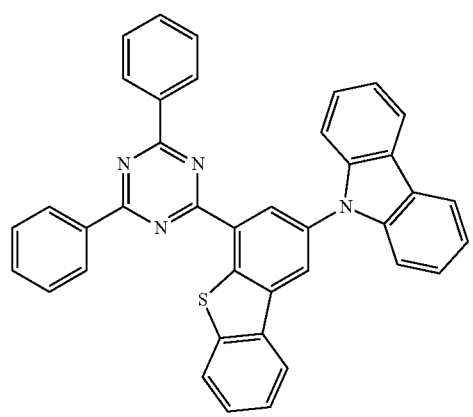

S1 level and T1 level of the Example Compounds and the Comparative Compounds were calculated by a non-empirical molecular orbital method. Particularly, the calculation was conducted using B3LYP as a functional, and 6-31G(d) as a basis function by using Gaussian09 of Gaussian Co. The results are shown in Table 1 below. $\Delta E_{ST}$ represents the difference between a singlet energy level and a triplet energy level.

TABLE 1

|  | S1 energy level (eV) | T1 energy level (eV) | $\Delta E_{ST}$ |
|---|---|---|---|
| Example Compound 1 | 2.84 | 2.75 | 0.11 |
| Example Compound 24 | 2.97 | 2.87 | 0.10 |
| Example Compound 107 | 2.97 | 2.90 | 0.07 |
| Example Compound 109 | 2.96 | 2.87 | 0.09 |
| Example Compound 23 | 2.91 | 2.81 | 0.10 |
| Example Compound 29 | 3.01 | 2.90 | 0.11 |
| Example Compound 131 | 2.92 | 2.85 | 0.07 |
| Example Compound 133 | 2.89 | 2.81 | 0.08 |
| Comparative Compound X-1 | 2.76 | 2.58 | 0.18 |
| Comparative Compound X-2 | 2.75 | 2.56 | 0.19 |
| Comparative Compound X-3 | 2.89 | 2.74 | 0.15 |

Referring to the results of Table 1, all Example Compounds exhibited low $\Delta E_{ST}$ values and are thought to be appropriately used as materials for thermally activated delayed fluorescence. The Comparative Compounds exhibited relatively high $\Delta E_{ST}$ values, and are not thought to be appropriately used as materials for thermally activated delayed fluorescence.

Each of the organic electroluminescence devices of Examples 1 to 8 and Comparative Examples 1 to 3 was manufactured by forming a first electrode using ITO to a thickness of about 150 nm, a hole injection layer using HAT-CN to a thickness of about 10 nm, a hole transport layer using NPB to a thickness of about 80 nm, an electron blocking layer using mCP to a thickness of about 5 nm, an emission layer using DPEPO doped with 18% of the Example Compound or the Comparative Compound to a thickness of about 20 nm, a hole blocking layer using DPEPO to a thickness of about 10 nm, an electron transport layer using TPBi to a thickness of about 30 nm, an electron injection layer using LiF to a thickness of about 0.5 nm, and a second electrode using Al to a thickness of about 100 nm. Each layer was formed by a deposition method in vacuum.

The maximum emission wavelength (e.g., wavelength of maximum emission) and external quantum efficiency of each of the organic electroluminescence devices according to Examples 1 to 8 and Comparative Examples 1 to 3 were measured and are shown in Table 2 below. EQE in Table 2 means values at about 10 mA/cm². For the evaluation of the emission properties of the organic electroluminescence devices thus manufactured, a luminous brightness measurement apparatus, C9920-11 of HAMAMATSU Photonics Co. was used.

TABLE 2

| | Emission layer dopant material | $\lambda_{max}$ (nm) | EQE (%) |
|---|---|---|---|
| Example 1 | Example Compound 1 | 470 | 9 |
| Example 2 | Example Compound 24 | 463 | 11 |
| Example 3 | Example Compound 107 | 459 | 14 |
| Example 4 | Example Compound 109 | 461 | 13 |
| Example 5 | Example Compound 23 | 460 | 13 |
| Example 6 | Example Compound 29 | 452 | 10 |
| Example 7 | Example Compound 131 | 464 | 15 |
| Example 8 | Example Compound 133 | 462 | 14 |
| Comparative Example 1 | Comparative Compound X-1 | 474 | 5 |
| Comparative Example 2 | Comparative Compound X-2 | 472 | 2 |
| Comparative Example 3 | Comparative Compound X-3 | 466 | 3 |

Referring to the results of Table 2, Examples 1 to 8 exhibited increased efficiency when compared with Comparative Examples 1 to 3. These results were thought to be obtained because an azine group functioned an electron acceptor and a carbazole group functioned an electron donor in the example compounds, and the Example Compounds showed the properties of a material for thermally activated delayed fluorescence. Further, the azine group and the carbazole group were bonded in an ortho relationship, and the electron acceptor and the electron donor were twisted, HOMO and LUMO were efficiently separated, and the properties of a material for thermally activated delayed fluorescence were shown.

Meanwhile, in Comparative Example 1, since an azine group and a carbazolyl group were not bonded in ortho relationship, the donor and the acceptor were insufficiently twisted, and TADF was not shown. In Comparative Examples 2 and 3, $\Delta E_{ST}$ values were relatively large and only one carbazole group was included. Thus, the function of an electron donor was weak, reverse intersystem crossing was insufficiently arisen, and the properties as a material for thermally activated delayed fluorescence were now exhibited.

The heterocyclic compound according to an embodiment may be utilized as a dopant of thermally activated delayed fluorescence for emitting deep blue color.

The organic electroluminescence device including the heterocyclic compound according to an embodiment may facilitate emission of deep blue color and may have excellent efficiency at the same time.

The organic electroluminescence device according to an embodiment may have excellent efficiency.

The heterocyclic compound according to an embodiment may be applied to an organic electroluminescence device and may contribute to high efficiency.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic electroluminescence device, comprising:
a first electrode;
a hole transport region on the first electrode;
an emission layer on the hole transport region;
an electron transport region on the emission layer; and
a second electrode on the electron transport region,
wherein:
the emission layer includes a heterocyclic compound that includes a nitrogen-containing monocycle, at least one linker, and two or more carbazole moieties,
the at least one linker is a substituted or unsubstituted dibenzofuran group or a substituted or unsubstituted dibenzothiophene group,
at least one of the carbazole moieties and the nitrogen-containing monocycle are bonded to the at least one linker in an ortho relationship to one of the six-membered rings of the dibenzofuran group of the substituted or unsubstituted dibenzofuran group or the dibenzothiophene group of the substituted or unsubstituted dibenzothiophene group, and
the other of the six-membered rings of the dibenzofuran group of the substituted or unsubstituted dibenzofuran group or the dibenzothiophene group of the substituted or unsubstituted dibenzothiophene group is not substituted with a heteroaryl group.

2. The organic electroluminescence device as claimed in claim 1, wherein the nitrogen-containing monocycle is a substituted or unsubstituted pyridine group, a substituted or unsubstituted pyrimidine group, or a substituted or unsubstituted triazine group.

3. The organic electroluminescence device as claimed in claim 1, wherein the heterocyclic compound includes one or two linkers.

4. The organic electroluminescence device as claimed in claim 1, wherein the nitrogen-containing monocycle is substituted with at least one substituted or unsubstituted phenyl group.

5. The organic electroluminescence device as claimed in claim 1, wherein:
the emission layer includes a host and a dopant, and
the dopant includes the heterocyclic compound.

6. The organic electroluminescence device as claimed in claim 5, wherein the dopant is a thermally activated delayed fluorescence dopant.

7. The organic electroluminescence device as claimed in claim 1, wherein the heterocyclic compound is represented by the following Formula 1:

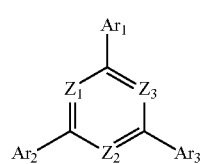

[Formula 1]

in Formula 1,
$Z_1$ to $Z_3$ are each independently $CR_1$ or N,
at least one of $Z_1$ to $Z_3$ is N, R₁ is a hydrogen atom, a deuterium atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, Ar₁ to Ar₃ are each independently a group represented by the following Formula 2, a substituted or unsubstituted aryl group having 6 to 30 ring carbon atoms, or a substituted or unsubstituted heteroaryl group having 2 to 30 ring carbon atoms, and at least one of Ar₁ to Ar₃ is a group represented by Formula 2:

[Formula 2]

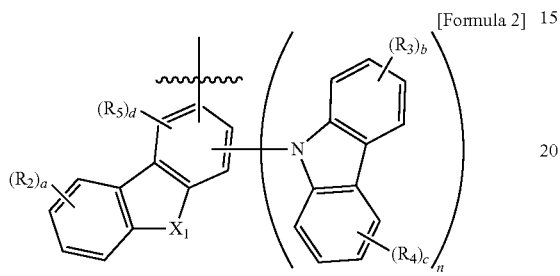

in Formula 2,

X₁ is O or S,

"n" is an integer of 1 to 3,

"a" to "c" are each independently an integer of 0 to 4,

"d" is an integer of 0 to 2, and

R₂ is a hydrogen atom, a deuterium atom, a halogen atom, a substituted or unsubstituted alkyl group having 1 to 10 carbon atoms, or a substituted or unsubstituted aryl group having 6 to 30 ring carbon atoms, and R₃ to R₅ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms.

8. The organic electroluminescence device as claimed in claim 7, wherein each of Z₁ to Z₃ is N.

9. The organic electroluminescence device as claimed in claim 7, wherein the compound represented by Formula 1 is represented by the following Formula 1-1:

[Formula 1-1]

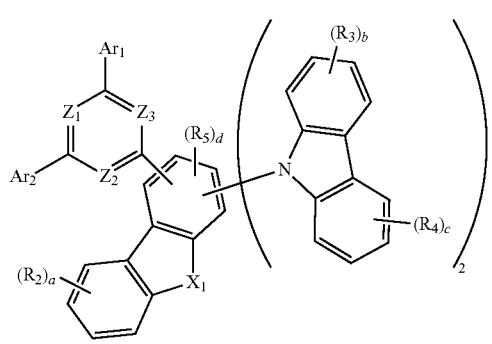

in Formula 1-1,

Z₁ to Z₃, Ar₁, Ar₂, R₂ to R₅, "a" to "c" and X₁ are defined the same as those of Formula 1 and Formula 2, and "d" is 0 or 1.

10. The organic electroluminescence device as claimed in claim 7, wherein the compound represented by Formula 1 is represented by the following Formula 1-2:

[Formula 1-2]

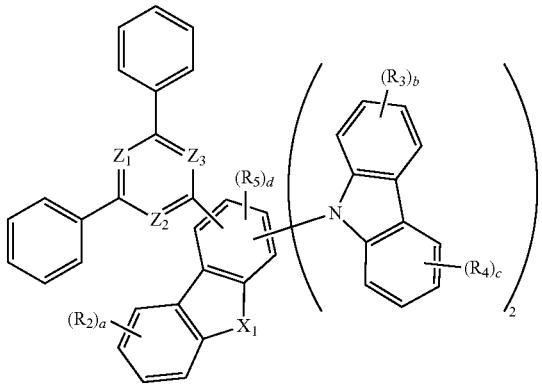

in Formula 1-2,

Z₁ to Z₃, R₂ to R₅, "a" to "c" and X₁ are defined the same as those of Formula 1 and Formula 2, and "d" is 0 or 1.

11. The organic electroluminescence device as claimed in claim 7, wherein the compound represented by Formula 1 is represented by the following Formula 1-3:

[Formula 1-3]

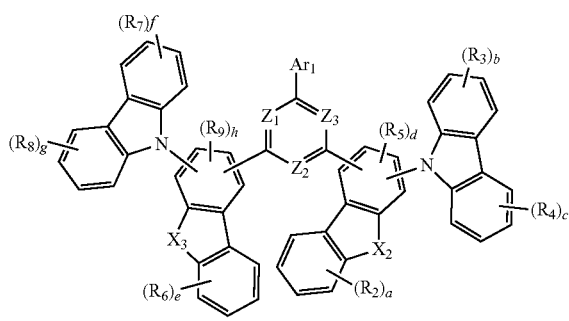

in Formula 1-3,

X₂ and X₃ are each independently O or S,

R₂ is a hydrogen atom, a deuterium atom, a halogen atom, a substituted or unsubstituted alkyl group having 1 to 10 carbon atoms, or a substituted or unsubstituted aryl group having 6 to 30 ring carbon atoms, R₃ to R₉ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, "a" to "c" and "e" to "g" are each independently an integer of 0 to 4, "d" and "h" are each independently an integer of 0 to 2, and Z₁ to Z₃, and Ar₁ are defined the same as those of Formula 1.

12. The organic electroluminescence device as claimed in claim 7, wherein the compound represented by Formula 1 is represented by the following Formula 1-4:

[Formula 1-4]

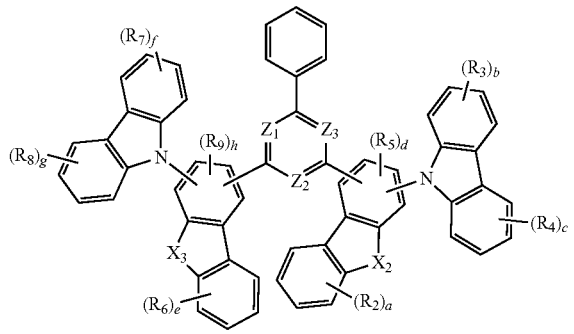

in Formula 1-4,

X$_2$ and X$_3$ are each independently O or S,

R$_2$ is a hydrogen atom, a deuterium atom, a halogen atom, a substituted or unsubstituted alkyl group having 1 to 10 carbon atoms, or a substituted or unsubstituted aryl group having 6 to 30 ring carbon atoms, R$_3$ to R$_9$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, "a" to "c" and "e" to "g" are each independently an integer of 0 to 4, "d" and "h" are each independently an integer of 0 to 2, and Z$_1$ to Z$_3$ are defined the same as those of Formula 1.

13. The organic electroluminescence device as claimed in claim 1, wherein the heterocyclic compound is a compound of the following Compound Group 1:

[Compound Group 1]

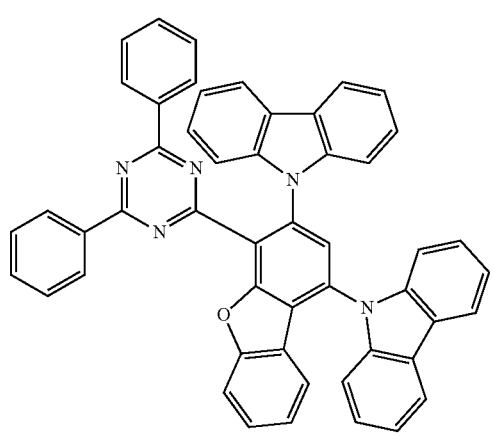

1

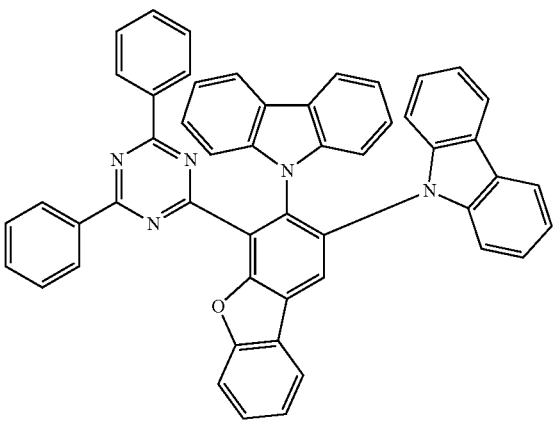

2

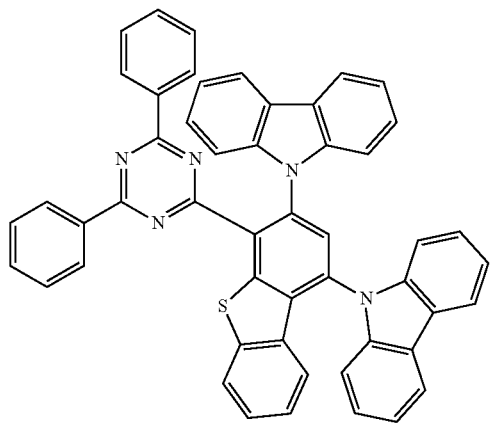

3

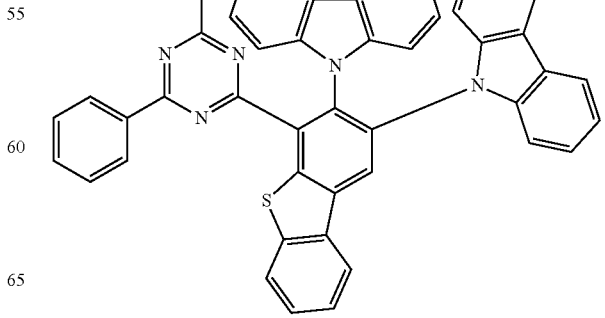

4

5
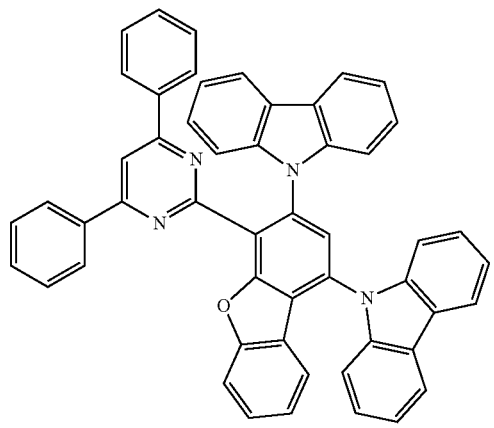
6
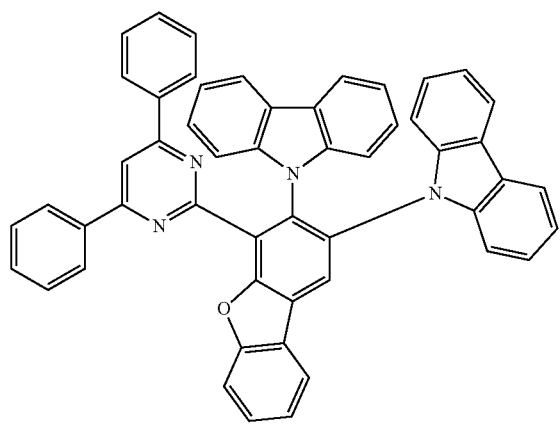
7
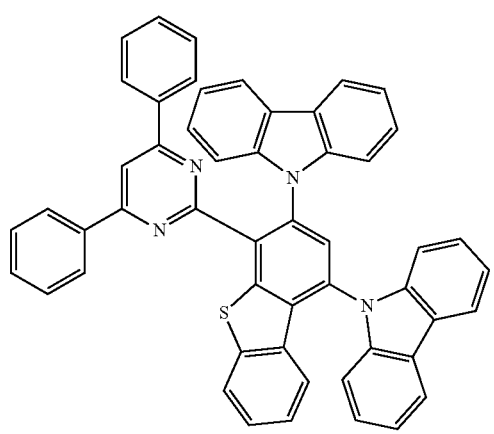
8
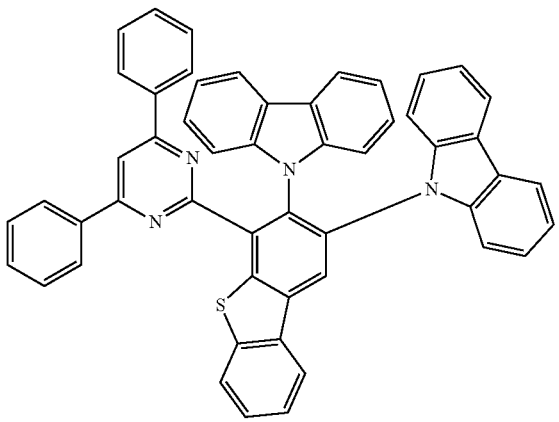
9
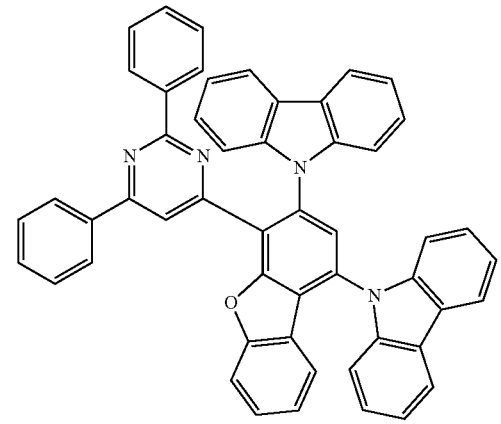
10
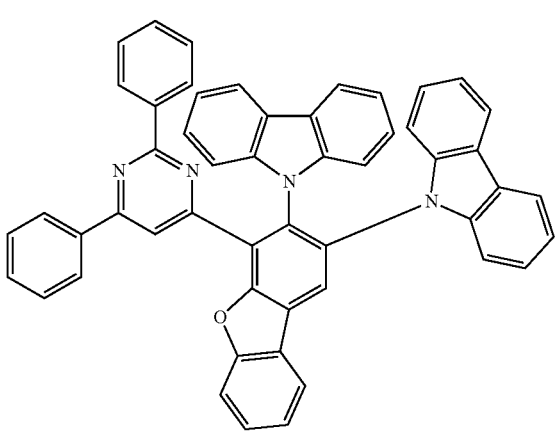

11
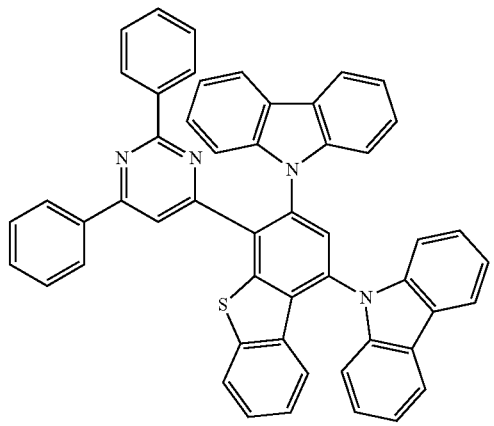
12
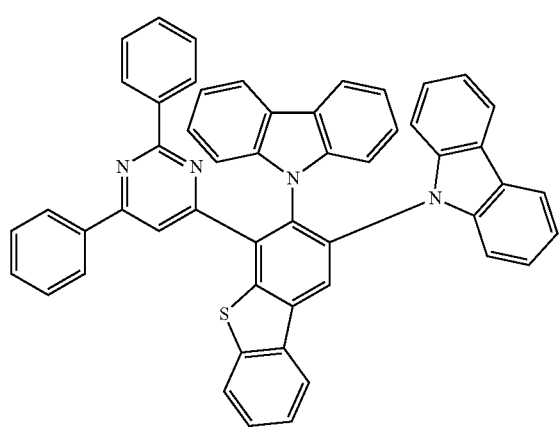
13
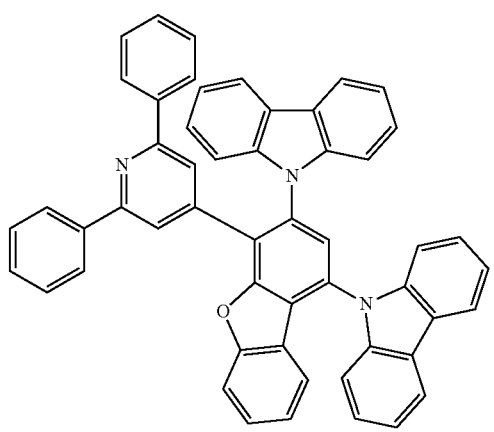
14
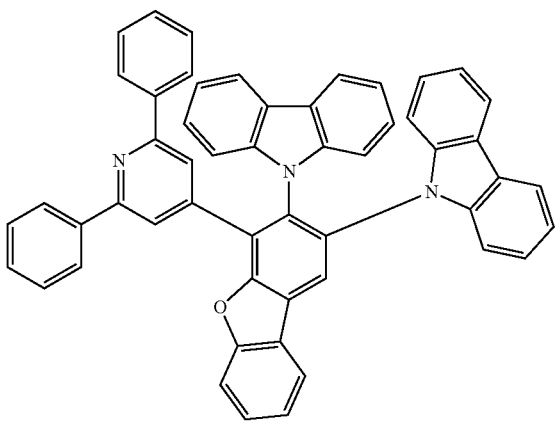
15
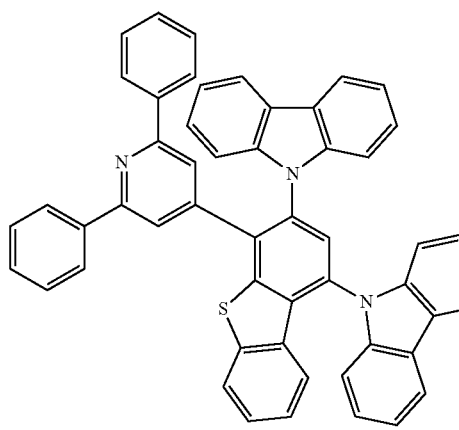
16
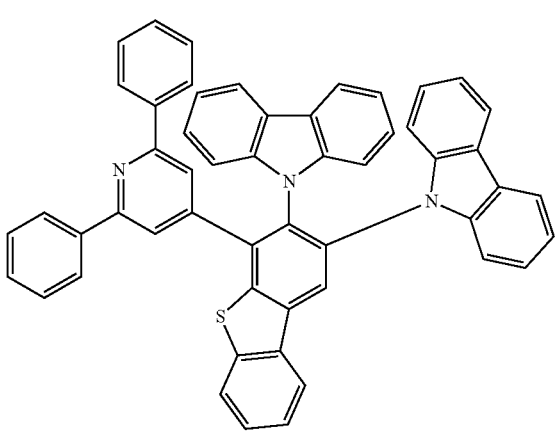

17
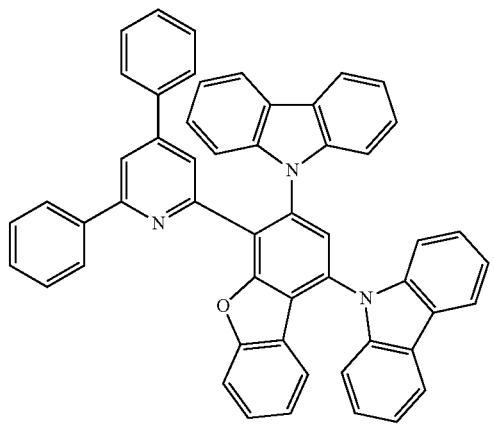
18
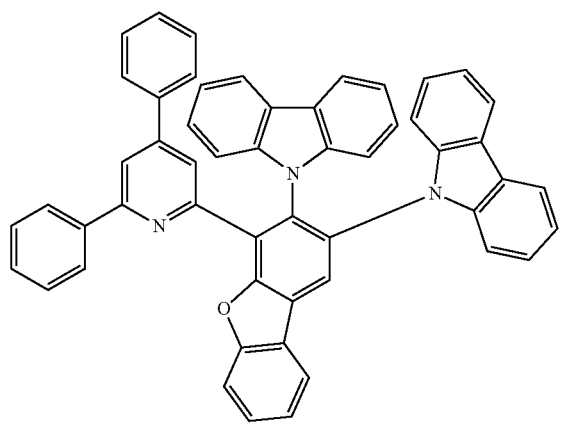
19
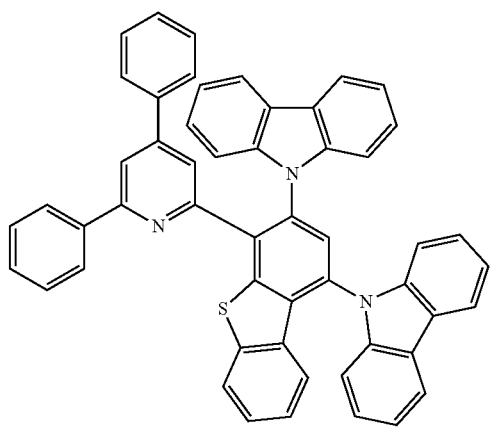
20
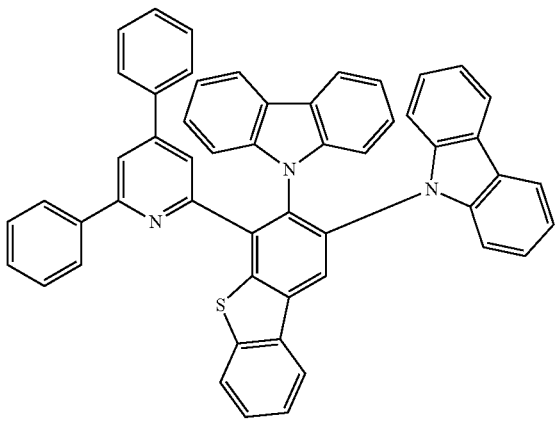
21
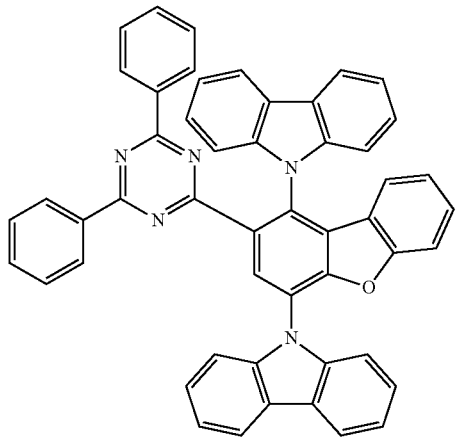
22
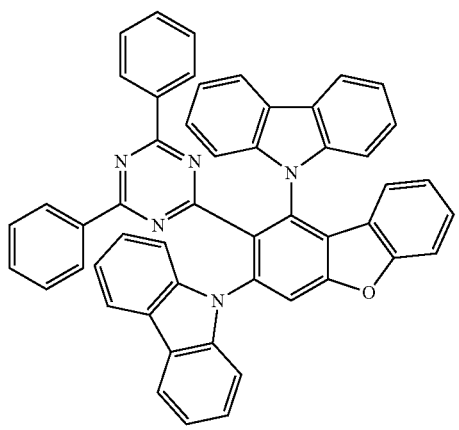

23
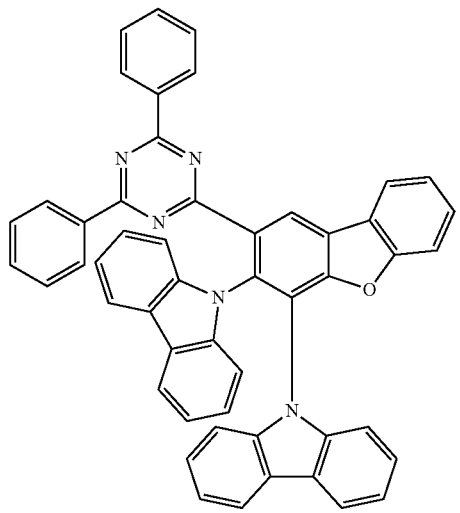
24
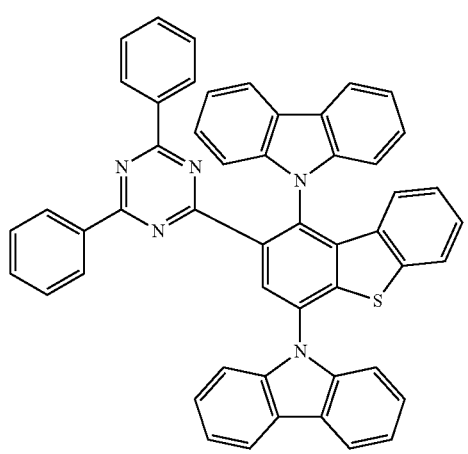
25
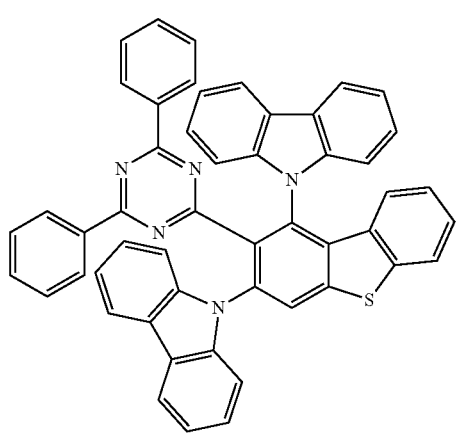
26
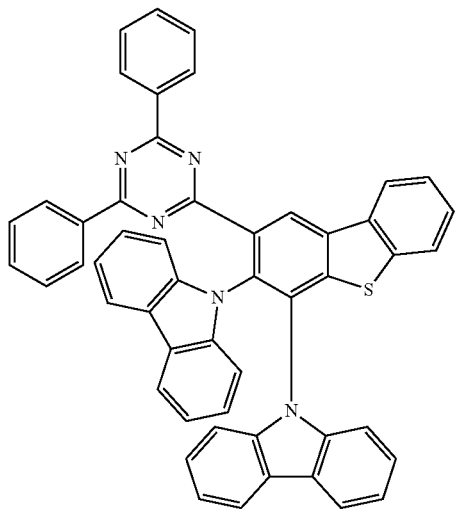
27
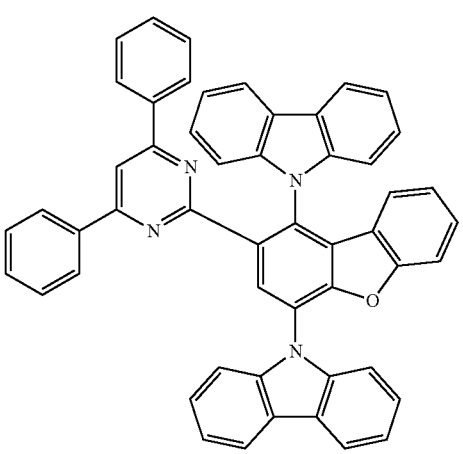
28
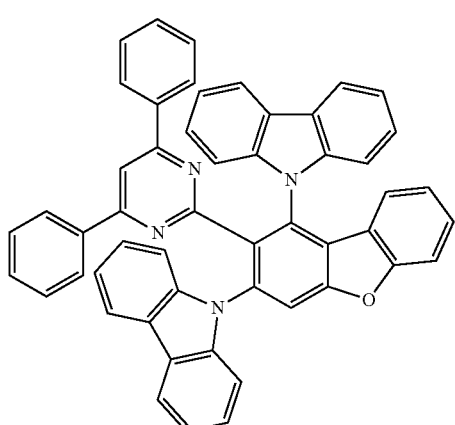

121
-continued
29
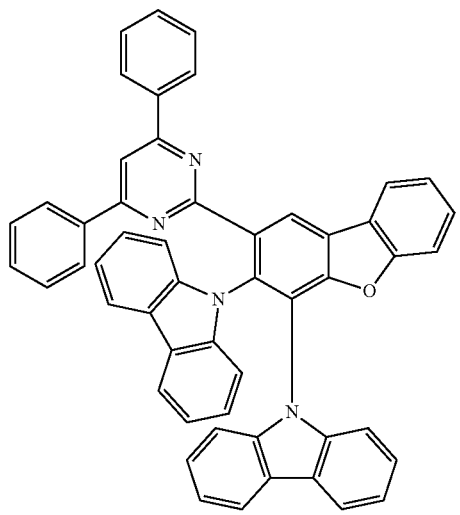
30
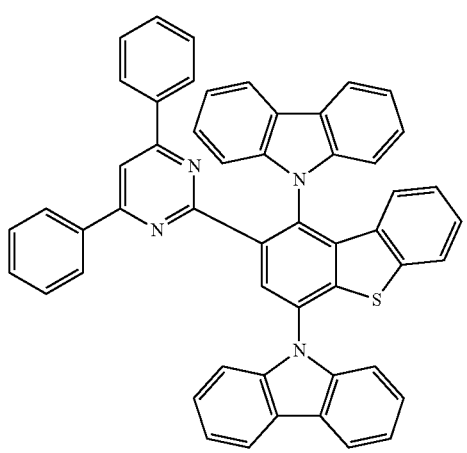
31
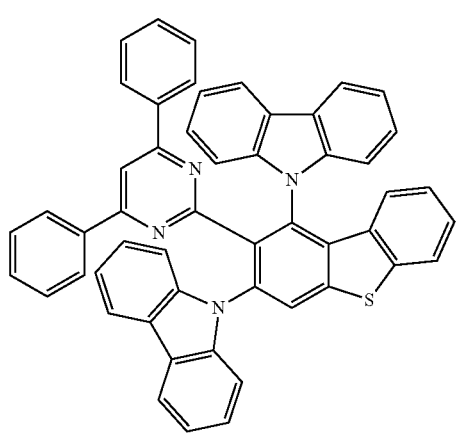
122
-continued
32
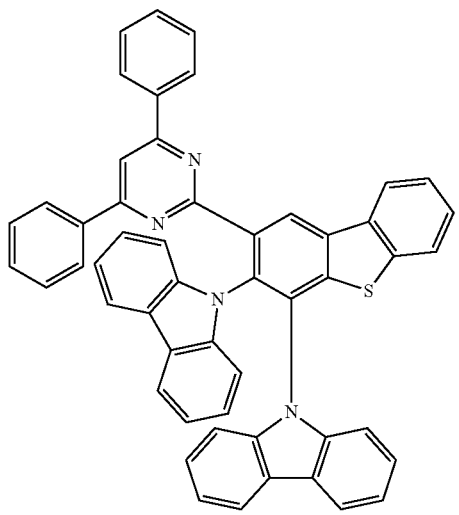
33
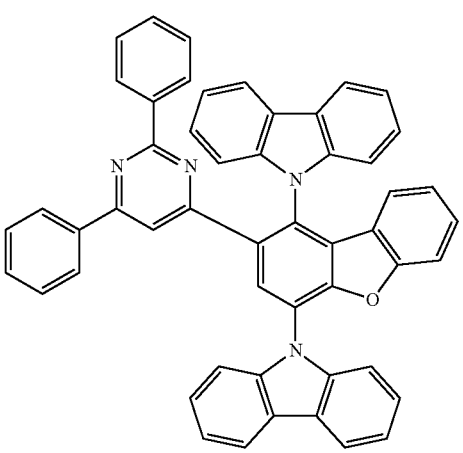
34
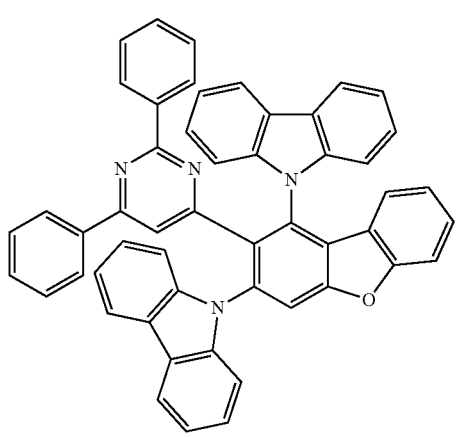

123
35
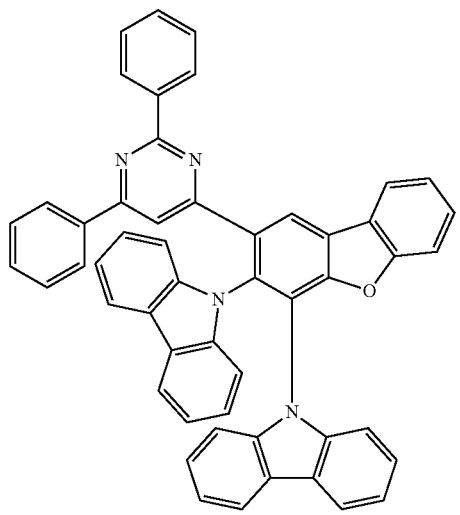
36
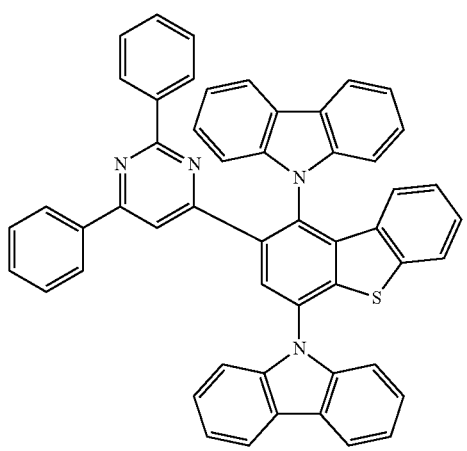
37
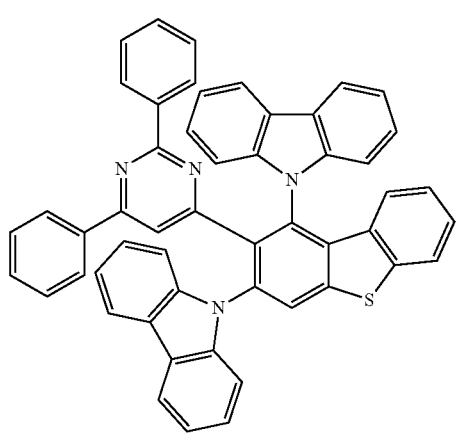
124
38
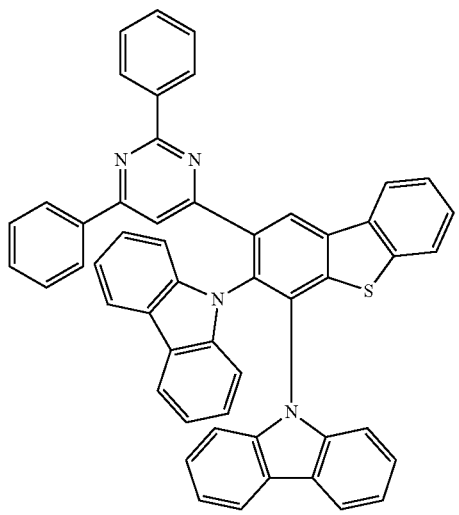
39
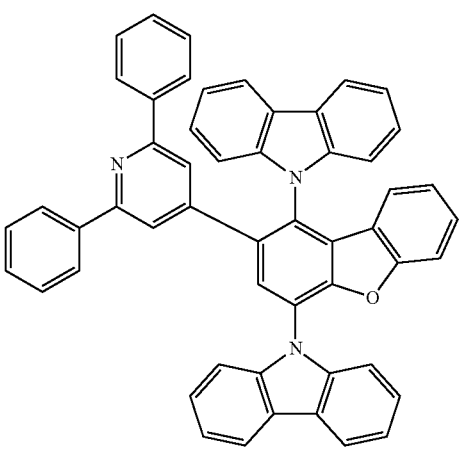
40
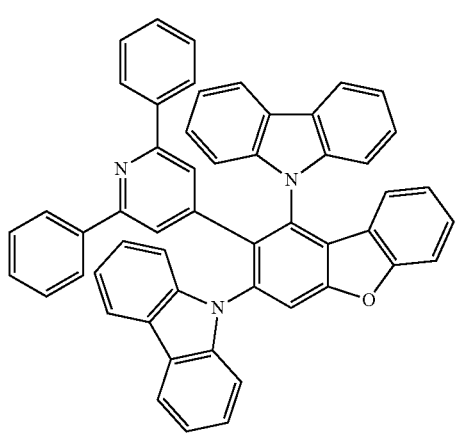

41
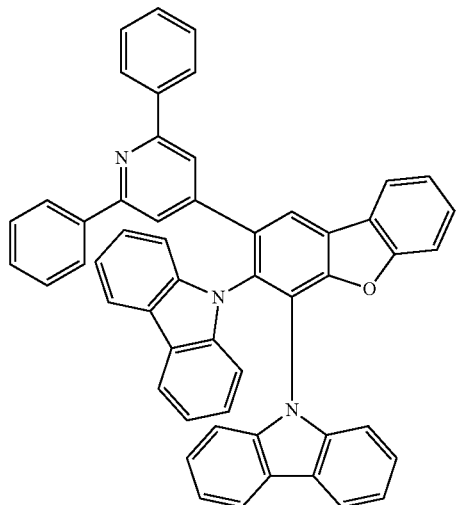
44
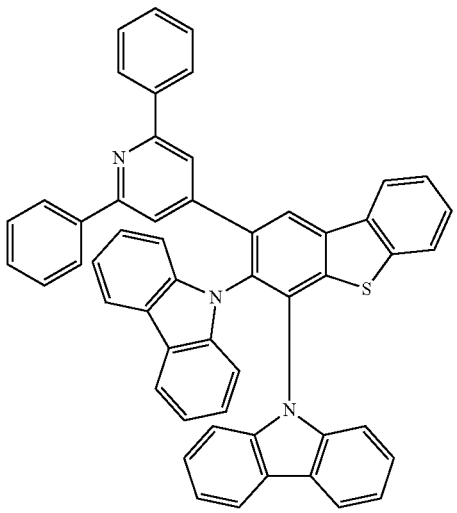
42
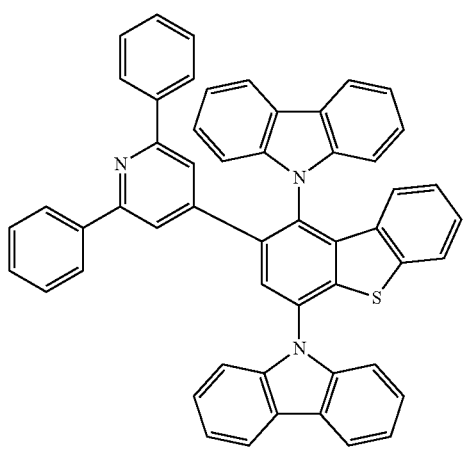
45
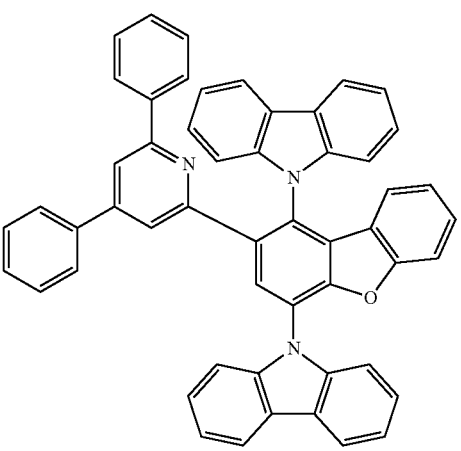
43
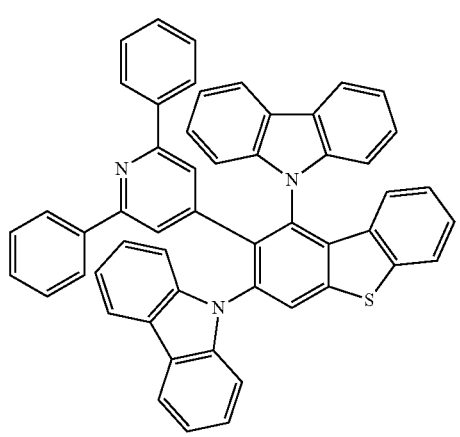
46
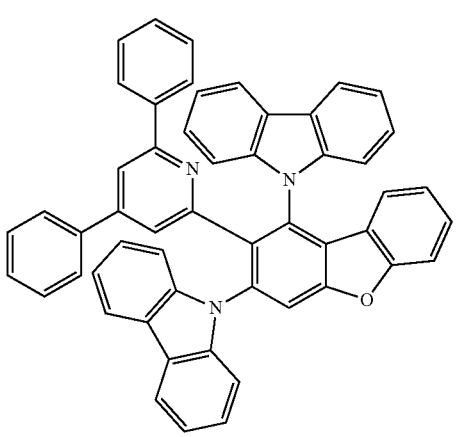

47
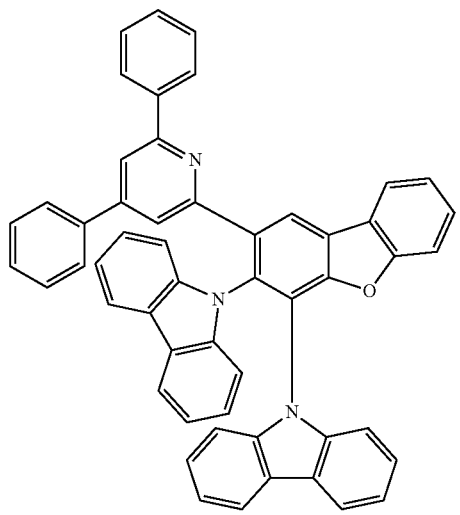
48
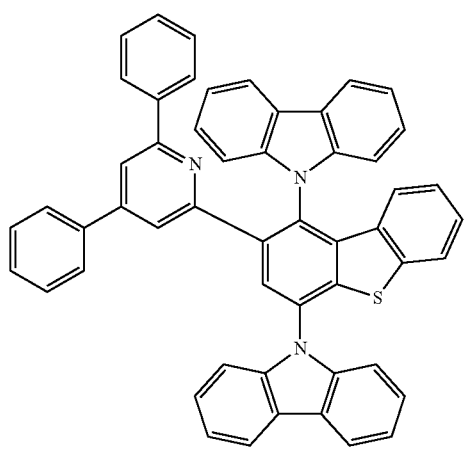
49
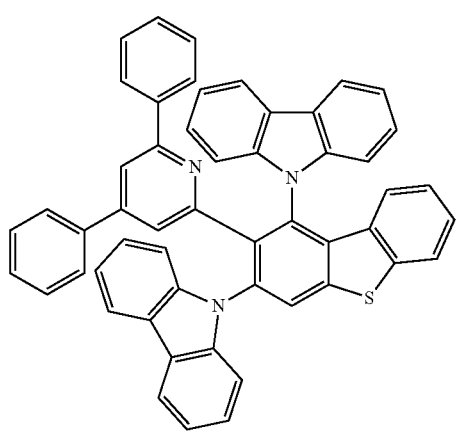
50
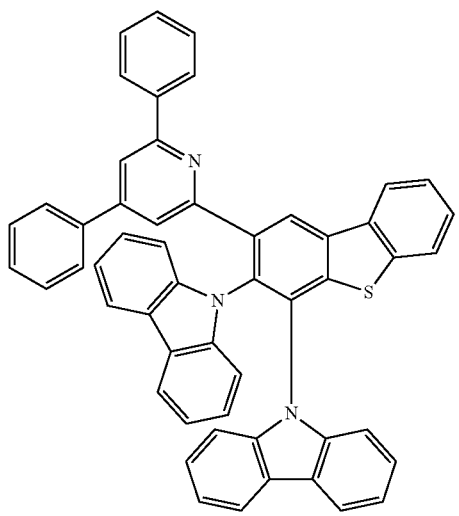
51
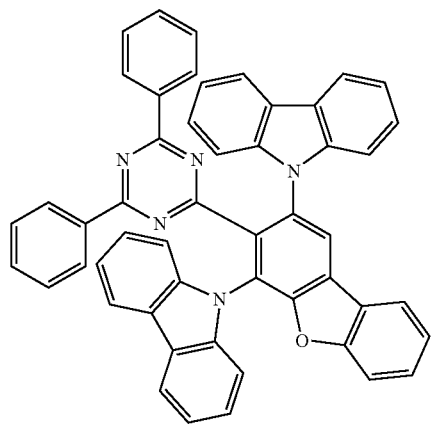
52
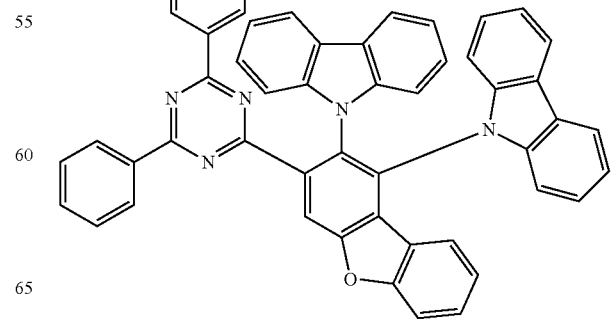

129
-continued
53
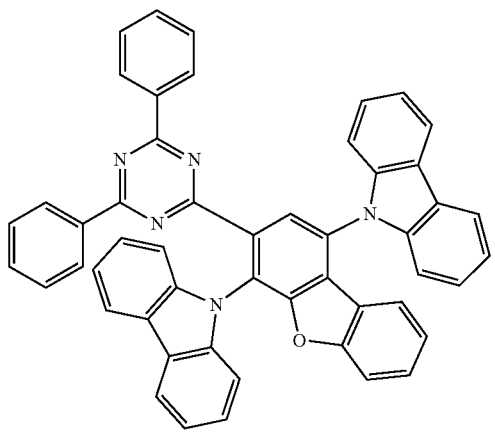
54
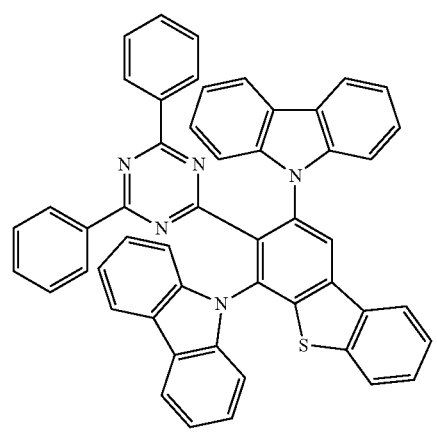
130
-continued
56
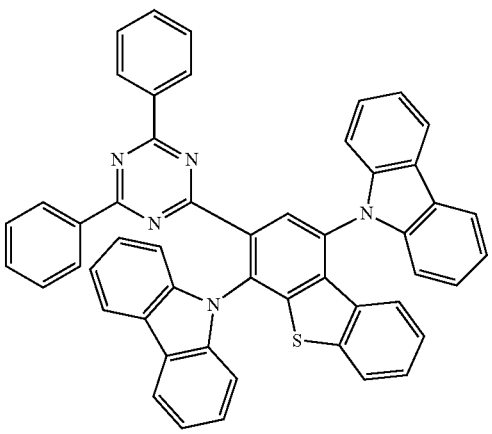
57
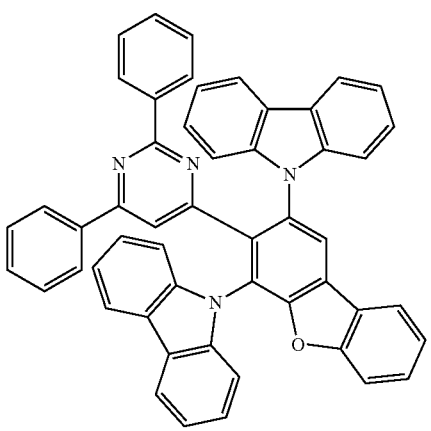
55
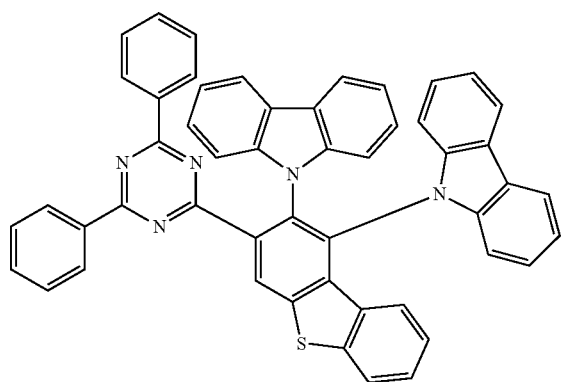
58
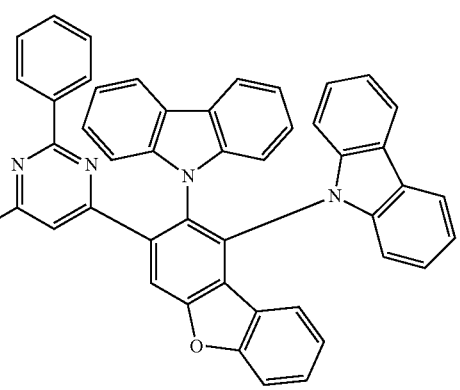

59
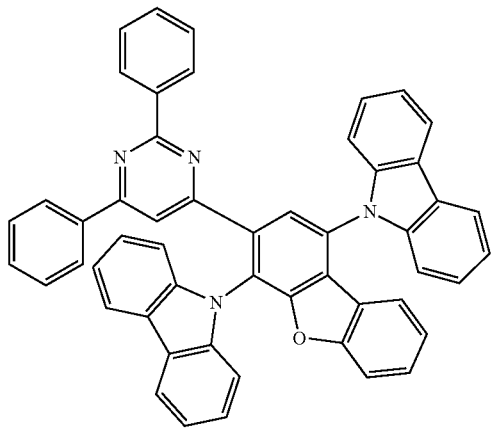
60
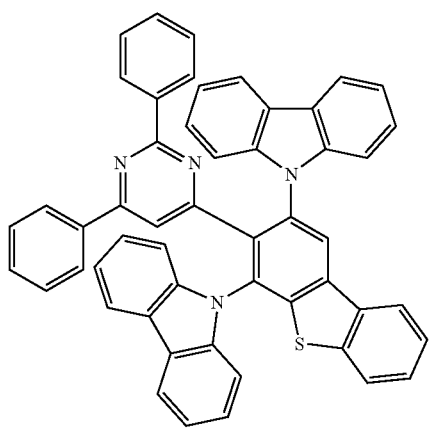
61
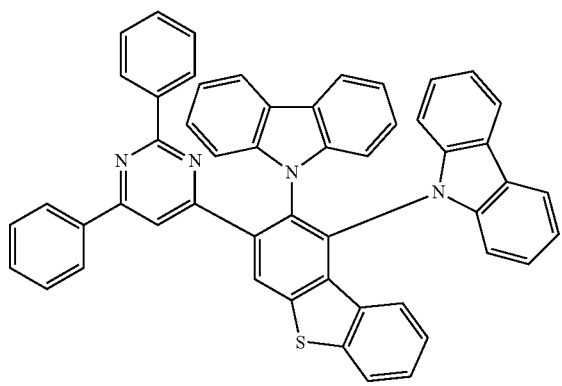
62
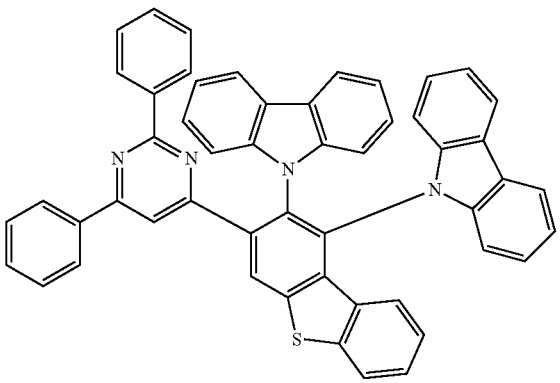
63
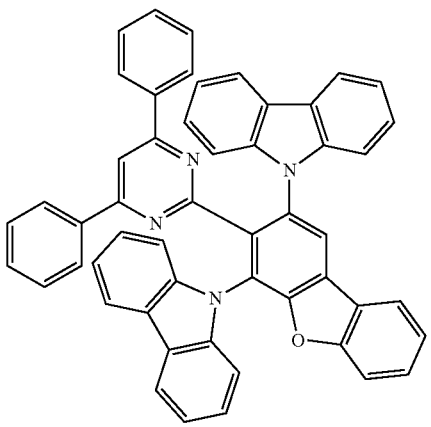
64
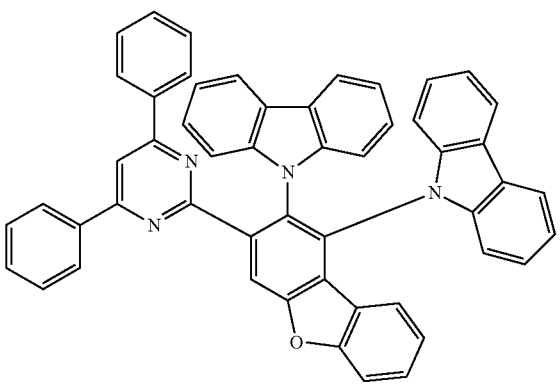

65
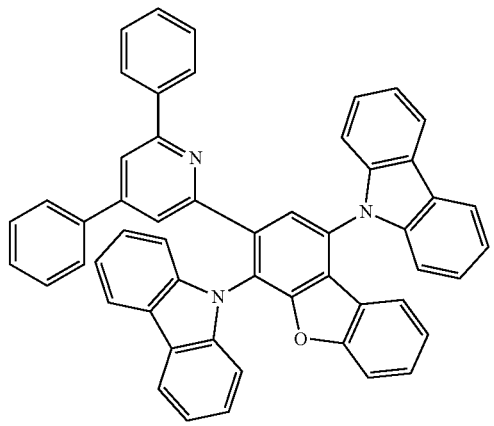
66
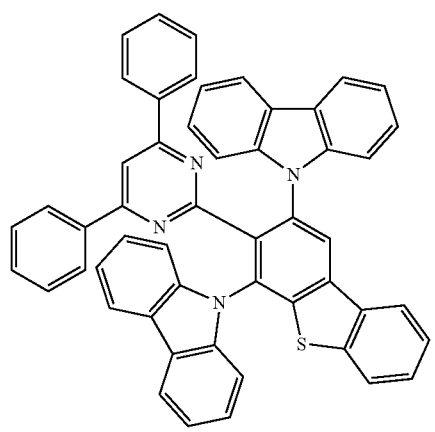
67
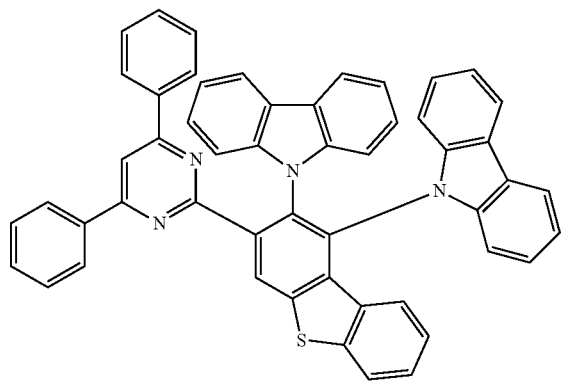
68
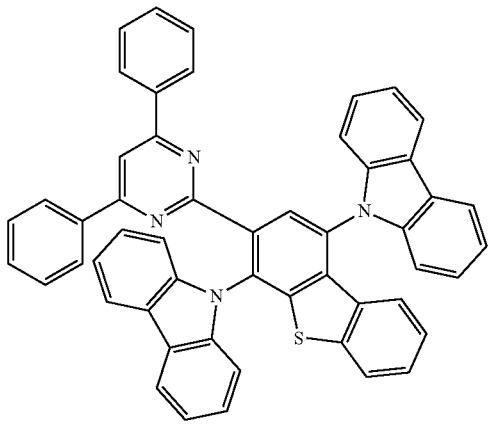
69
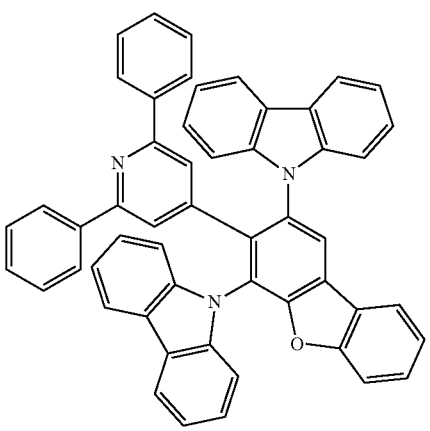
70
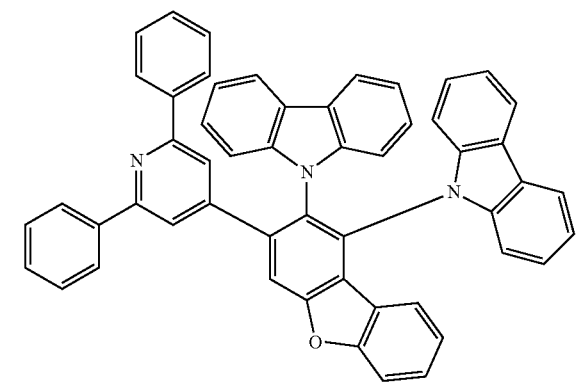

71
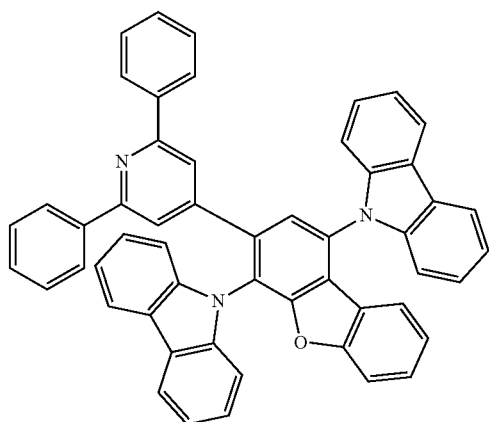
74
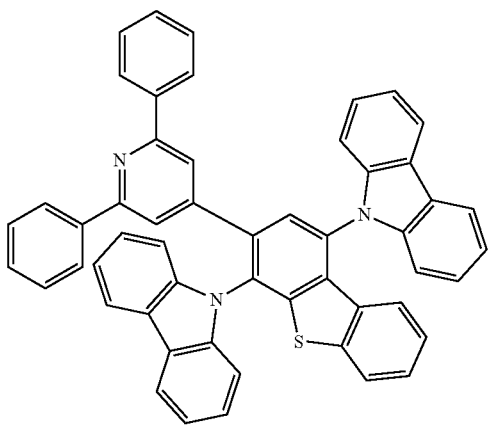
72
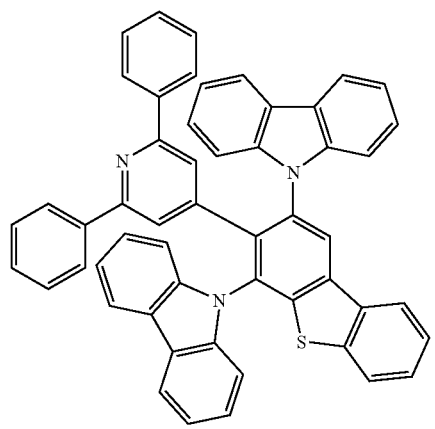
75
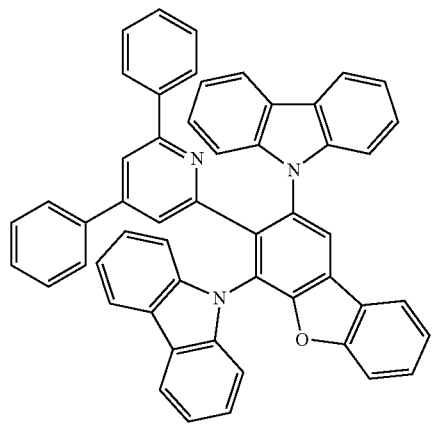
73
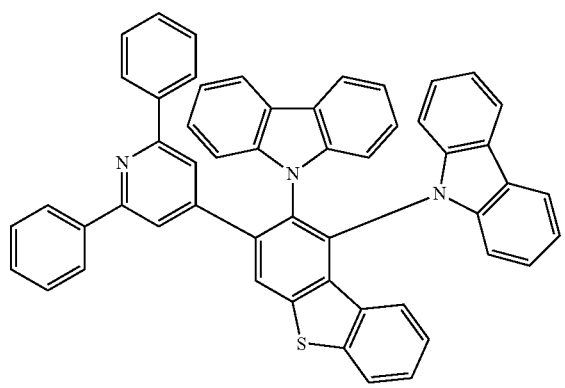
76
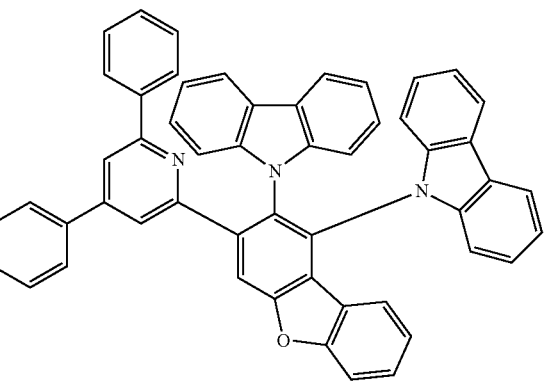

77
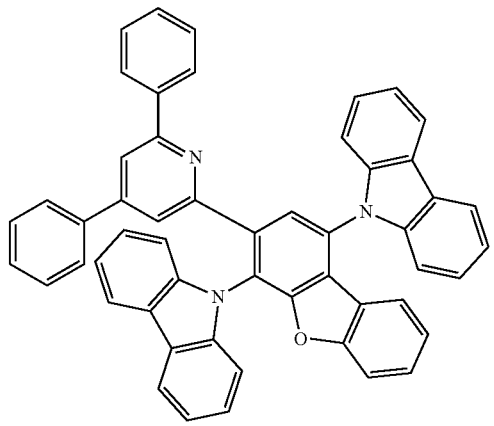
80
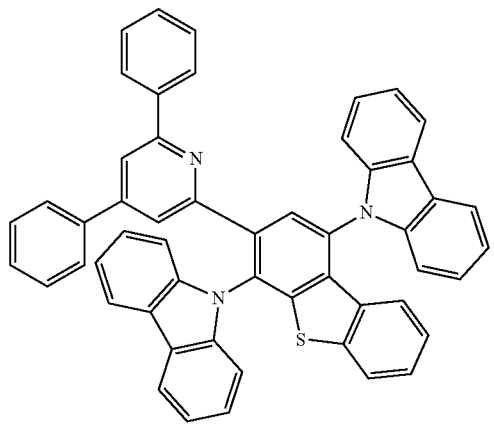
78
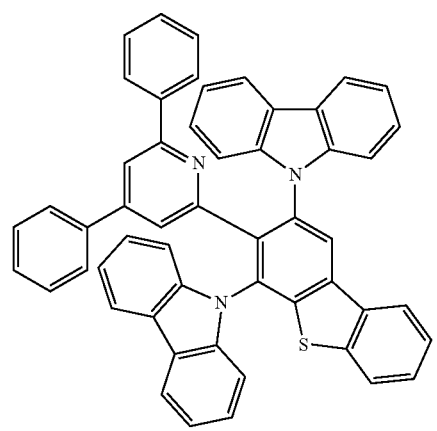
81
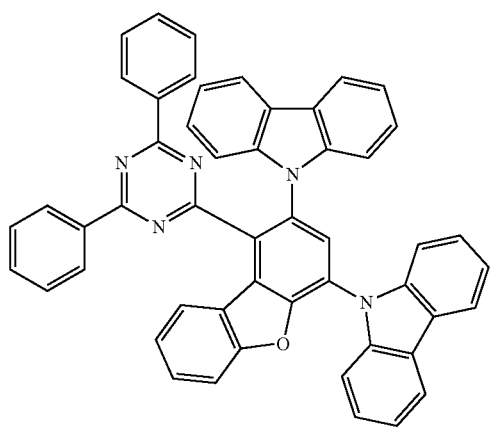
79
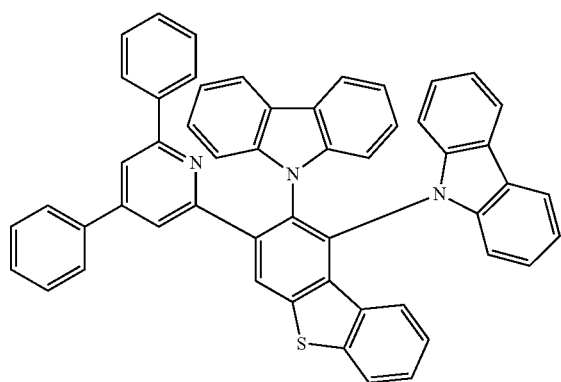
82
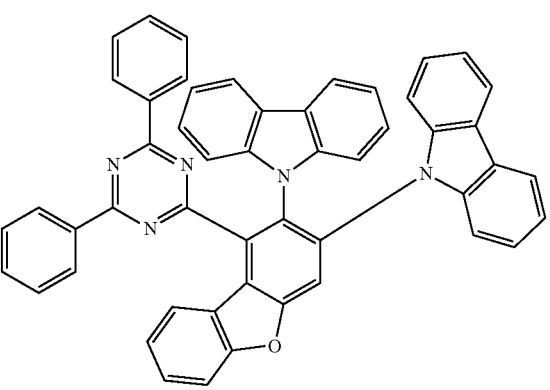

83
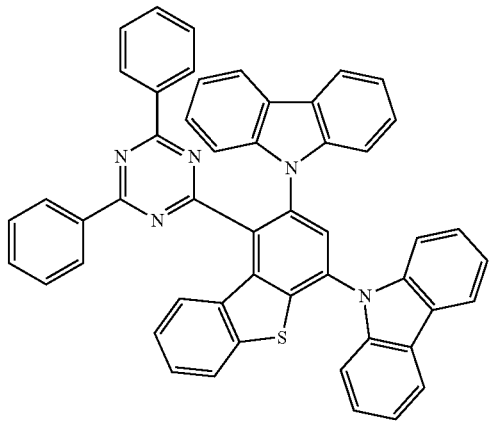
84
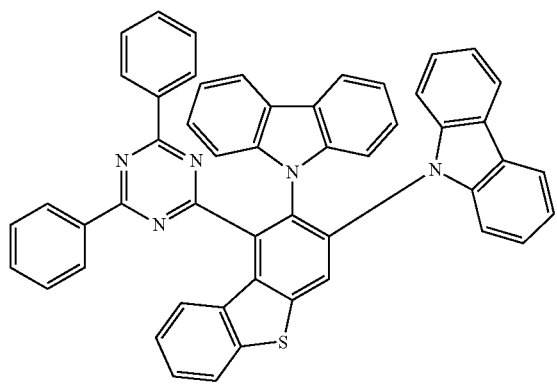
85
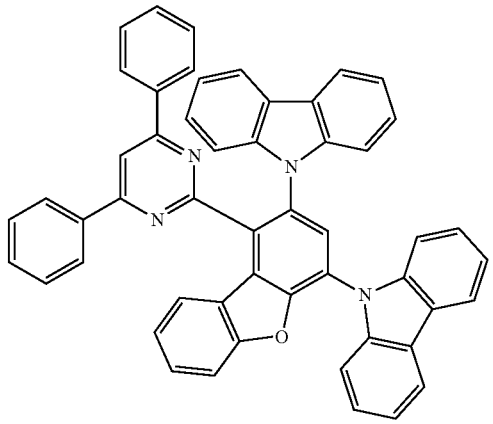
86
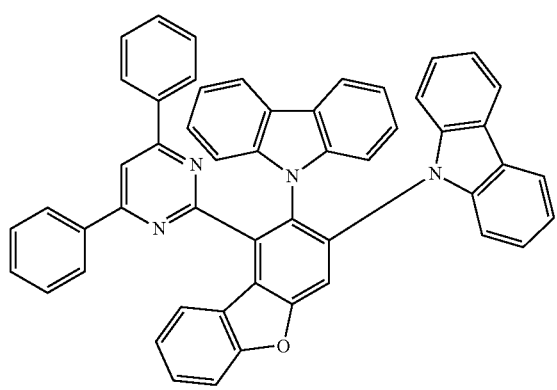
87
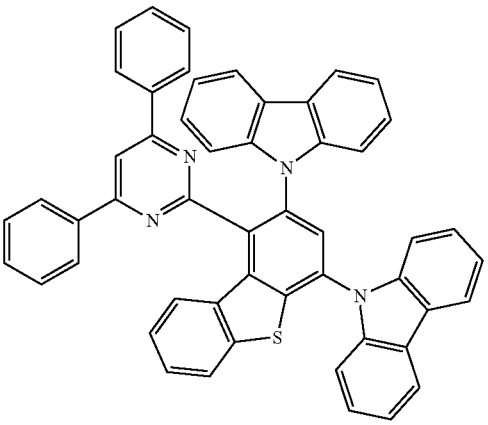
88
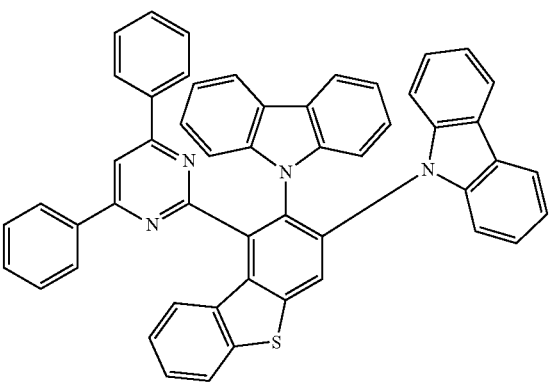
89
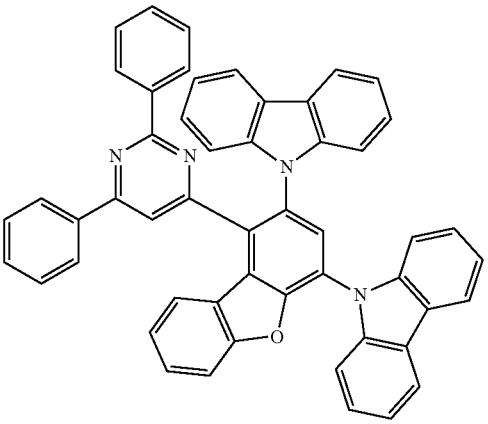
90
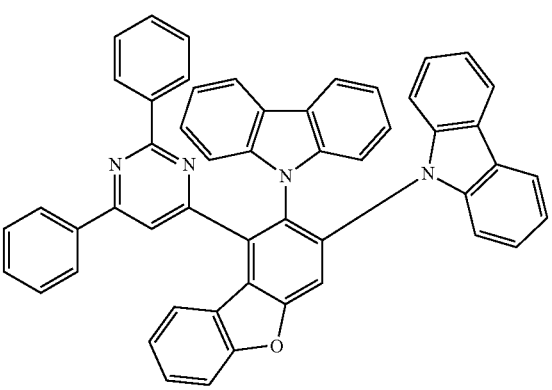

91
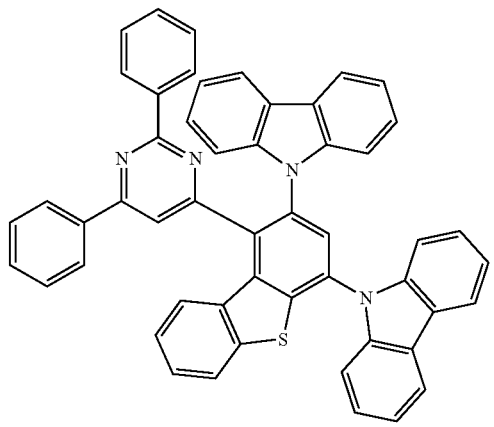
95
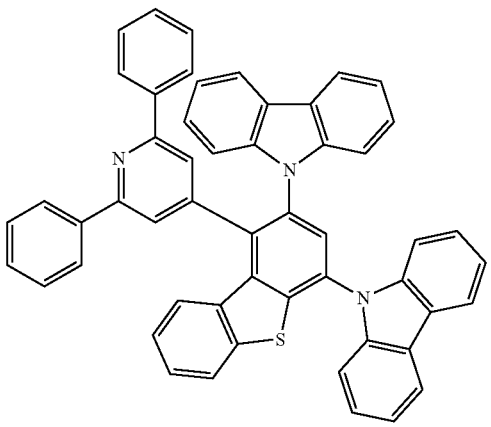
92
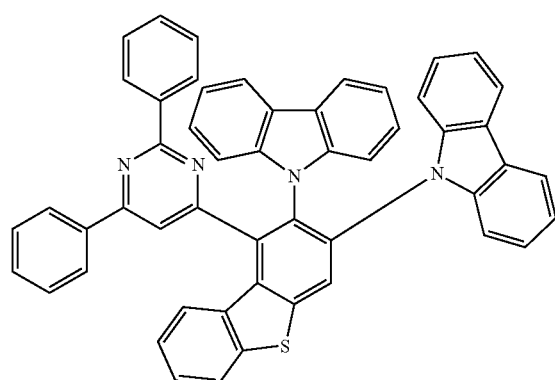
96
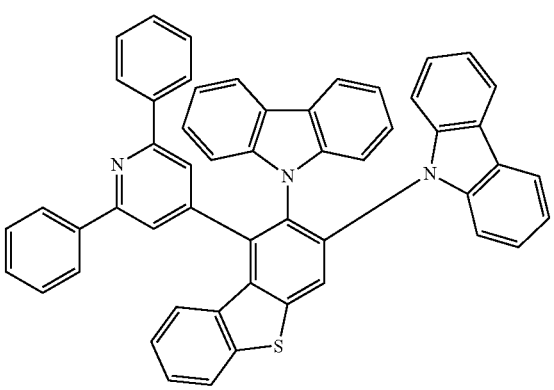
93
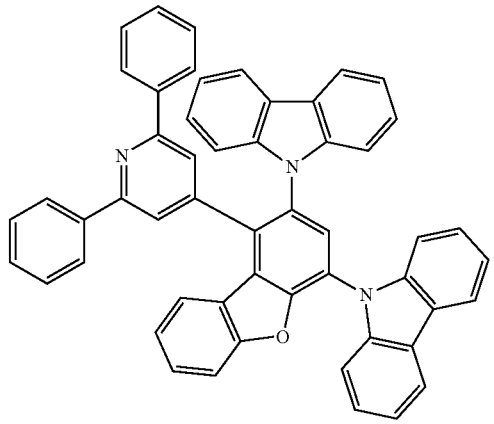
97
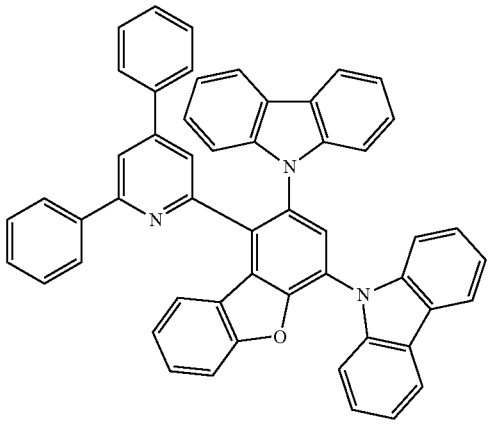
94
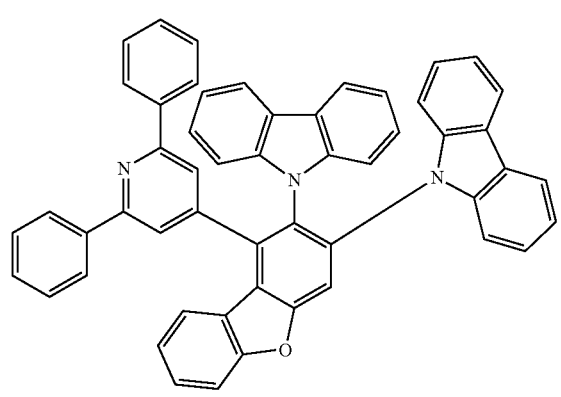
98
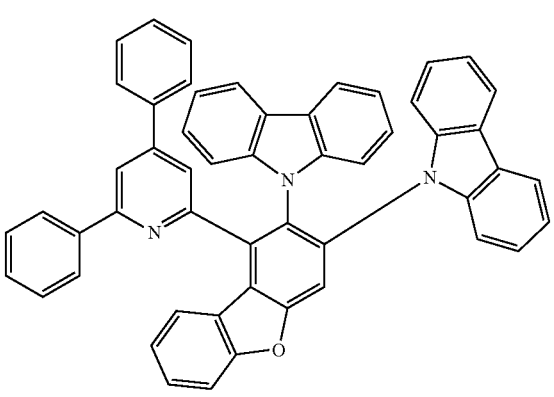

99
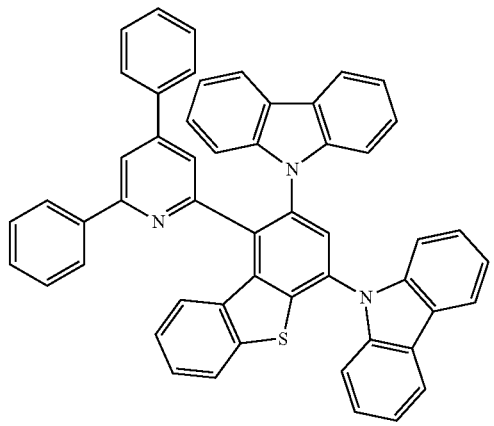
100
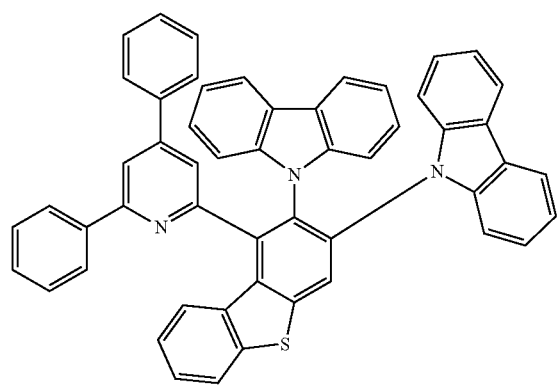
101
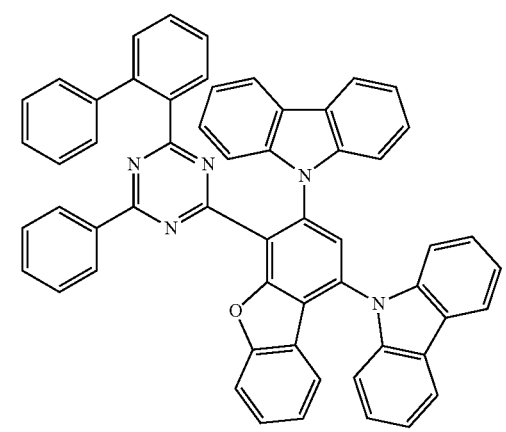
102
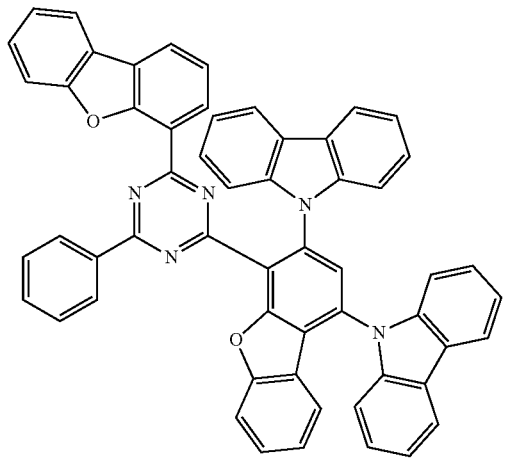
103
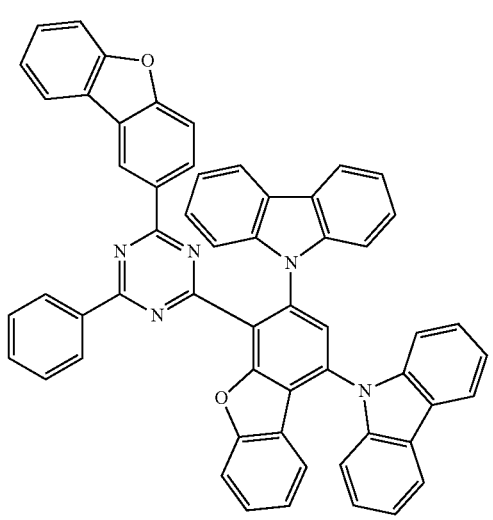
104
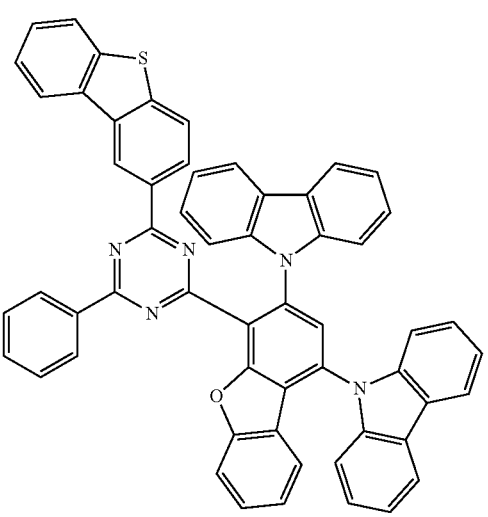

105
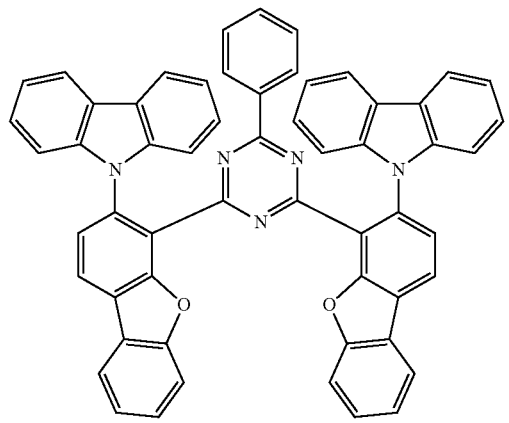
106
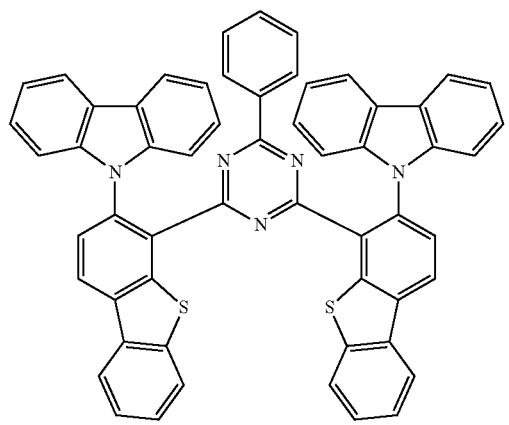
107
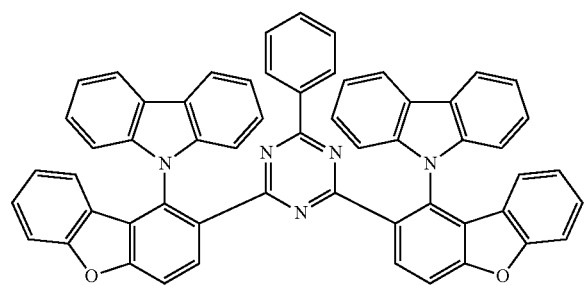
108
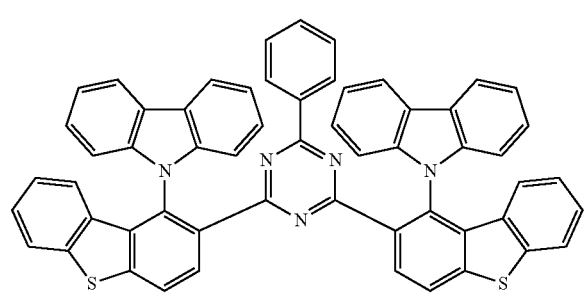
109
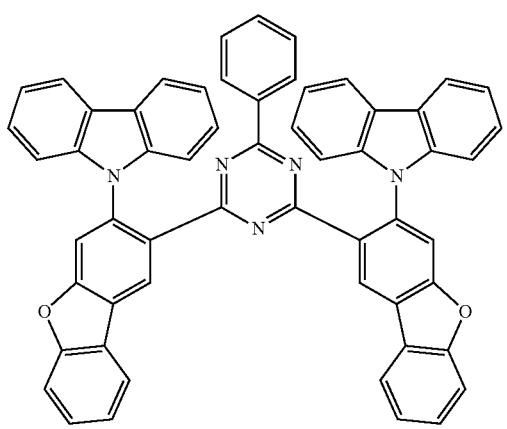
110
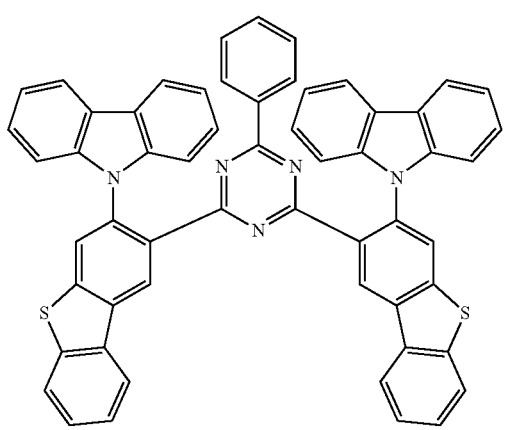
111
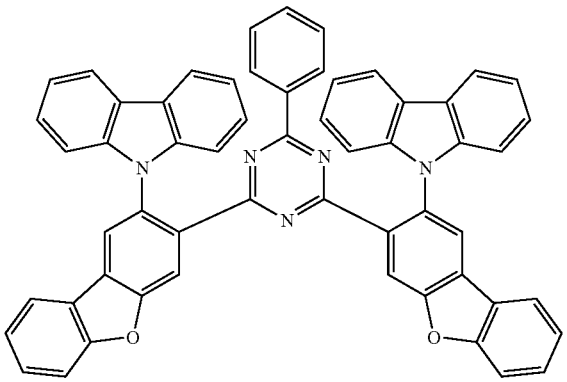

112
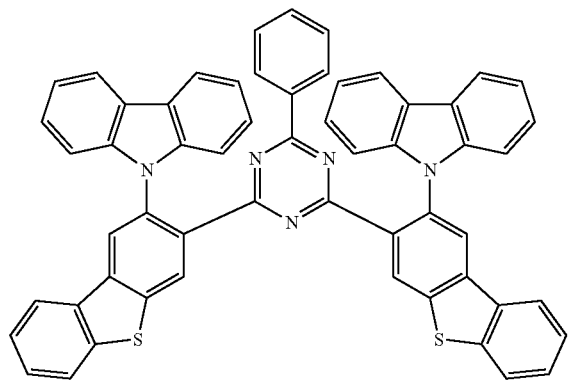
113
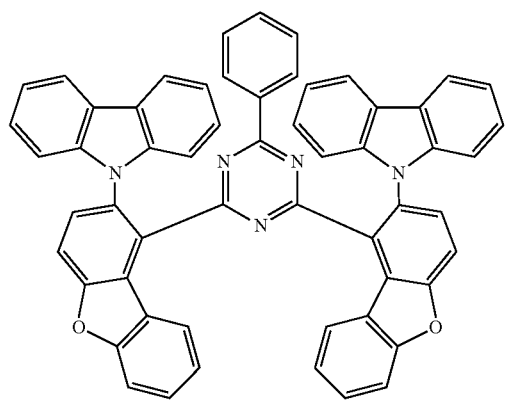
114
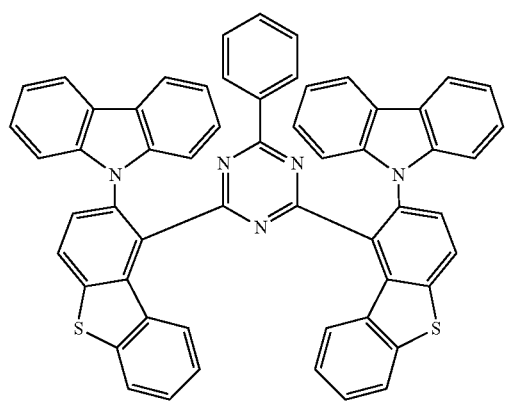
115
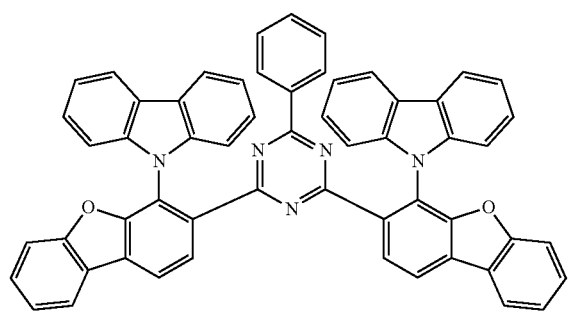
116
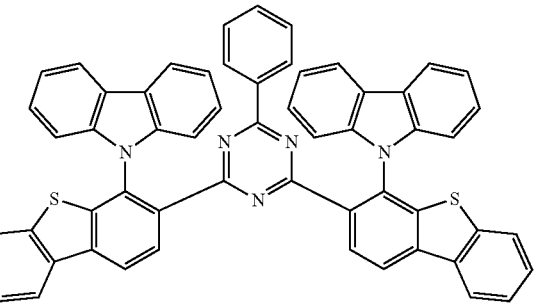
117
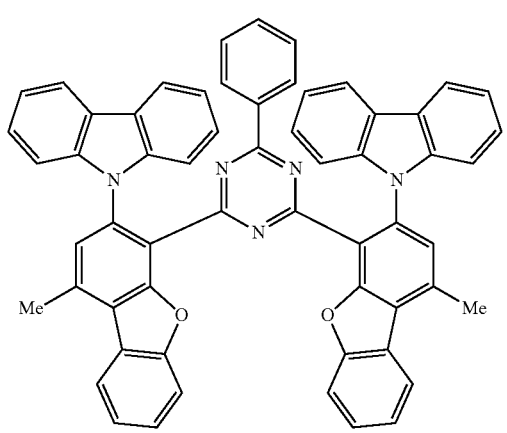
118
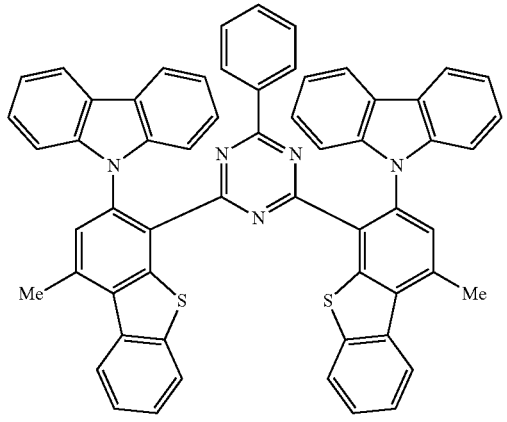
119
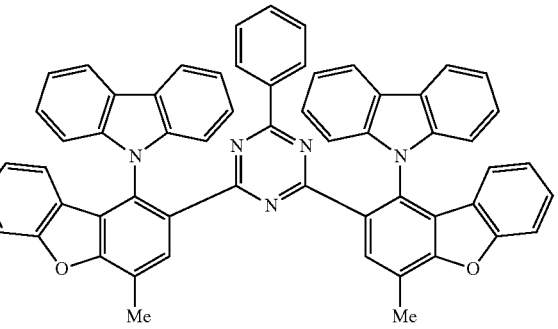

-continued
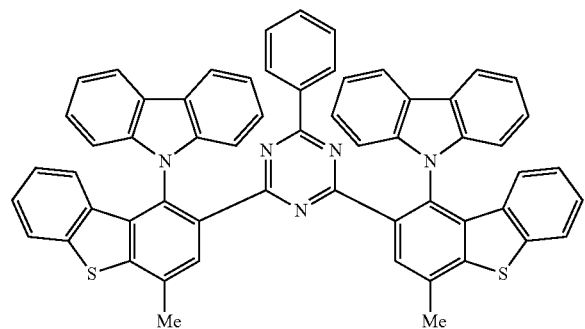
120
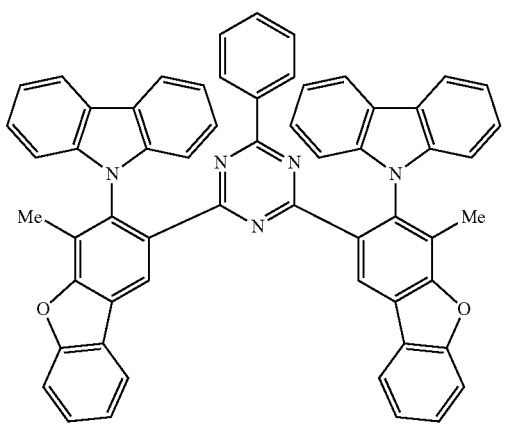
121
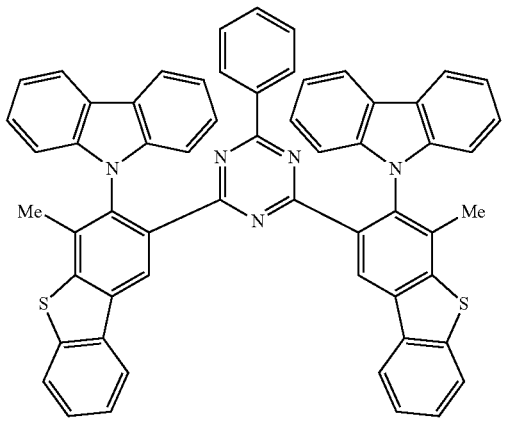
122
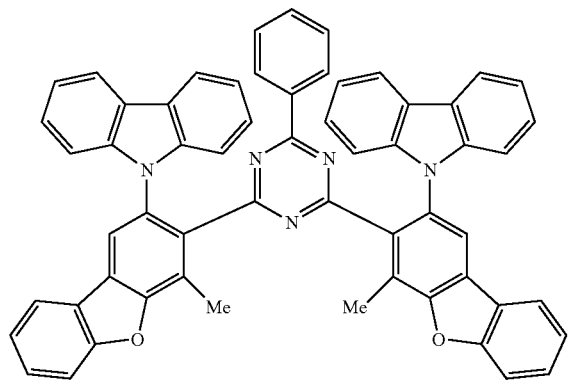
123
-continued
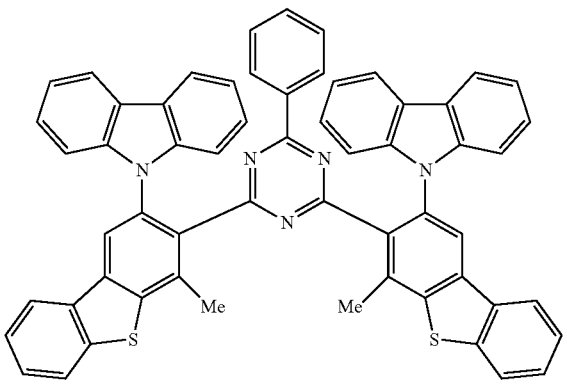
124
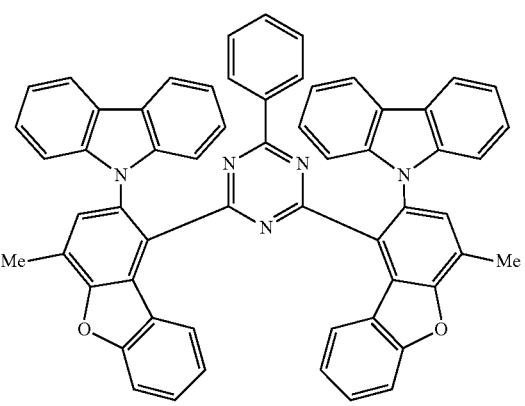
125
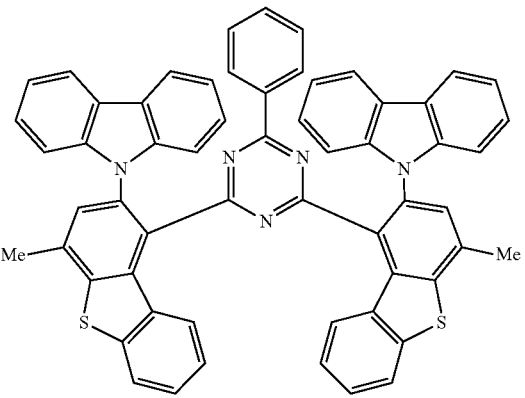
126
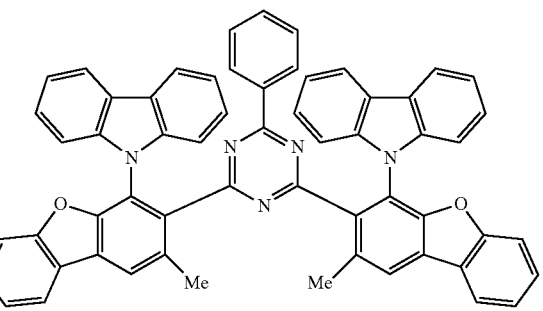
127

128
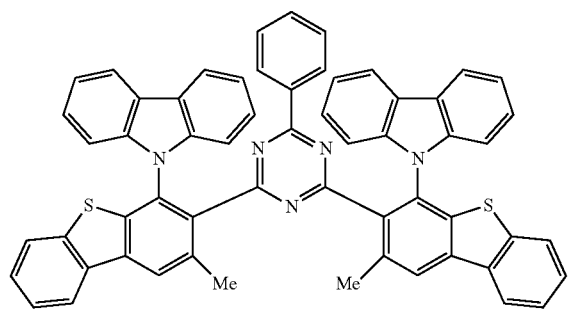
129
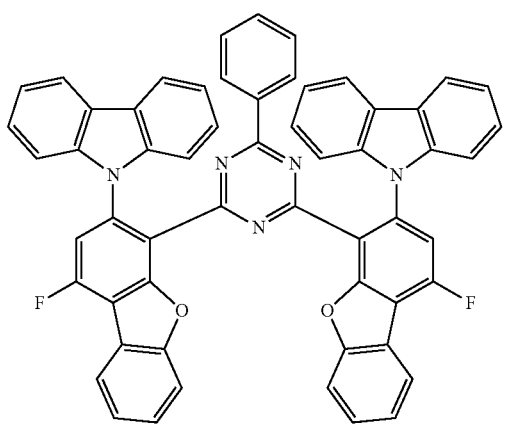
130
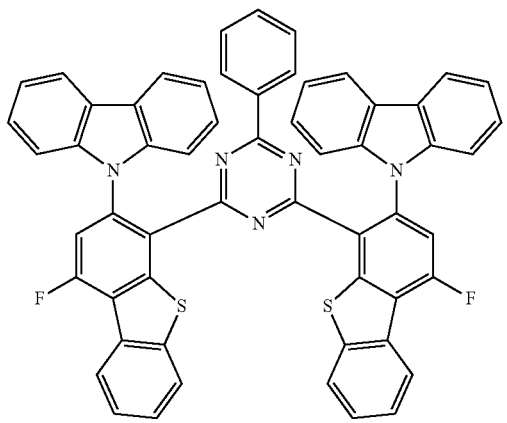
131
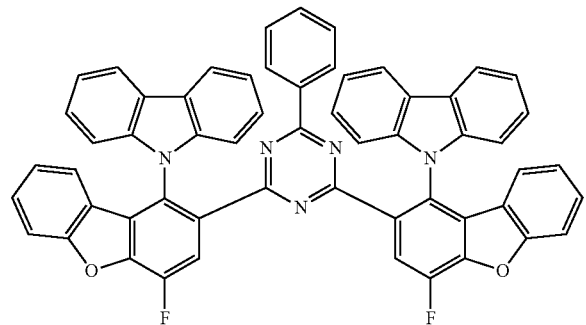
132
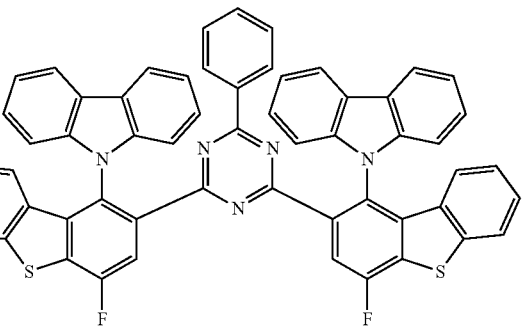
133
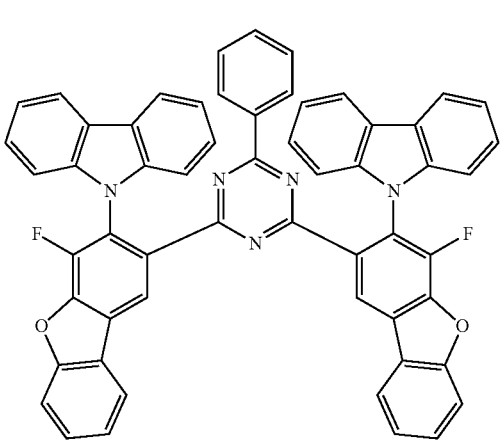
134
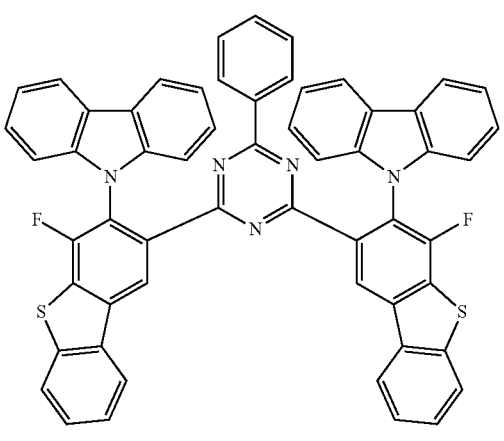
135
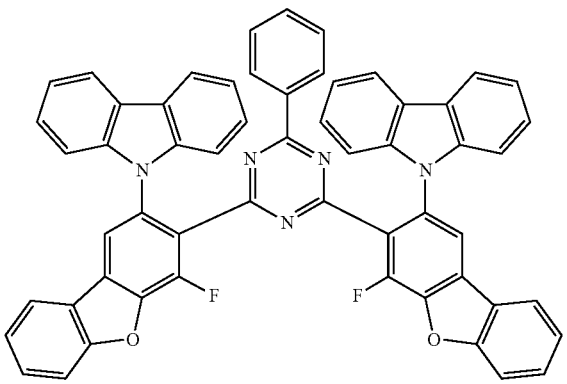

153
-continued
136
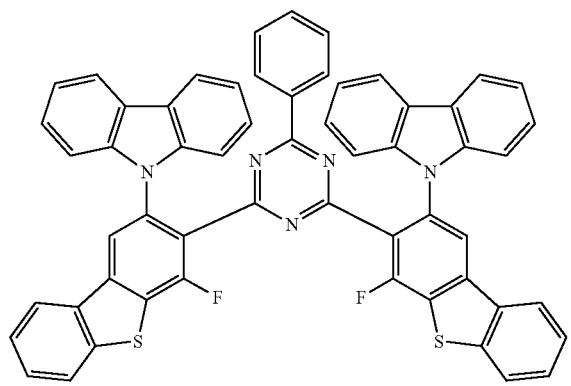
137
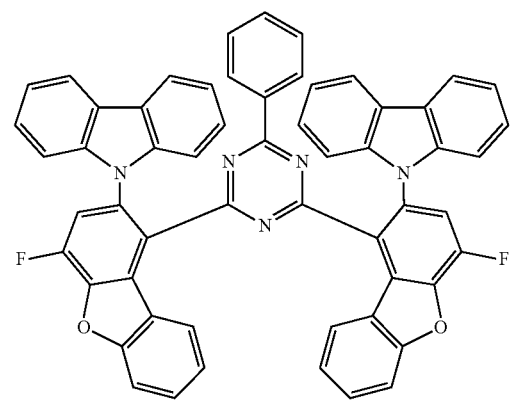
138
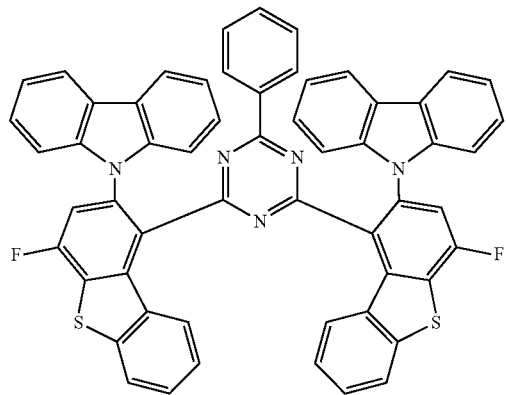
139
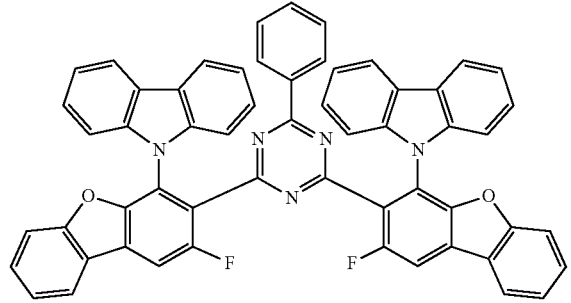
154
-continued
140
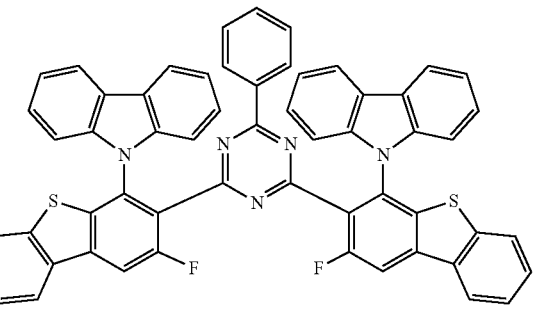
141
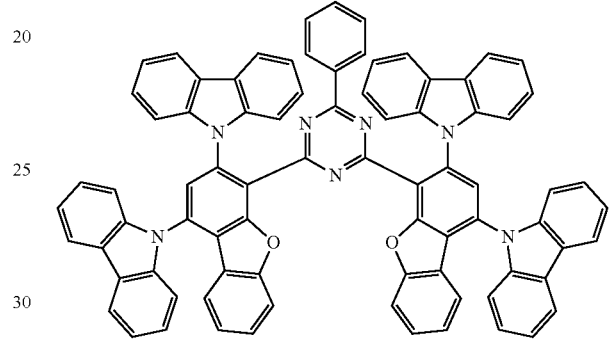
142
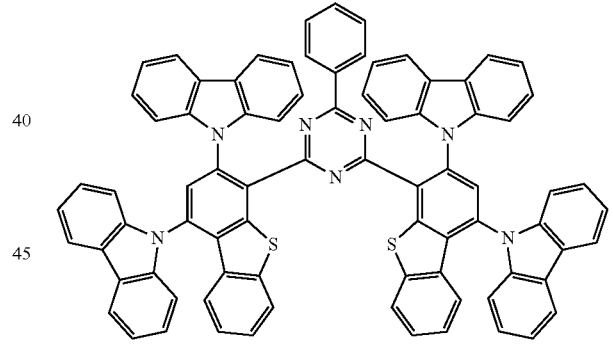
143
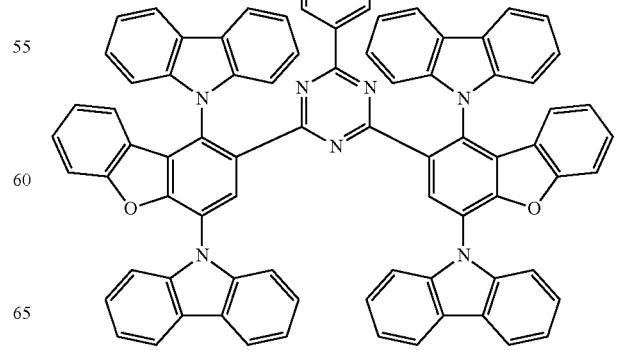

144
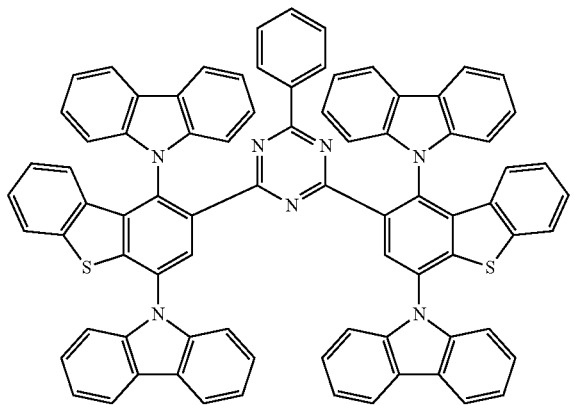
145
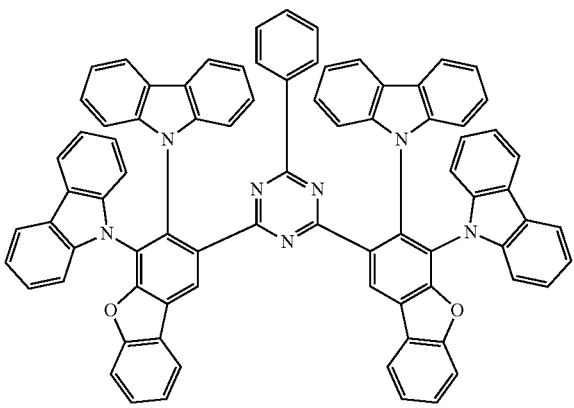
146
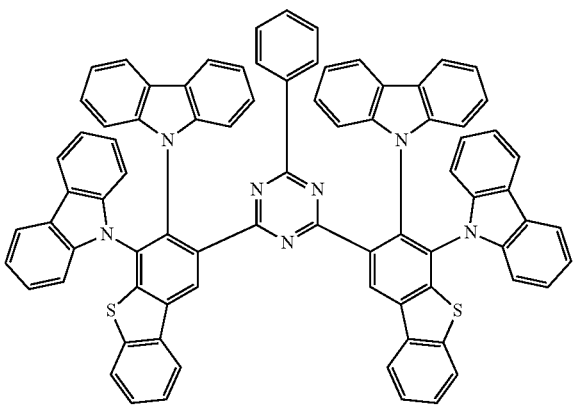
147
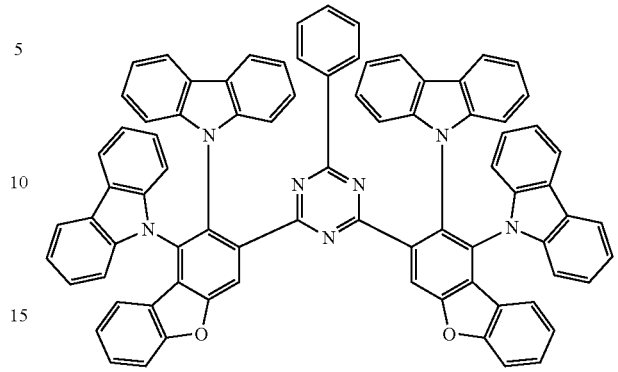
148
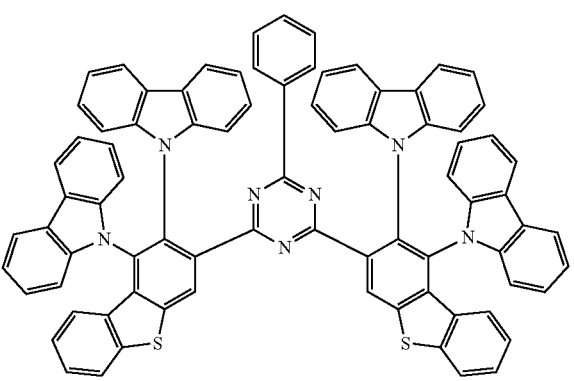
149
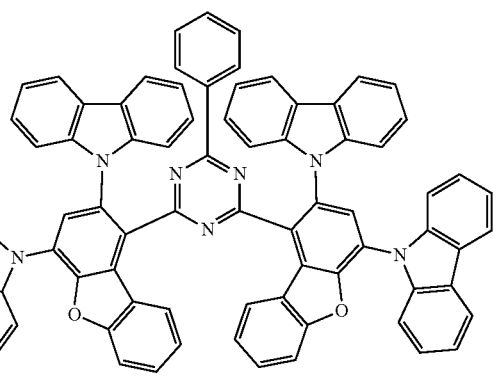
150
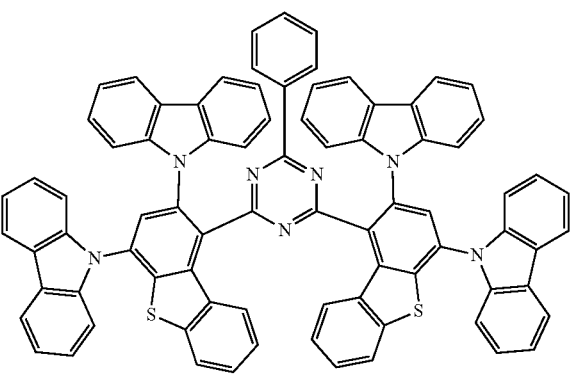

157
-continued
151
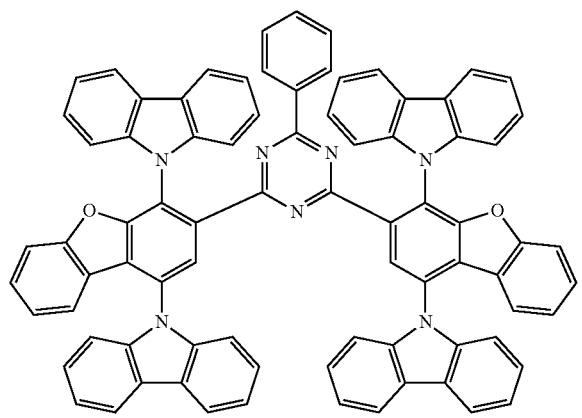
152
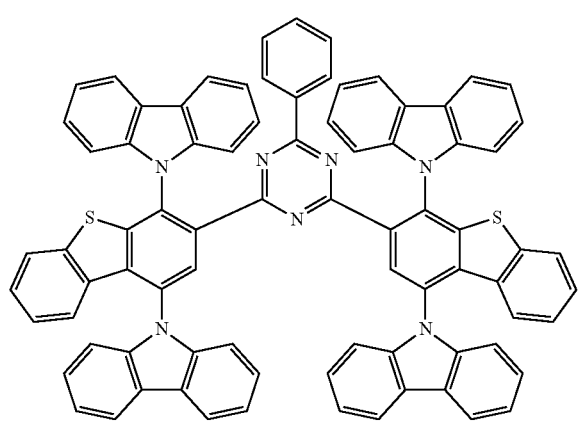
153
158
-continued
154
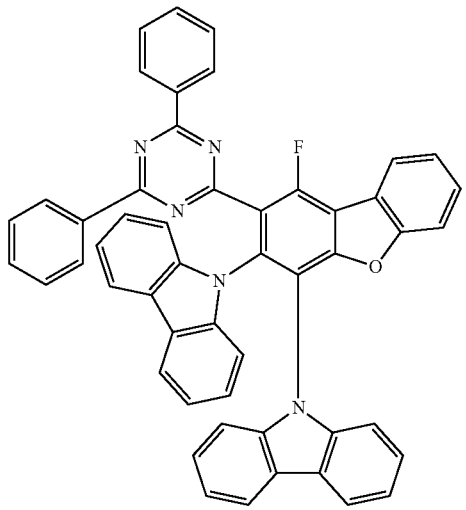
155
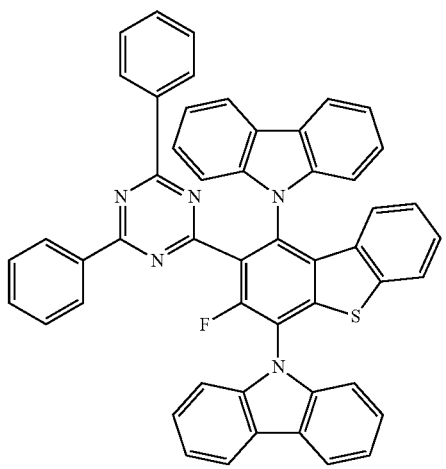
156
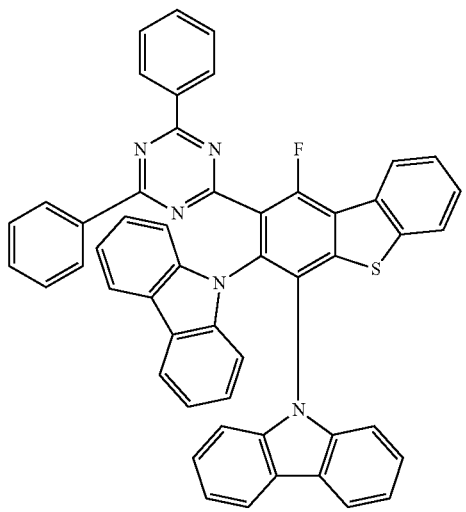

157
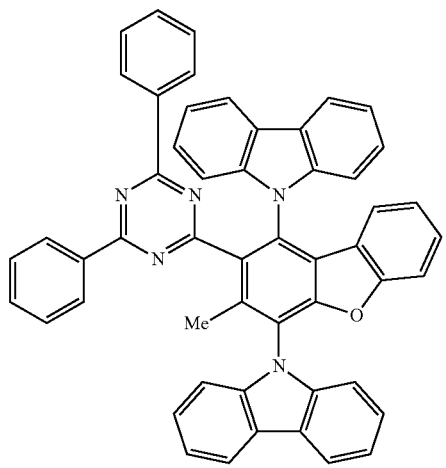
158
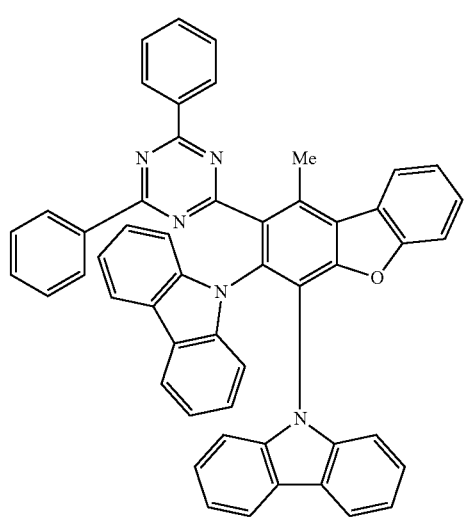
159
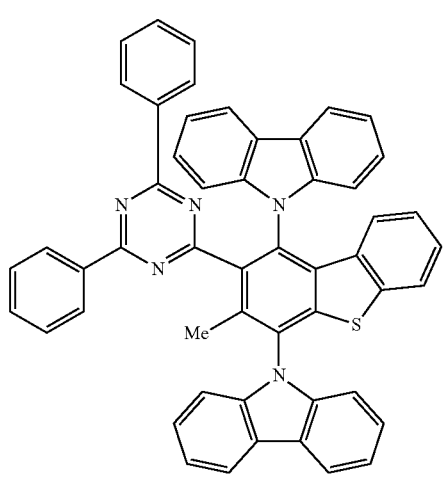
160
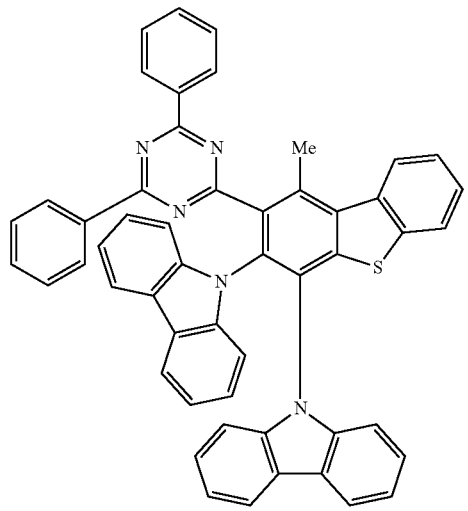
161
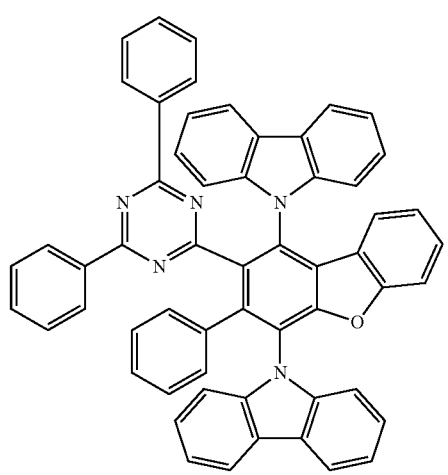
162
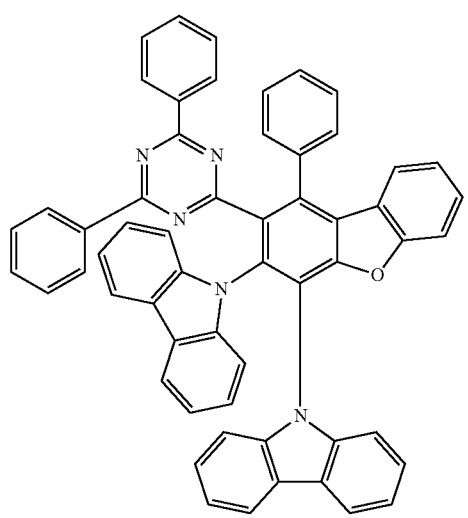

161
-continued
163
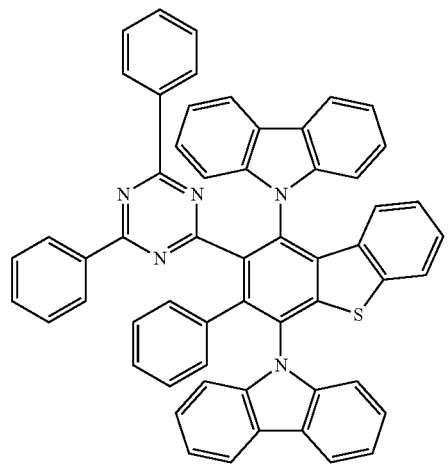
164
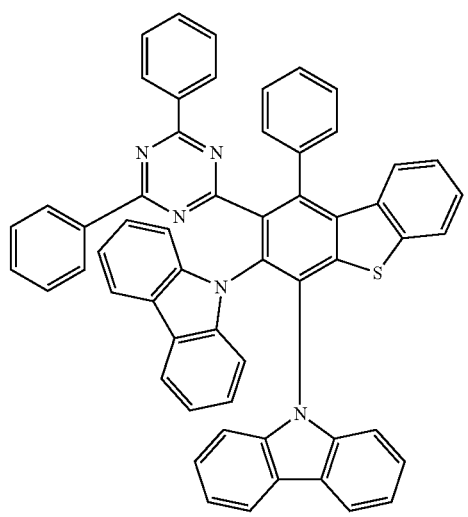
165
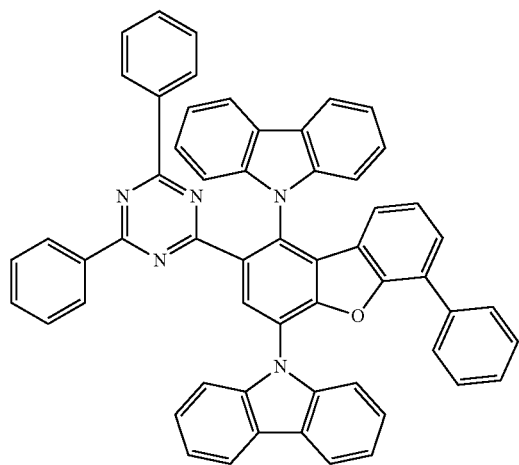
162
-continued
166
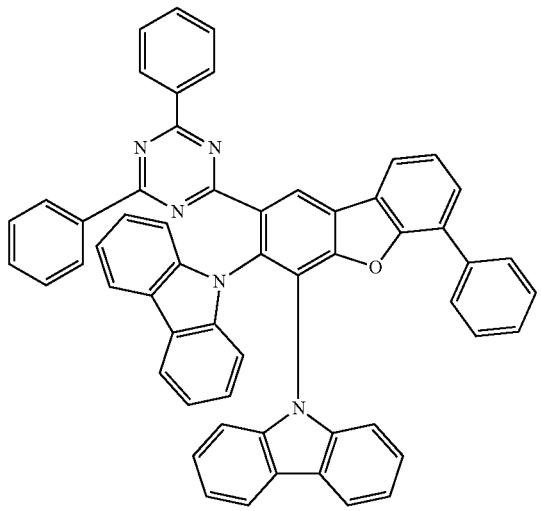
167
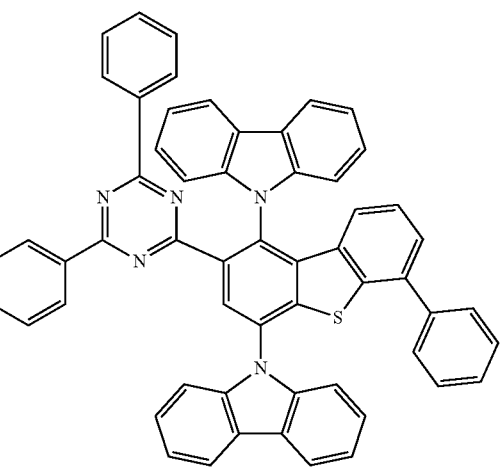
168
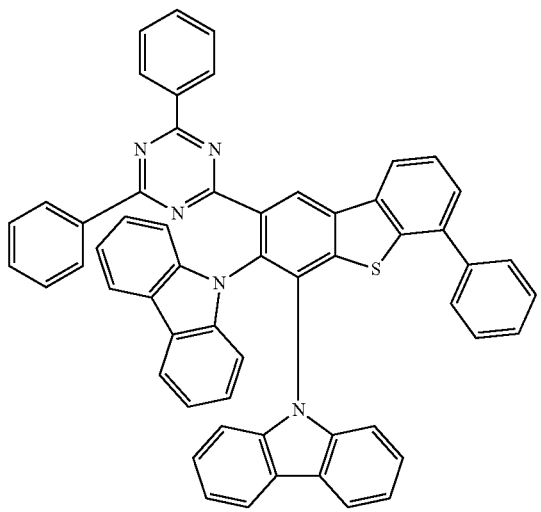

163
-continued
169
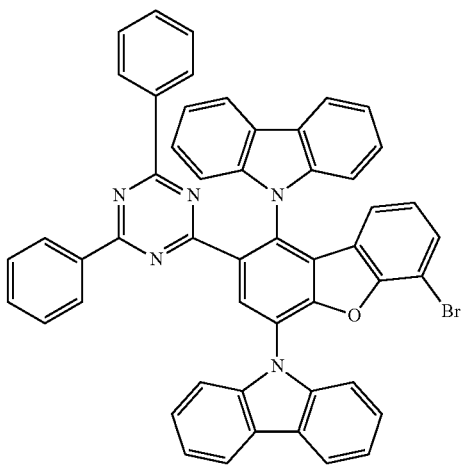
170
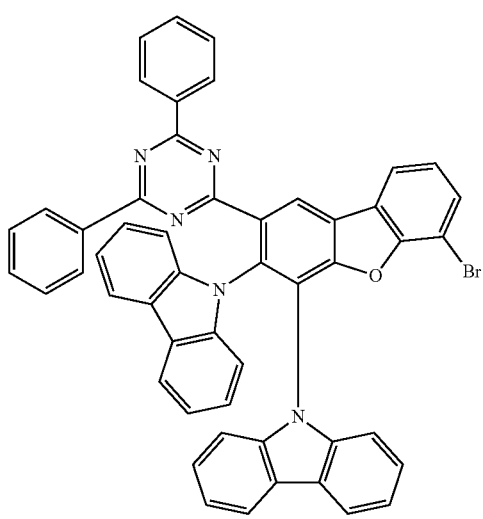
171
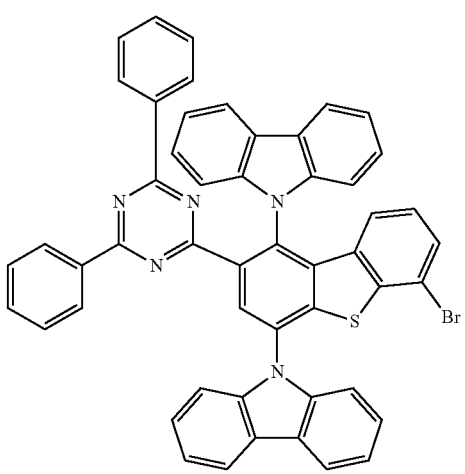
164
-continued
172
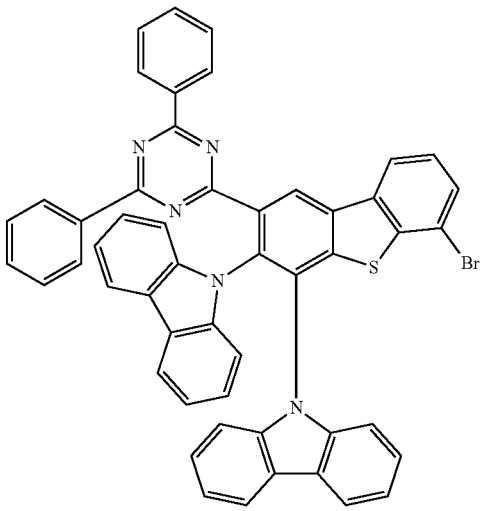
173
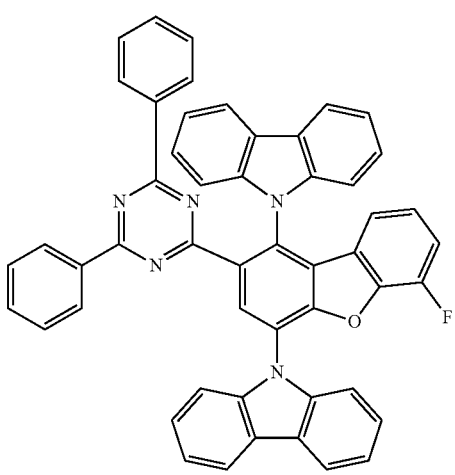
174
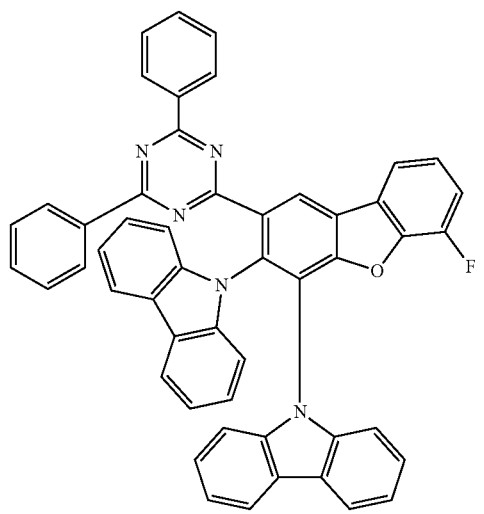

165
-continued
175
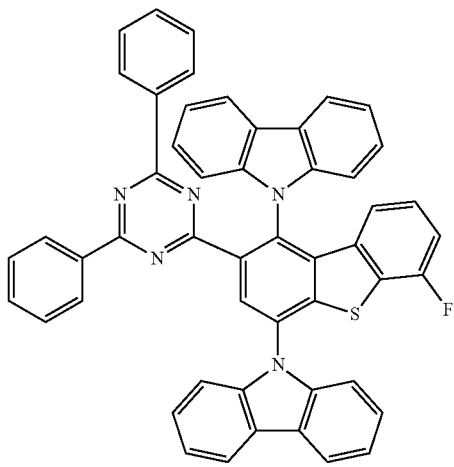
176
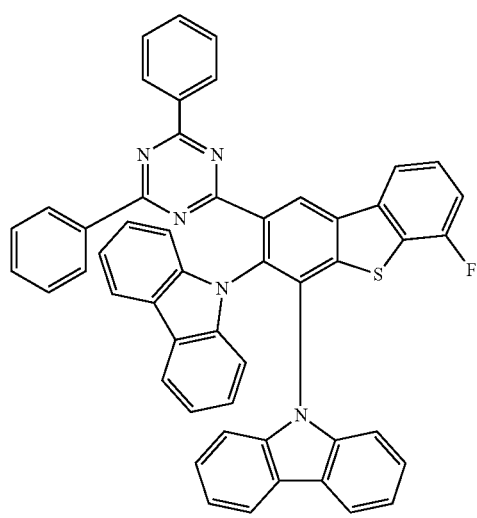
177
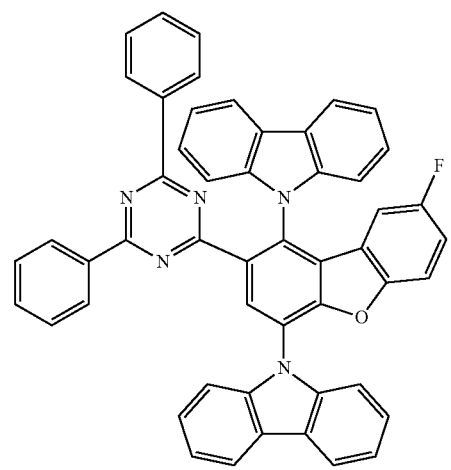
166
-continued
178
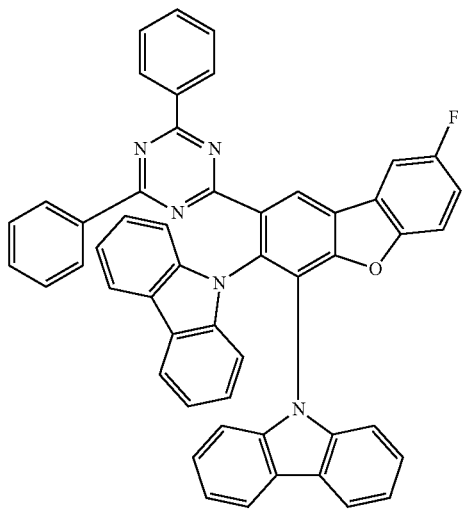
179
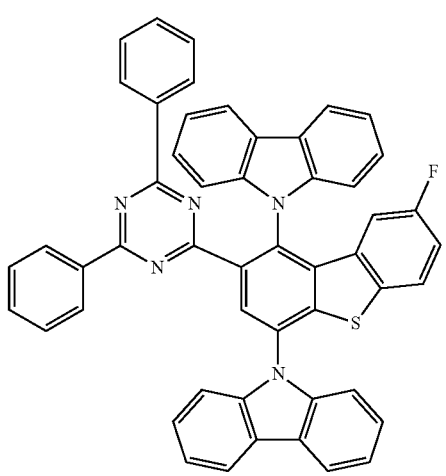
180
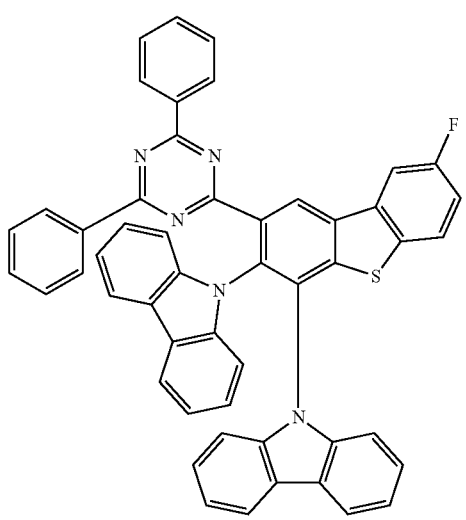

181 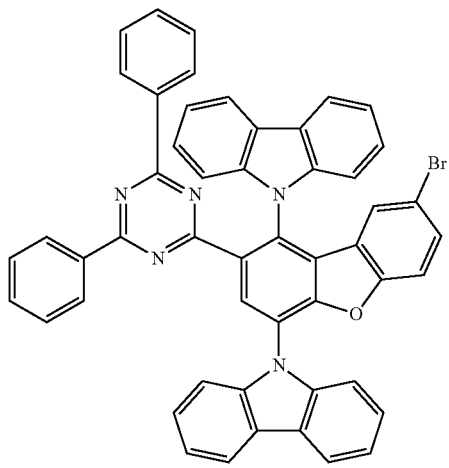
184 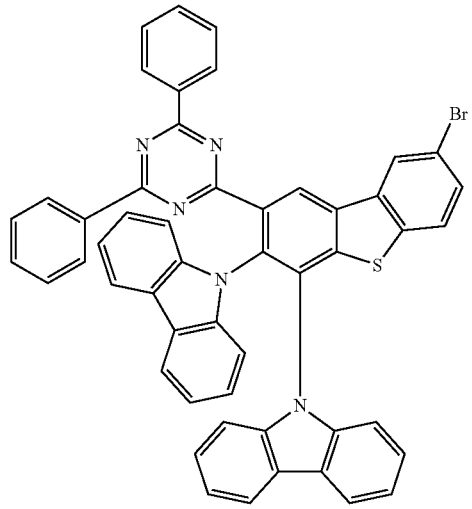
182 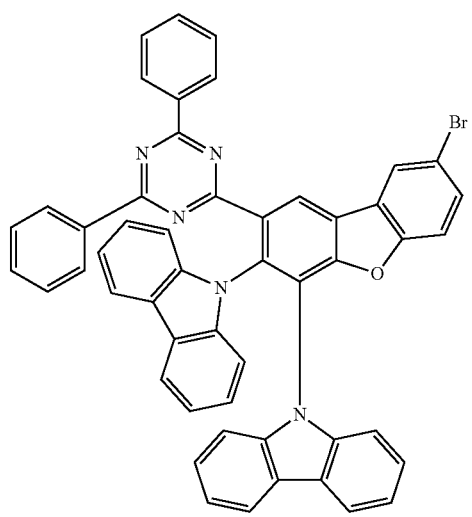
185 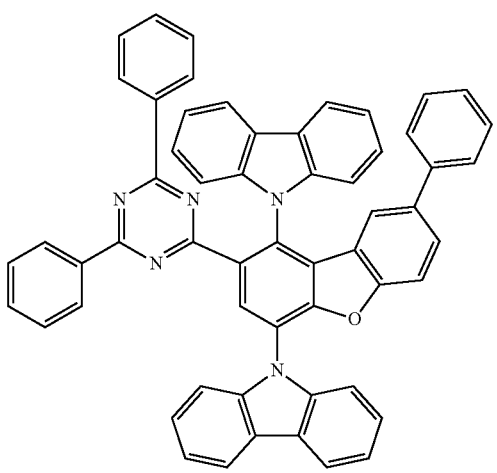
183 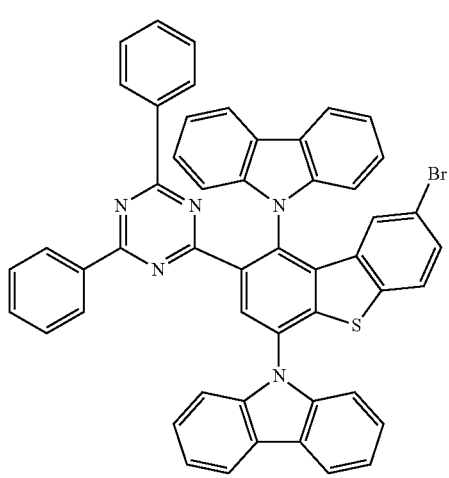
186 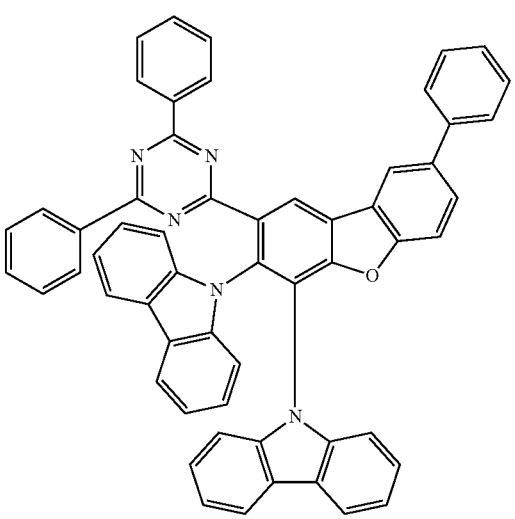

-continued

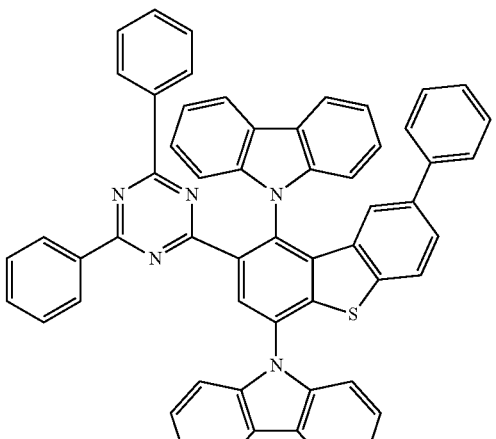

187

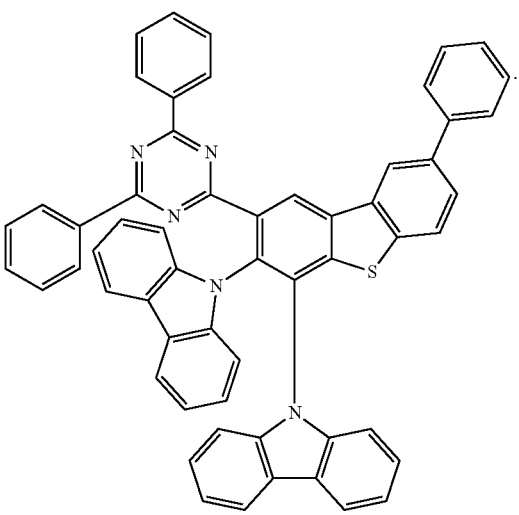

188

14. An organic electroluminescence device, comprising:
a first electrode;
a hole transport region on the first electrode;
an emission layer on the hole transport region;
an electron transport region on the emission layer; and
a second electrode on the electron transport region,
wherein the emission layer includes a heterocyclic compound represented by the following Formula 1:

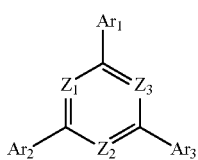

[Formula 1]

in Formula 1,
$Z_1$ to $Z_3$ are each independently $CR_1$ or N,
at least one of $Z_1$ to $Z_3$ is N,
$R_1$ is a hydrogen atom, a deuterium atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, $Ar_1$ to $Ar_3$ are each independently a group represented by the following Formula 2, a substituted or unsubstituted aryl group having 6 to 30 ring carbon atoms, or a substituted or unsubstituted heteroaryl group having 2 to 30 carbon atoms for forming a ring, and
at least one of $Ar_1$ to $Ar_3$ is a group represented by Formula 2:

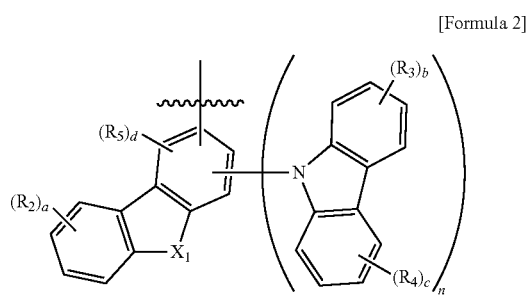

[Formula 2]

in Formula 2,
$X_1$ is O or S,
"n" is an integer of 1 to 3,
"a" to "c" are each independently an integer of 0 to 4,
"d" is an integer of 0 to 2, and
$R_2$ is a hydrogen atom, a deuterium atom, a halogen atom, a substituted or unsubstituted alkyl group having 1 to 10 carbon atoms, or a substituted or unsubstituted aryl group having 6 to 30 ring carbon atoms,
$R_3$ to $R_5$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
when only one of $Ar_1$ to $Ar_3$ is a group represented by Formula 2 above, "n" is 2 or 3, and
at least one of the carbazole moieties in Formula 2 is bonded in an ortho relationship with respect to the nitrogen-containing monocycle of Formula 1.

15. The organic electroluminescence device as claimed in claim 14, wherein each of $Z_1$ to $Z_3$ is N.

16. The organic electroluminescence device as claimed in claim 14, wherein the compound represented by Formula 1 is represented by Formula 1-1 or Formula 1-3:

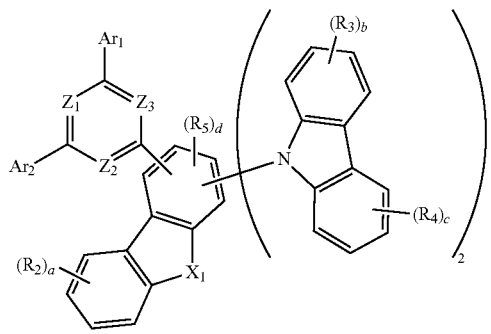

[Formula 1-1]

-continued

[Formula 1-3]

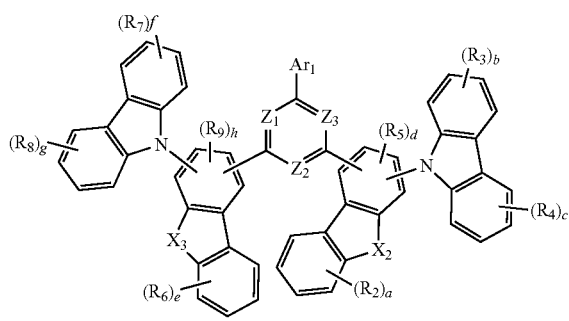

in Formulae 1-1 and 1-3, $Z_1$ to $Z_3$, $Ar_1$, $Ar_2$, $R_2$ to $R_5$, "a" to "d" and $X_1$ are defined the same as those of Formula 1 and Formula 2, and in Formula 1-3, $X_2$ and $X_3$ are each independently O or S, $R_6$ to $R_9$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, "e" to "g" are each independently an integer of 0 to 4, and "h" is an integer of 0 to 2.

17. The organic electroluminescence device as claimed in claim 14, wherein the compound represented by Formula 1 is represented by the following Formula 1-2 or Formula 1-4:

[Formula 1-2]

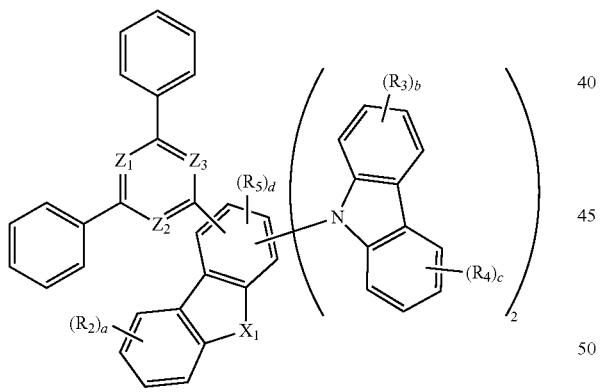

[Formula 1-4]

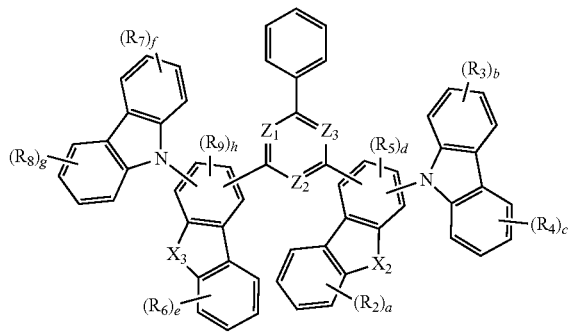

in Formulae 1-2 and 1-4, $Z_1$ to $Z_3$, $R_2$ to $R_5$, "a" to "d" and $X_1$ are defined the same as those of Formulae 1 and 2, and in Formula 1-4, $X_2$ and $X_3$ are each independently O or S, $R_6$ to $R_9$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, "e" to "g" are each independently an integer of 0 to 4, and "h" is an integer of 0 to 2.

18. The organic electroluminescence device as claimed in claim 14, wherein the heterocyclic compound is a compound of the following Compound Group 1:

[Compound Group 1]

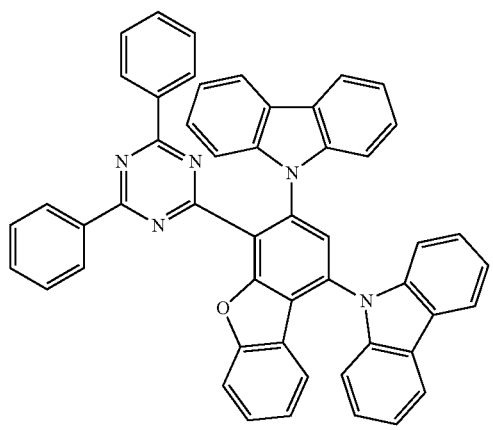

1

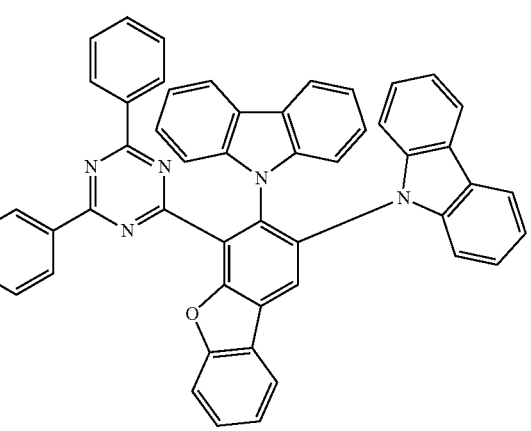

2

3
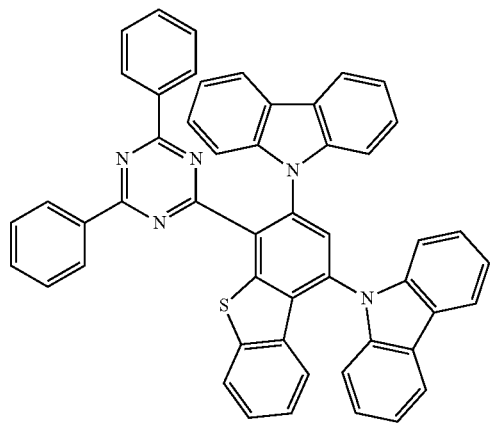
4
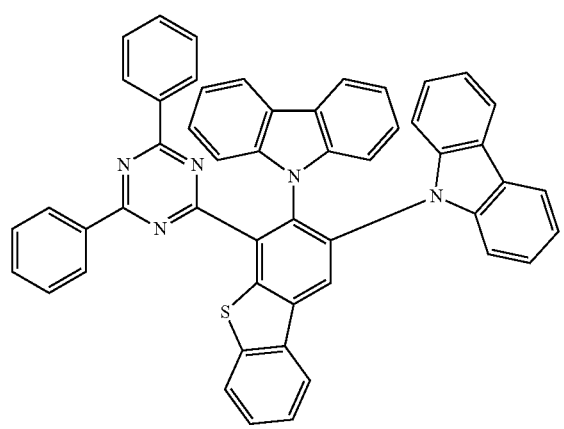
5
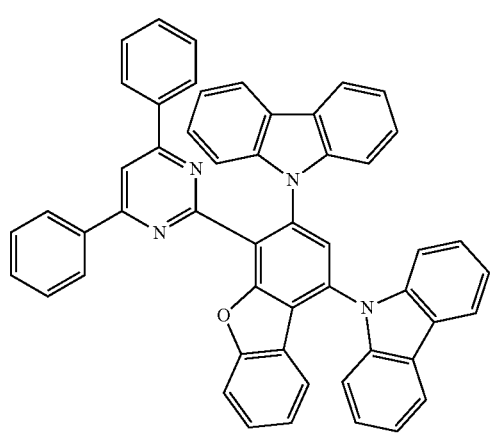
6
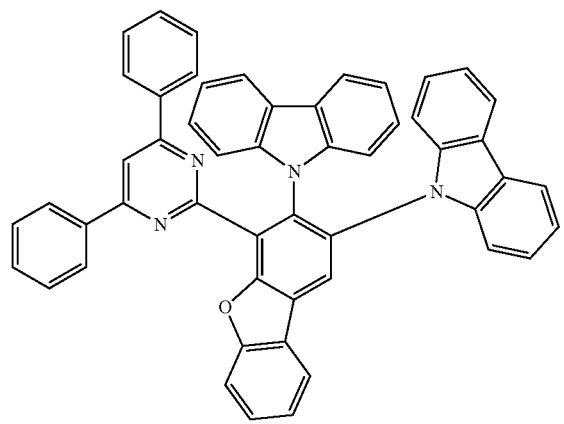
7
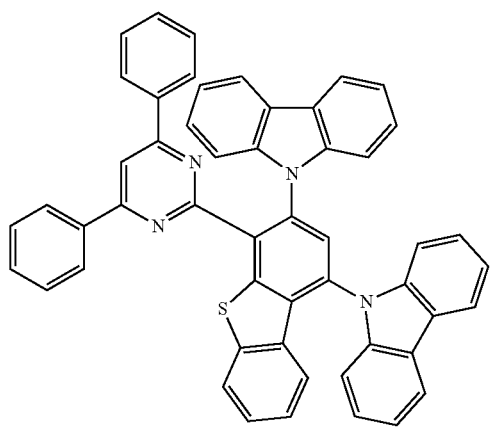
8
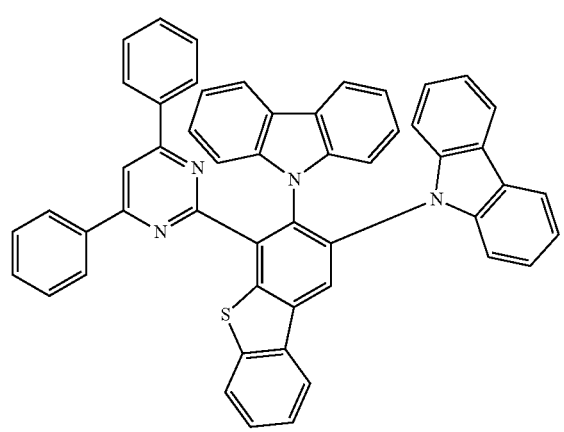

9
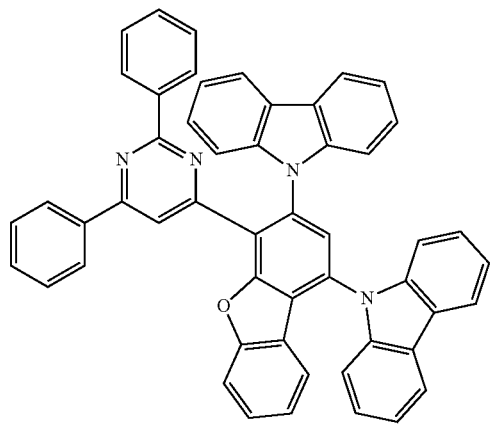
10
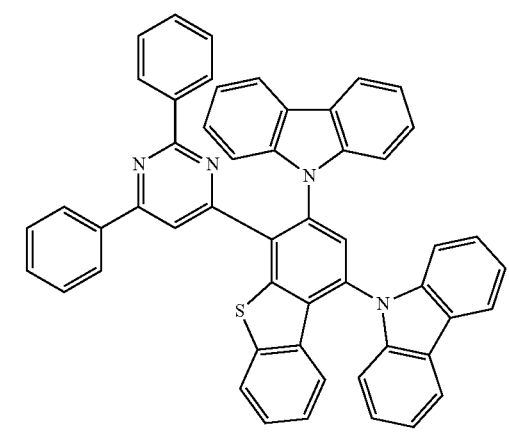
11
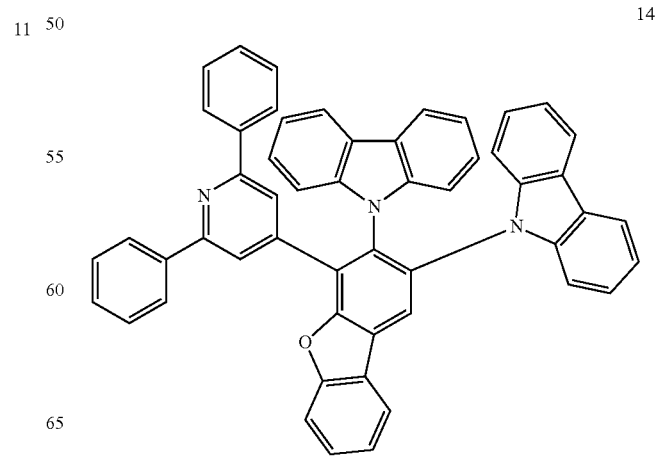
12
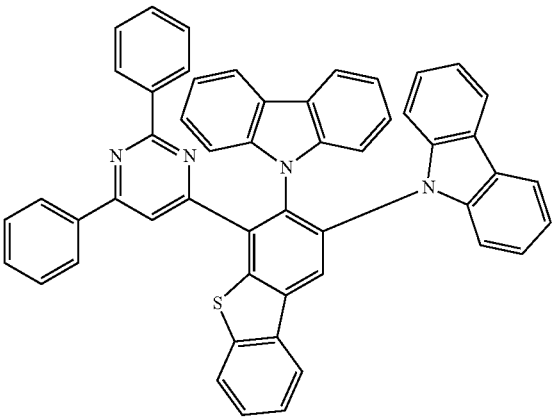
13
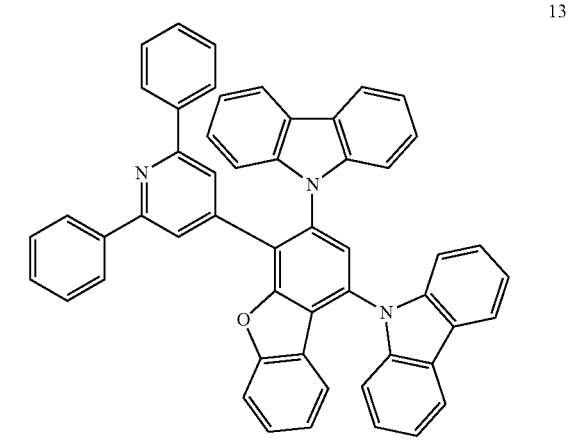
14

15
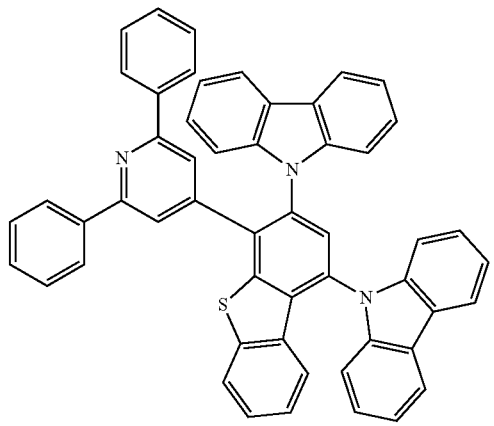
16
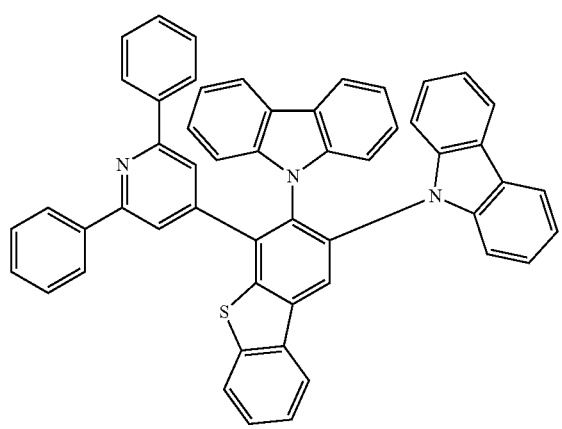
17
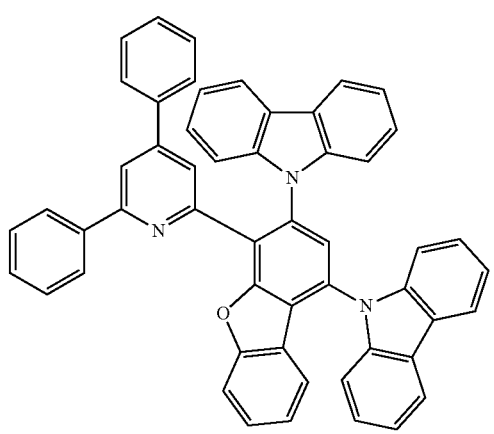
18
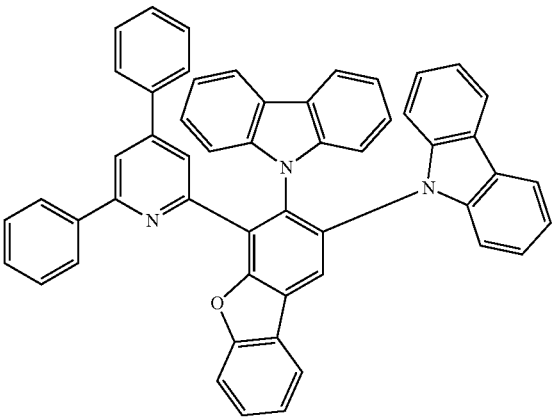
19
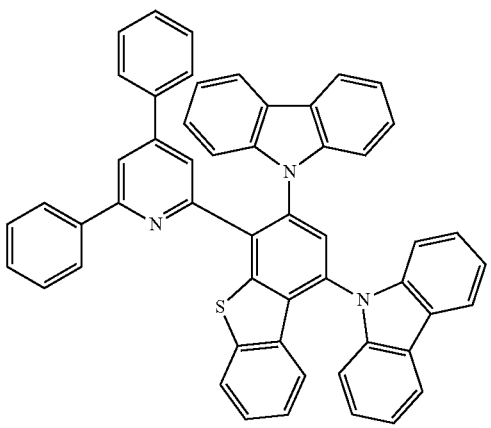
20
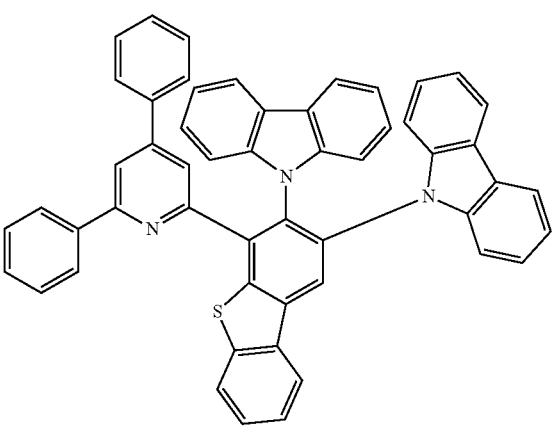

-continued
21
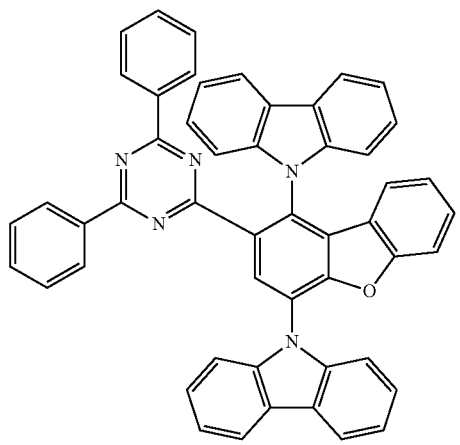
22
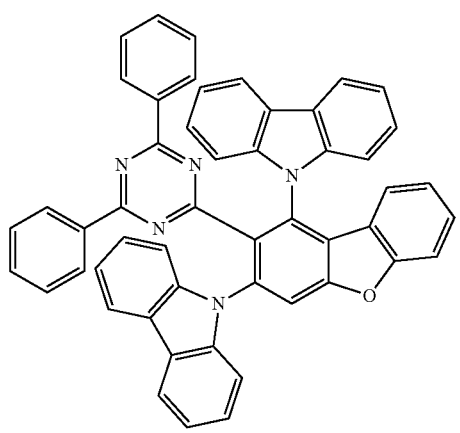
23
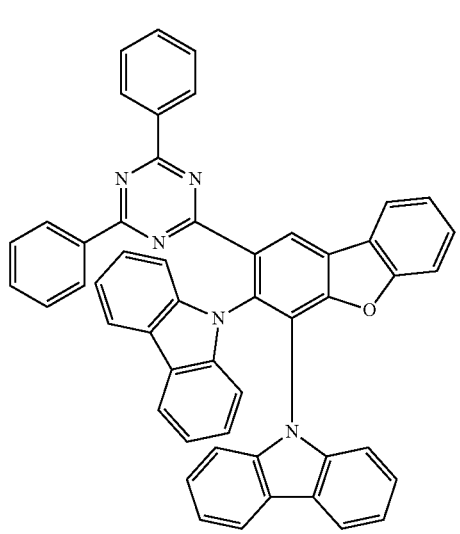
-continued
24
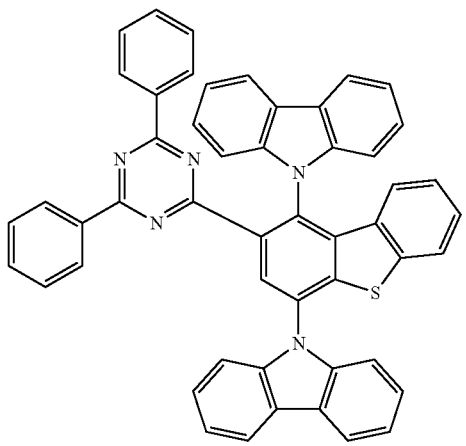
25
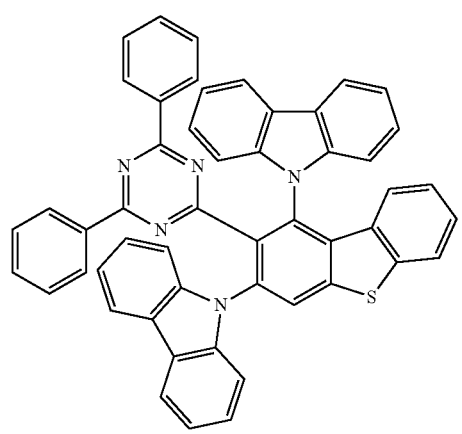
26
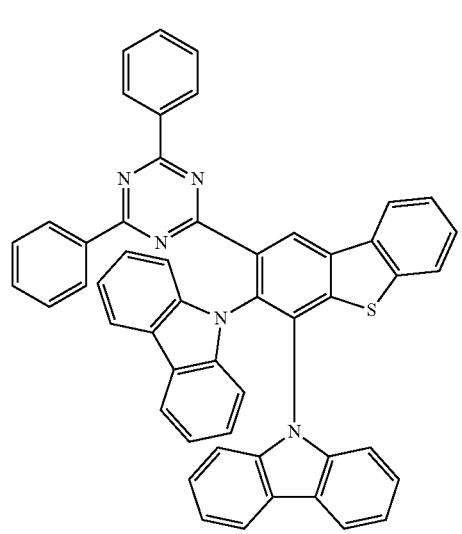

27
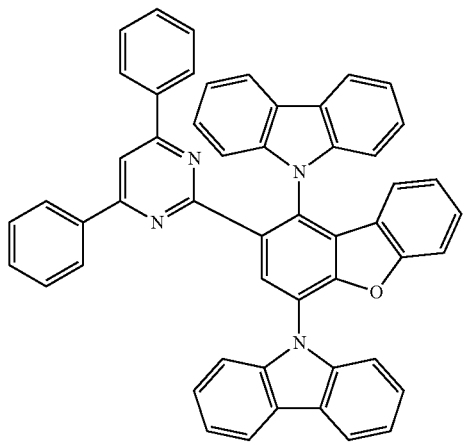
28
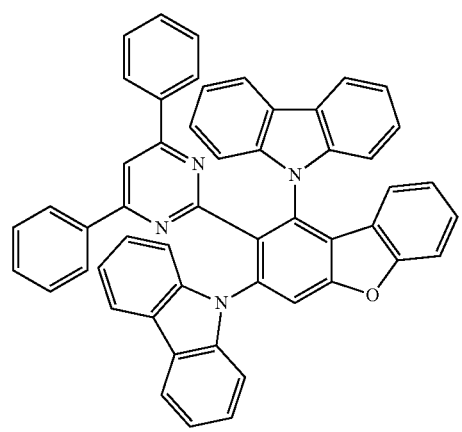
29
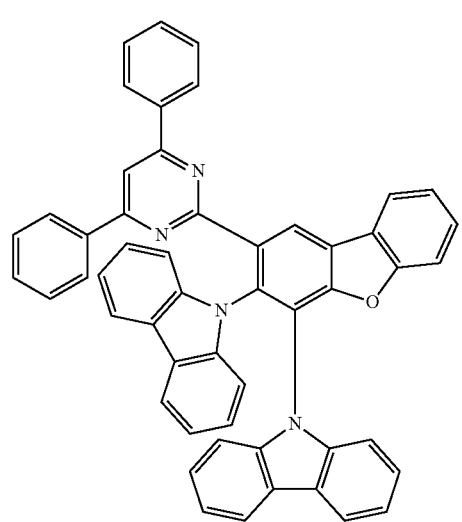
30
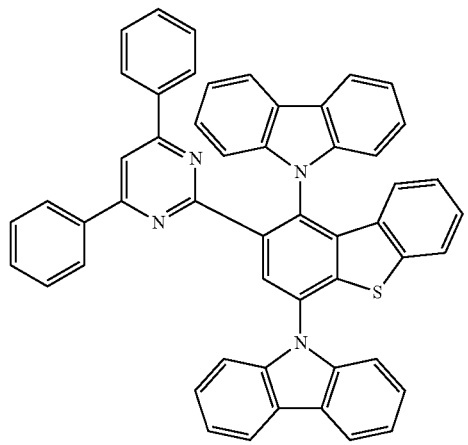
31
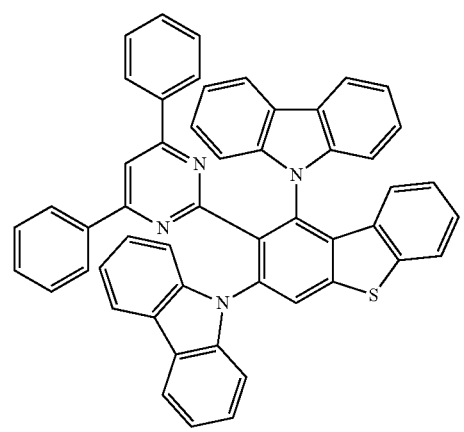
32
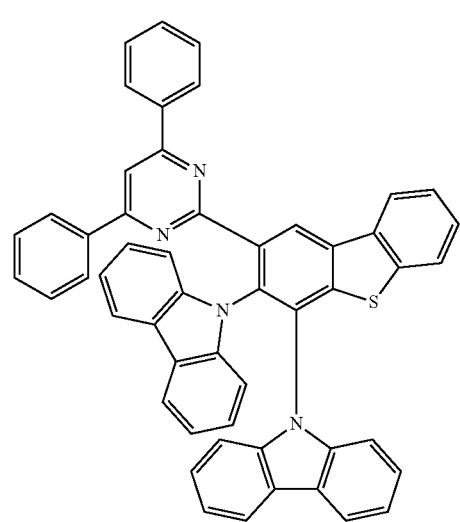

-continued
33
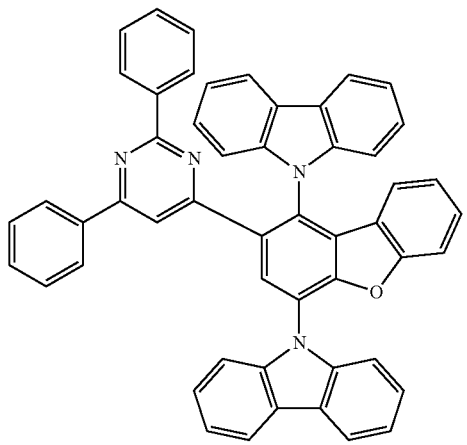
34
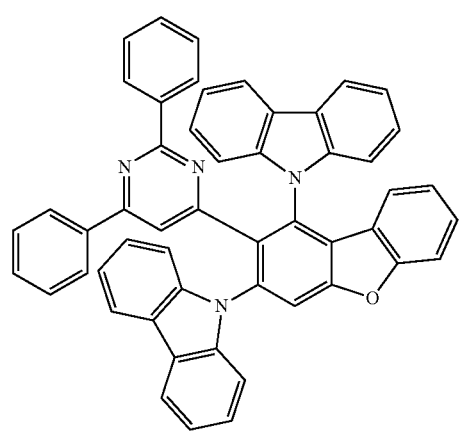
35
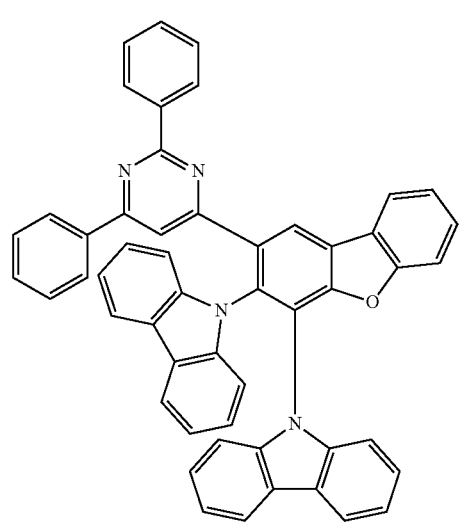
-continued
36
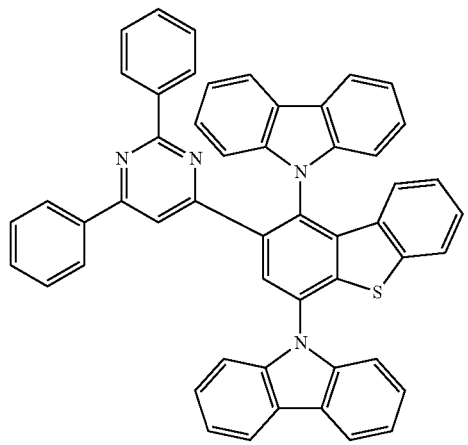
37
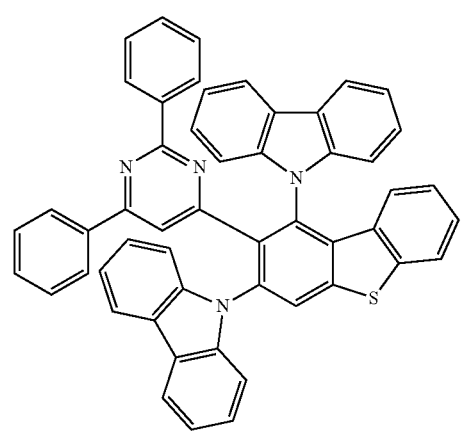
38
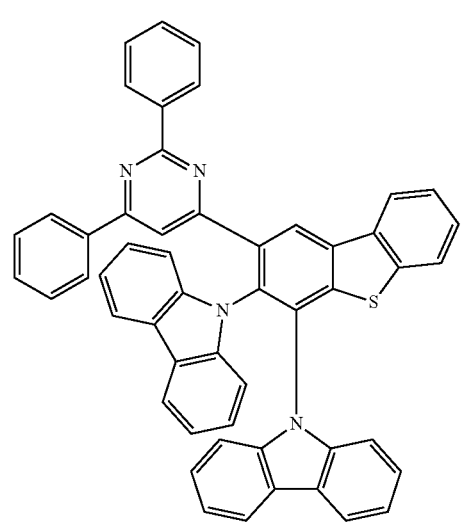

-continued
39
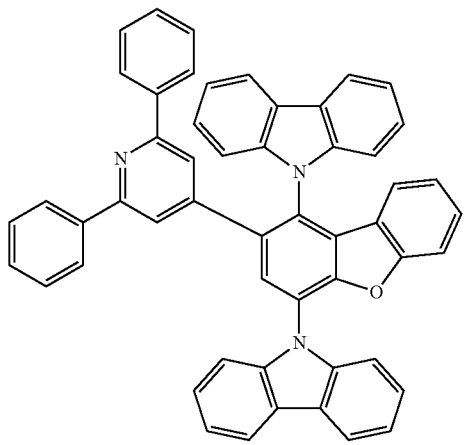
40
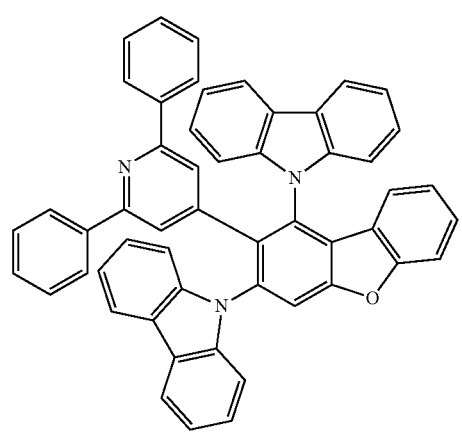
41
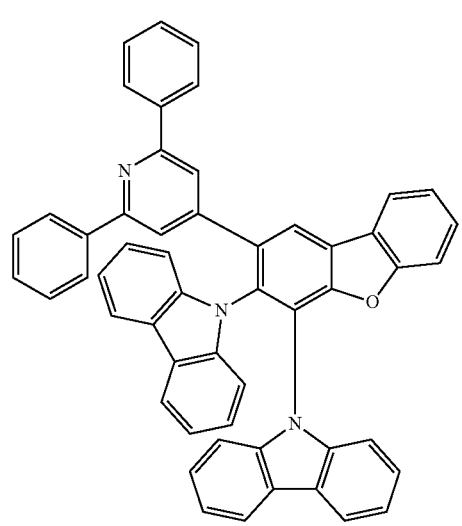
-continued
42
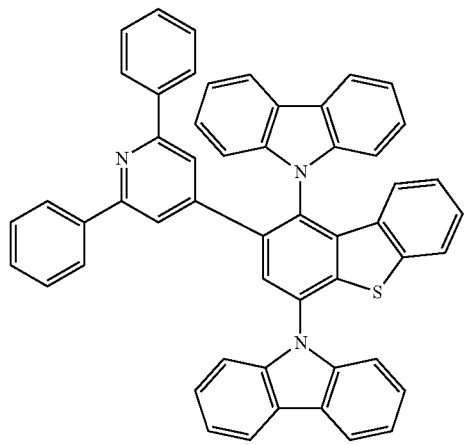
43
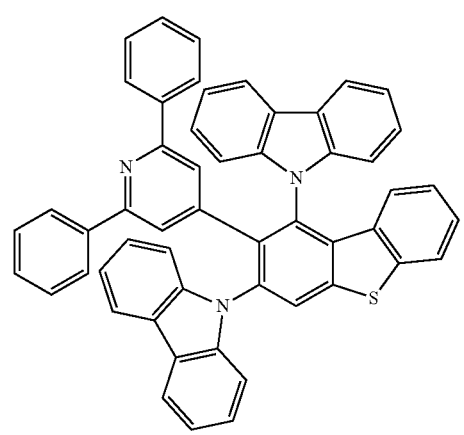
44
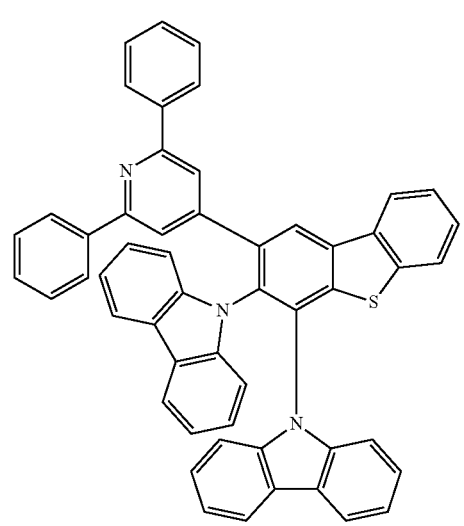

187
-continued
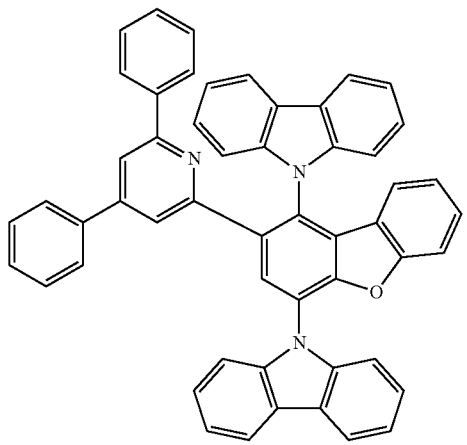
45
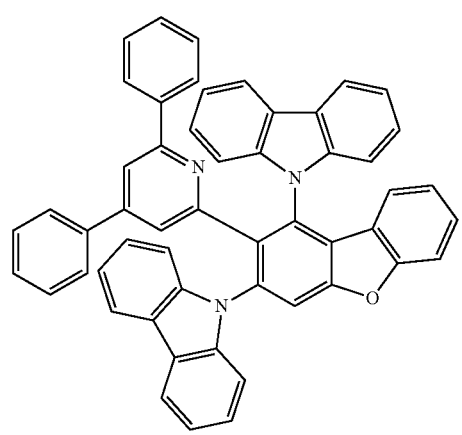
46
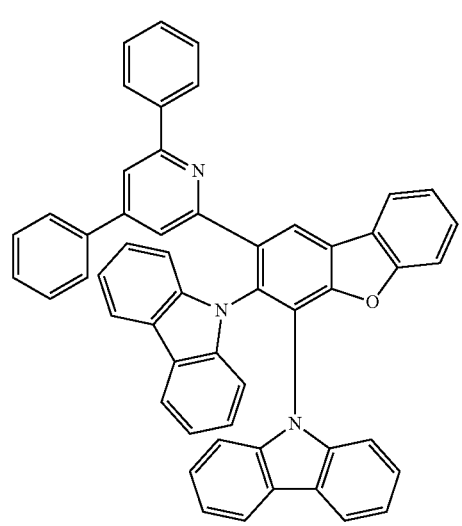
47
188
-continued
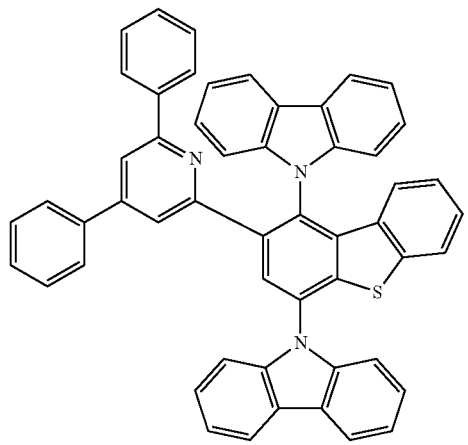
48
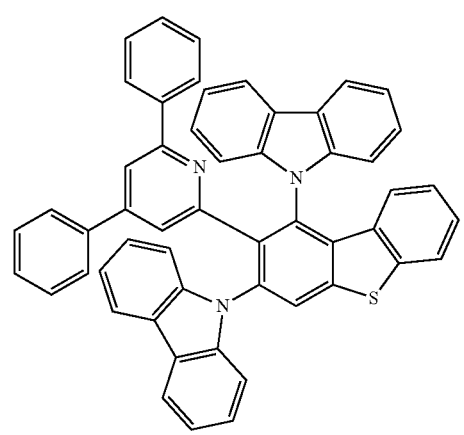
49
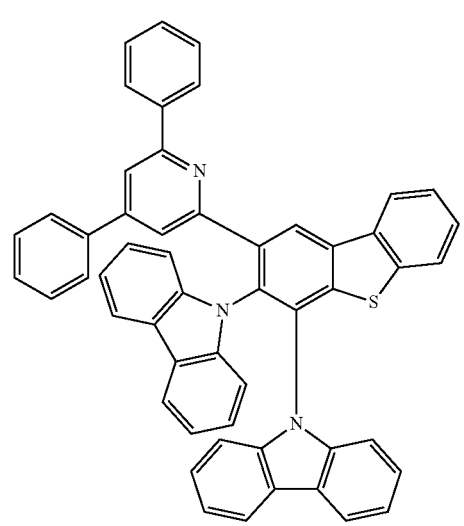
50

51
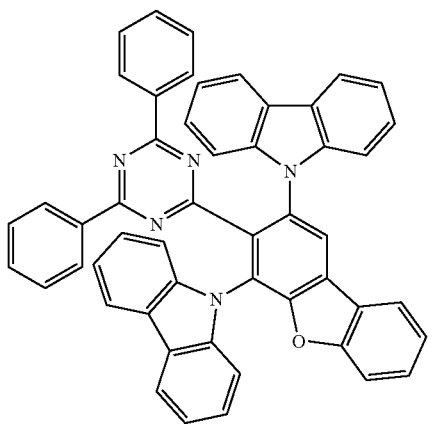
52
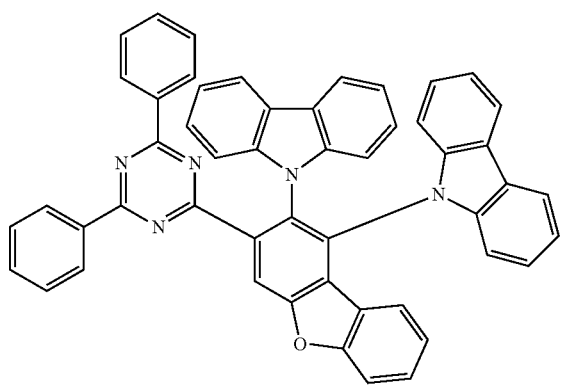
53
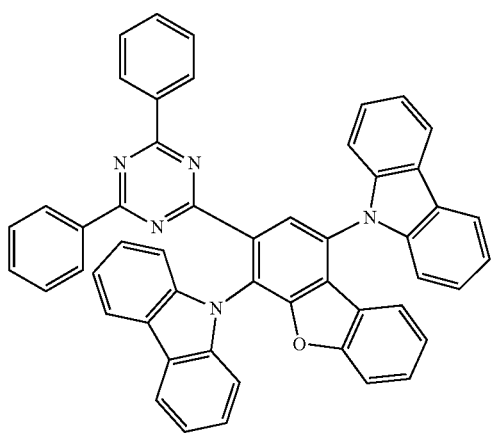
54
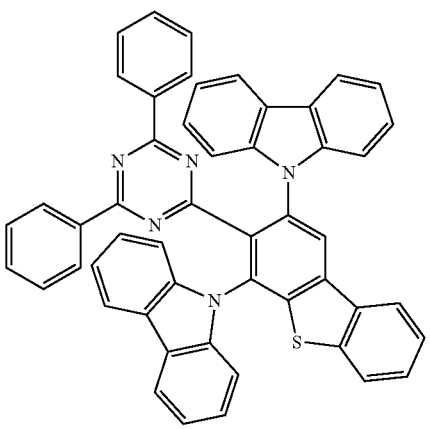
55
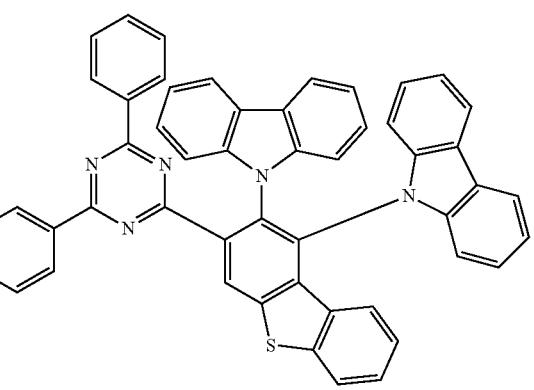
56
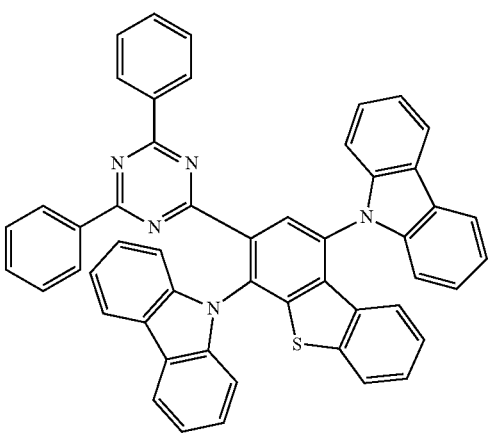

57
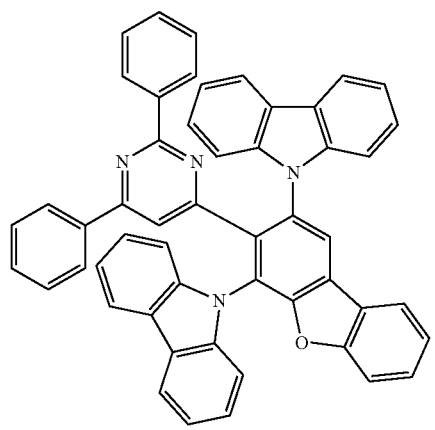
58
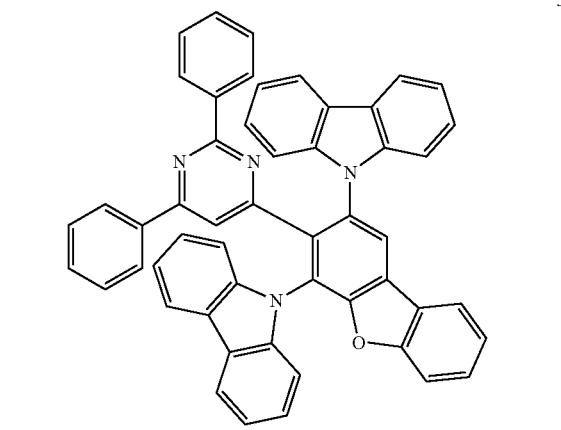
59
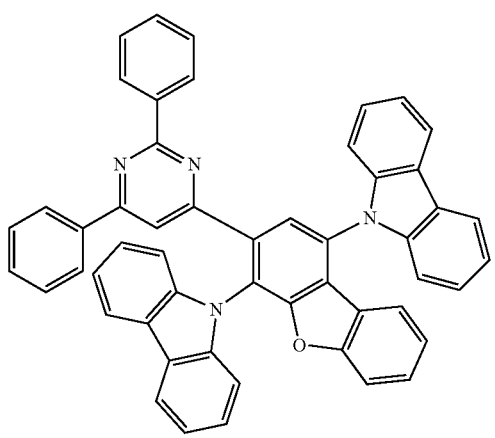
60
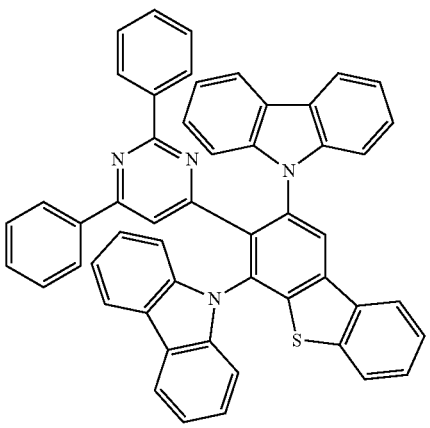
61
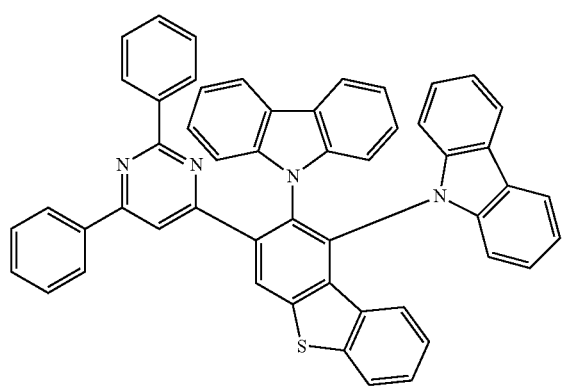
62
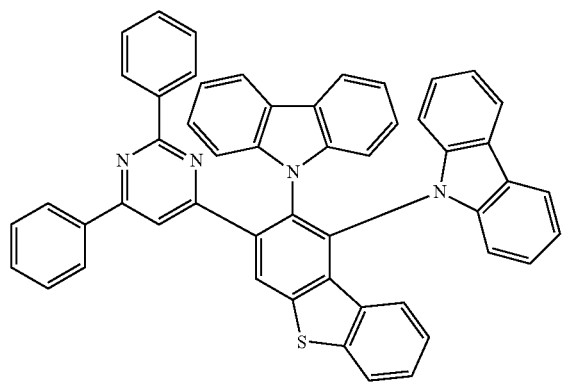
63
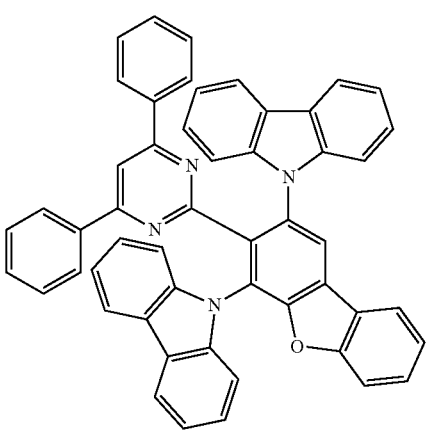

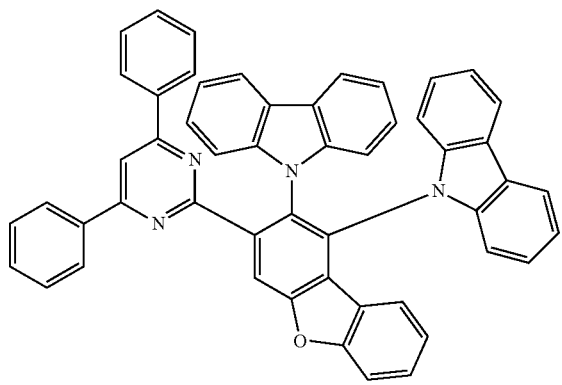
64
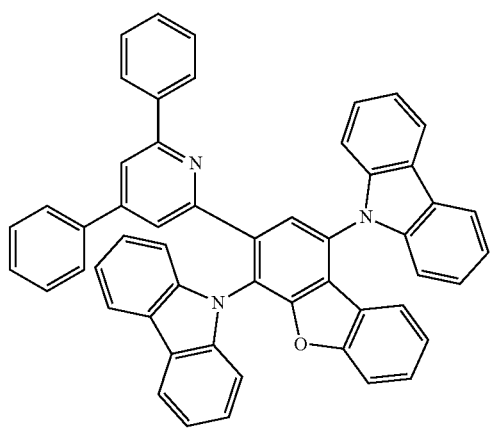
65
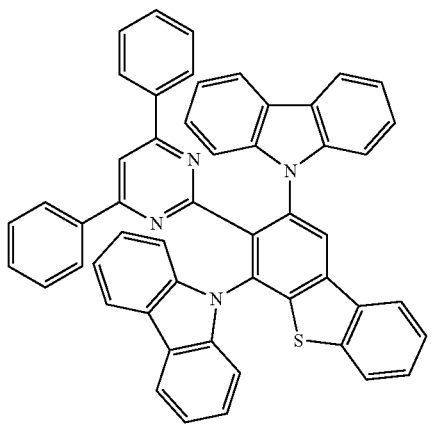
66
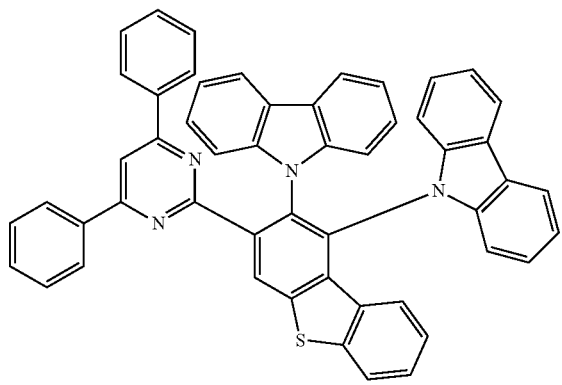
67
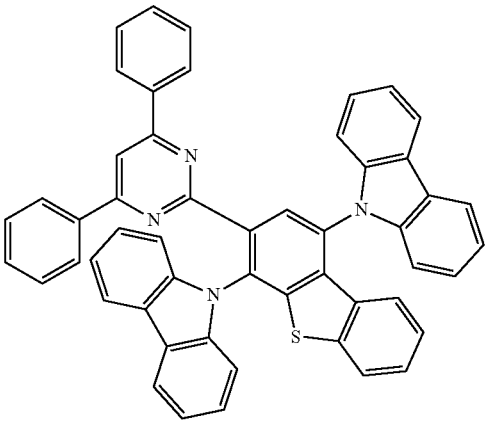
68
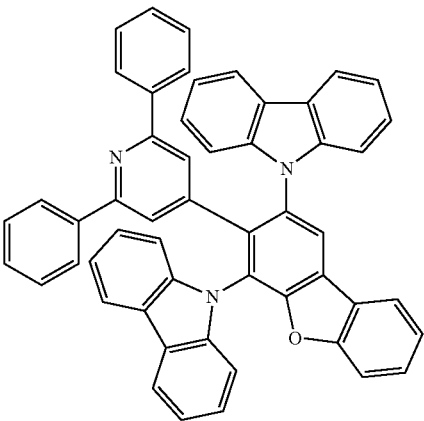
69
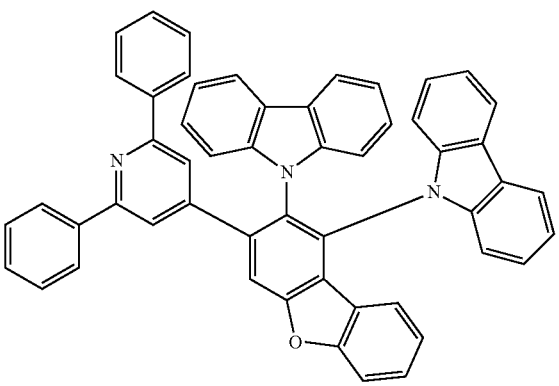
70

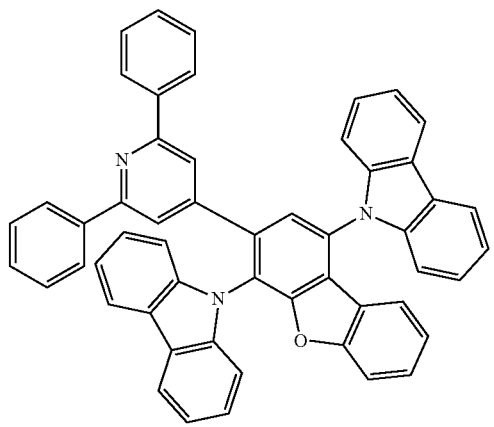
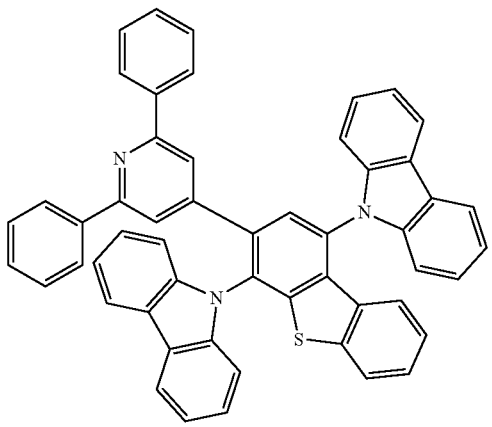

197
-continued
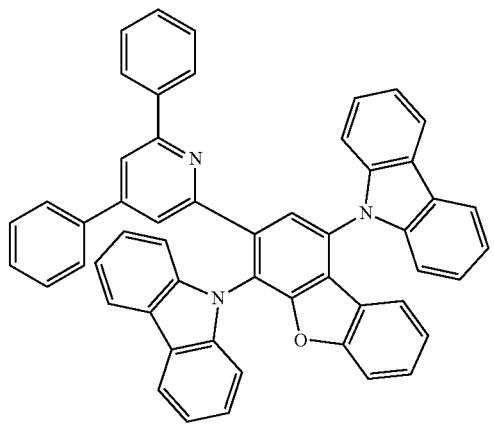
77
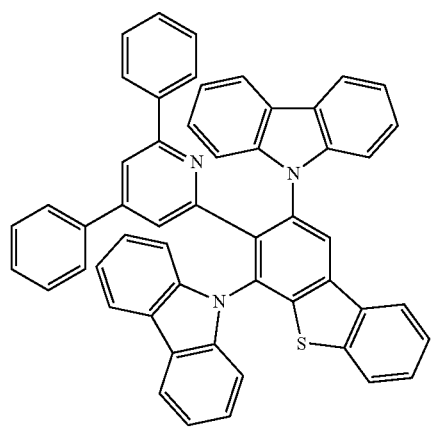
78
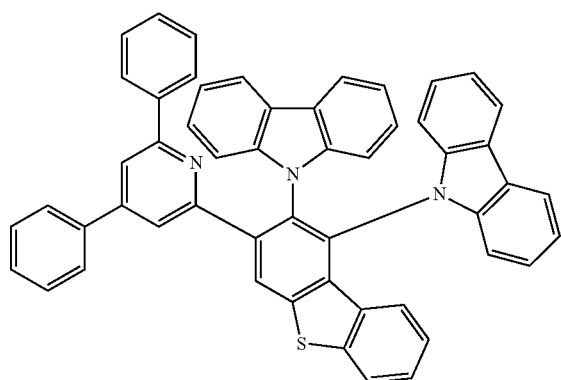
79
198
-continued
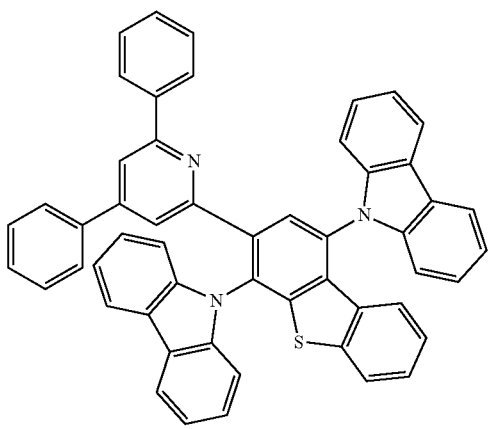
80
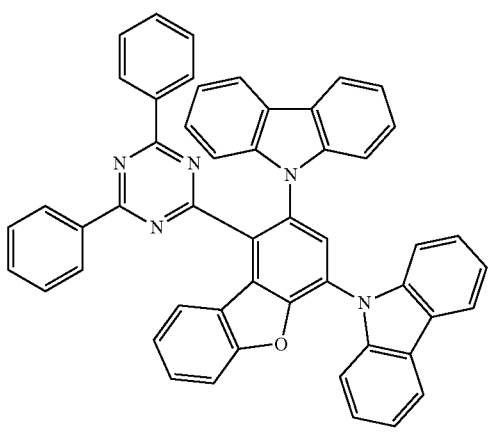
81
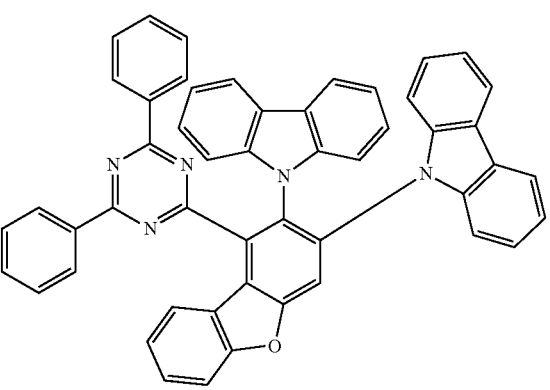
82

199
-continued
83
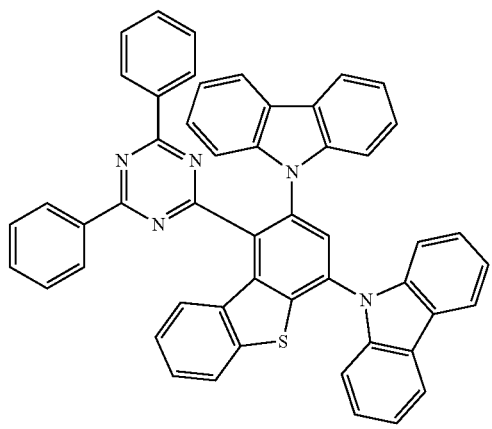
84
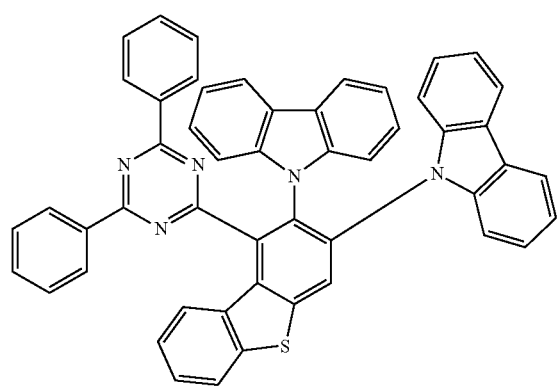
85
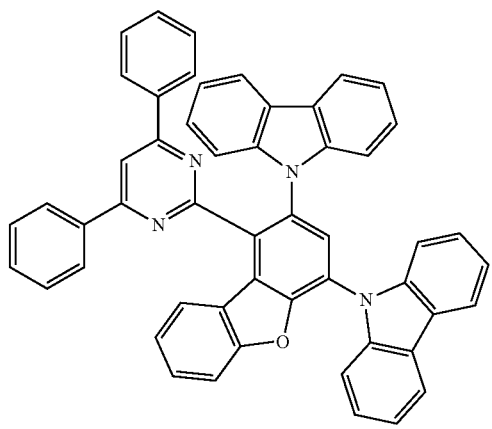
86
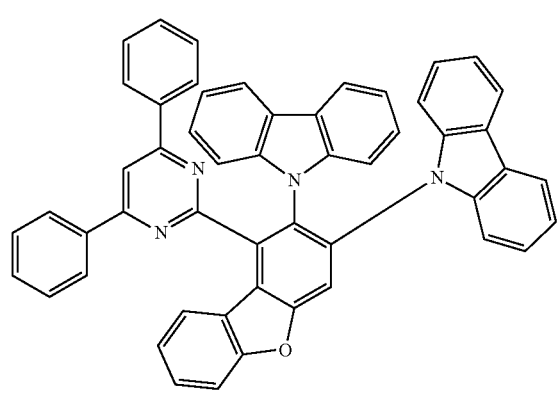
200
-continued
87
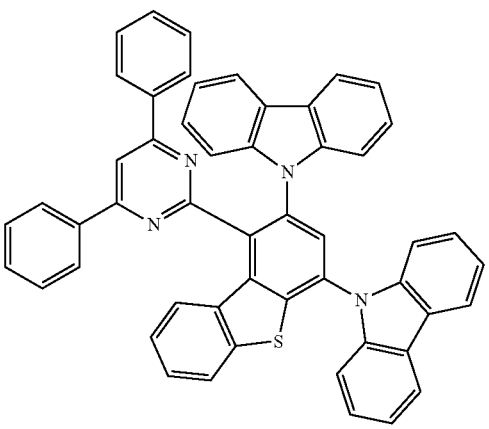
88
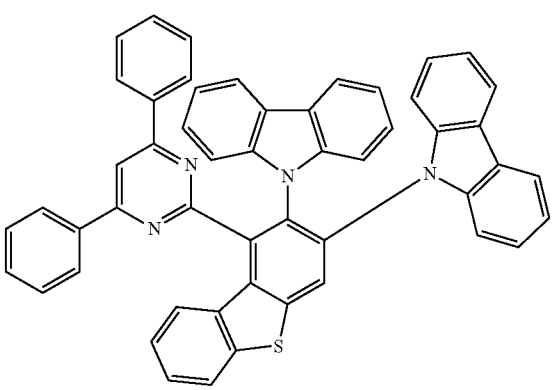
89
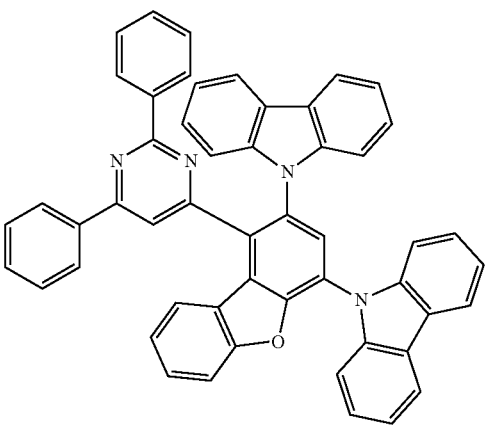
90
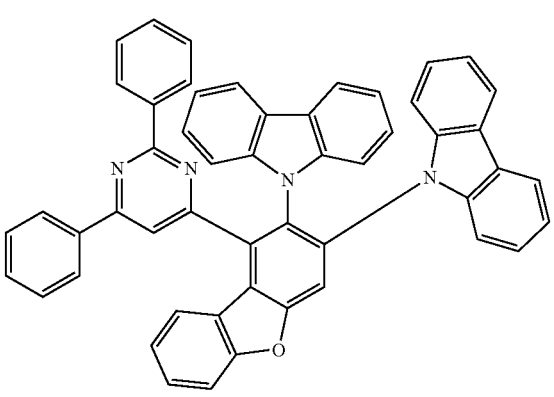

91
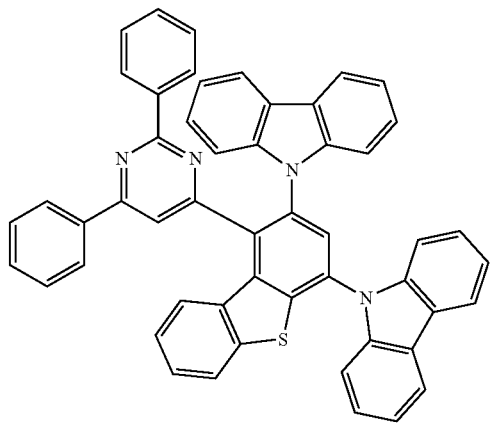
92
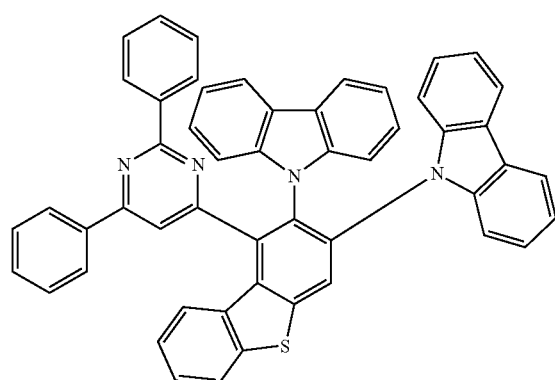
93
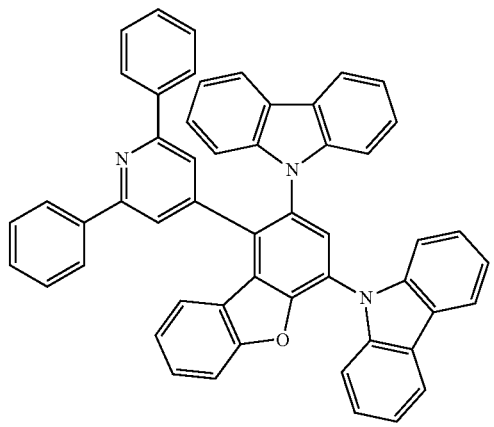
94
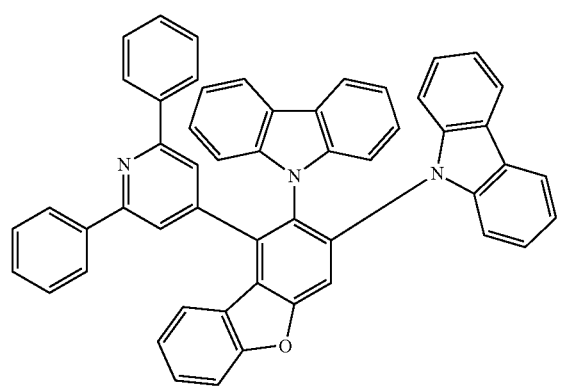
95
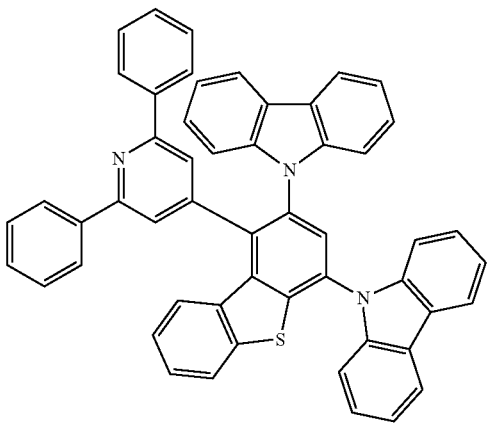
96
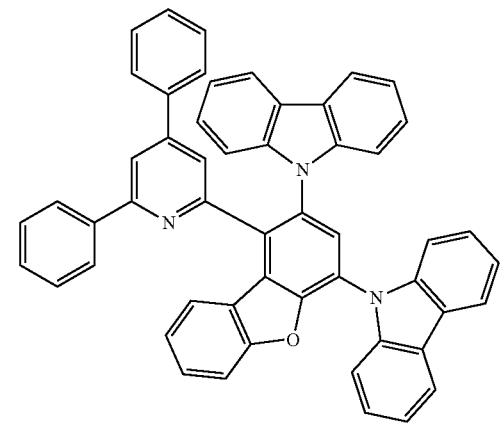
97
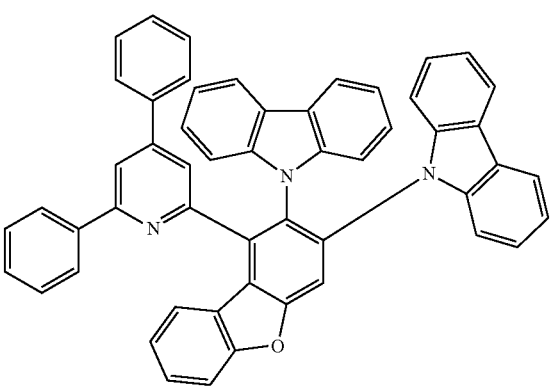
98

203
-continued
99
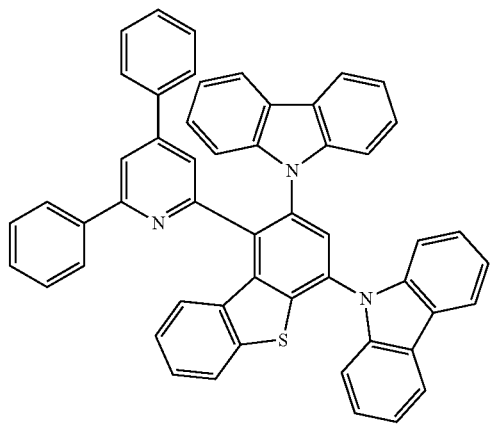
100
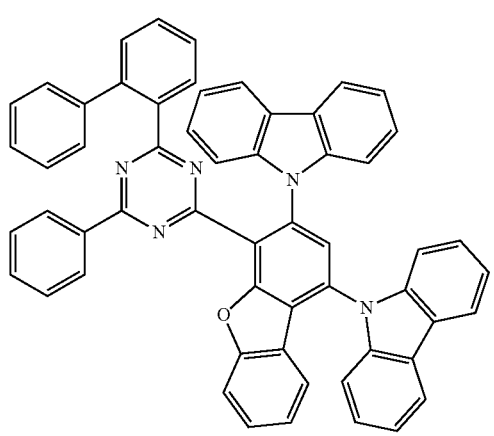
101
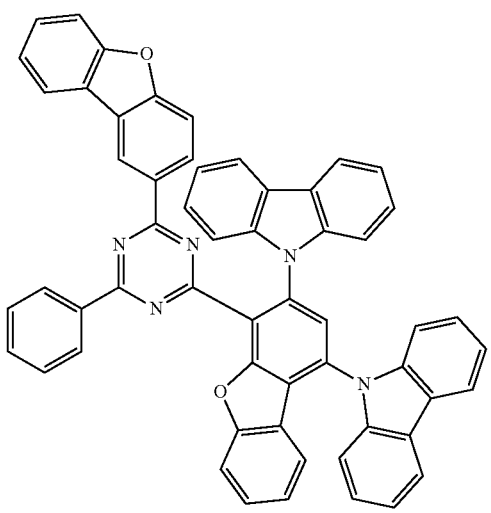
204
-continued
102
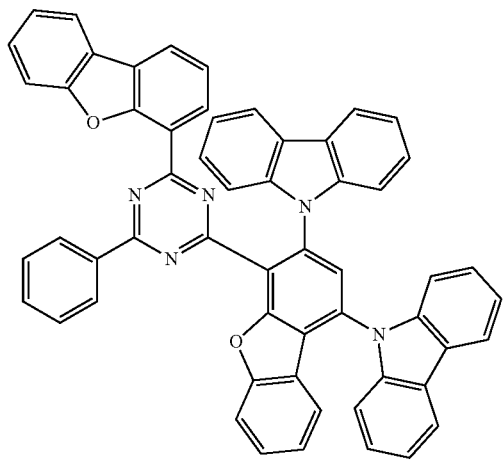
103
104
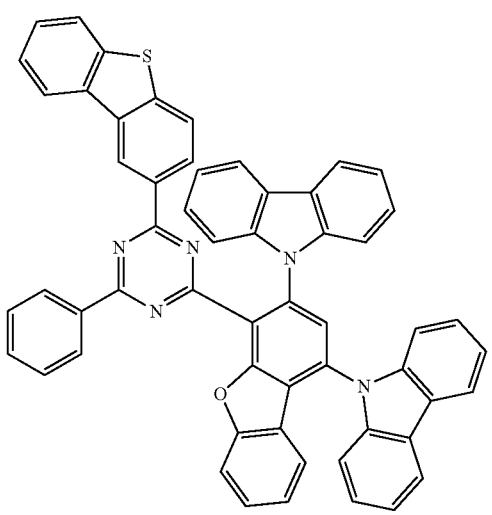

105
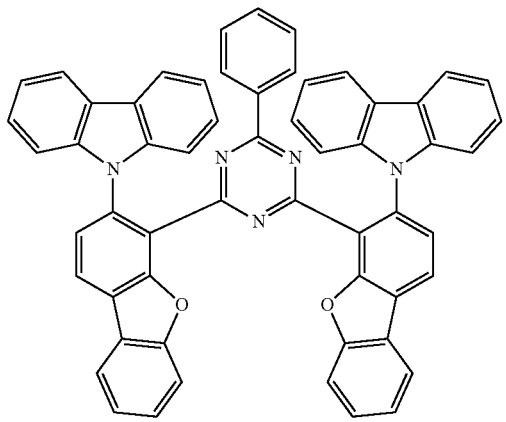
106
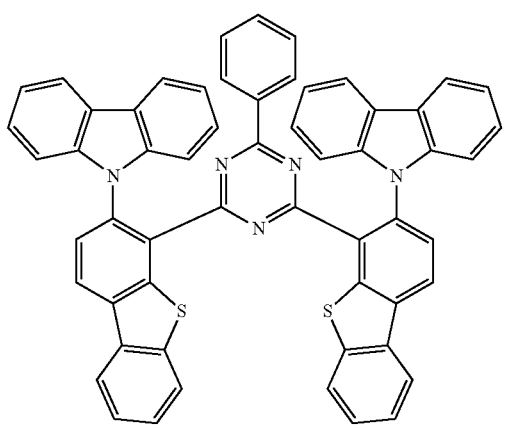
107
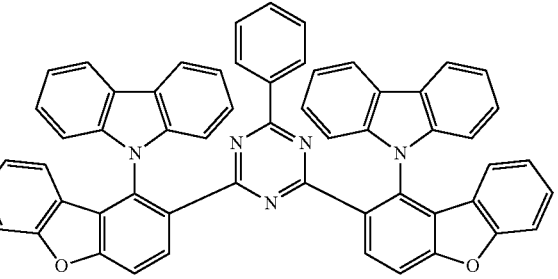
108
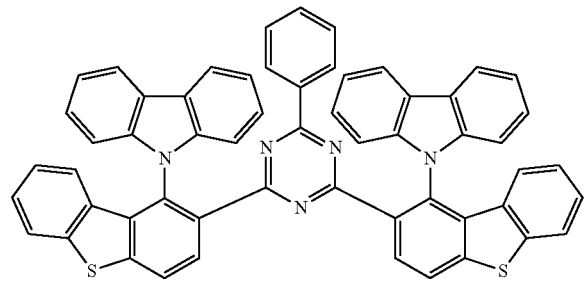
109
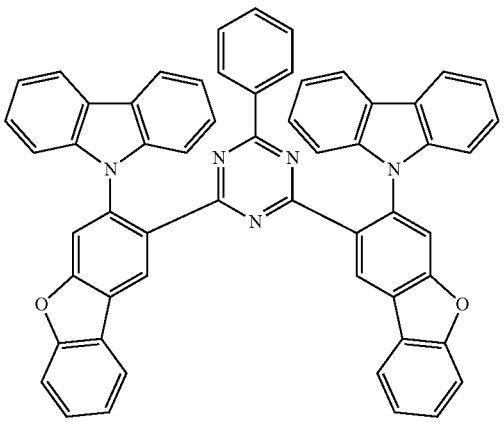
110
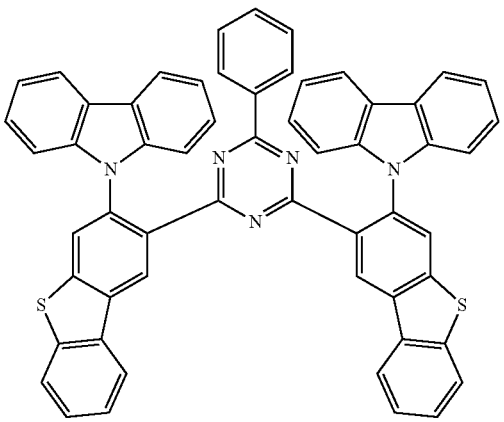
111
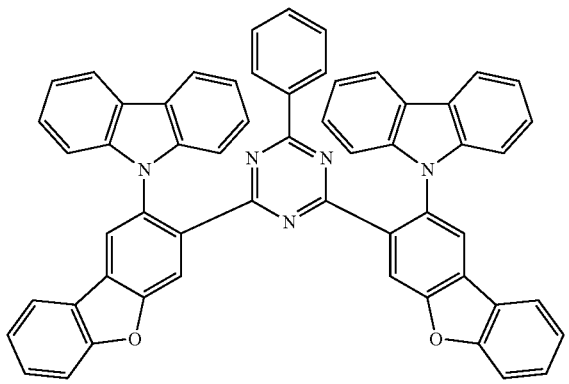
112
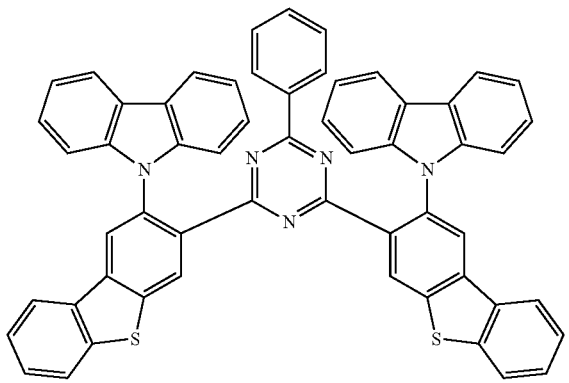

113
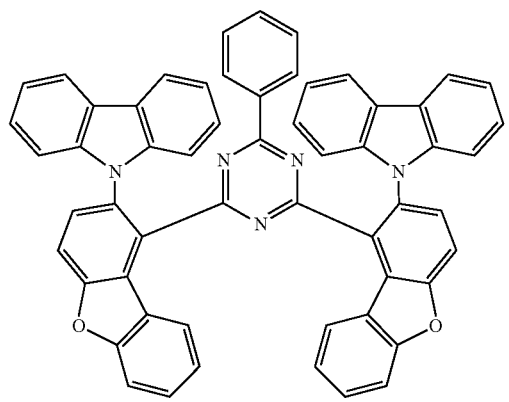
114
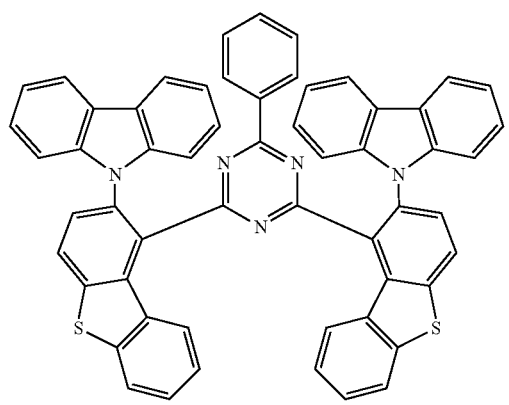
117
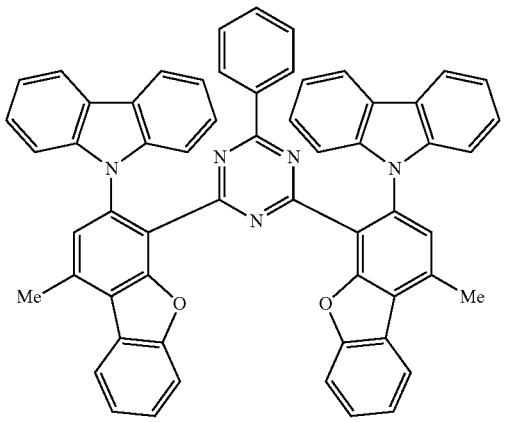
118
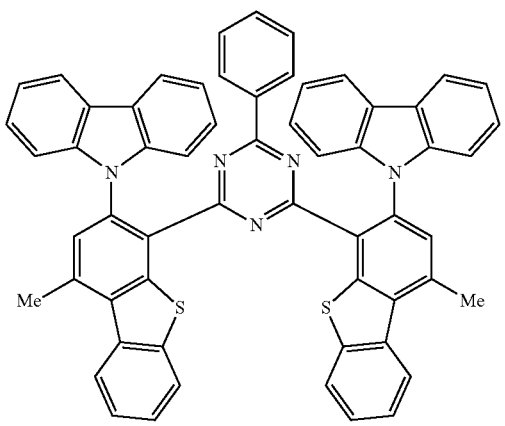
115
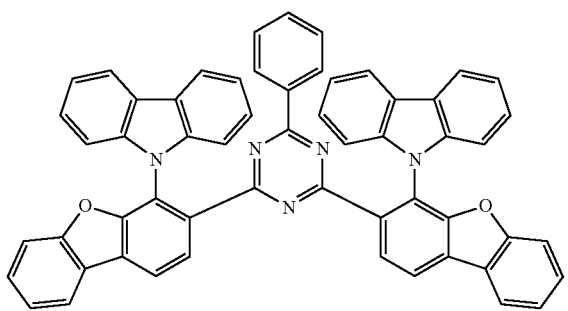
119
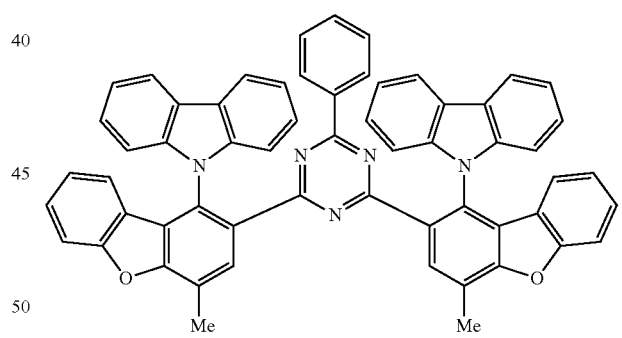
116
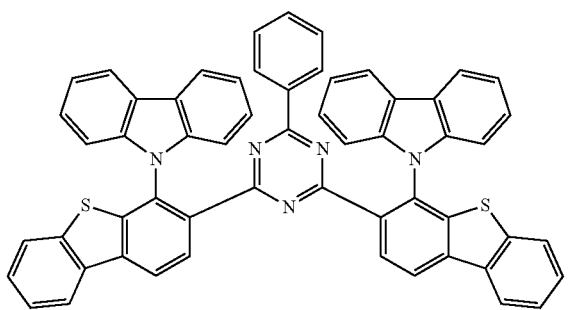
120
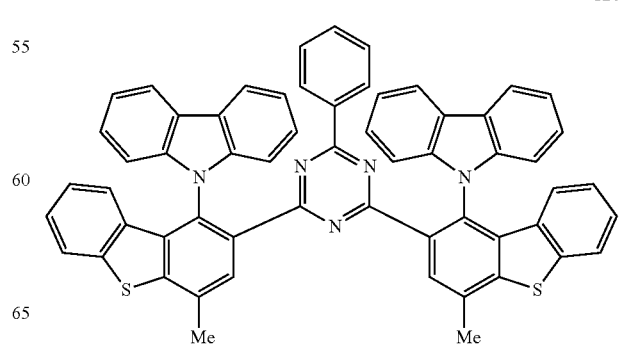

121
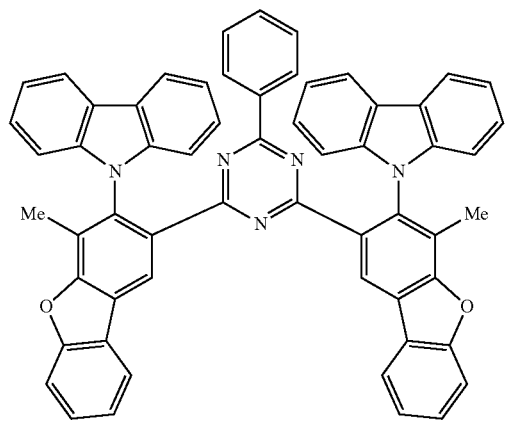
122
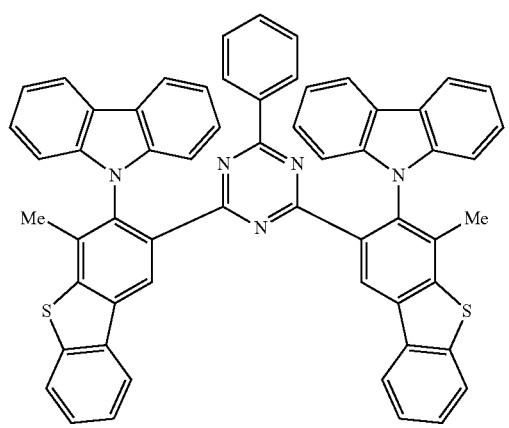
123
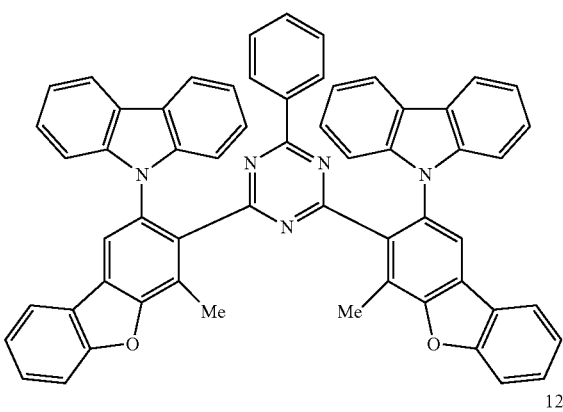
124
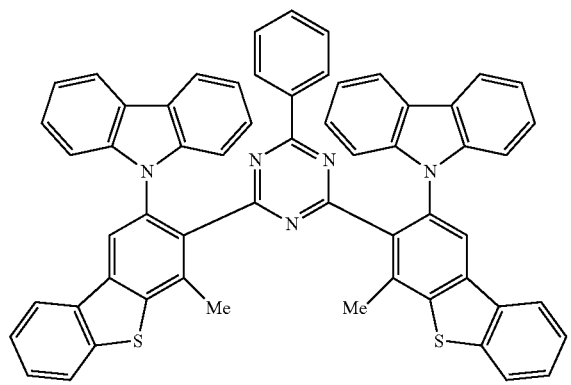
125
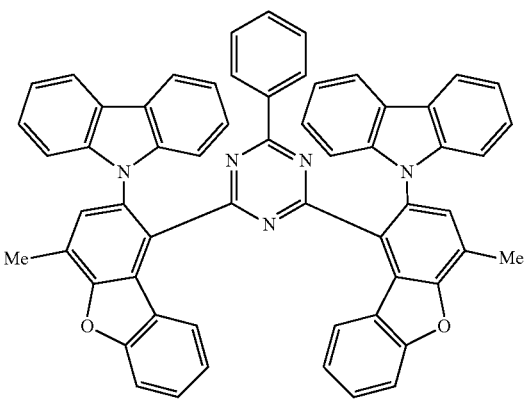
126
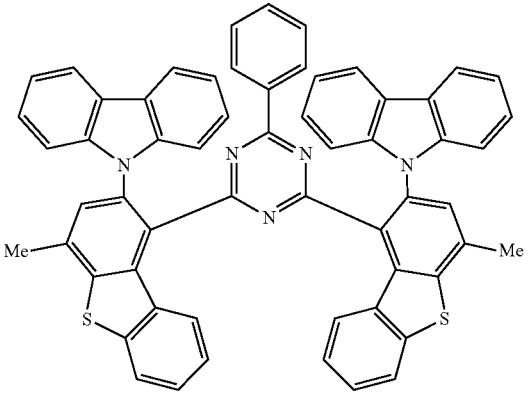
127
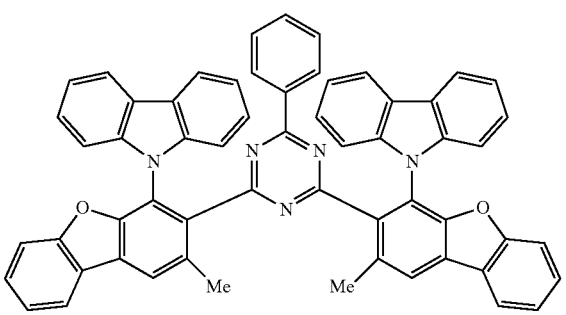
128
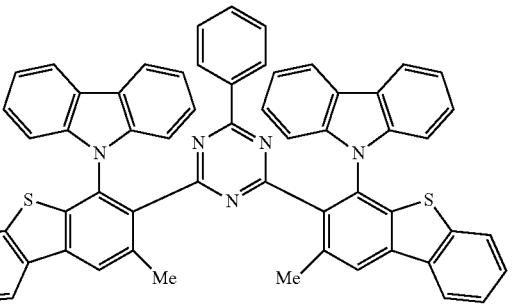

129
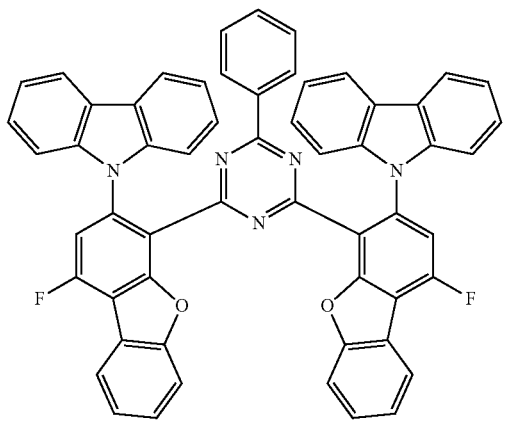
130
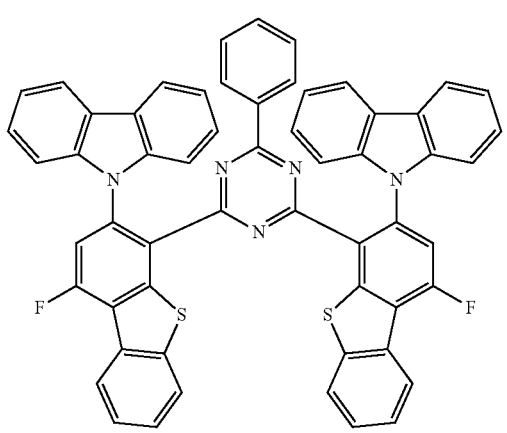
131
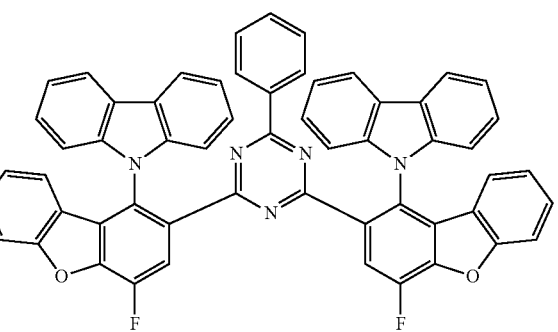
132
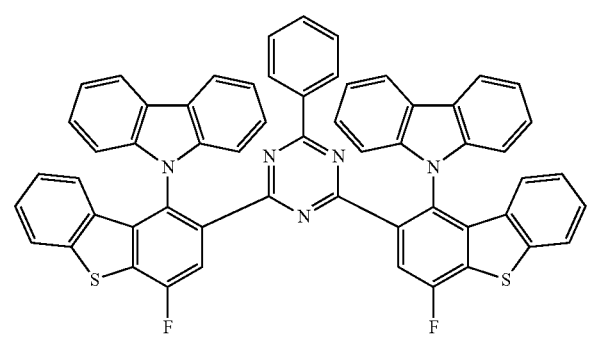
133
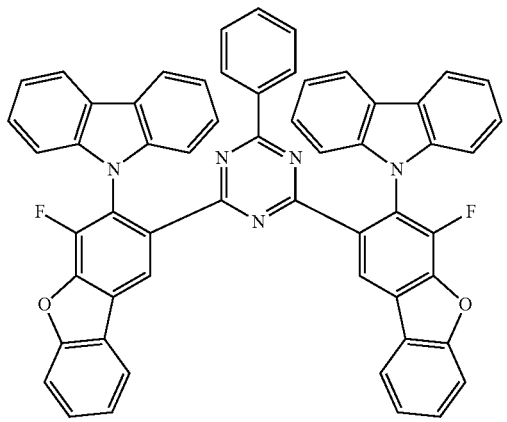
134
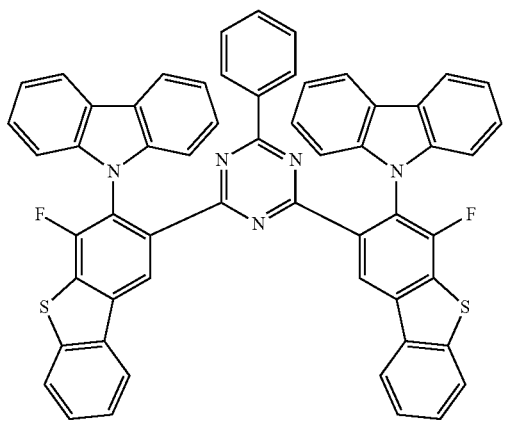
135
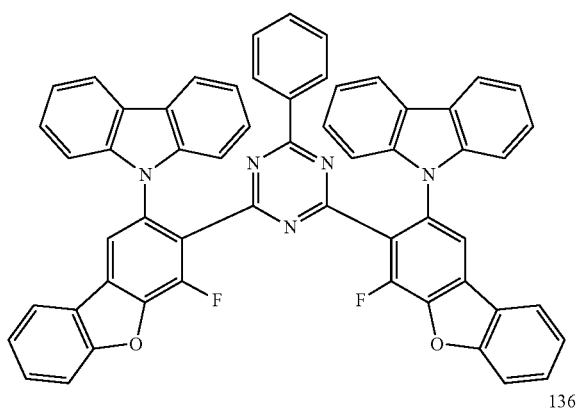
136
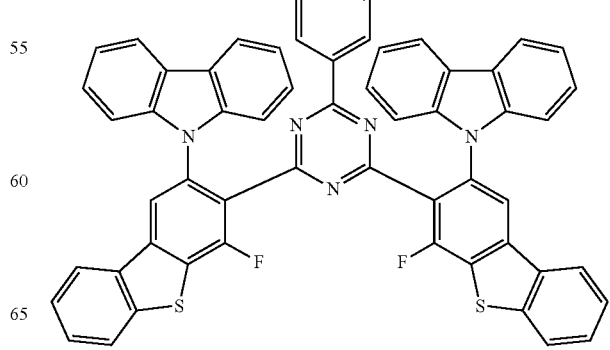

213
-continued
137
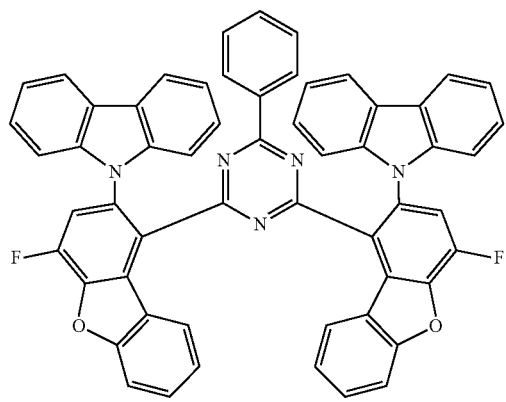
138
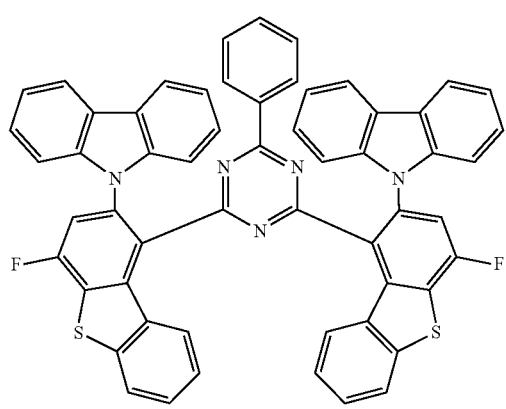
139
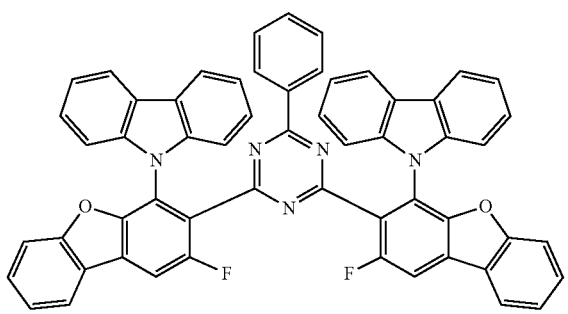
140
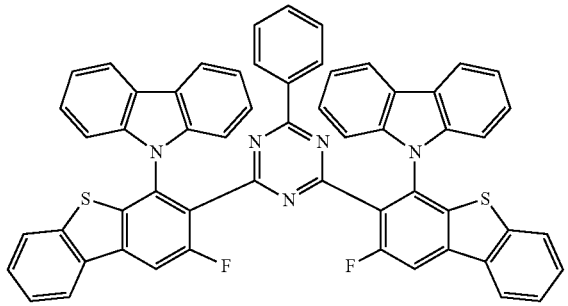
214
-continued
141
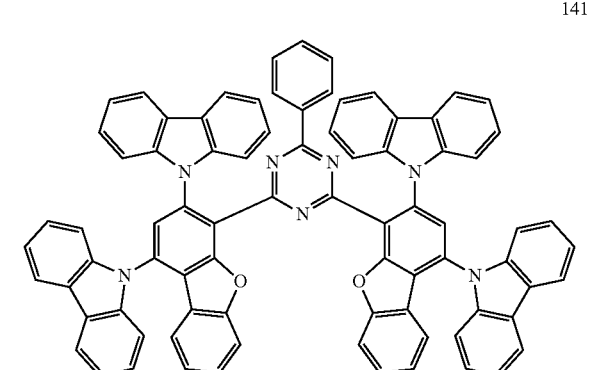
142
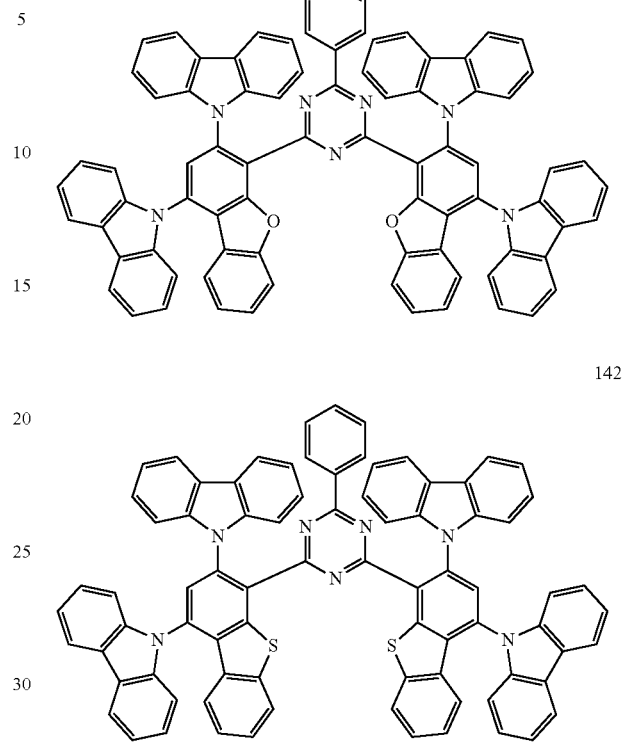
143
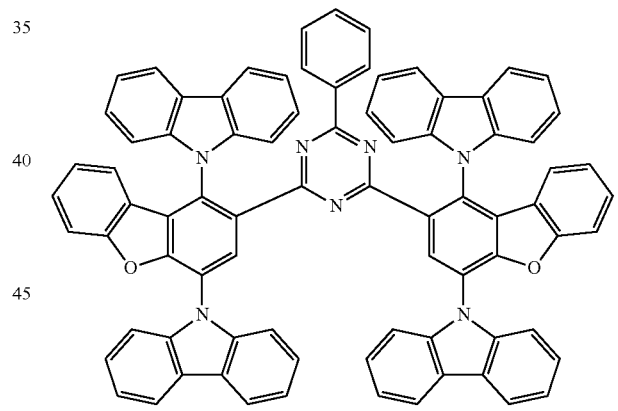
144
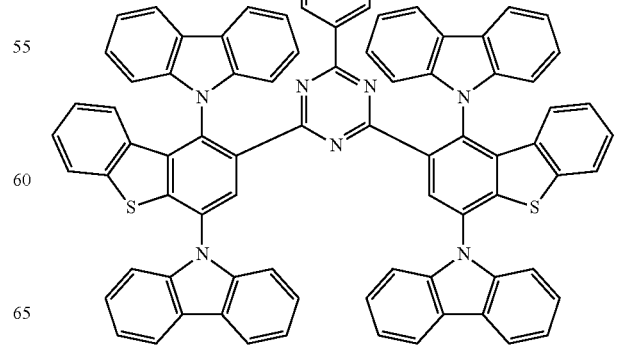

145
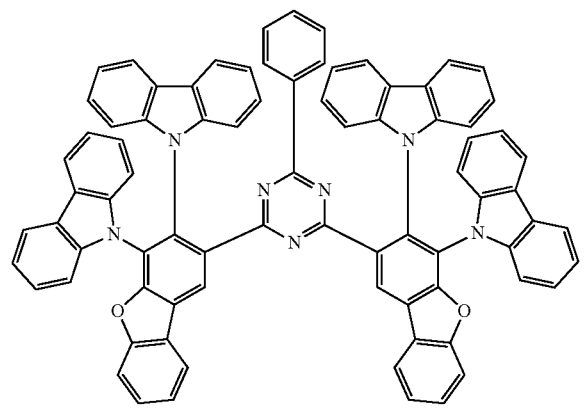
146
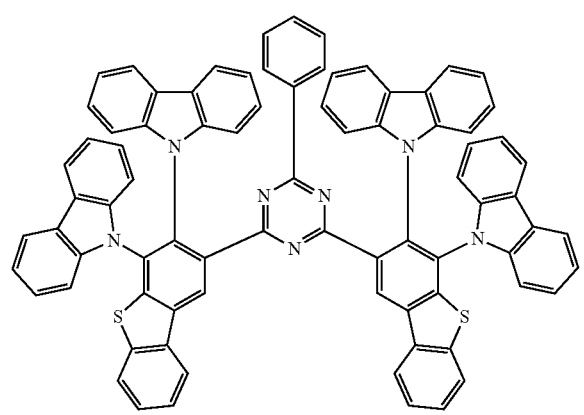
147
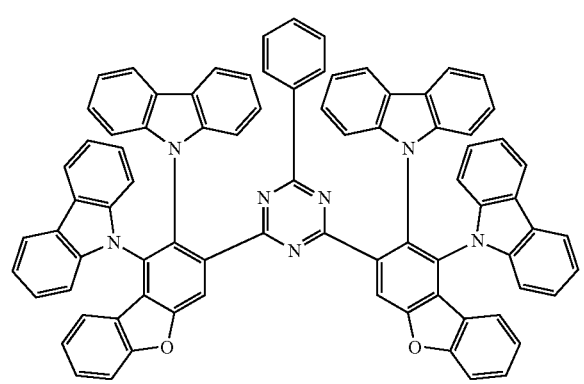
148
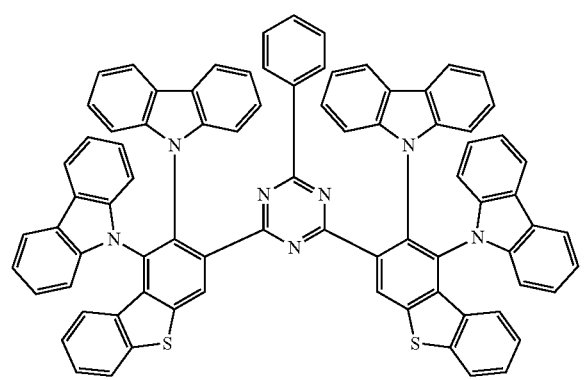
149
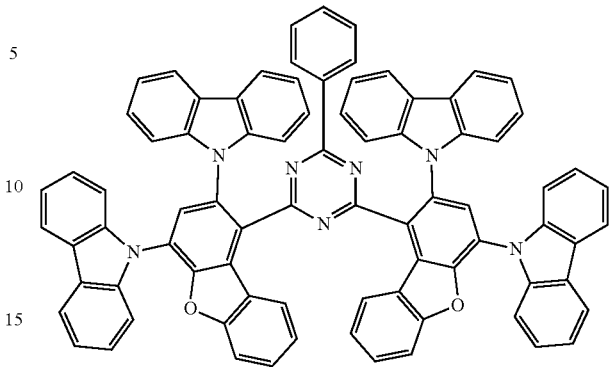
150
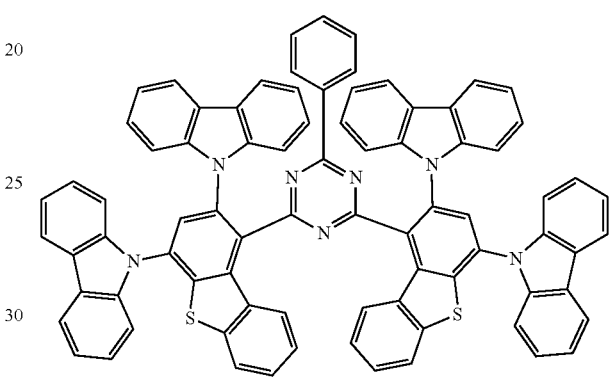
151
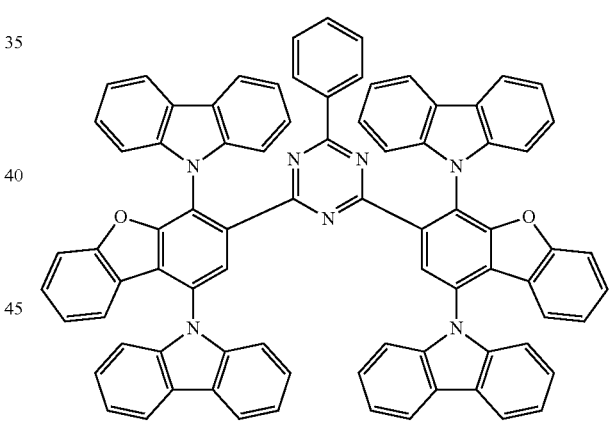
152
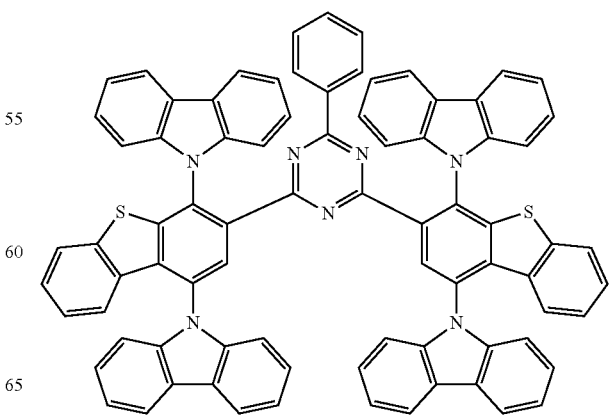

217
-continued
153
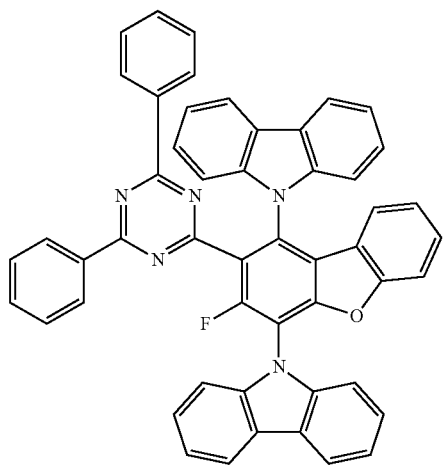
154
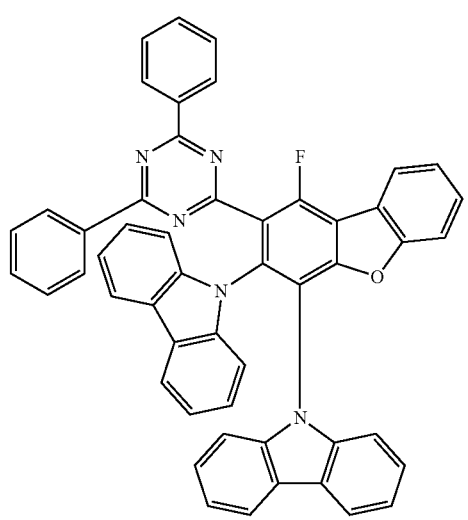
155
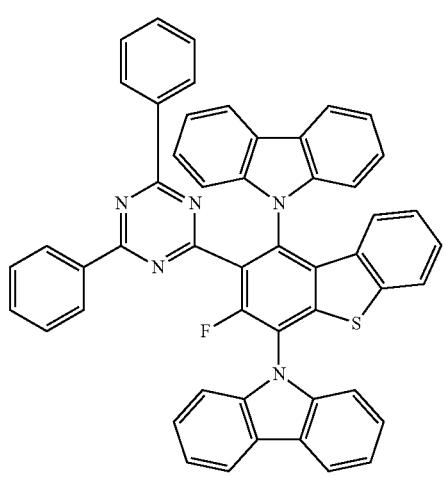
218
-continued
156
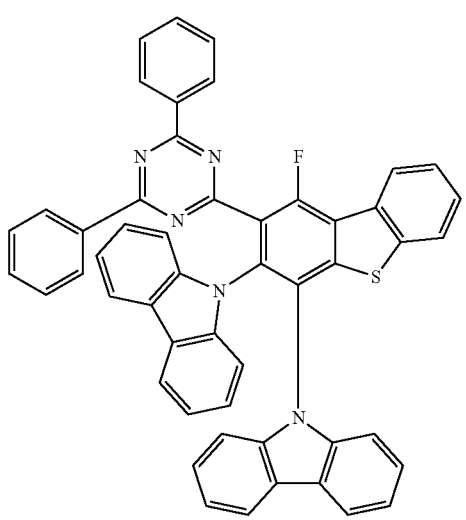
157
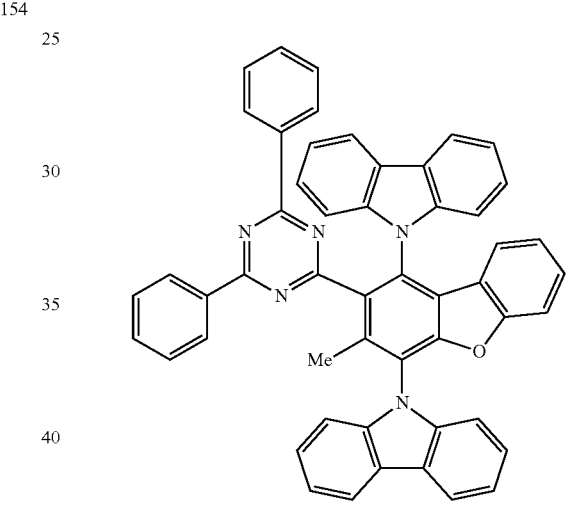
158
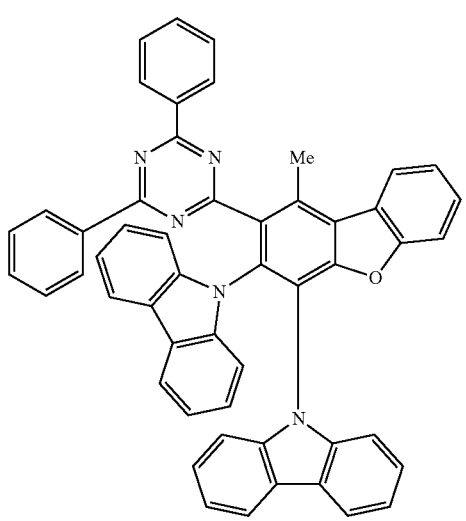

159
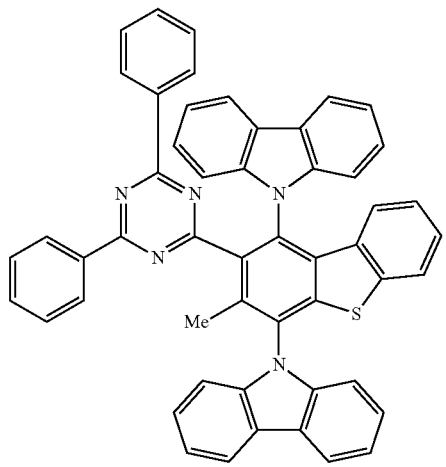
160
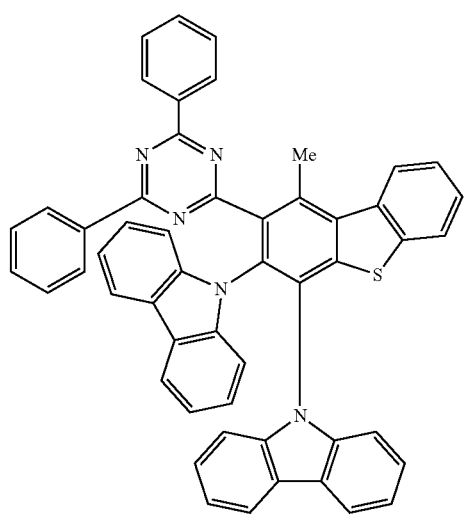
161
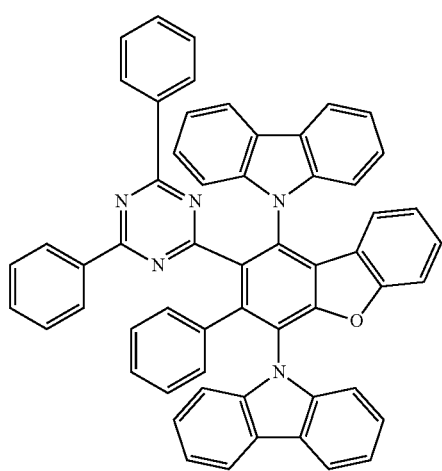
162
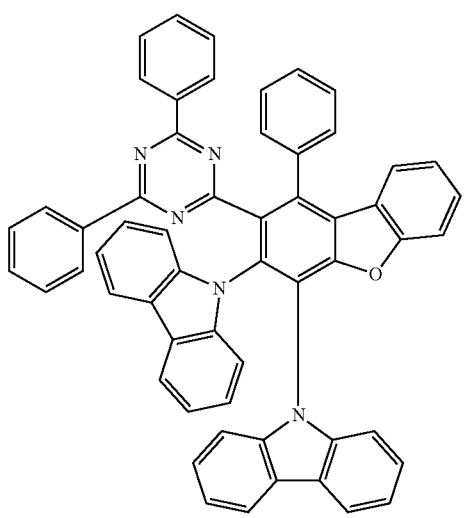
163
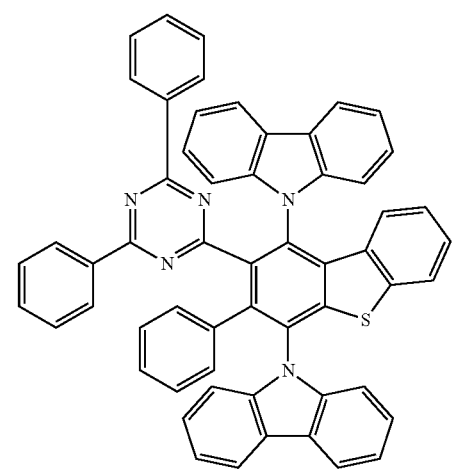
164
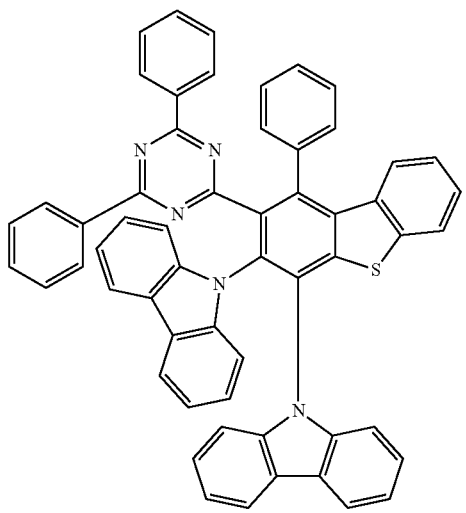

221
-continued
165
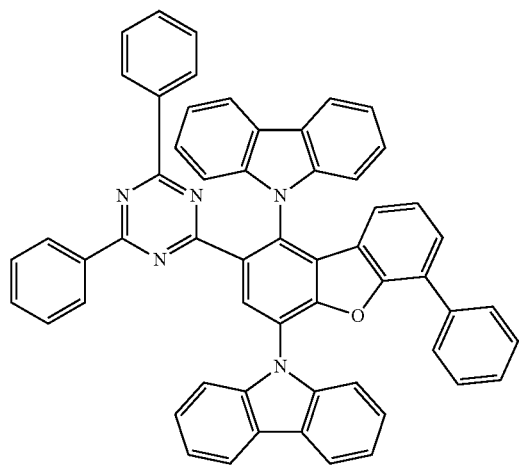
166
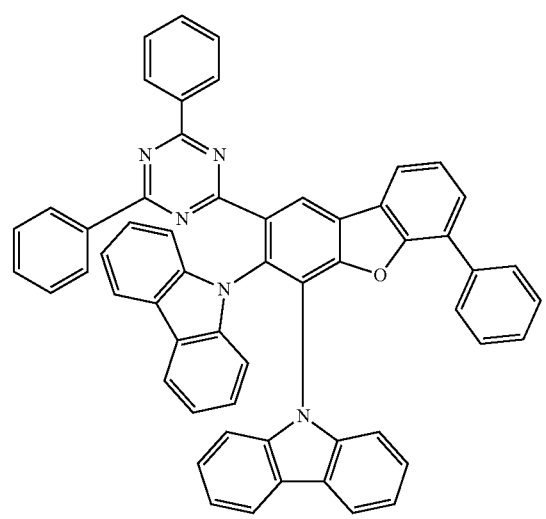
167
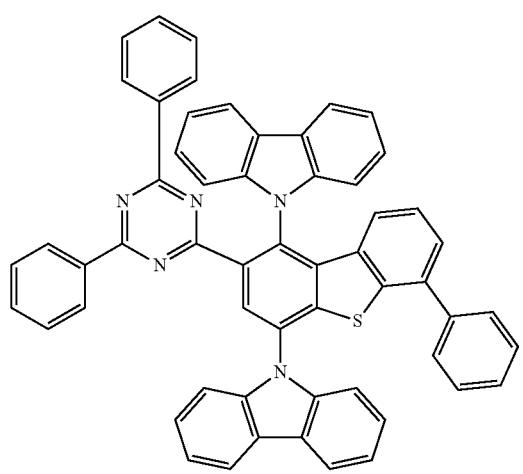
222
-continued
168
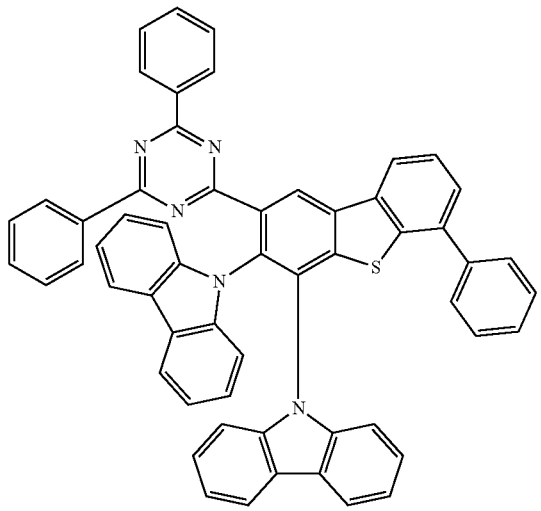
169
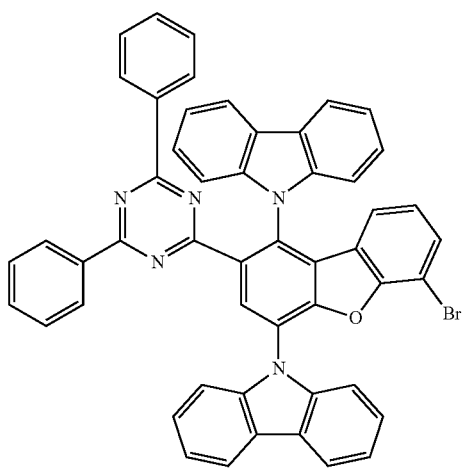
170
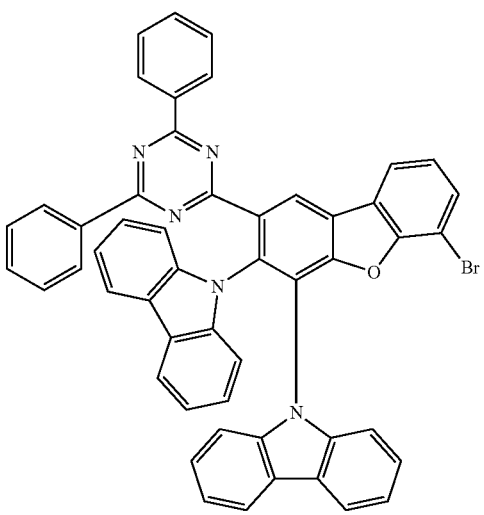

223
-continued
171
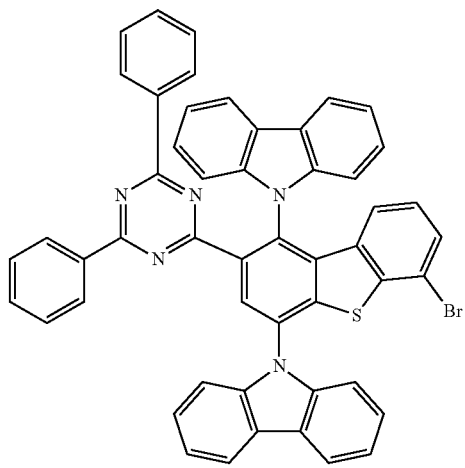
172
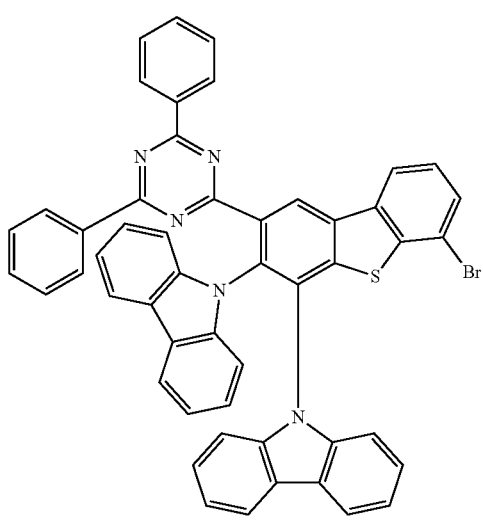
173
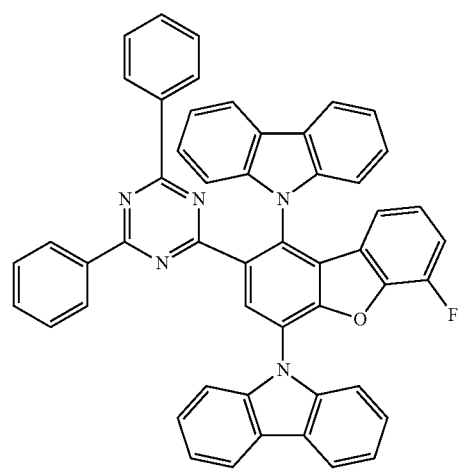
224
-continued
174
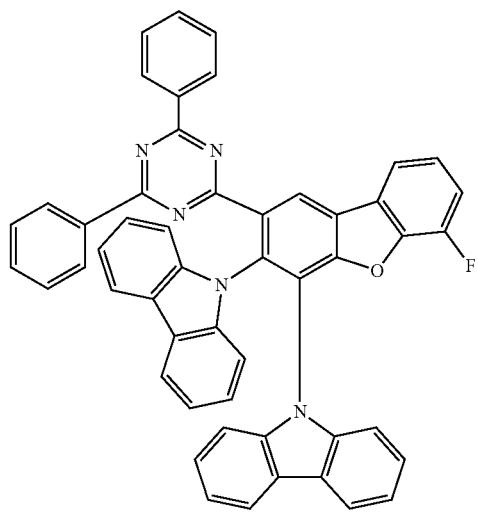
175
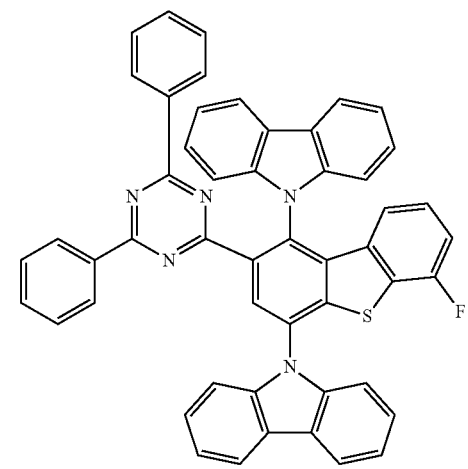
176
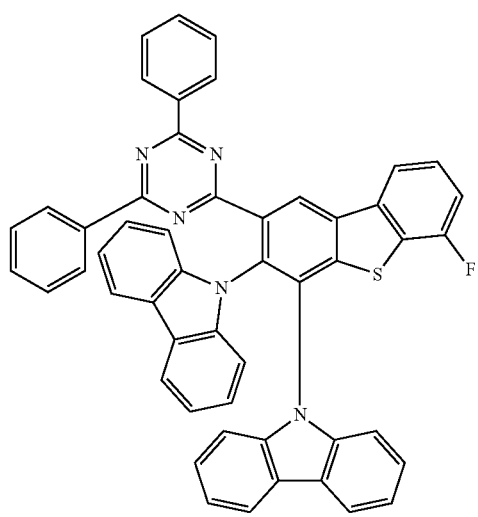

225
-continued
177
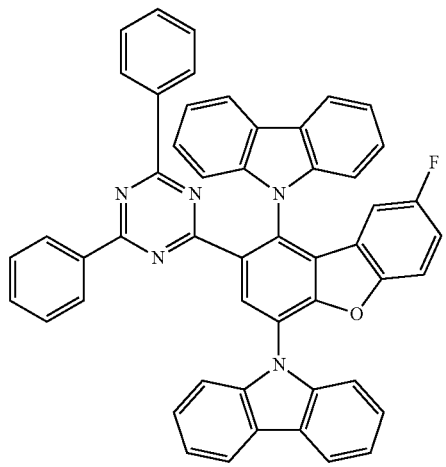
178
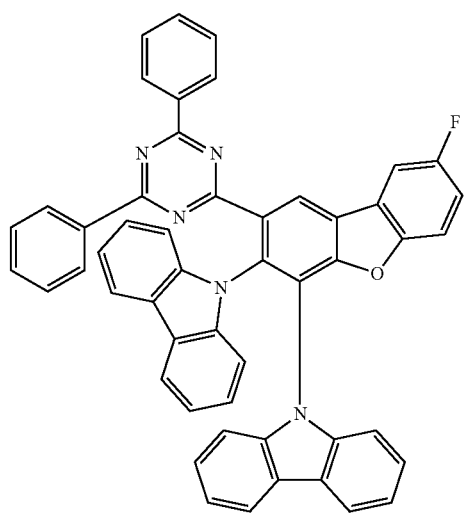
179
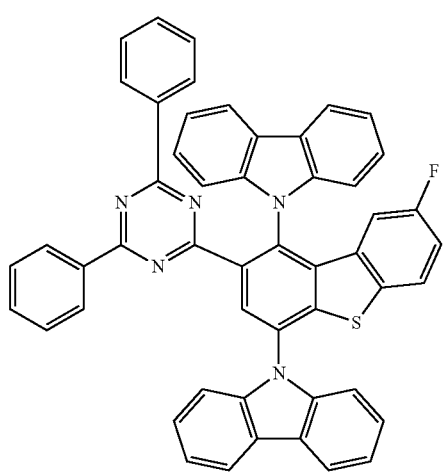
226
-continued
180
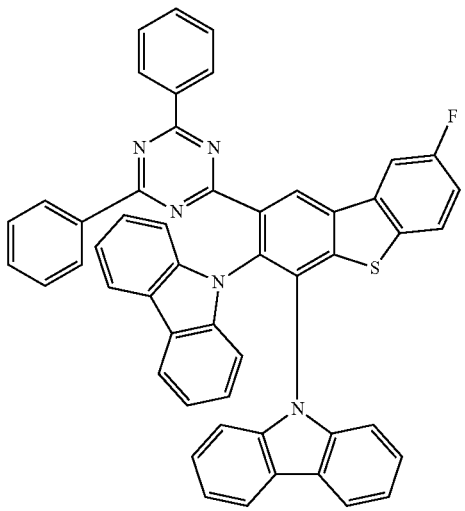
181
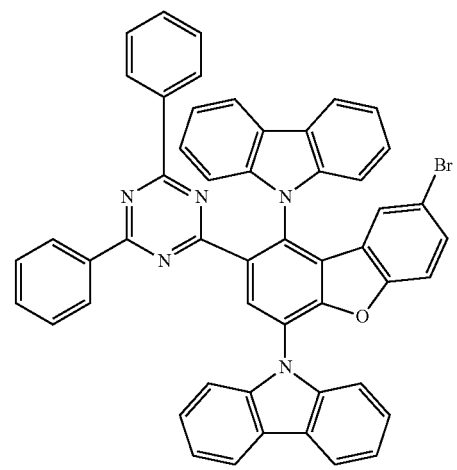
182
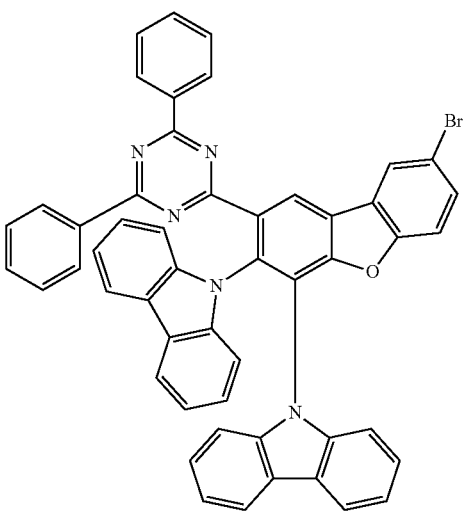

227 -continued
183
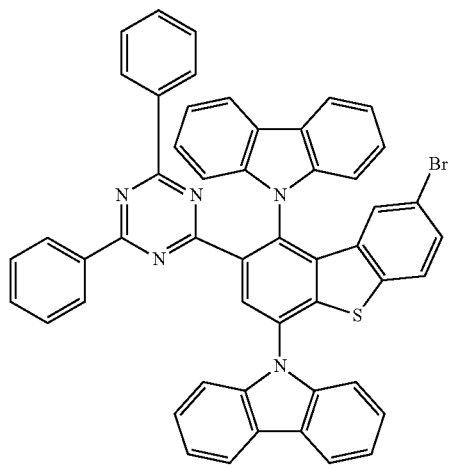
184
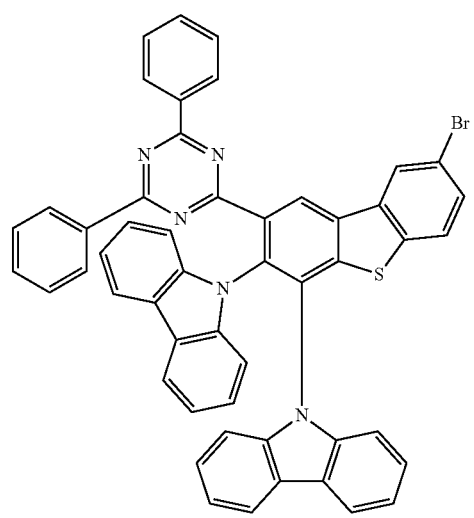
185
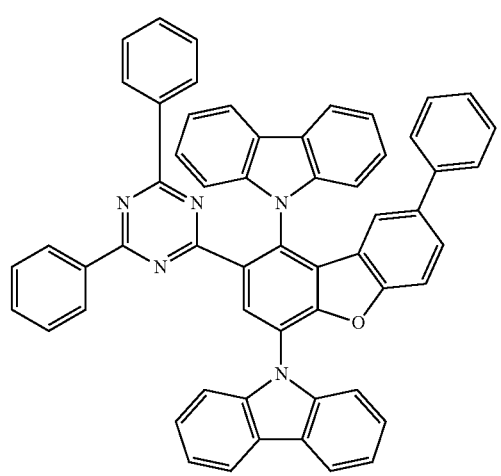
228 -continued
186
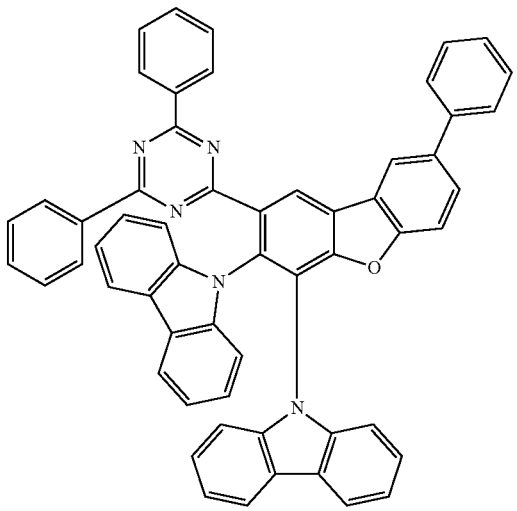
187
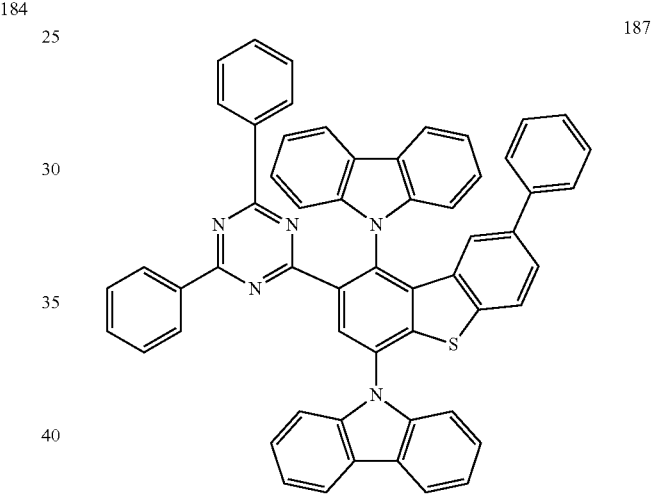
188
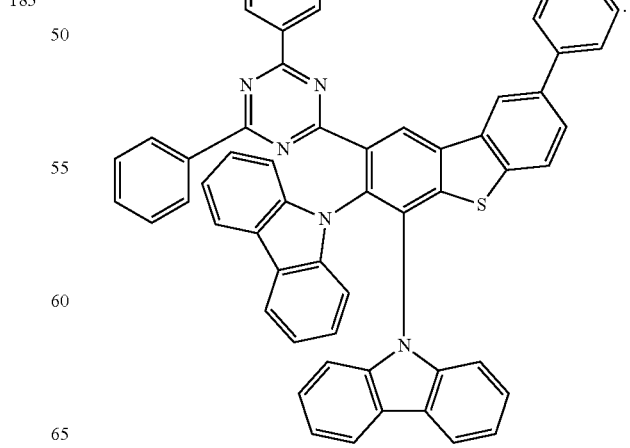

19. A heterocyclic compound represented by the following Formula 1:

[Formula 1]

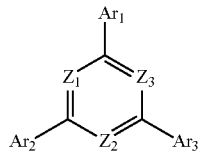

wherein, in Formula 1,
$Z_1$ to $Z_3$ are each independently $CR_1$ or N,
at least one of $Z_1$ to $Z_3$ is N,
$R_1$ is a hydrogen atom, a deuterium atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
$Ar_1$ to $Ar_3$ are each independently a group represented by the following Formula 2, a substituted or unsubstituted aryl group having 6 to 30 ring carbon atoms, or a substituted or unsubstituted heteroaryl group having 2 to 30 ring carbon atoms, and
at least one of $Ar_1$ to $Ar_3$ is a group represented by Formula 2:

[Formula 2]

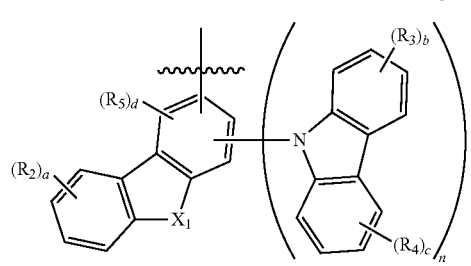

in Formula 2,
$X_1$ is O or S,
"n" is an integer of 1 to 3,
"a" to "c" are each independently an integer of 0 to 4,
"d" is an integer of 0 to 2, and
$R_2$ is a hydrogen atom, a deuterium atom, a halogen atom, a substituted or unsubstituted alkyl group having 1 to 10 carbon atoms, or a substituted or unsubstituted aryl group having 6 to 30 ring carbon atoms,
$R_3$ to $R_5$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
when only one of $Ar_1$ to $Ar_3$ is a group represented by Formula 2 above, "n" is 2 or 3, and
at least one of the carbazole moieties in Formula 2 is bonded in an ortho relationship with respect to the nitrogen-containing monocycle of Formula 1.

20. The heterocyclic compound as claimed in claim 19, wherein each of $Z_1$ to $Z_3$ is N.

21. The heterocyclic compound as claimed in claim 19, wherein the compound represented by Formula 1 is represented by the following Formula 1-1 or Formula 1-3:

[Formula 1-1]

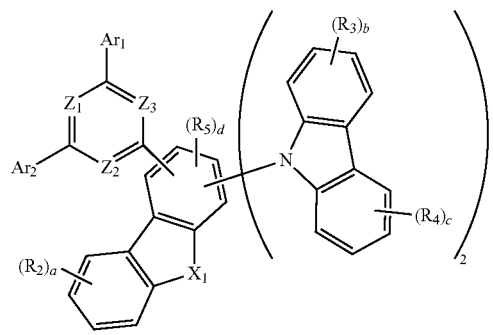

[Formula 1-3]

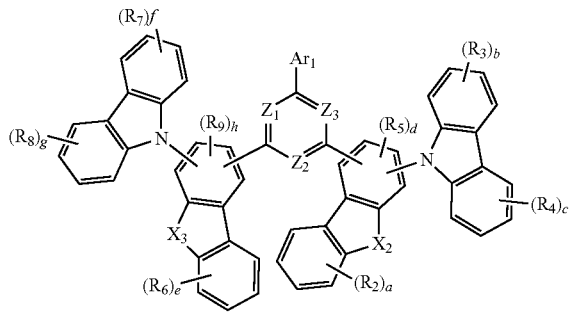

in Formulae 1-1 and 1-3,
$Z_1$ to $Z_3$, $Ar_1$, $Ar_2$, $R_2$ to $R_5$, "a" to "d" and $X_1$ are defined the same as those of Formulae 1 and 2, and
in Formula 1-3,
$X_2$ and $X_3$ are each independently O or S,
$R_6$ to $R_9$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms,
"e" to "g" are each independently an integer of 0 to 4, and
"h" is an integer of 0 to 2.

22. The heterocyclic compound as claimed in claim 19, wherein the compound represented by Formula 1 is represented by the following Formula 1-2 or Formula 1-4:

[Formula 1-2]

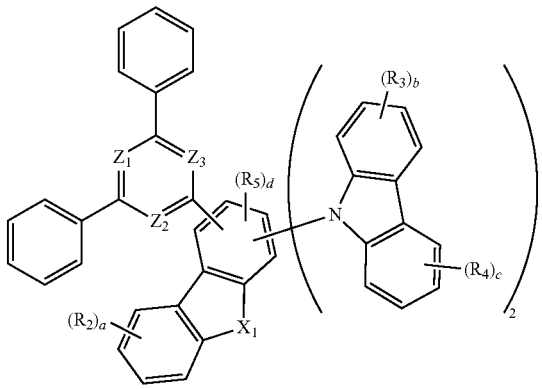

[Formula 1-4]

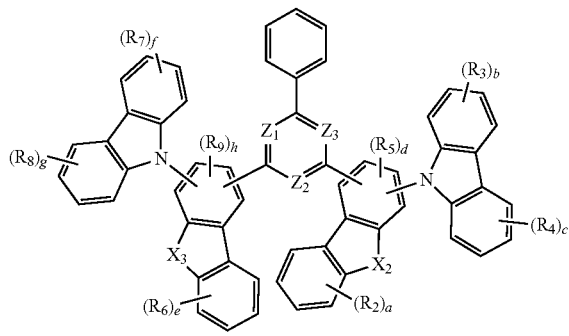

in Formulae 1-2 and 1-4, $Z_1$ to $Z_3$, $R_2$ to $R_5$, "a" to "d" and $X_1$ are defined the same as those of Formulae 1 and 2, and in Formula 1-4, $X_2$ and $X_3$ are each independently O or S, $R_6$ to $R_9$ are each independently a hydrogen atom, a deuterium atom, a halogen atom, a substituted or unsubstituted alkyl group having 1 to 10 carbon atoms, a substituted or unsubstituted aryl group having 6 to 30 ring carbon atoms, or a substituted or unsubstituted heteroaryl group having 2 to 30 ring carbon atoms, "e" to "g" are each independently an integer of 0 to 4, and "h" is an integer of 0 to 2.

23. The heterocyclic compound as claimed in claim 19, wherein the heterocyclic compound is a compound of the following Compound Group 1:

[Compound Group 1]

1

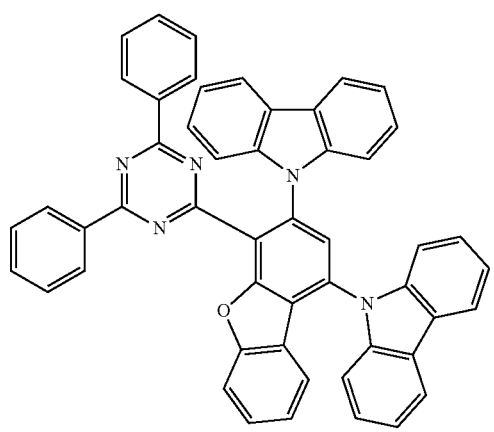

2

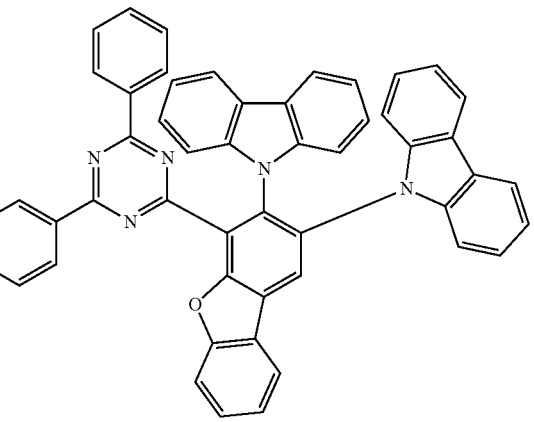

3

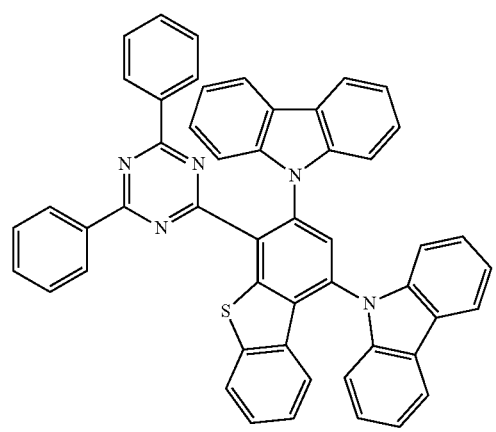

4

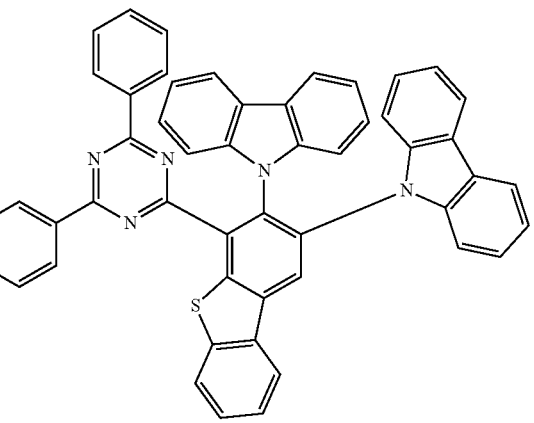

233
-continued
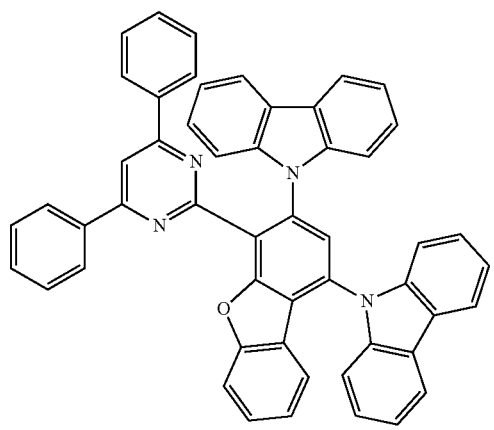
5
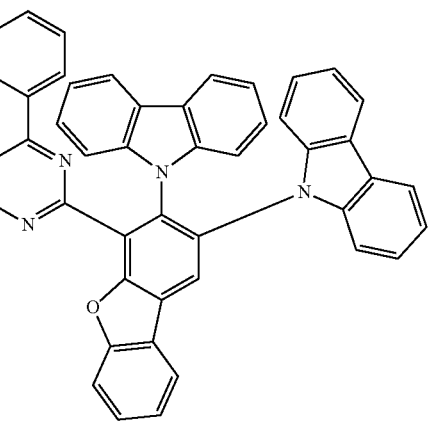
6
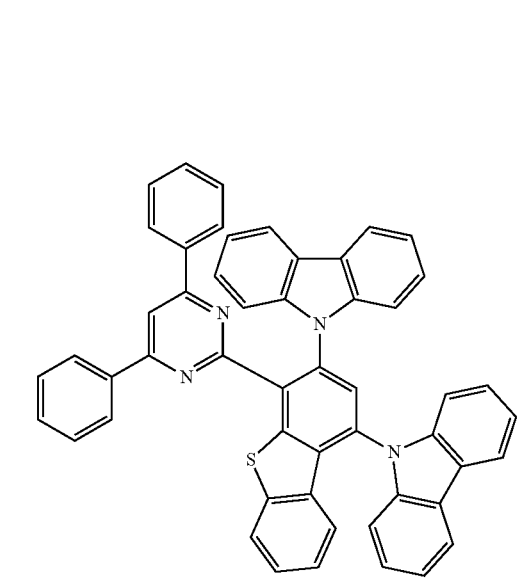
7
234
-continued
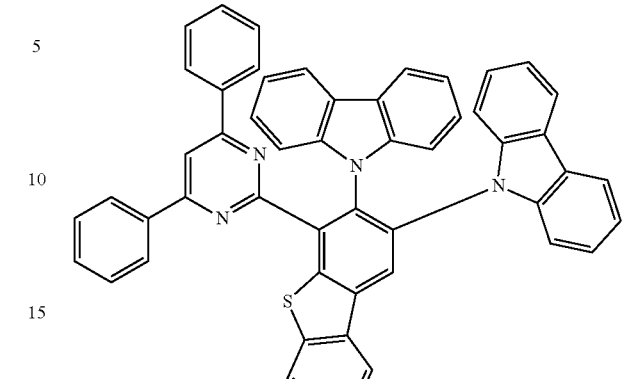
8
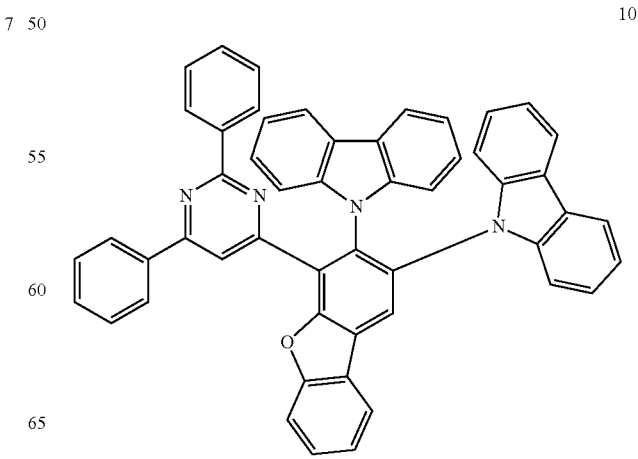
9
10

11
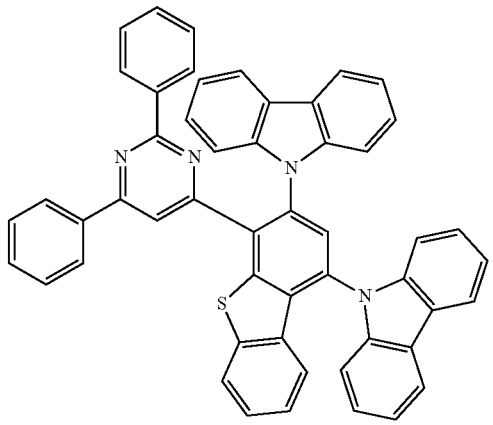
12
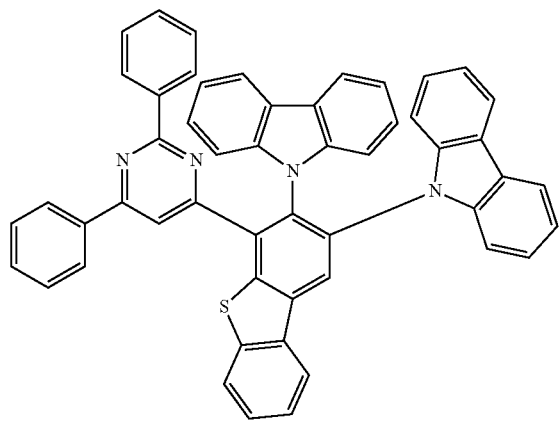
13
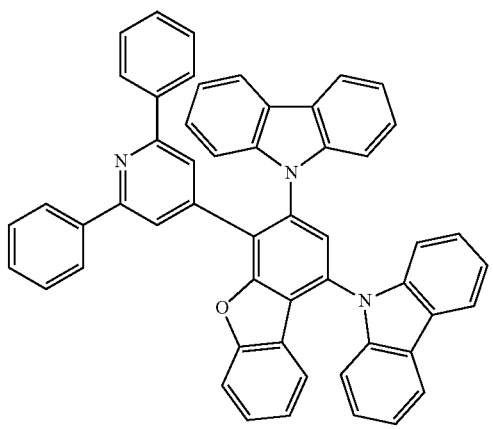
14
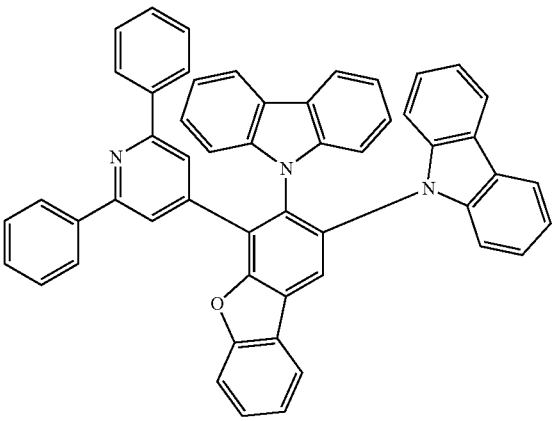
15
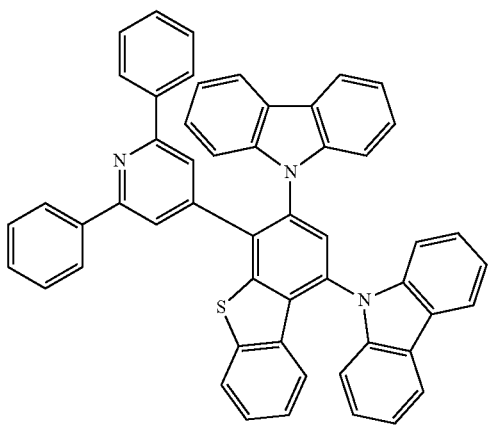
16
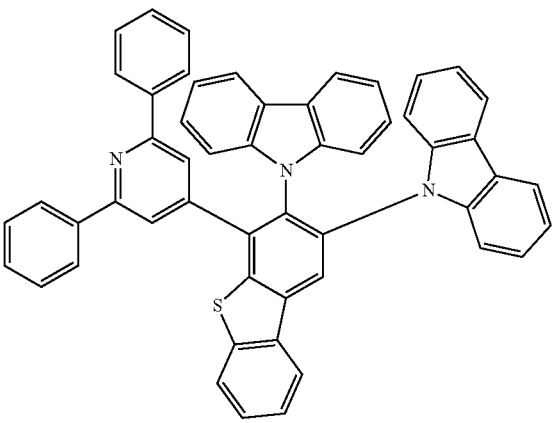

17
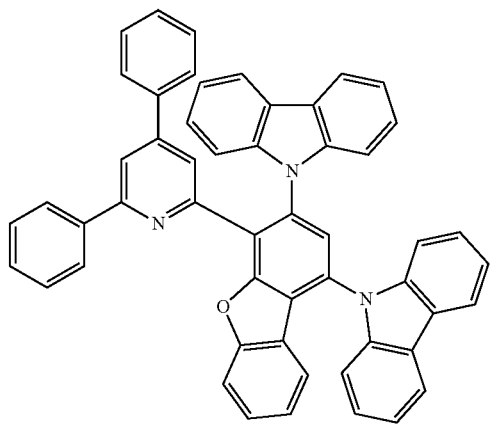
18
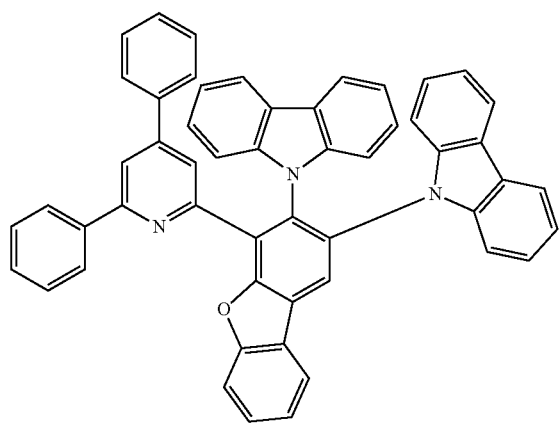
19
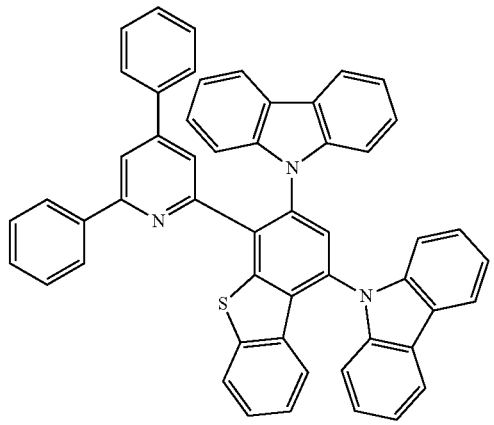
20
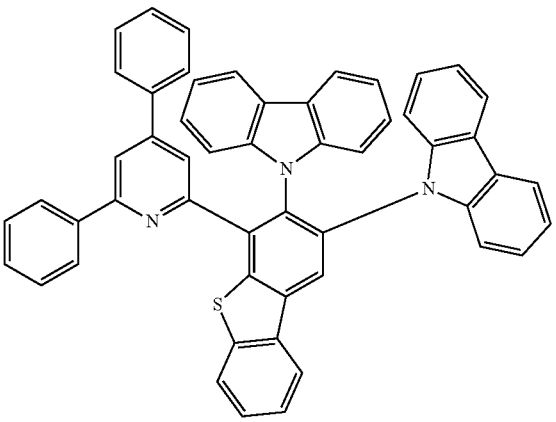
21
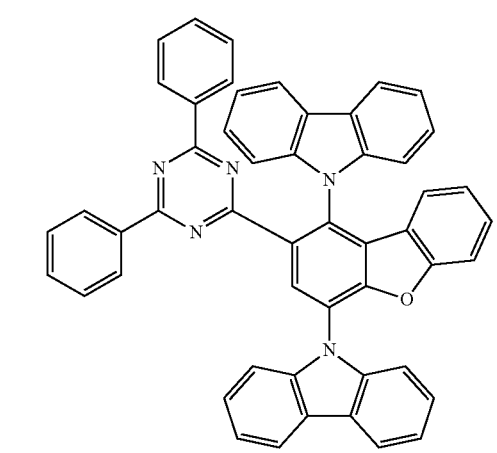
22
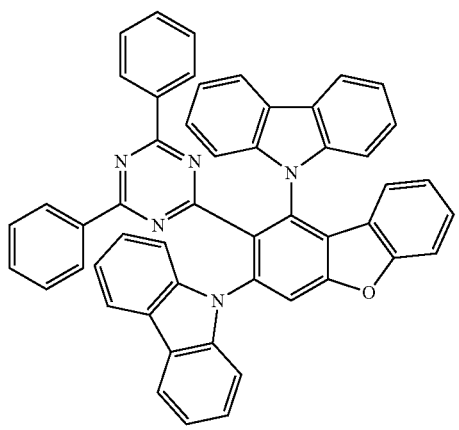

23
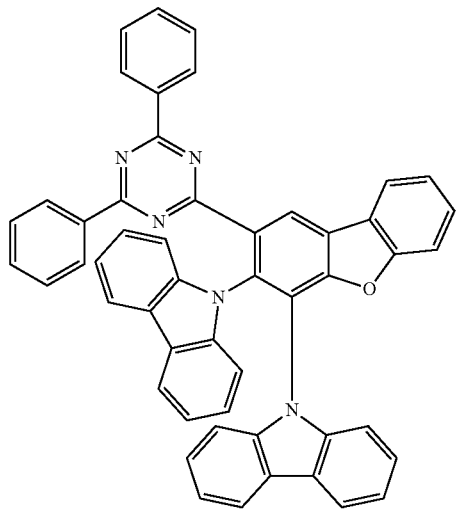
24
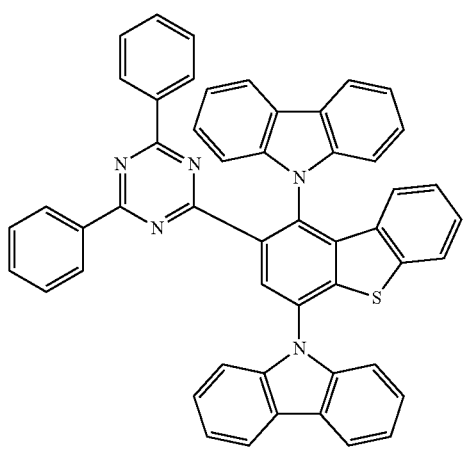
25
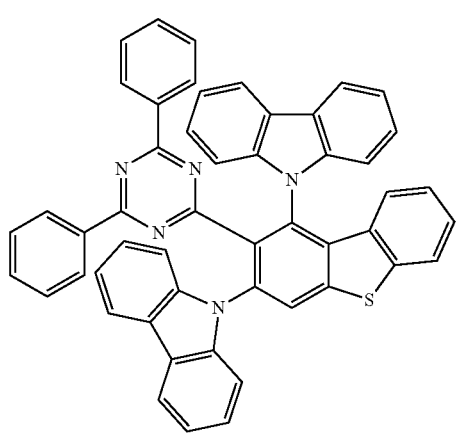
26
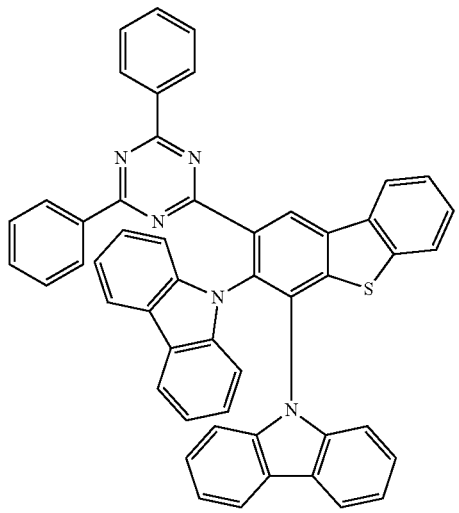
27
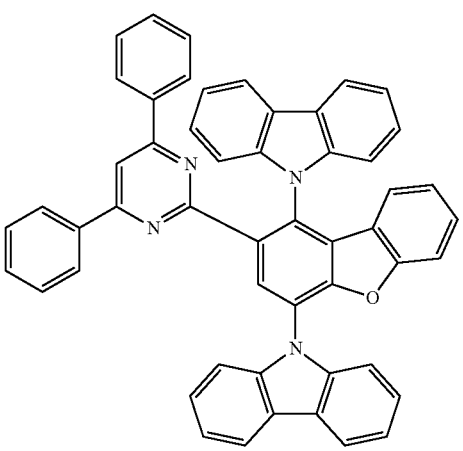
28
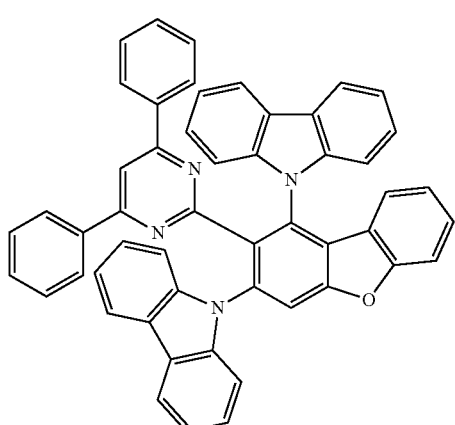

29
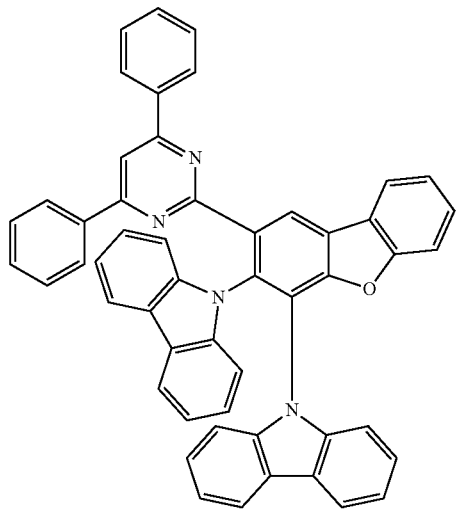
32
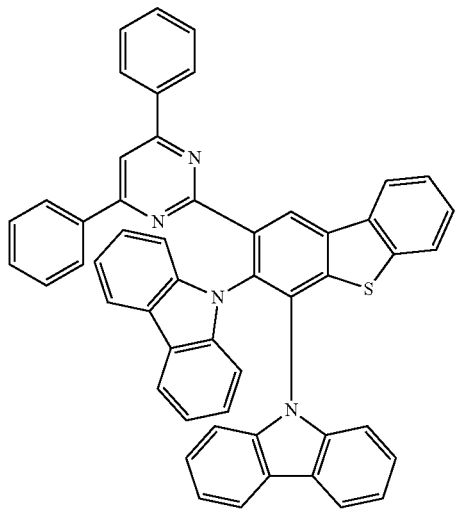
30
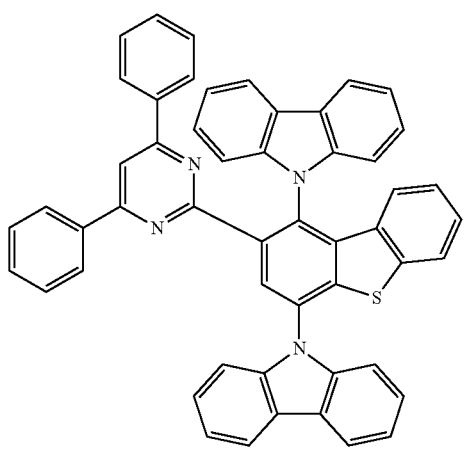
33
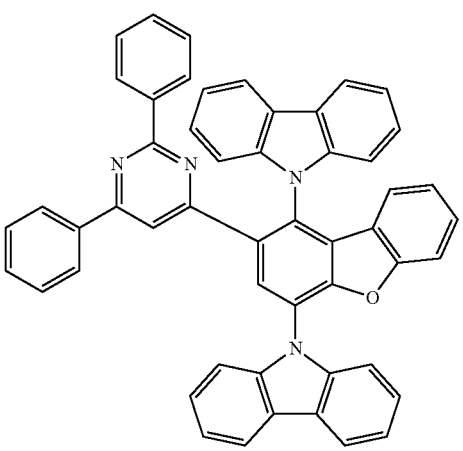
31
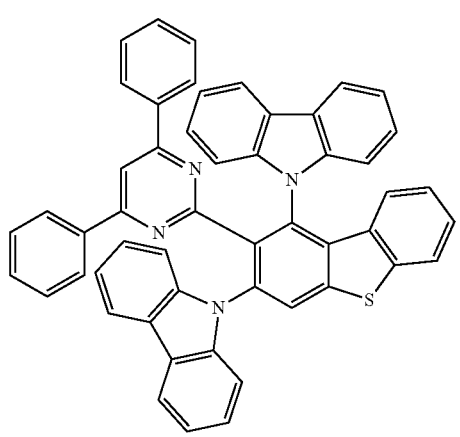
34
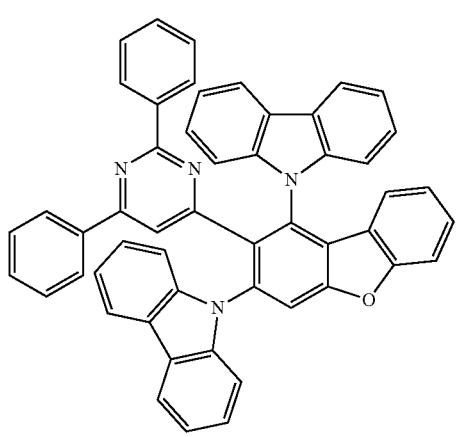

35
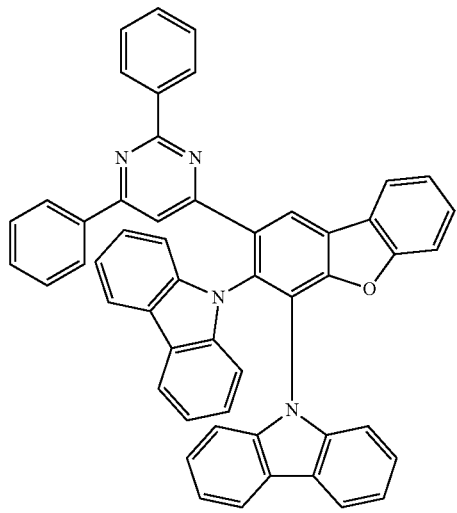
36
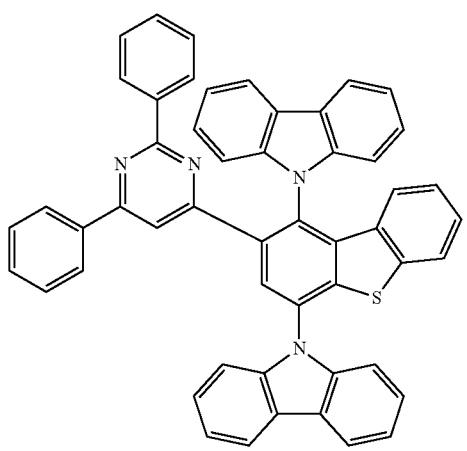
37
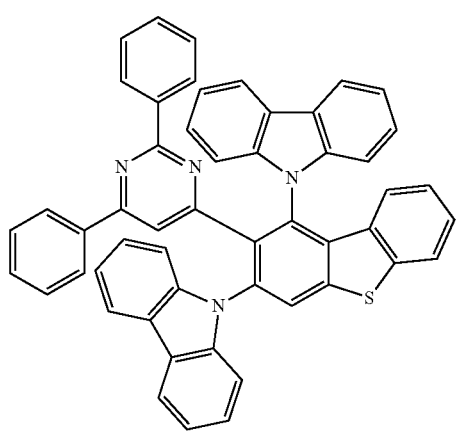
38
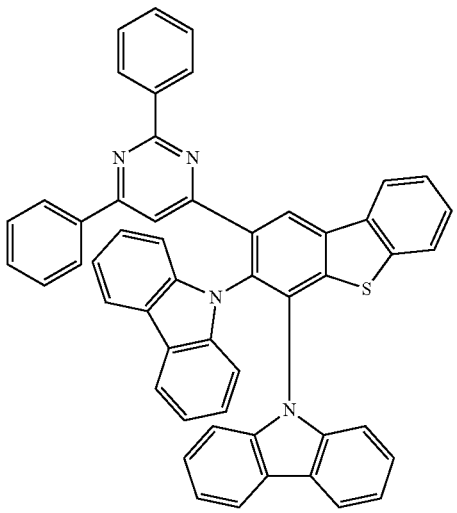
39
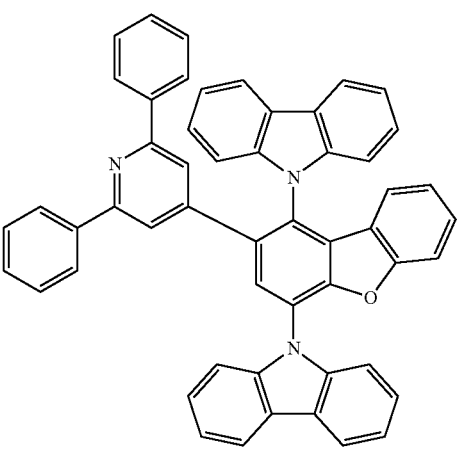
40
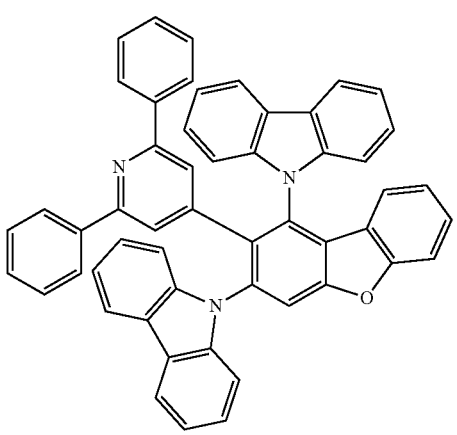

41
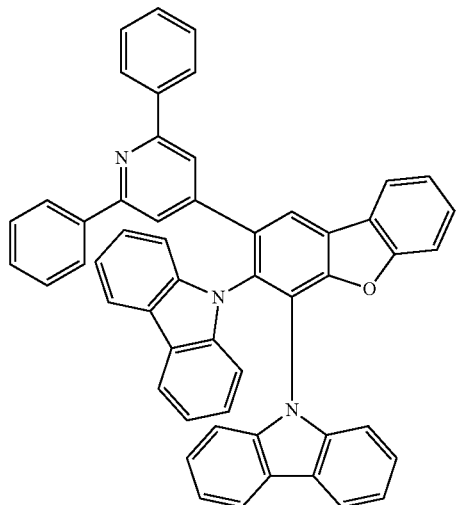
42
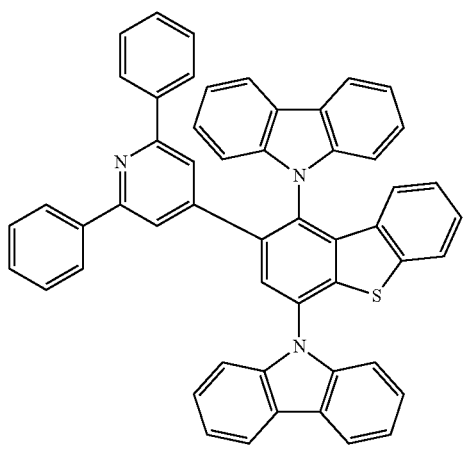
43
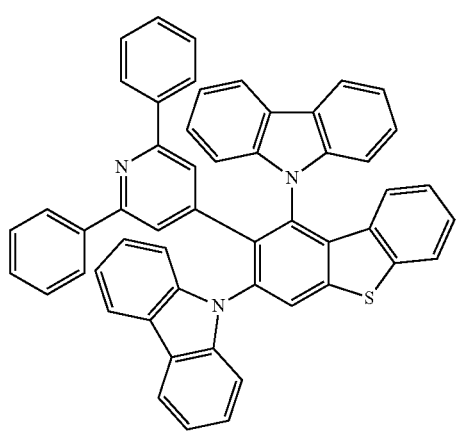
44
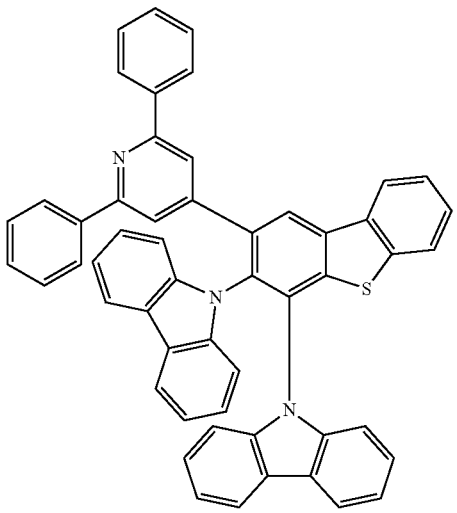
45
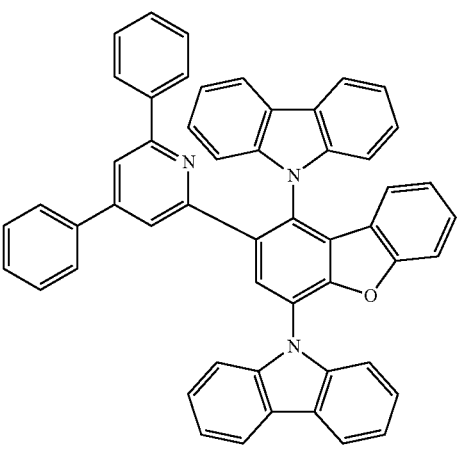
46
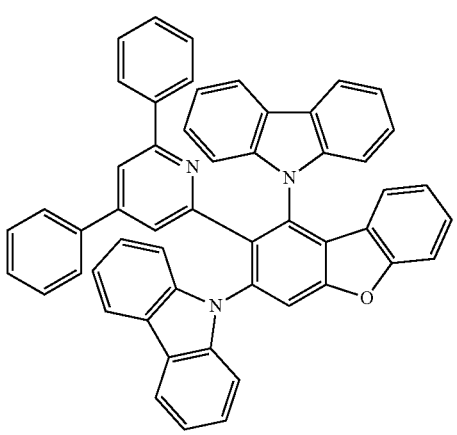

47
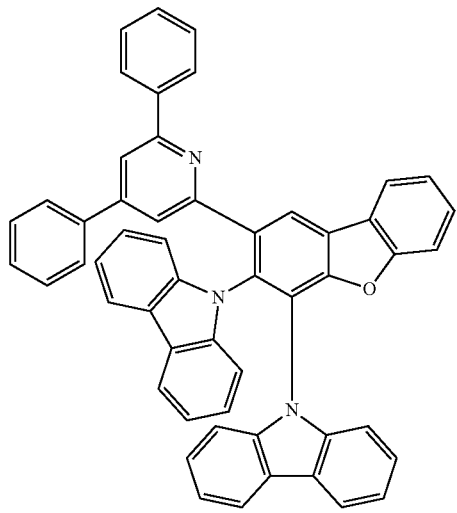
48
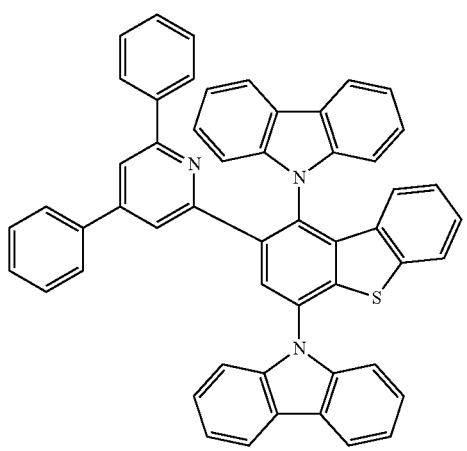
49
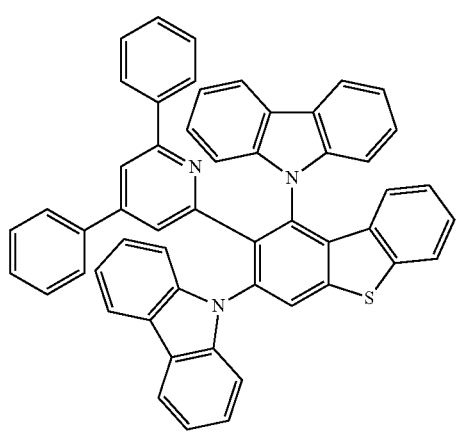
50
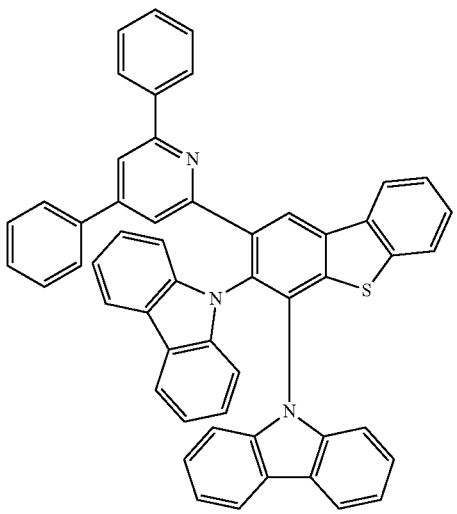
51
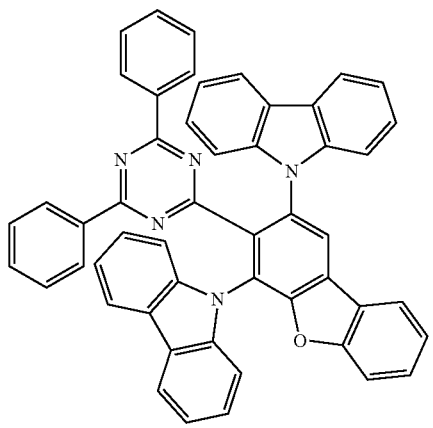
52
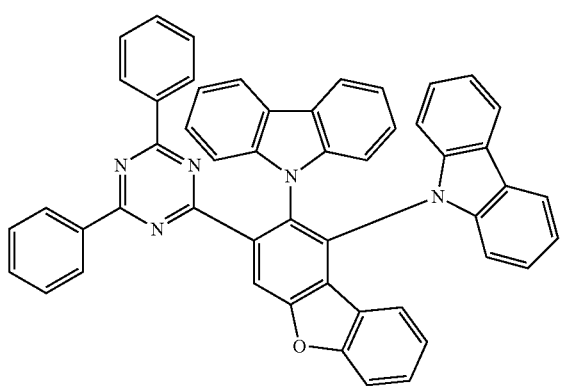

-continued
53
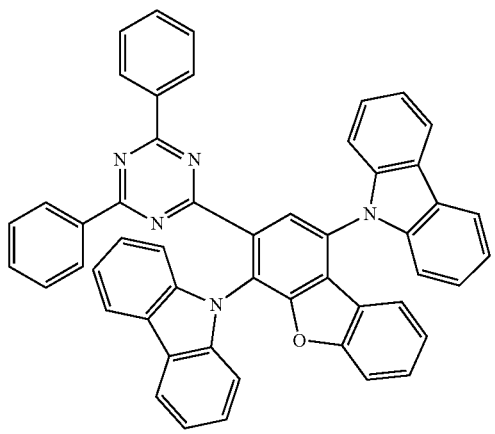
54
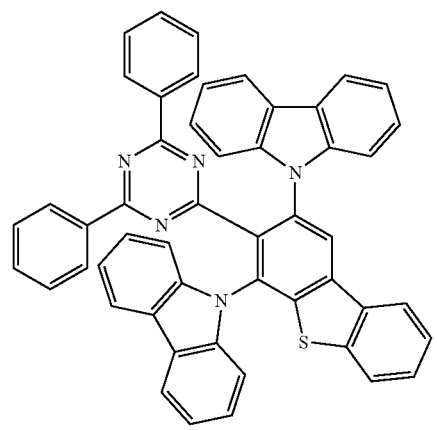
55
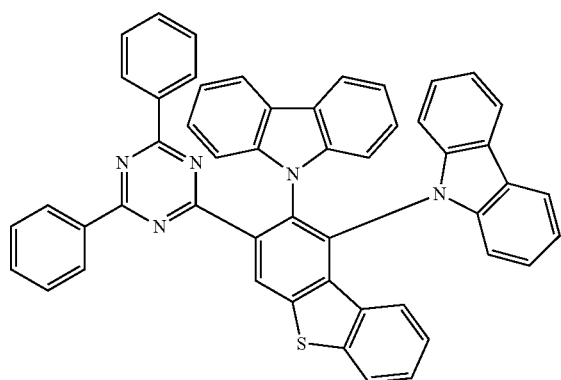
-continued
56
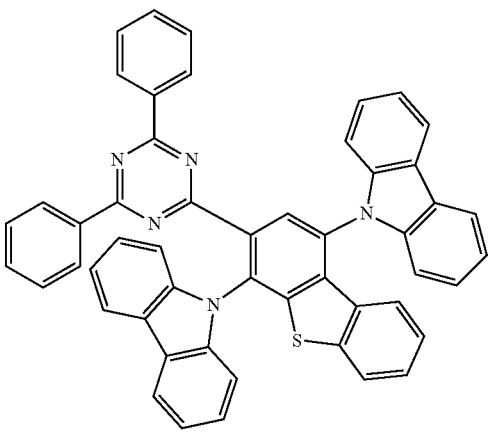
57
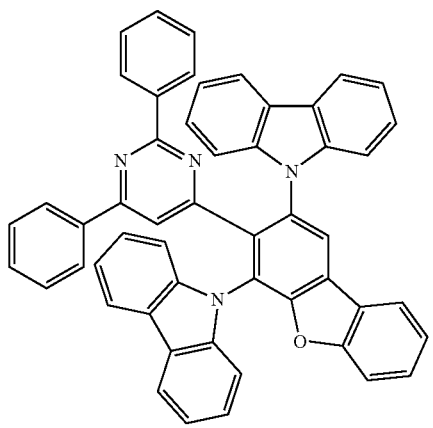
58
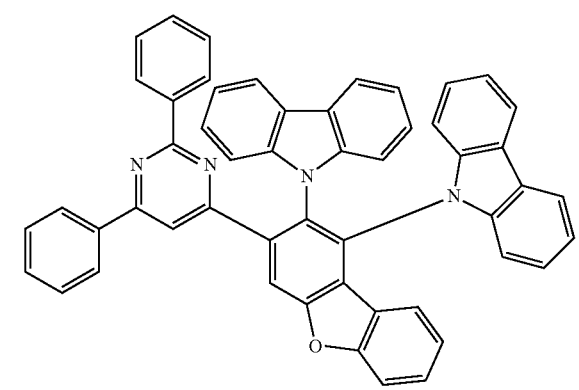

59
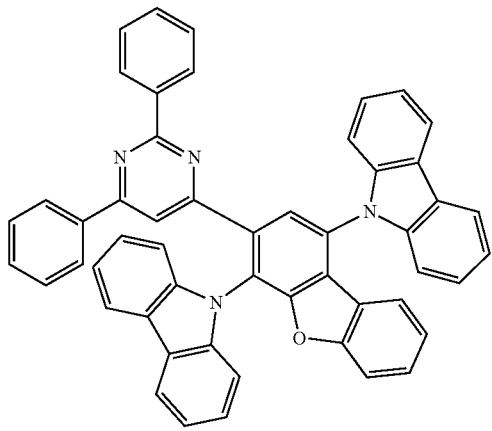
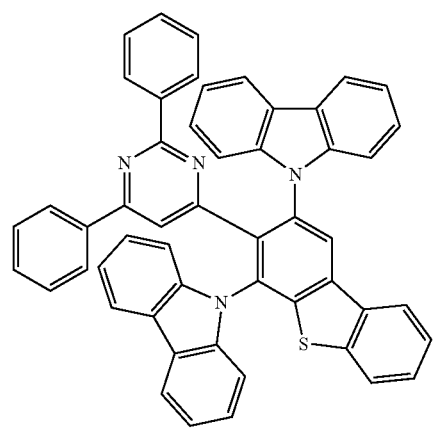
60
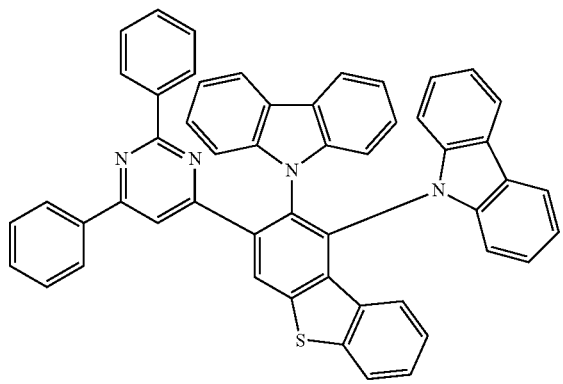
62
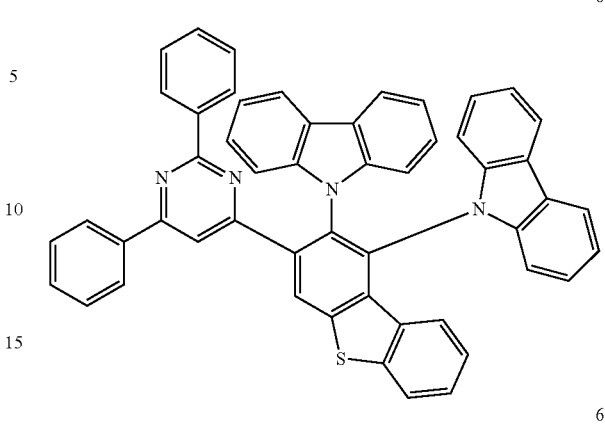
63
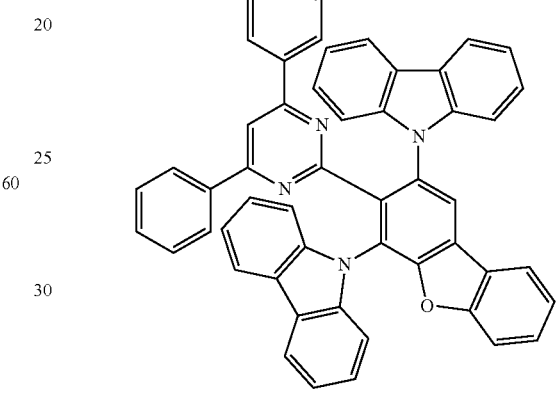
64
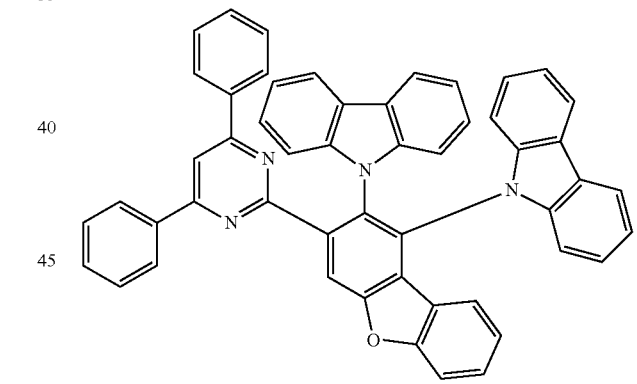
65
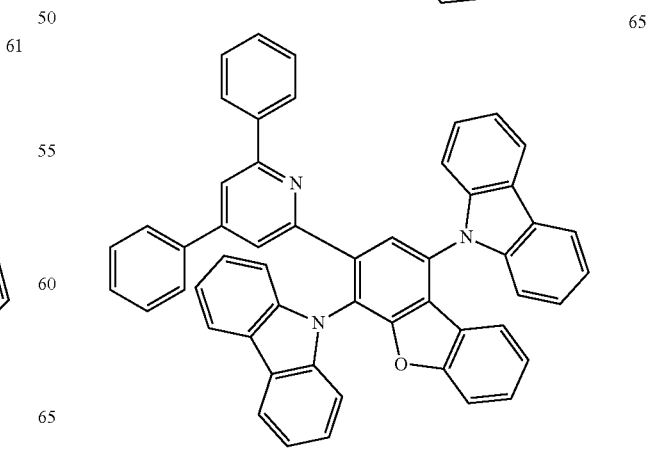

66
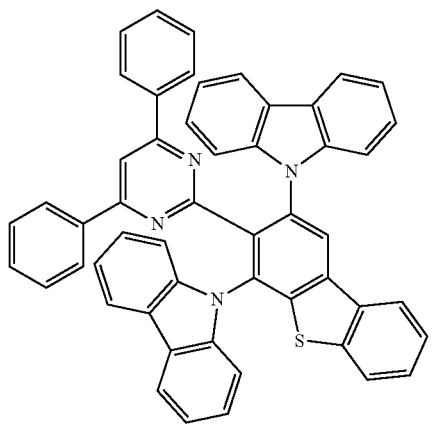
67
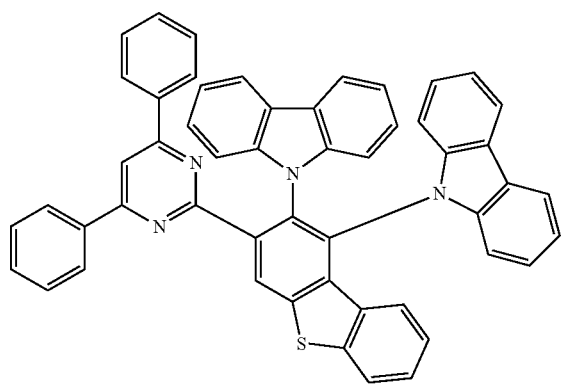
68
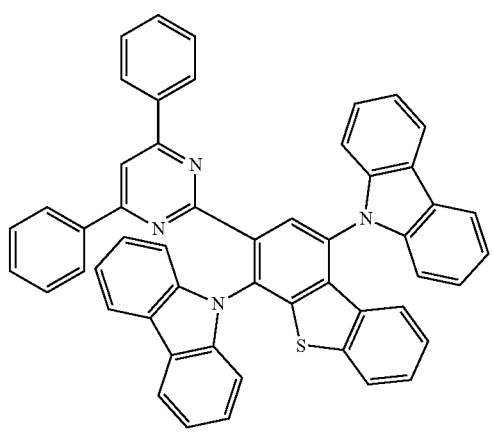
69
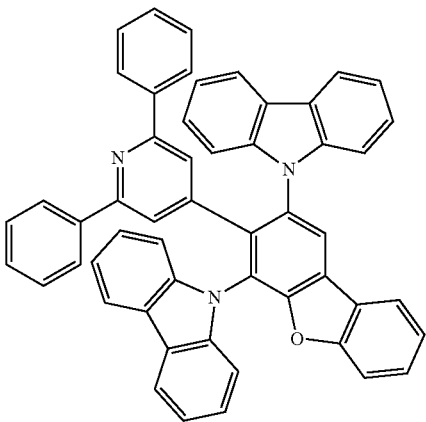
70
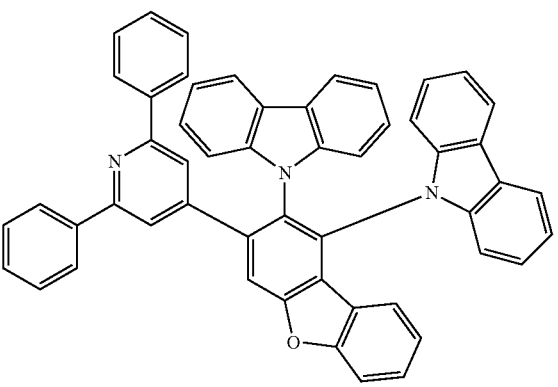
71
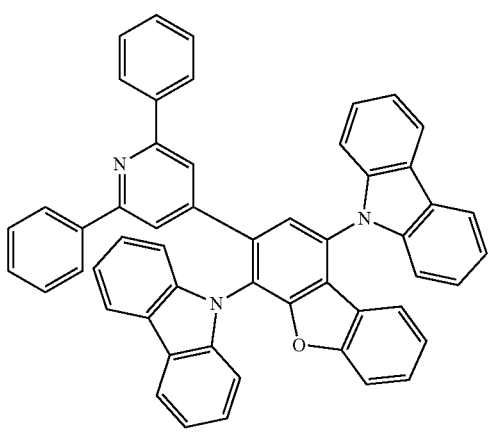

72
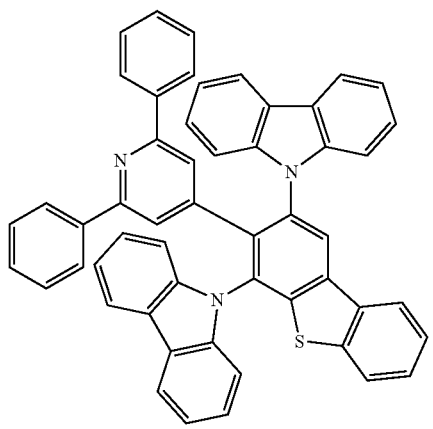
75
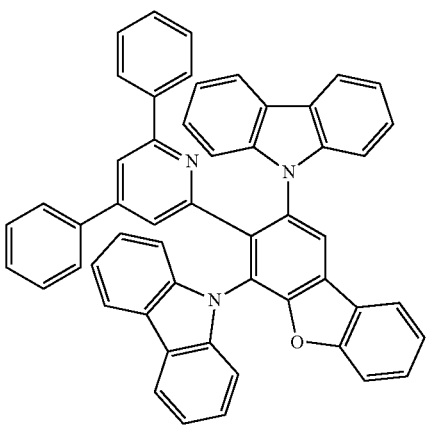
73
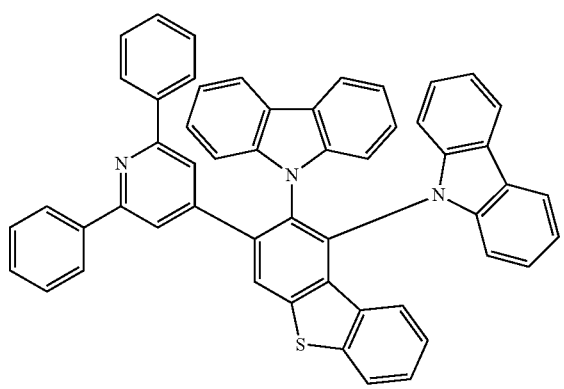
76
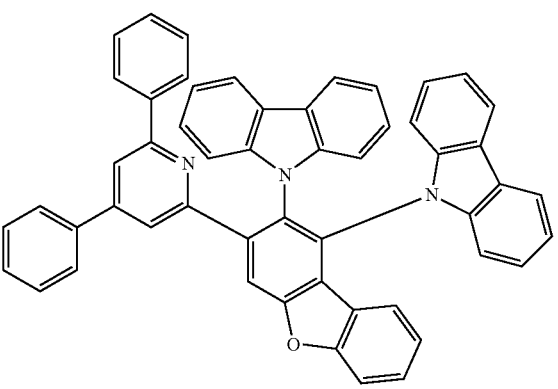
74
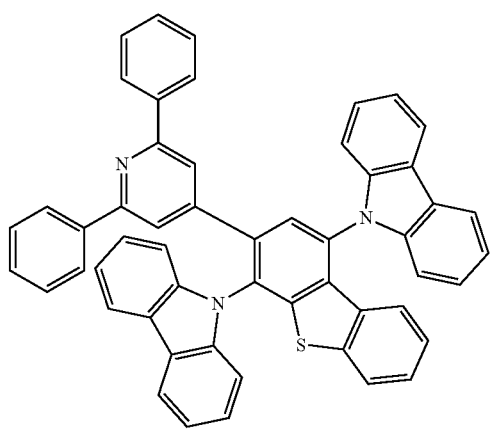
77
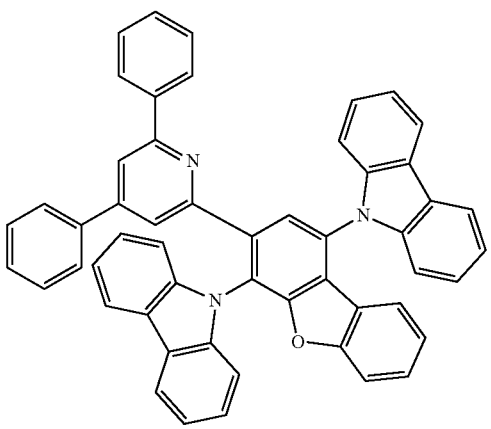

78
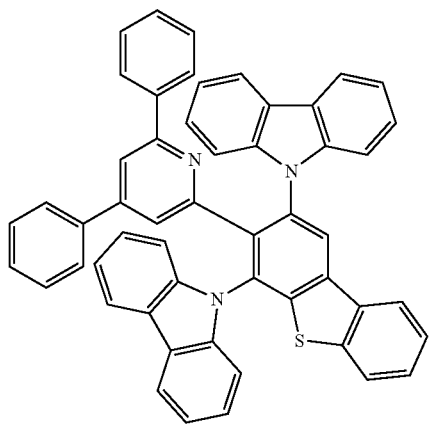
79
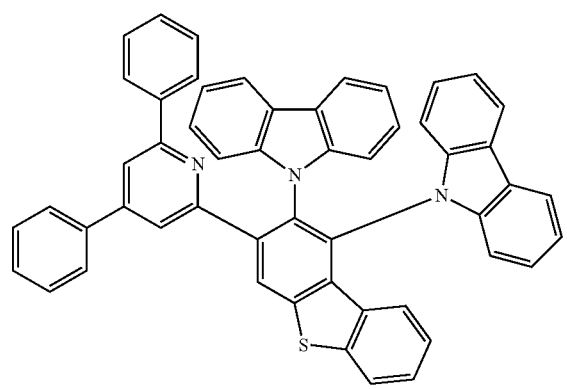
80
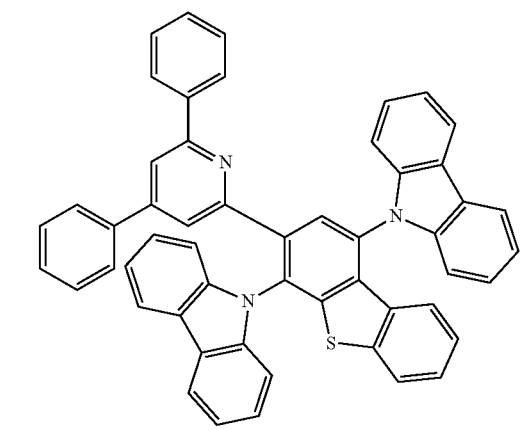
81
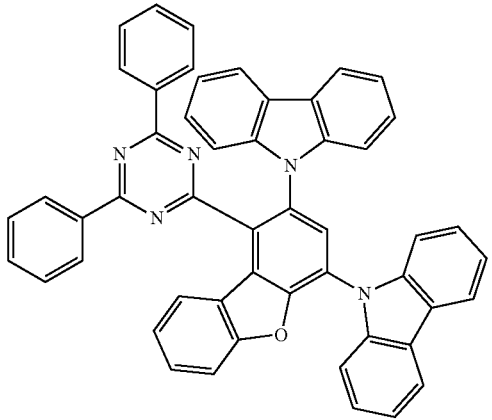
82
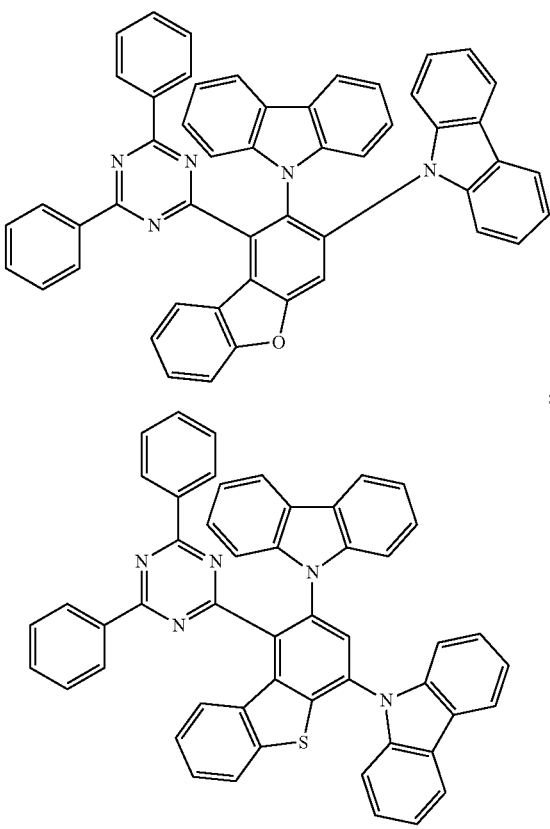
83
84
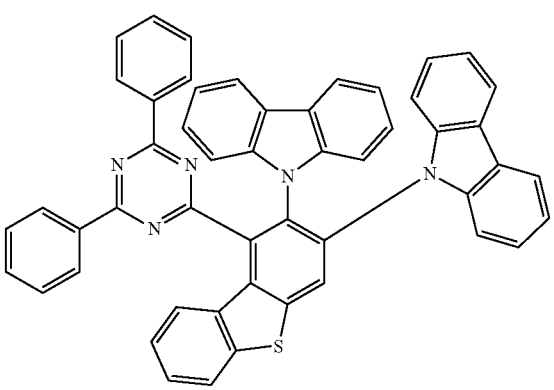

259
-continued
85
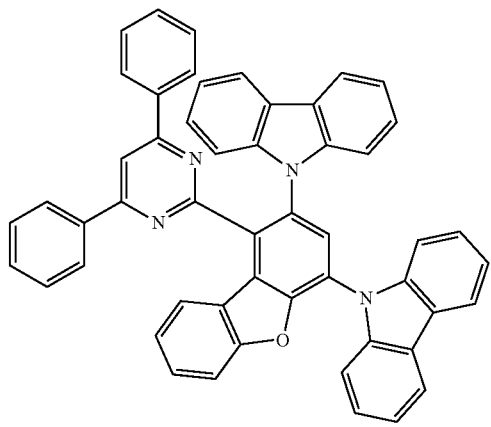
86
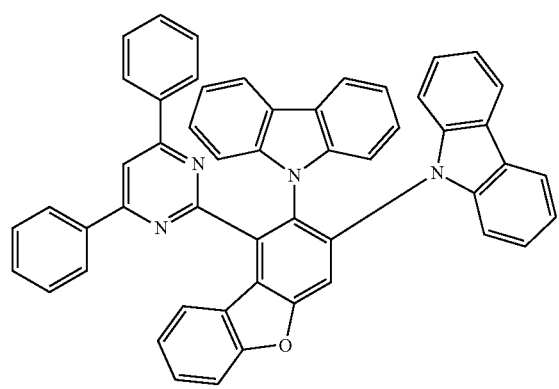
87
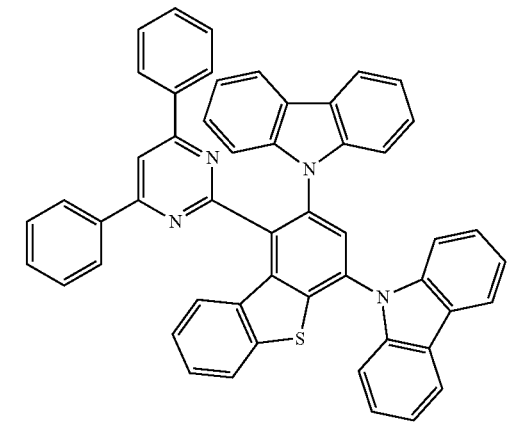
88
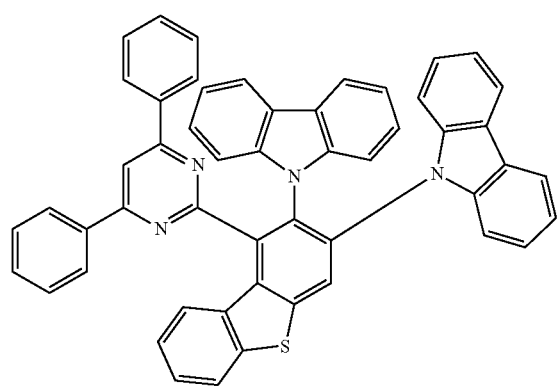
260
-continued
89
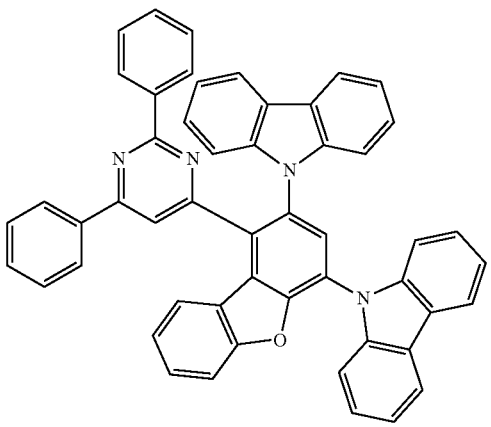
90
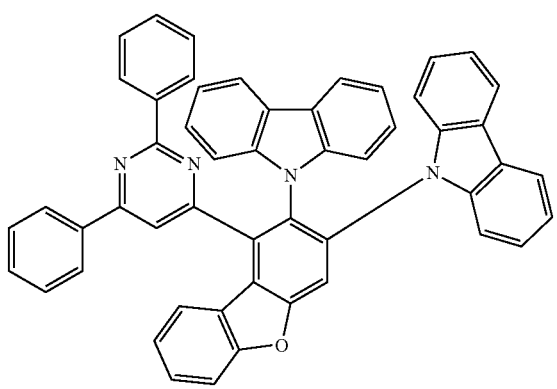
91
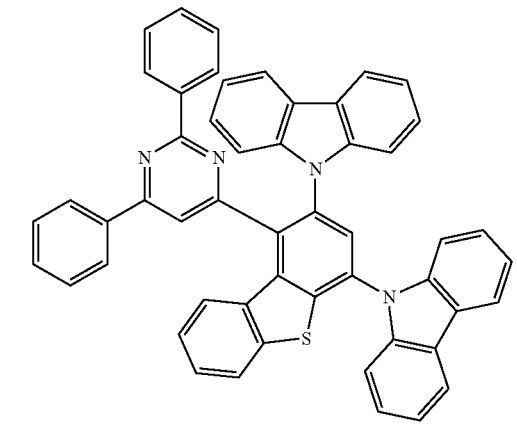
92
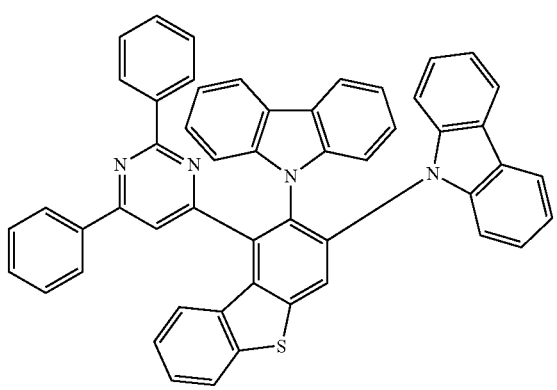

-continued
93
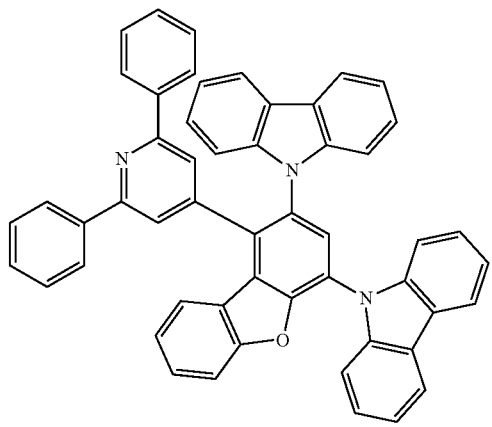
94
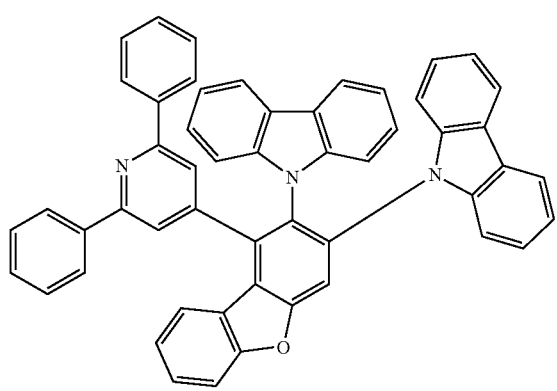
95
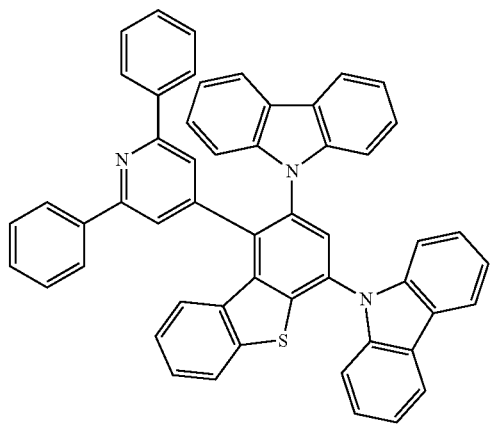
96
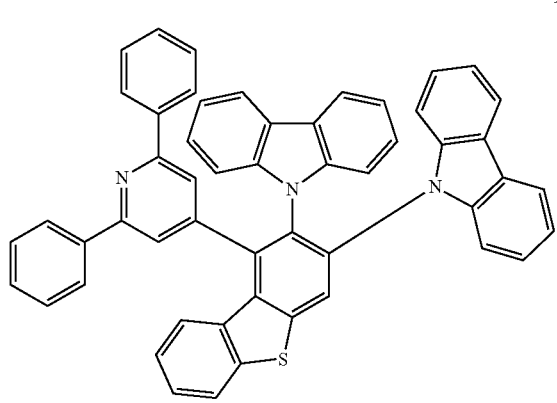
-continued
97
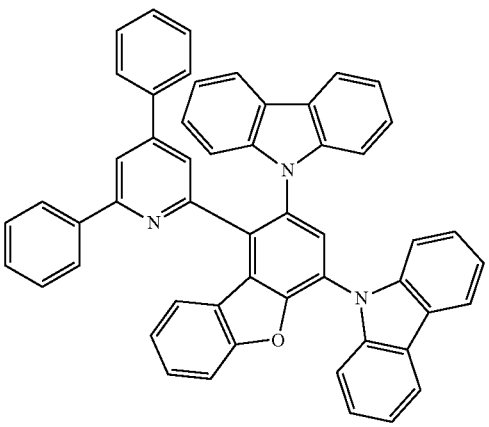
98
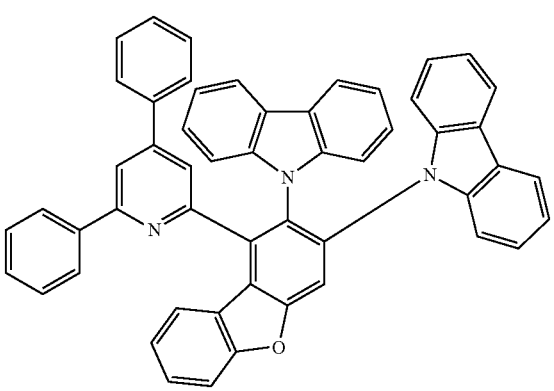
99
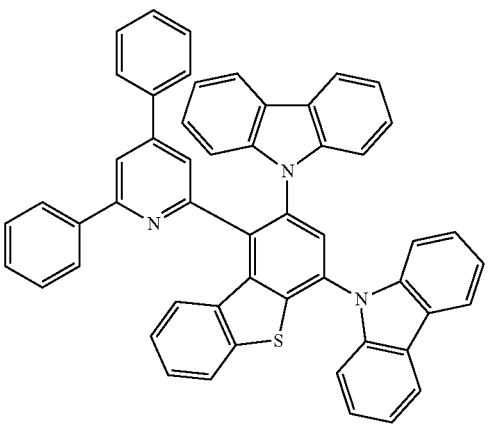
100
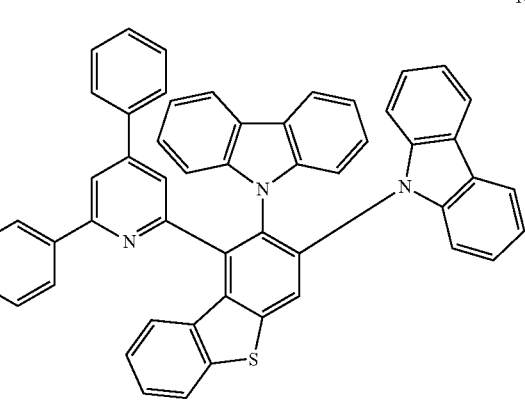

101
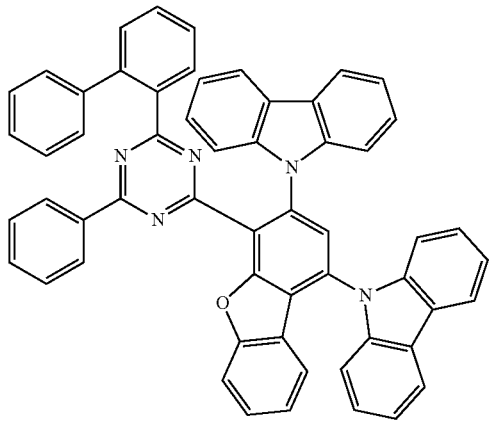
102
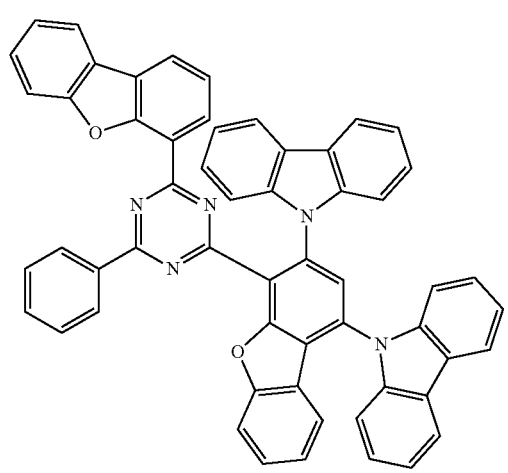
103
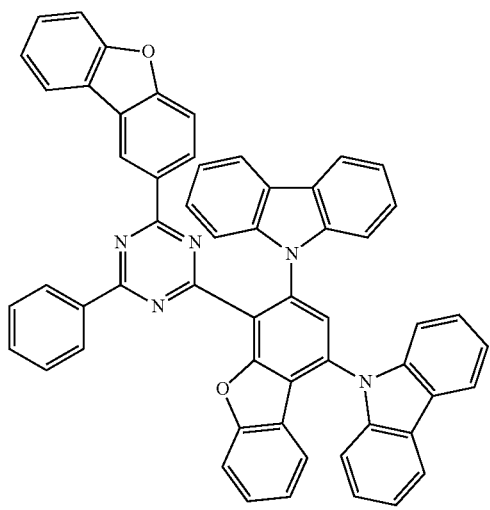
104
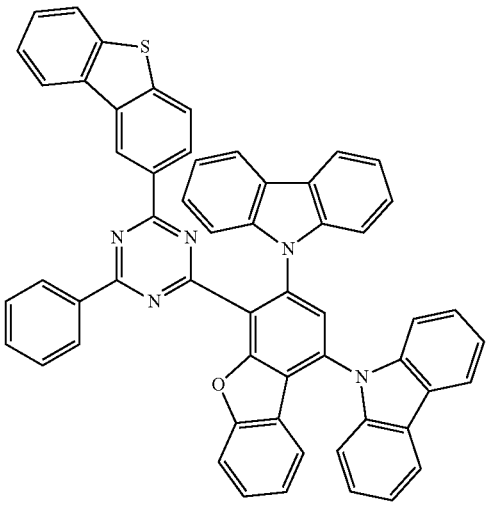
105
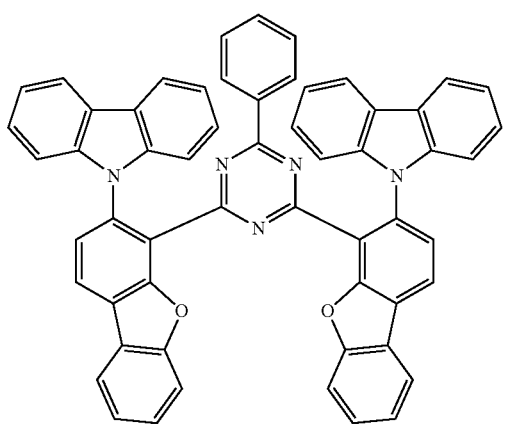
106
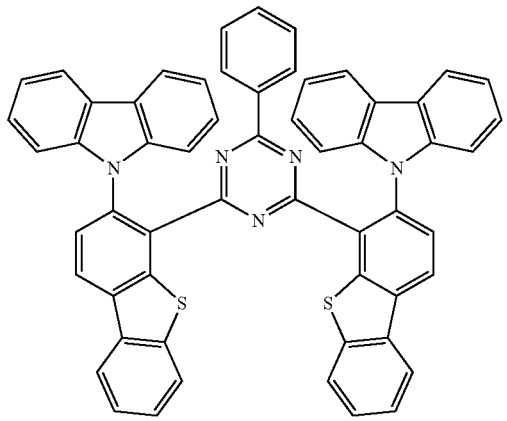
107
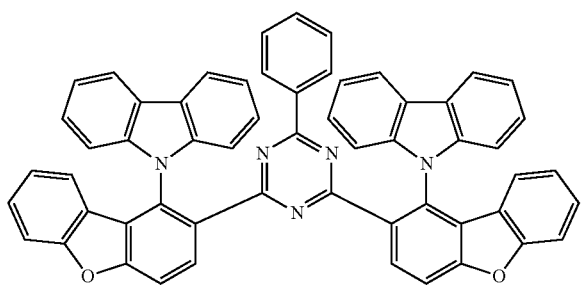

265
-continued
108
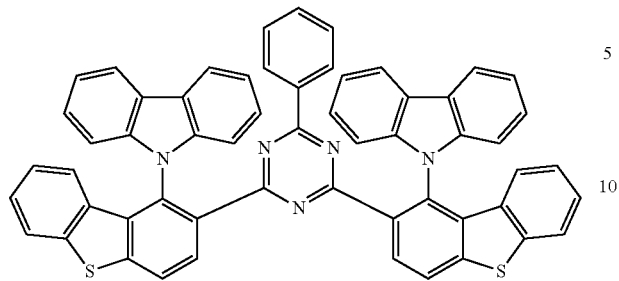
109
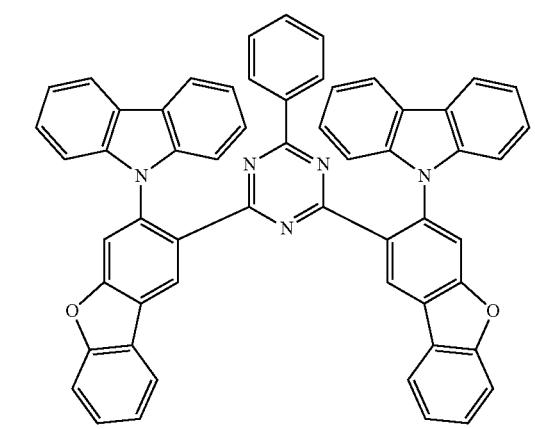
110
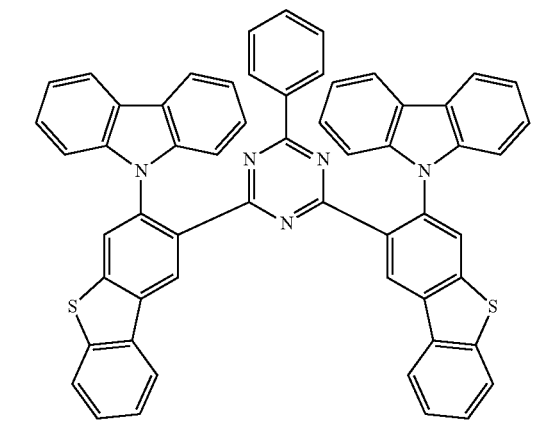
111
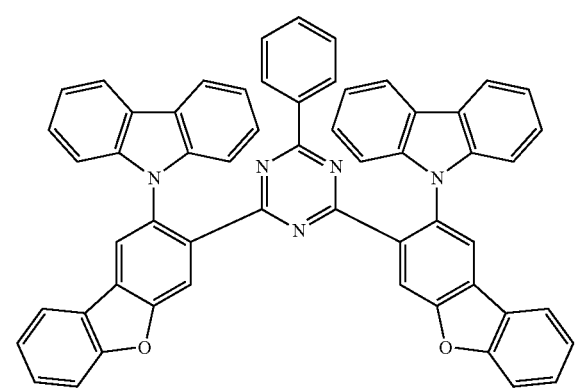
266
-continued
112
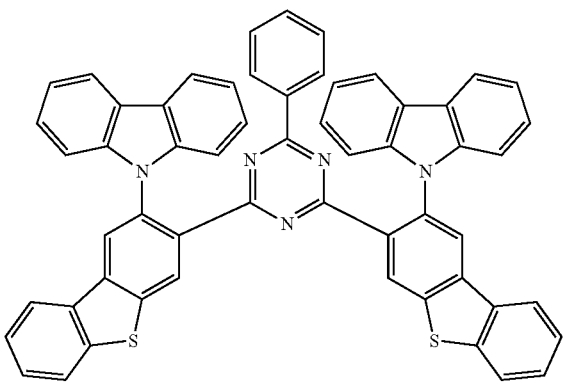
113
114
115
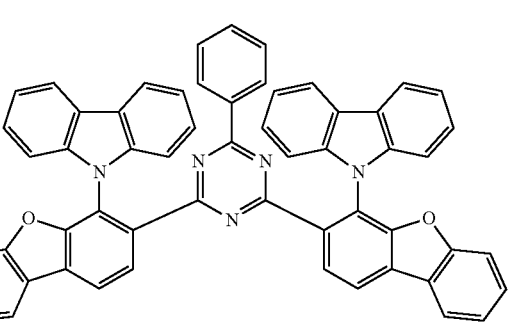

116
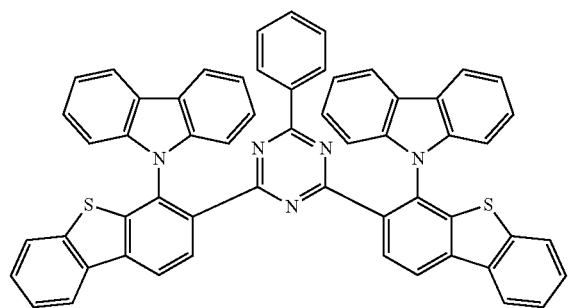
117
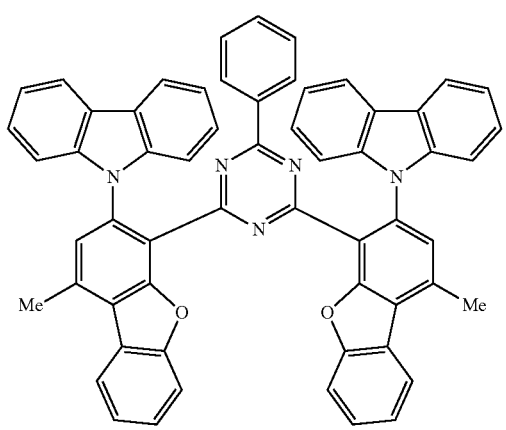
118
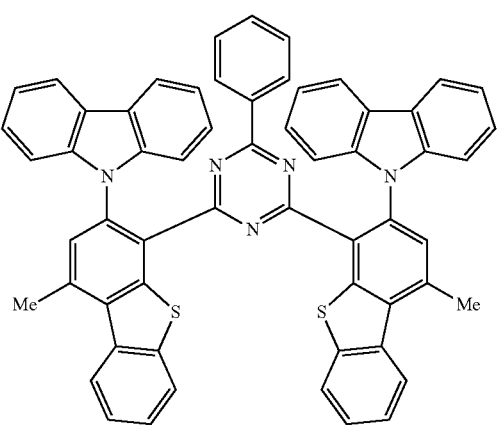
119
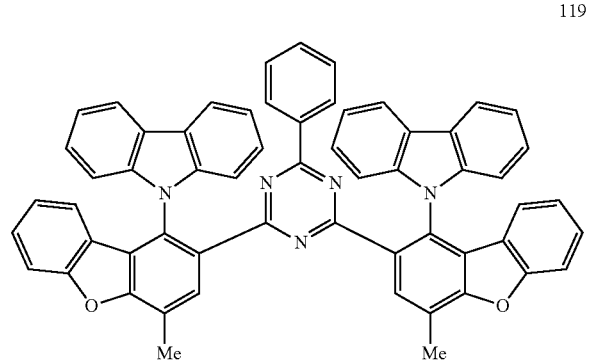
120
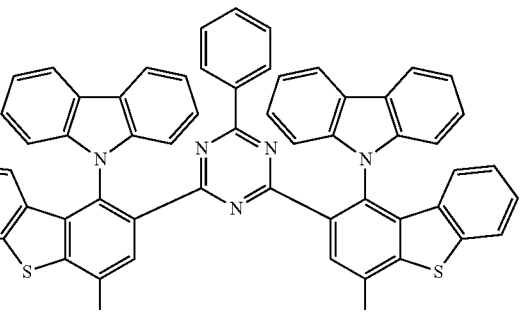
121
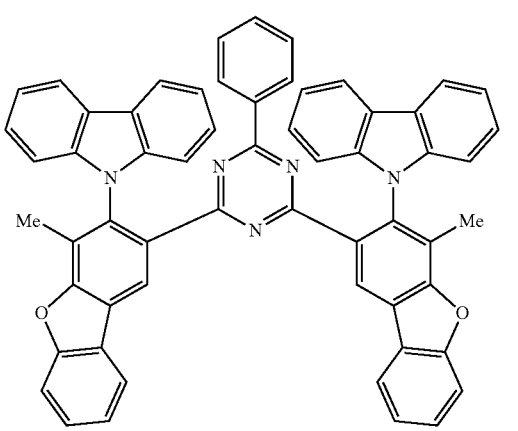
122
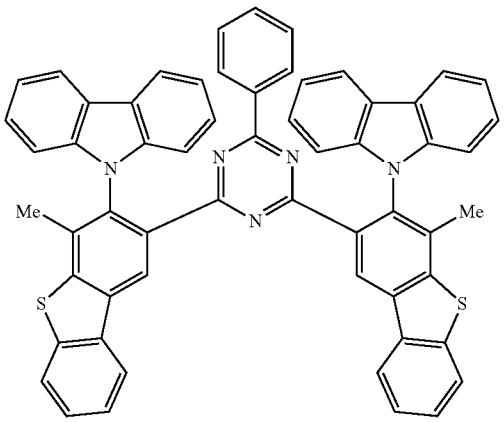
123
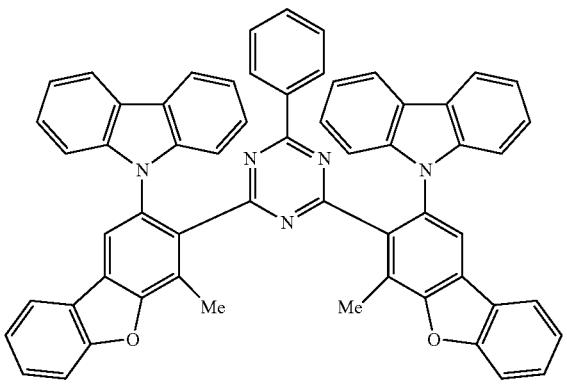

-continued
124
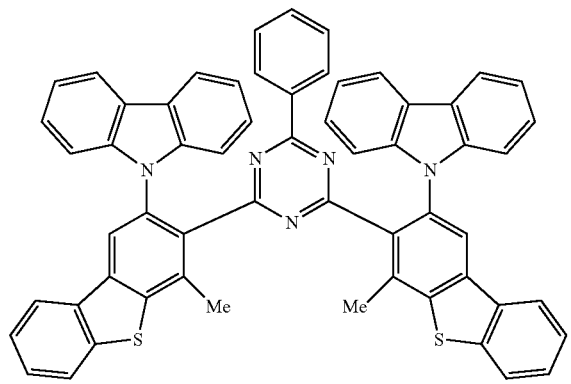
125
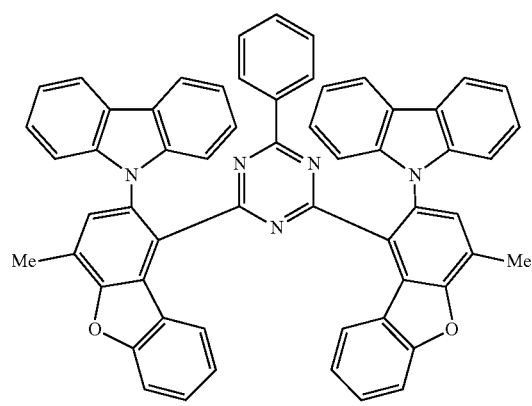
126
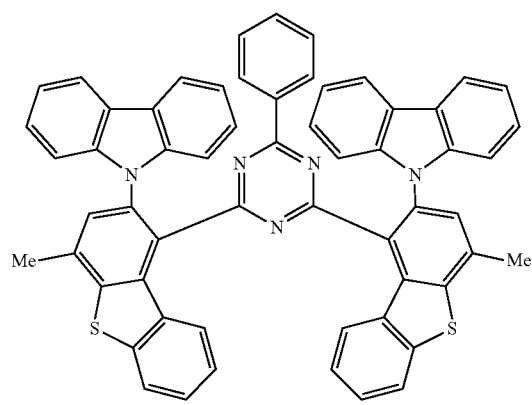
127
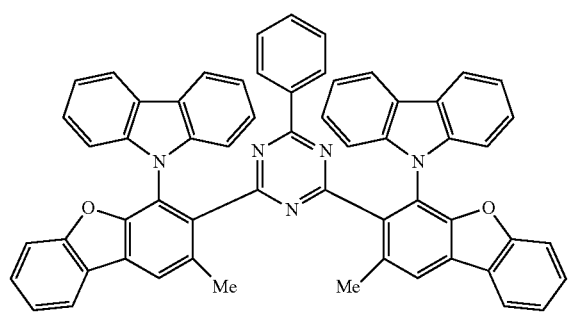
-continued
128
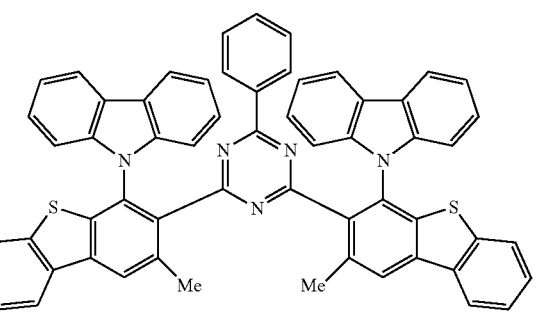
129
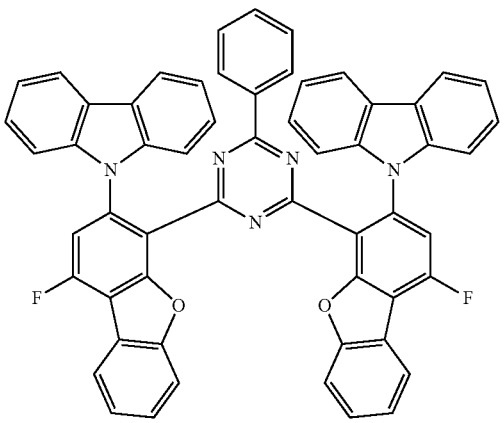
130
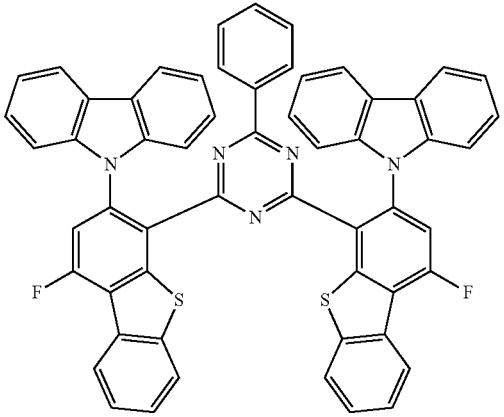
131
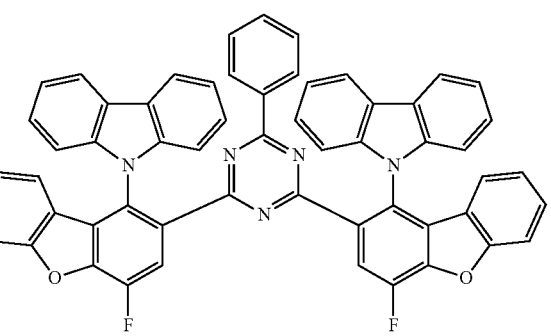

132
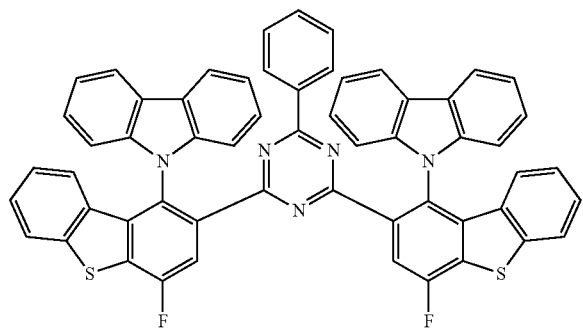
133
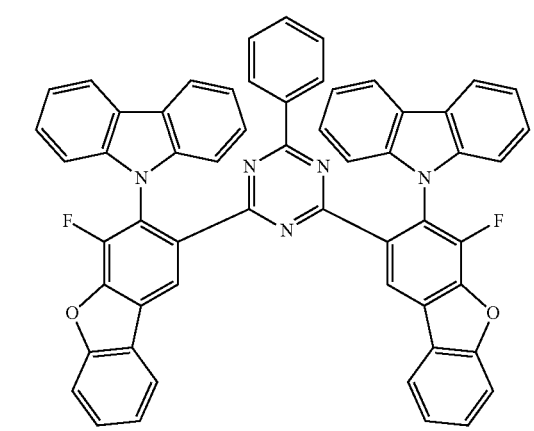
134
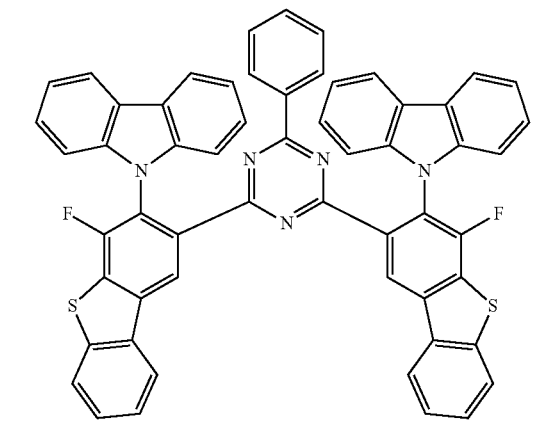
135
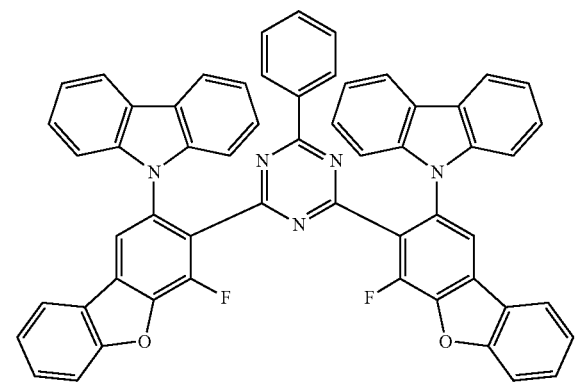
136
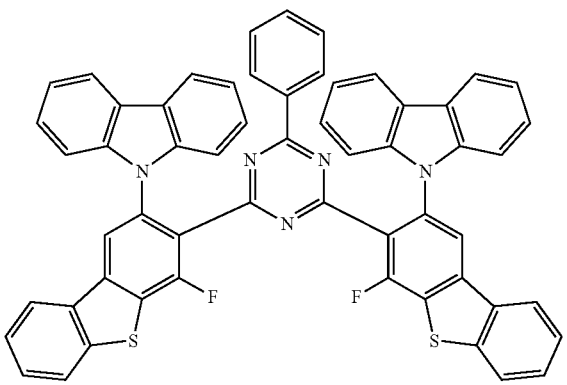
137
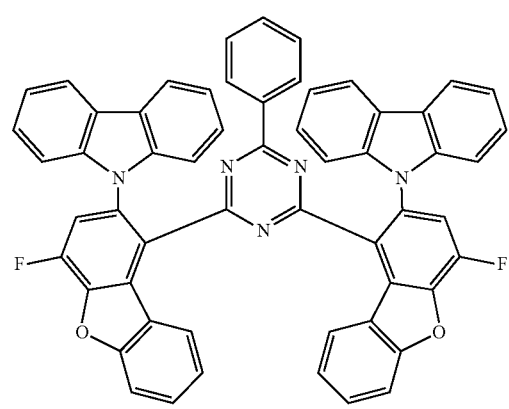
138
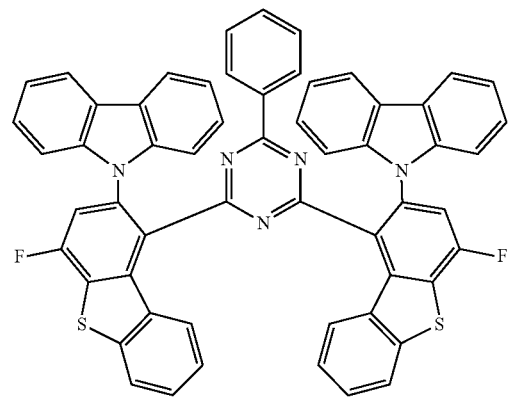
139
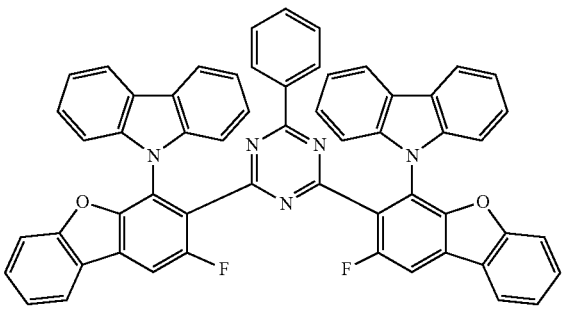

140
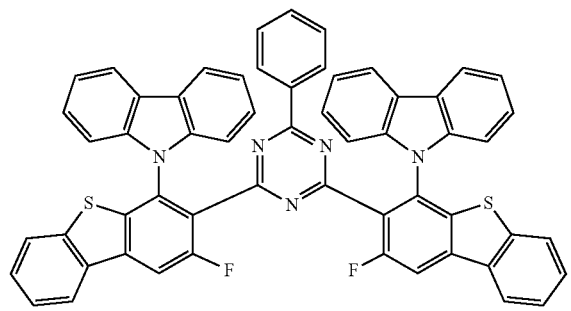
141
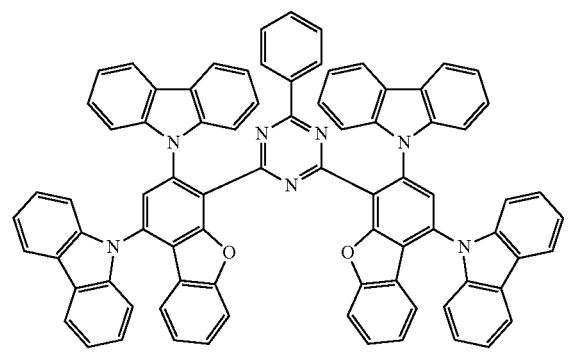
142
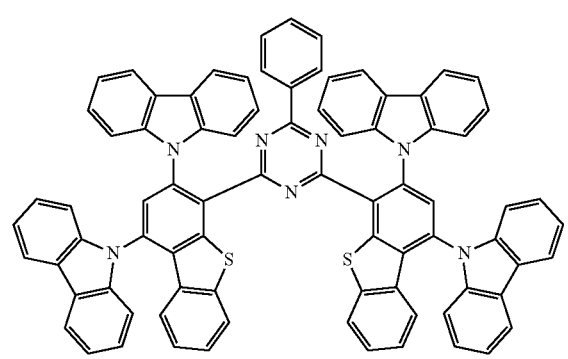
143
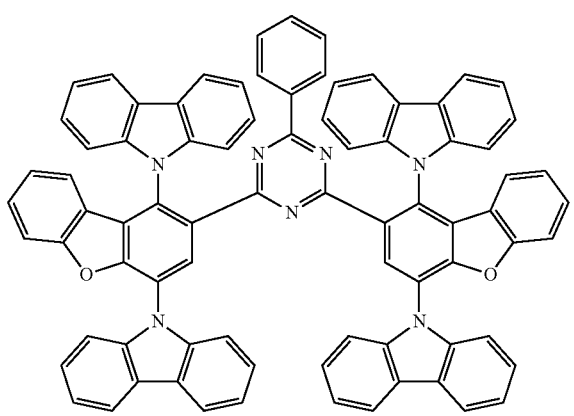
144
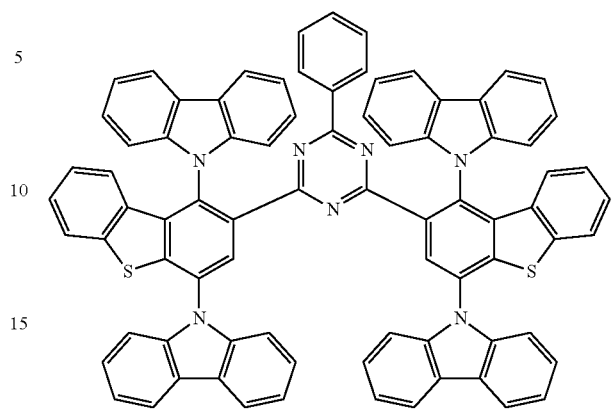
145
146
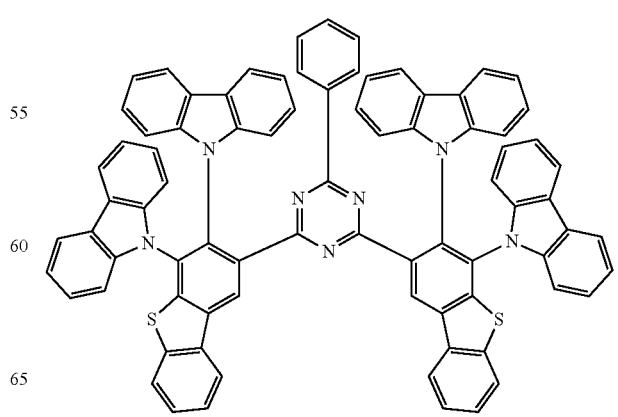

275
-continued
147
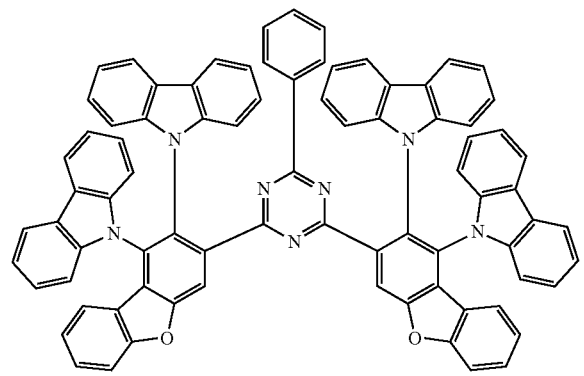
148
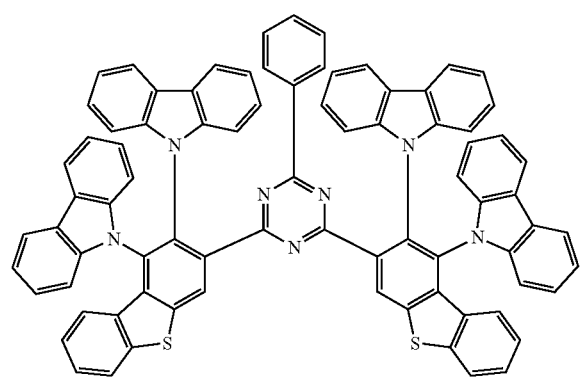
149
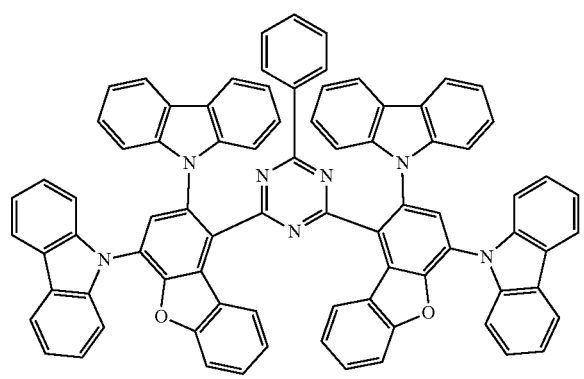
150
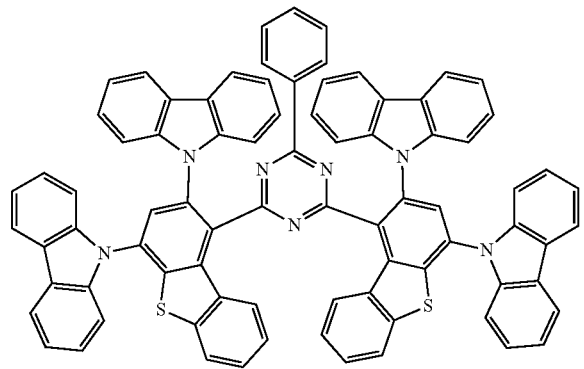
276
-continued
151
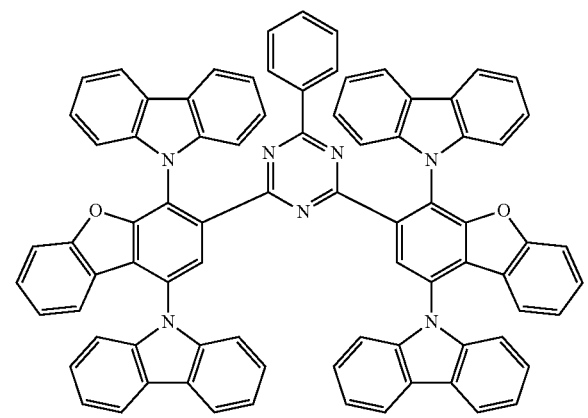
152
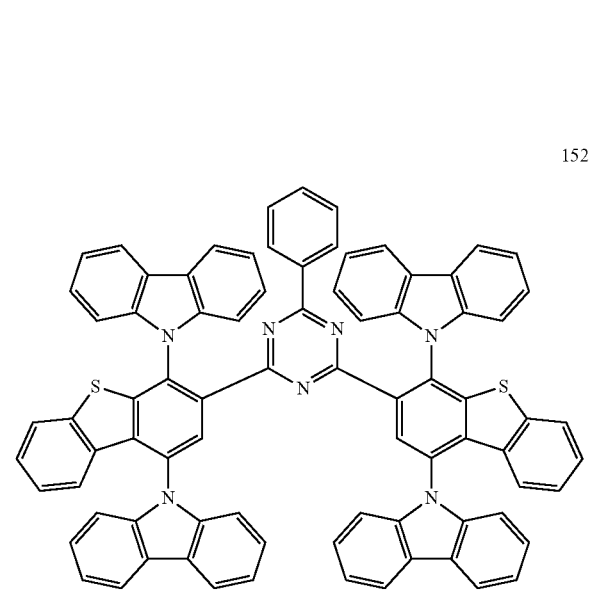
153
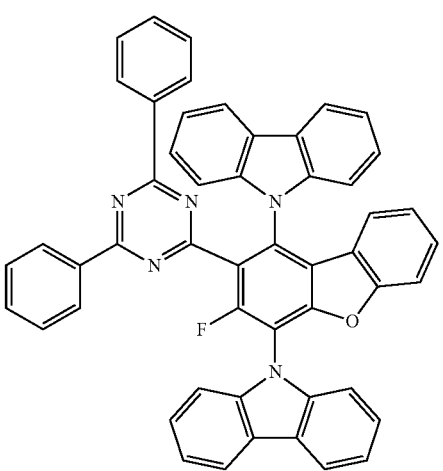

277
-continued
154
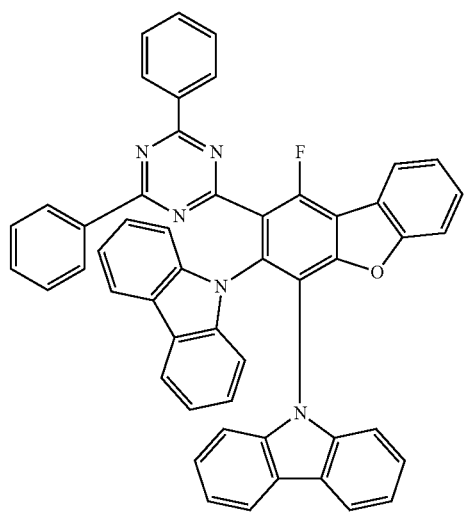
155
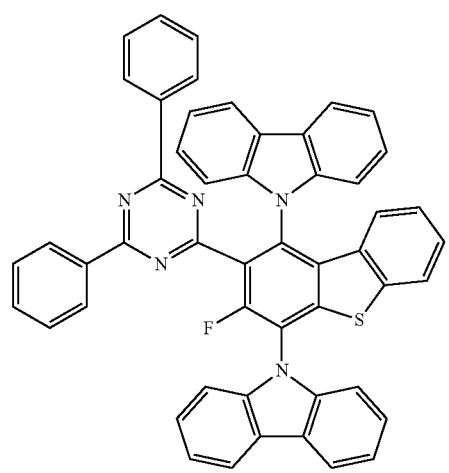
156
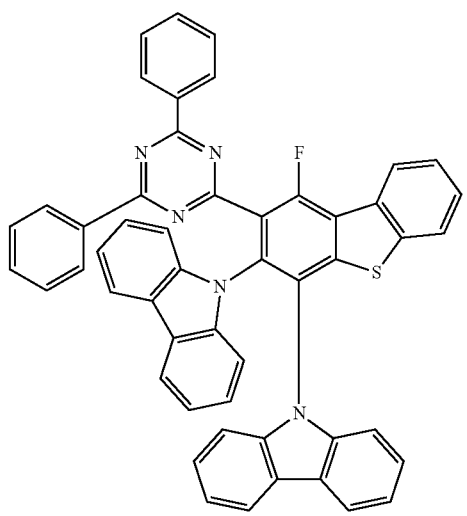
278
-continued
157
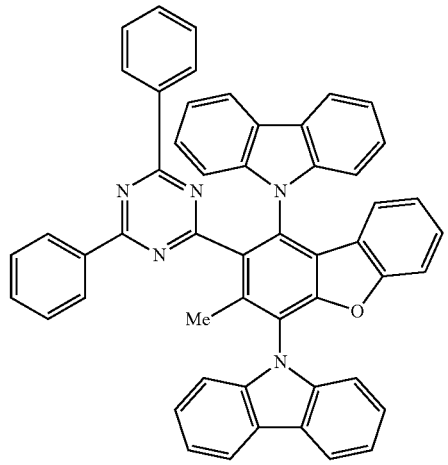
158
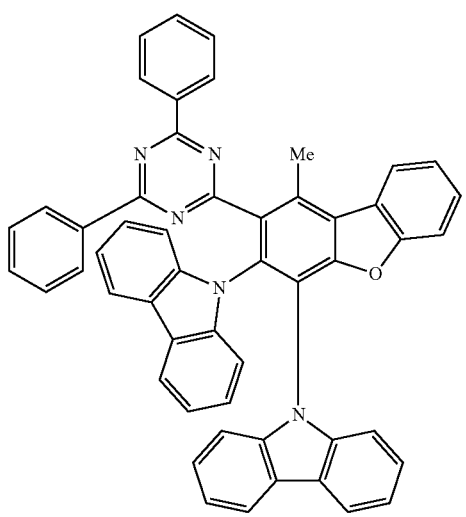
159
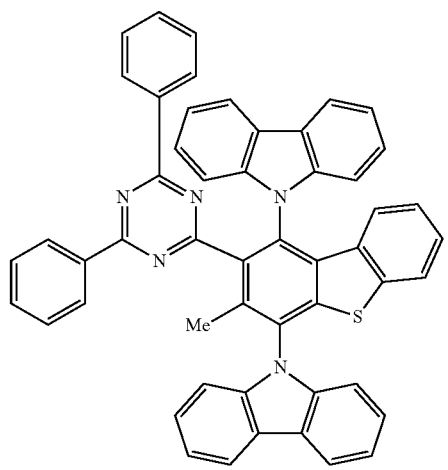

279
-continued
160
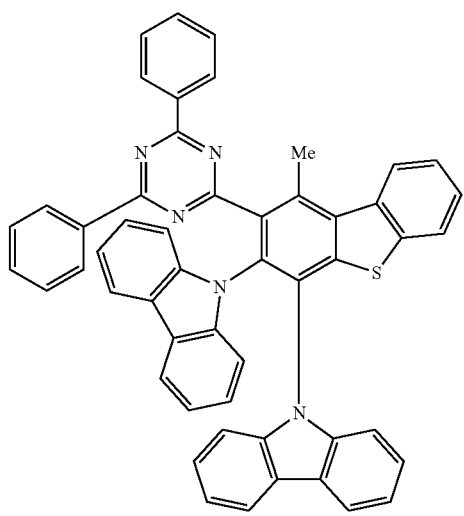
161
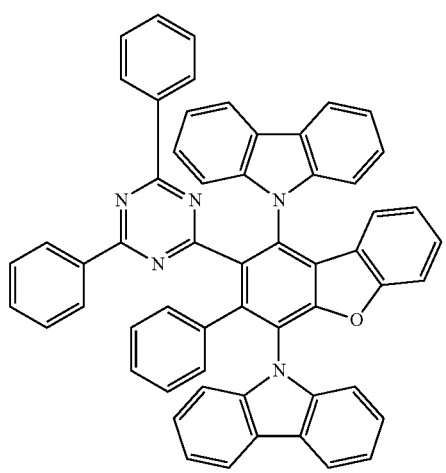
162
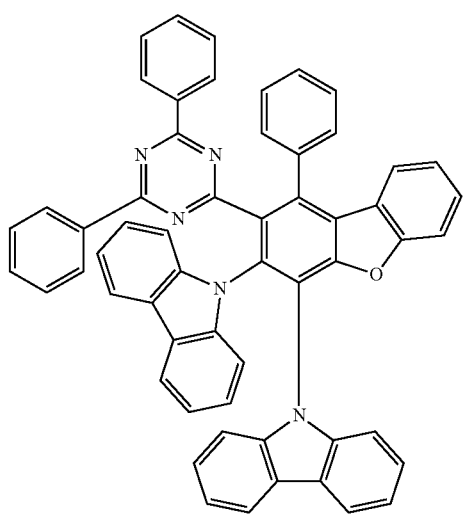
280
-continued
163
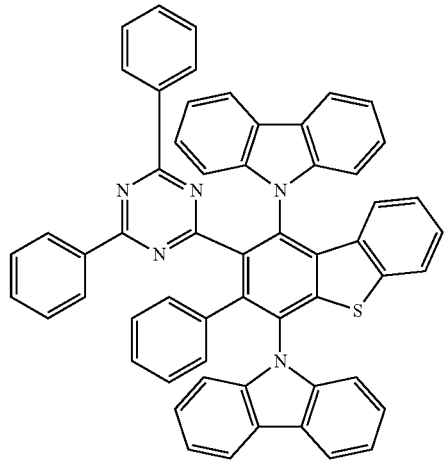
164
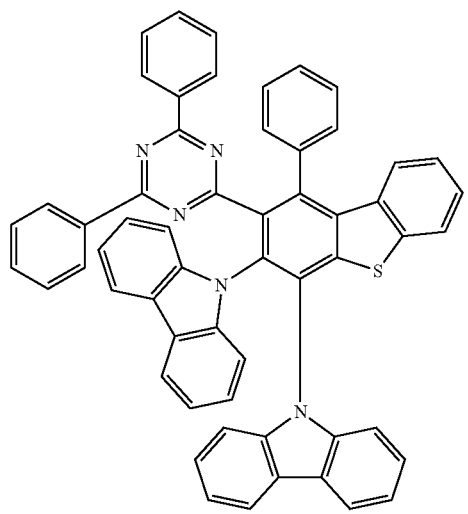
165
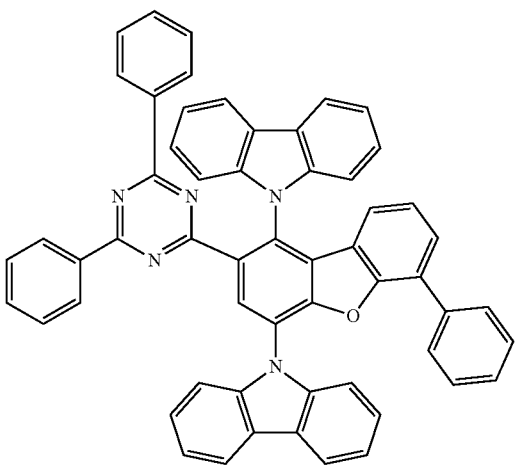

281
-continued
166
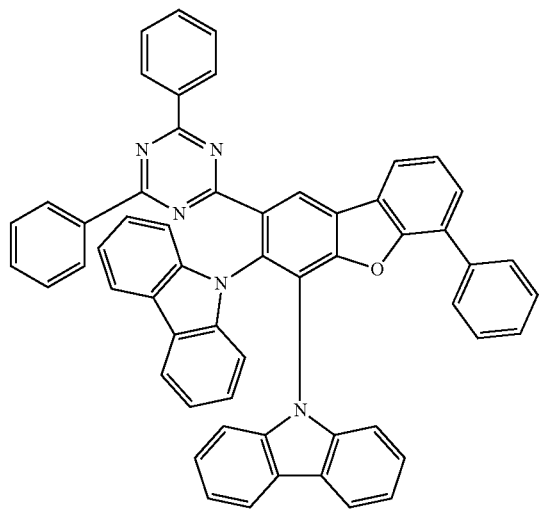
167
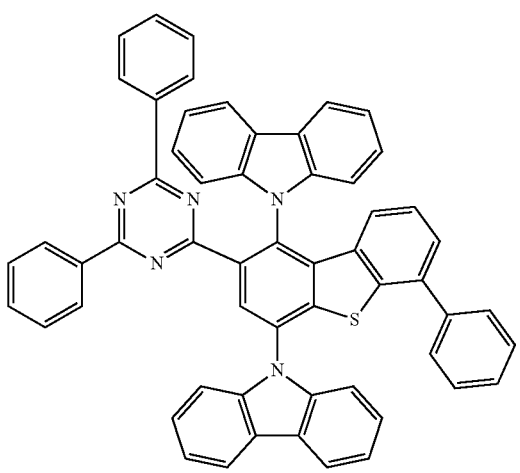
168
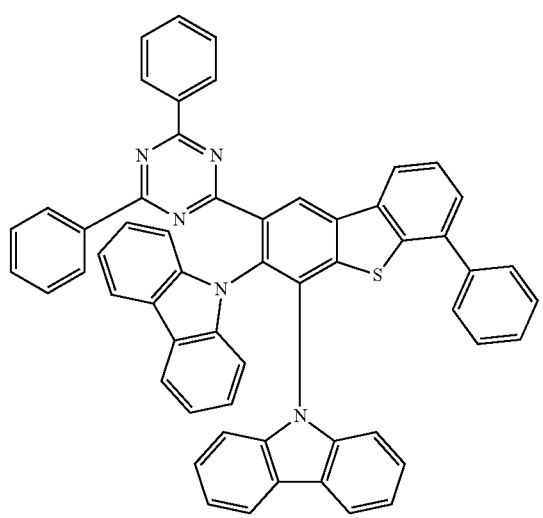
282
-continued
169
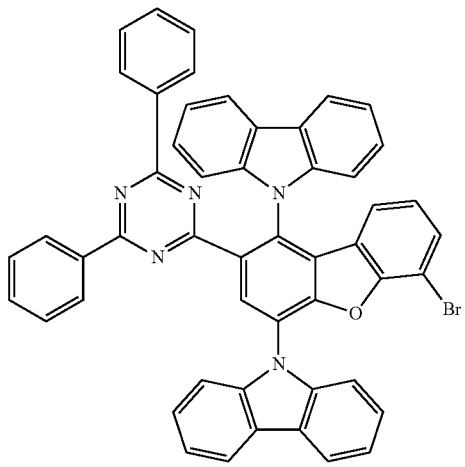
170
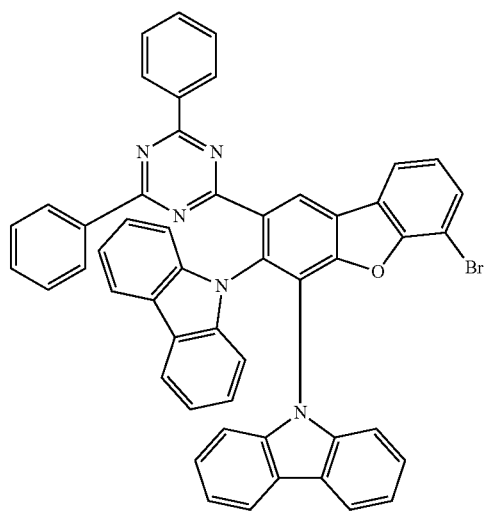
171
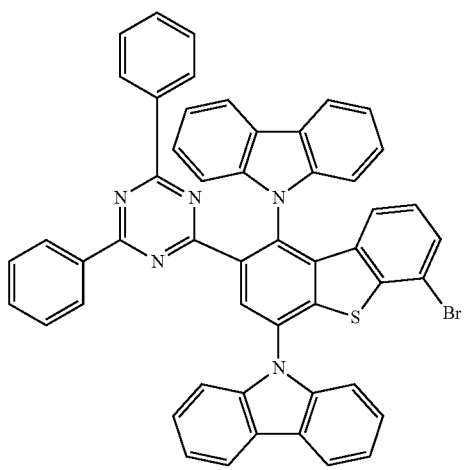

172
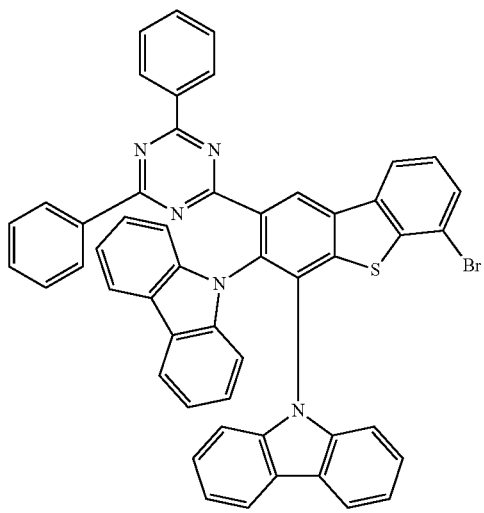
173
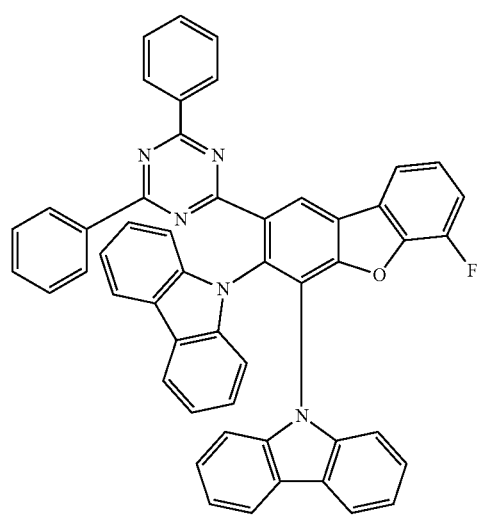
174
175
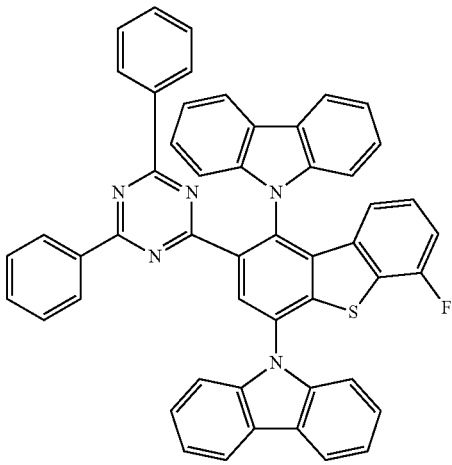
176
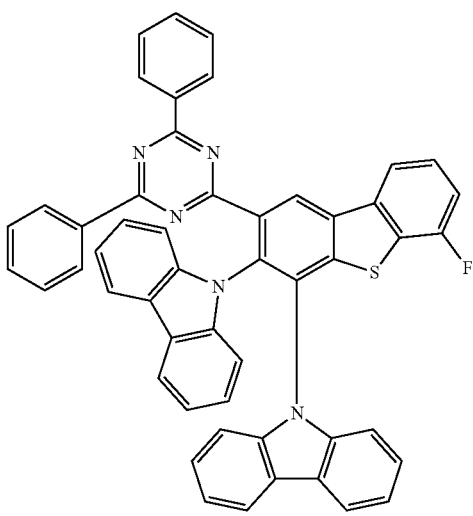
177
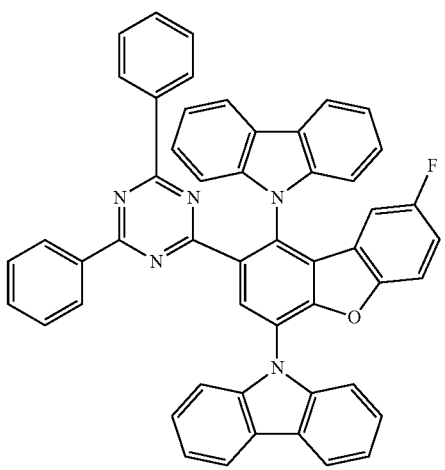

285
-continued
178
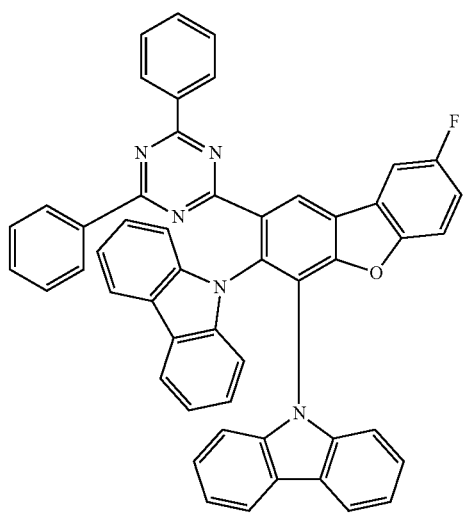
179
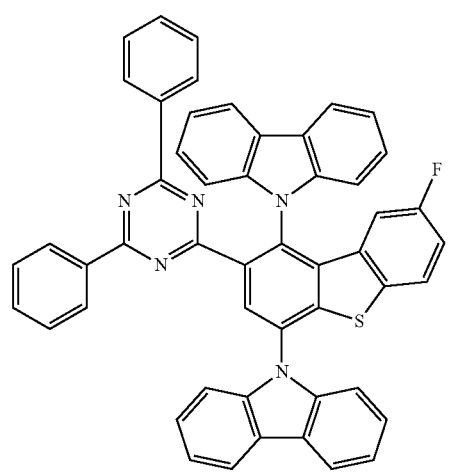
180
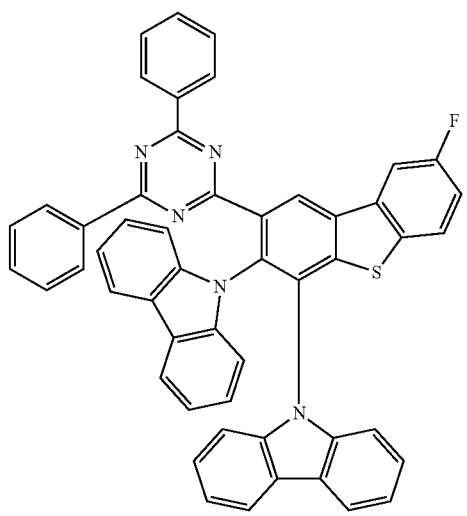
286
-continued
181
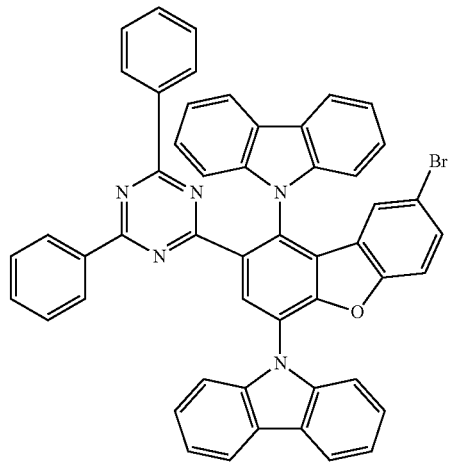
182
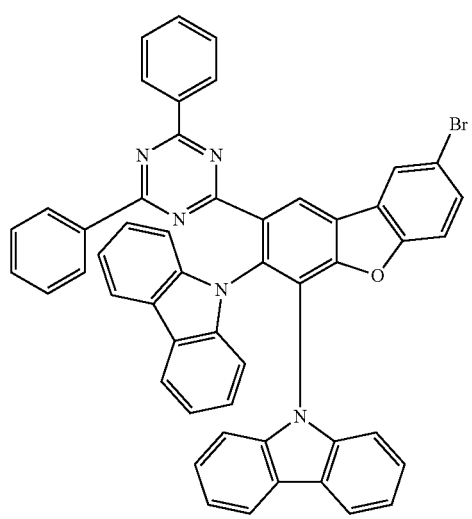
183
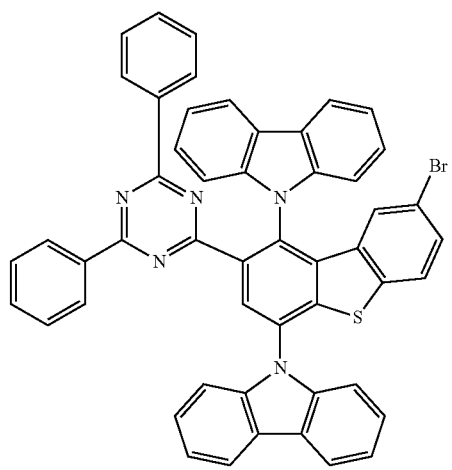

287
-continued
184
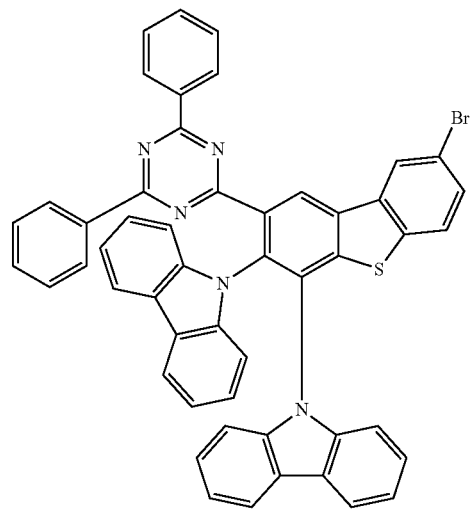
185
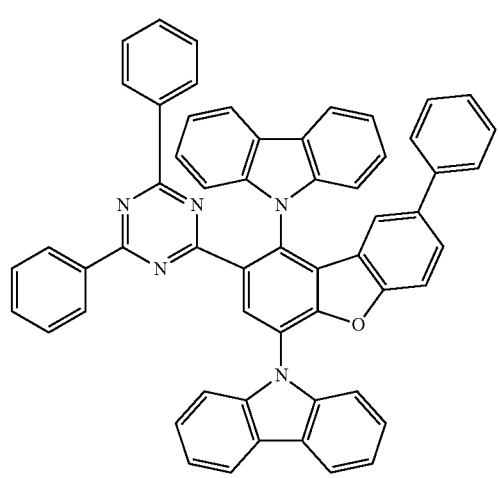
186
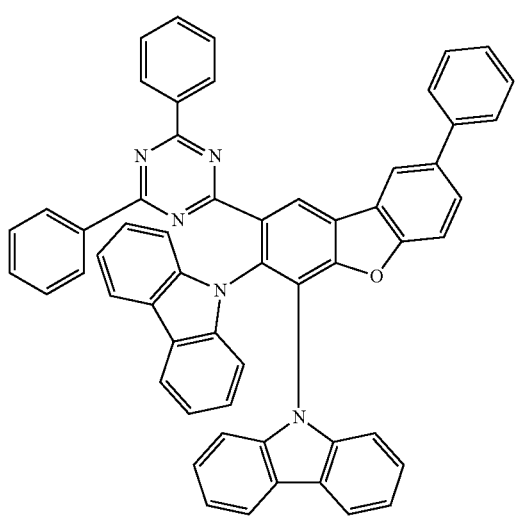
288
-continued
187
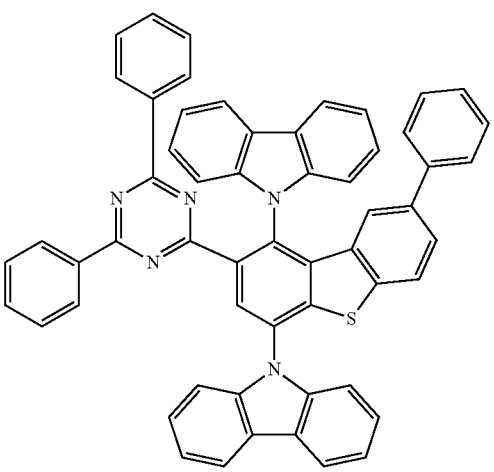
188
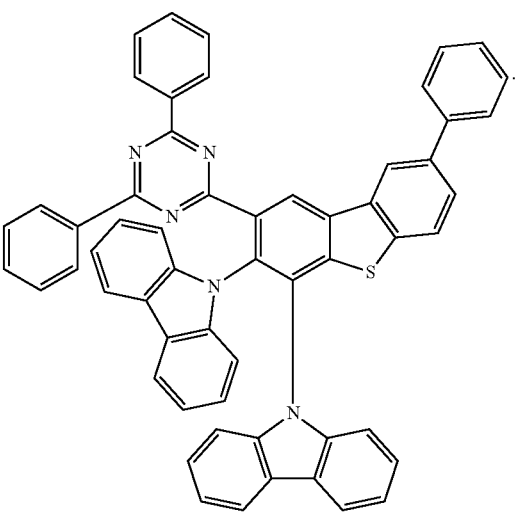
* * * * *